US006777418B2

(12) United States Patent
Lapierre et al.

(10) Patent No.: US 6,777,418 B2
(45) Date of Patent: Aug. 17, 2004

(54) RETINOID COMPOUNDS (I)

(75) Inventors: Jean-Marc Lapierre, Mountain View, CA (US); David Mark Rotstein, Sunnyvale, CA (US); Eric Brian Sjogren, Mountain View, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/968,425

(22) Filed: Oct. 1, 2001

(65) Prior Publication Data

US 2002/0082265 A1 Jun. 27, 2002

Related U.S. Application Data

(60) Provisional application No. 60/237,459, filed on Oct. 2, 2000.

(51) Int. Cl.$^7$ .................. A01N 43/54; A01N 43/64; A01N 43/40; A61K 31/505; A61K 31/445
(52) U.S. Cl. .................. 514/256; 514/274; 514/319; 514/359; 514/363; 514/365; 514/367; 514/369; 514/406; 514/427; 514/438; 514/448; 514/567; 514/569; 544/318; 544/335; 546/205; 548/136; 548/266.4; 548/255; 548/170; 548/187; 548/204; 548/374.1; 548/376.1; 548/373.1; 548/562; 549/79; 562/427; 562/442; 562/466
(58) Field of Search .................. 514/256, 274, 514/319, 359, 363, 365, 367, 369, 406, 427, 438, 448, 567, 569; 544/318, 335, 106; 546/205, 243; 548/136, 266.4, 255, 170, 187, 204, 374.1, 376.1, 373.1, 562, 578, 373, 1, 129, 264, 2, 251, 165, 573.1, 264.2, 483.71; 549/59, 483, 71, 506; 562/427, 442, 466; 560/466, 427, 442

(56) References Cited

U.S. PATENT DOCUMENTS

| 4,578,498 A | * 3/1986 | Frickel et al. .................. 560/8 |
| 5,324,840 A | 6/1994 | Chandraratna |
| 5,527,945 A | 6/1996 | Janssen et al. |
| 5,700,836 A | 12/1997 | Klaus et al. |
| 5,750,515 A | 5/1998 | Shibata et al. |
| 5,962,508 A | 10/1999 | Billoni et al. |
| 6,046,220 A | 4/2000 | Bernardon |

FOREIGN PATENT DOCUMENTS

| WO | WO 95/33745 | 12/1995 |
| WO | WO 96/32101 | 10/1996 |
| WO | WO 97/24116 | 7/1997 |

OTHER PUBLICATIONS

Randolph, Tim R., "Acute Promyelocytic Leukemia (AML–M3)—Part 1: Pathophysiology, Clinical Diagnosis, and Differentiation Therapy" Clinical Laborotory Science, vol. 13(2), pp. 98–105 (2000 Spring).*
Contreras et al, "Retionoides: su aplication en las lesiones precancerosas y el cancer oral" Medicina Oral, vol. 6(2), pp. 114 123 (Mar.–Apr. 2001).*
Hansel, Trevor T., "Smoking–Related Lung Disease: Prospect for New Drug Therapy" Drug News Perspectives, vol. 14(3), pp. 175–180 (Apr. 2001).*
McGowan, Stephen E., "Contributions of Retinoids to the Generation and Repair of the Pulmonary Alveolus" CHEST, vol. 121 suppl.), pp. 206S–208S (May 2002).*
Soprano, K.J. and Soprano, D.R., "Retinoic Acid Receptors and Cancer" J. Nutrit., vol. 132(12), pp. 3809S–3813S (2002).*
Crowe, D.L., "Receptor Selective Synthetic Retinoids as Potential Cancer Chemotherapy Agents" Current Cancer Drug Target vol. 2, pp. 77–86 (2002).*
Orfanos et al., "Current Use and Future Potential Role of the Retinoids in Dermatology" Drugs, vol. 53(3), pp. 358–388 (1997.*
Zouboulis, C., "Retinoids—Which Dermatological Indications Will Benefit in the Near Future!" Skin Pharmacol. and Applied Sk Physiol., vol. 14, p. 303–315 (2001).*
DiGiovanna, J.J., "Systemic Retinoid Therapy" Dermatologic Clinics, vol. 19(1), pp. 161–167 (2001).*
Ling, M.R., "Acitretin: Optimal Dosing Strategies" J. Amer. Acad. Of Dermatol., vol. 41 (No. 3, part 2), p. S13–S17 (1999.*
Kagechika et al., "Affinity Gels for Purification of Retinoid–Specific Binding Protein (RSBP)", *Biochemical and Biophysical Research Communications*, vol. 155(1), (1988), pp. 503–508.
Douguet et al., "Quantitative structure–activity relationship studies of RAR α, β, χ retinoid agonists", *QSAR Wiley–VCH*, vol. 18 (1999), pp. 107–123.

* cited by examiner

Primary Examiner—Richard L. Raymond
Assistant Examiner—Zachary C. Tucker
(74) Attorney, Agent, or Firm—Brian L. Buckwalter

(57) ABSTRACT

The current invention provide novel retinoid compounds and methods for their synthesis, methods of treating or preventing emphysema, cancer and dermatological disorders and pharmaceutical compositions suitable for the treatment or prevention of emphysema, cancer and dermatological disorders.

98 Claims, No Drawings

RETINOID COMPOUNDS (I)

CROSS-REFERENCE

This application claims the benefit of priority of U.S. Provisional Patent Application Serial No. 60/237,459 filed Oct. 2, 2000, which is incorporated herein by reference in its entirety.

FIELD OF THE INVENTION

The invention relates to novel retinoid compounds and methods of synthesis thereof. The invention also relates to methods of using these novel retinoid compounds and pharmaceutical compositions thereof.

BACKGROUND OF THE INVENTION

Retinoids

The retinoids are structural analogues of vitamin A and include both natural and synthetic compounds. Retinoid compounds such as all trans retinoic acid ("ATRA"), 9-cis-retinoic acid, trans 3–4 didehydroretinoic acid, 4-oxo retinoic acid, 13-cis-retinoic acid and retinol are pleiotrophic regulatory compounds that influence a large number of inflammatory, immune and structural cells.

For example, retinoids modulate epithelial cell proliferation, morphogenesis in lung and differentiation through a series of hormone nuclear receptors that belong to the steroid/thyroid receptor superfamily. The retinoid receptors are classified into the retinoic acid receptors (RAR) and the retinoid X receptors (RXR) each of which consists of three distinct subtypes ($\alpha$, $\beta$ and $\gamma$).

ATRA is the natural ligand for the retinoic acid receptors and binds with similar affinity to the $\alpha$, $\beta$ and $\gamma$ subtypes. A quantitative structure-activity relationship has been established for a number of synthetic RAR $\alpha$, $\beta$ and $\gamma$ retinoid agonists, which has elucidated the principal electronic and structural characteristics that provide selective affinity for each RAR subtype (Douget et al., *Quant. Struct. Act. Relat.*, 18, 107, 1999).

ATRA does not bind to RXR, for which 9-cis-retinoic acid is the natural ligand. A number of synthetic RXR $\alpha$, $\beta$ and $\gamma$ retinoid agonists have also been described in the art (See, e.g., Billoni et al., U.S. Pat. No. 5,962,508; Klaus et al., U.S. Pat. No. 5,986,131.

Therapeutic uses of Retinoids in Dermatology and Cancer

In tissues other than pulmonary tissues, retinoids typically have anti-inflammatory effects, can alter the progression of epithelial cell differentiation and may inhibit stromal cell matrix production. These biological effects of retinoids have led to the development of many topical agents for dermatological disorders such as psoriasis, acne, and hypertrophic cutaneous scars. Retinoids have also been used in the treatment of light and age damaged skin, the healing of wounds caused, for example, by surgery and burns (Mustoe et al., *Science* 237, 1333 1987; Sprugel et al., *J. Pathol.*, 129, 601, 1987; Boyd, *Am. J. Med.*, 86, 568, 1989) and as anti-inflammatory agents for treatment of arthritis. Other medicinal applications of retinoids include the control of acute promyelocytic leukemia, adeno and squamous cell carcinoma and hepatic fibrosis. Retinoids have also been used extensively in treatment of premalignant epithelial lesions and malignant tumors (carcinomas) of epithelial origin (Bollag et al., U.S. Pat. No. 5,248,071; Sporn et al., *Fed. Proc.* 1976, 1332; Hong et al., "Retinoids and Human Cancer" in *The Retinoids: Biology, Chemistry and Medicine*, M. B. Sporn, A. B. Roberts and D. S. Goodman (eds.) Raven Press, New York, 1994, 597–630). However, many retinoids previously studied often lack selectivity and consequently exert harmful pleiotrophic effects and may cause patient death when used in therapeutically effective amounts. Thus, the therapeutic use of retinoids in diseases other then cancer has been limited by toxic side effects. A general review of retinoids can be found in Goodman & Gilman's "The Pharmacological Basis of Therapeutics", $9^{th}$ edition (1996, McGraw-Hill) Chapters 63–64.

Emphysema

Chronic Obstructive Pulmonary Disease ("COPD") refers to a large group of lung diseases which prevent normal respiration. Approximately 11% of the population of the United States has COPD and available data suggests that the incidence of COPD is increasing. Currently, COPD is the fourth leading cause of mortality in the United States.

COPD is a disease in which the lungs are obstructed due to the presence of at least one disease selected from asthma, emphysema and chronic bronchitis. The term COPD was introduced because these conditions often co-exist and in individual cases it may be difficult to ascertain which disease is responsible for causing the lung obstruction (1987 *Merck Manual*). Clinically, COPD is diagnosed by reduced expiratory flow from the lungs that is constant over several months and in the case of chronic bronchitis persists for two or more consecutive years. The most severe manifestations of COPD typically include symptoms characteristic of emphysema.

Emphysema is a disease where the gas-exchange structures (e.g., alveoli) of the lung are destroyed, which causes inadequate oxygenation that may lead to disability and death. Anatomically, emphysema is defined by permanent airspace enlargement distal to terminal bronchioles (e.g., breathing tubes) which is characterized by reduced lung elasticity, decreased alveolar surface area and gas exchange and alveolar destruction that results in decreased respiration. Thus, the characteristic physiological abnormalities of emphysema are reduced gas exchange and expiratory gas flow.

Cigarette smoking is the most common cause of emphysema although other environmental toxins may also contribute to alveoli destruction. The injurious compounds present in these harmful agents can activate destructive processes that include, for example, the release of excessive amounts of proteases that overwhelm normal protective mechanisms, such as protease inhibitors present in the lung. The imbalance between proteases and protease inhibitors present in the lung may lead to elastin matrix destruction, elastic recoil loss, tissue damage, and continuous lung function decline. The rate of lung damage may be decreased by reducing the amounts of toxins in the lung (i.e., by quitting smoking). However, the damaged alveolar structures are not repaired and lung function is not regained. At least four different types of emphysema have been described according to their locations in the secondary lobule: panlobar emphysema, centrilobular emphysema, distal lobular emphysema and paracicatrical emphysema.

The major symptom of emphysema is chronic shortness of breath. Other important symptoms of emphysema include but are not limited to chronic cough, coloration of the skin caused by lack of oxygen, shortness of breath with minimal physical activity and wheezing. Additional symptoms that may be associated with emphysema include but are not limited to vision abnormalities, dizziness, temporary cessation of respiration, anxiety, swelling, fatigue, insomnia and memory loss. Emphysema is typically diagnosed by a physical examination that shows decreased and abnormal breathing sounds, wheezing and prolonged exhalation. Pulmonary function tests, reduced oxygen levels in the blood and a chest X-ray may be used to confirm a diagnosis of emphysema.

No effective methods for reversing the clinical indications of emphysema currently exist in the art. In some instances, medications such as bronchodilators, β-agonists, theophylline, anticholinergics, diuretics and corticosteroids delivered to the lung by an inhaler or nebulizer may improve respiration impaired by emphysema. Oxygen treatment is frequently used in situations where lung function has been so severely impaired that sufficient oxygen cannot be absorbed from the air. Lung reduction surgery may be used to treat patients with severe emphysema. Here, damaged portions of the lung are removed, which allows the normal portions of the lung to expand more fully and benefit from increased aeration. Finally, lung transplantation is another surgical alternative available to individuals with emphysema, which may increase quality of life but does not significantly improve life expectancy.

Lung Development, Alveolar Septation and use of Retinoids in Treating Emphysema

Alveoli are formed during development by division of sacchules that constitute the gas-exchange elements of the immature lung. The precise mechanisms governing formation of septa and their spacing remain currently unknown in primates. Retinoids such as ATRA, which is a multifunctional modulator of cellular behavior that may alter both extracellular matrix metabolism and normal epithelial differentiation, have a critical regulatory role in mammals such as the rat. For example, ATRA modulates critical aspects of lung differentiation through binding to specific retinoic acid receptors that are selectively temporally and spatially expressed. Coordinated activation of different retinoic acid receptors subtypes has been associated with lung branching, alveolization/septation and gene activation of tropoelastin in neonatal rats.

During alveolar septation, retinoic acid storage granules increase in the fibroblastic mesenchyme surrounding alveolar walls (Liu et al., Am. J. Physiol. 1993, 265, L430; McGowan et al., Am. J. Physiol., 1995, 269, L463) and retinoic acid receptor expression in the lung peaks (Ong et al., Proc. Natl. Acad. of Sci., 1976, 73, 3976; Grummer et al., Pediatr. Pulm. 1994, 17, 234). The deposition of new elastin matrix and septation parallels depletion of these retinoic acid storage granules. Postnatal administration of retinoic acid has been shown to increase the number of alveoli in rats, which supports the concept that ATRA and other retinoids may induces alveoli formation (Massaro et al., Am. J. Physiol., 270, L305, 1996). Treatment of newborn rat pups with dexamethasone, a glucocorticosteroid, prevents septation and decreases expression of some sub-types of retinoic acid receptor. Supplemental amounts of ATRA have been shown to prevent dexamethasone inhibition of alveoli formation. Further, ATRA prevents dexamethasone from diminishing retinoic acid receptor expression and subsequent alveolar septation in developing rat lung.

ATRA has been reported to induce formation of new alveoli and returns elastic recoil in the lung to approximately normal values in animal models of emphysema (Massaro et al., Nature Med., 1997, 3, 675; "Strategies to Augment Alveolization," National Heart, Lung, and Blood Institute, RFA: HL-98-011, 1998; Massaro et al., U.S. Pat. No. 5,998,486). However, the mechanism of action of ATRA in these studies remains undefined, although Massaro reports that ATRA generates new alveoli. More importantly, the use of ATRA presents several toxicity or adverse effects concerns.

Thus, novel retinoid agonists useful for treating dermatological disorders, emphysema and cancer without the toxicity problems of ATRA or other retinoids are highly desirable.

SUMMARY OF THE INVENTION

The current invention provides novel retinoid agonists, methods of treating or preventing emphysema, cancer and dermatological disorders, pharmaceutical compositions suitable for the treatment or prevention of emphysema, cancer and dermatological disorders and methods for delivering formulations of novel retinoids into the lung of a mammal suffering from emphysema, cancer and dermatological disorders.

In one embodiment, the invention provides compounds having the structural formula (I):

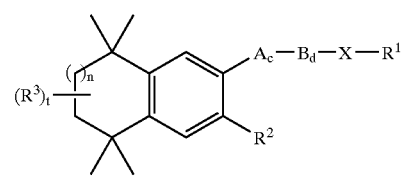

or a pharmaceutically acceptable salt, solvate hydrate or prodrug thereof wherein:

n is an integer from 0 to 2;

c is 0 or 1;

d is 0 or 1;

A is —C(=O)—, —C(=CH$_2$)—, —C(=NR$^4$)— or —CR$^5$R$^6$—;

R$^4$ is hydrogen, alkyl, hydroxy, alkoxy or amino; and R$^5$ and R$^6$ are independently hydrogen, alkyl or together, along with the carbon to which they are both attached, are cycloalkyl;

B is —C(O)O—, —OC(O)—, —C(O)NH—, —NHC(O)—, —NHC(O)NH—, —CR$^7$=CR$^8$—, —R$^7$C=CR$^8$—C(O)—, —C≡C—, —C≡C—C(O)—, —CH$_2$O—, —CH$_2$S—, —OCH$_2$—, —SCH$_2$—, —COCH$_2$—, or —CH$_2$CO—;

R$^7$ and R$^8$ are independently hydrogen or alkyl;

with the provisos that:
when A is —C(=O)—, or —C(=NR$^4$)—, then B is not —OC(O)—; and
when A is —C(=CH$_2$)—, then B is not —OC(O)—;

X is aryl or heteroaryl;

R$^1$ is —C(=O)—R$^9$;

R$^9$ is alkyl, cycloalkyl, cycloalkyl-alkyl, hydroxy, alkoxy, aryloxy, cycloalkyloxy, cycloalkyl-alklyloxy, arylalkyloxy, amino, alkylamino, dialkylamino, heteroalkyloxy, heteroalkylamino, heteroalkylthio, heterocyclyl or heterocyclylalkyl; and R$^2$ is:

(a) —(CR$^{10}$R$^{11}$)$_m$—Y$_p$—R$^{12}$;

m is an integer from 1 to 10;

p is 0 or 1;

$R^{10}$ and $R^{11}$ are independently hydrogen, alkyl, hydroxy or hydroxyalkyl;

Y is —O—, —S(O)$_q$— or —NR$^{13}$—; and q is an integer from 0 to 2; and $R^{13}$ is hydrogen or alkyl;

$R^{12}$ is hydrogen, alkyl, cycloalkyl, cycloalkyl-alkyl, aryl, arylalkyl, heteroaryl, heteroarylalkyl, acyl, alkoxycarbonyl, carbamoyl, substituted cycloalkyl, heteroalkyl, heteroalkylsubstituted cycloalkyl, hetero substituted cycloalkyl, hetero substituted cycloalkyl-alkyl, heterocyclyl or heterocyclylalkyl;

with the proviso that when p=0, then $R^{12}$ is not hydrogen or alkyl;

(b) heteroaryl;

(c) —Z—L; where:

Z is —CR$^{14}$=CR$^{15}$—, —C≡C—, —O—, —NR$^{16}$—, or —C(=O) or —S(O)$_q$—;

$R^{14}$, $R^{15}$ and $R^{16}$ are independently hydrogen or alkyl; and

L is heteroaryl, heteroarylalkyl or heteroalkyl with the proviso that when A$_c$—B$_d$ is —C(=O)—CR$^7$=CR$^8$—, then L is not heteroalkyl; or (d) —CR$^{14}$=CR$^{15}$—L$_1$ where L$_1$ is S(O)$_2$R$^{17}$ or SO$_2$NR$^{18}$R$^{19}$ where $R^{17}$ is alkyl and $R^{18}$ and $R^{19}$ are independently hydrogen or alkyl;

each $R^3$ is independently hydrogen, alkyl, hydroxy or oxo; and t is 1 or 2.

In a preferred embodiment, the invention provides compounds having the structural formula (II):

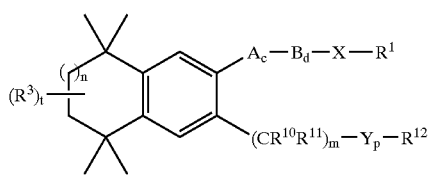

II or a pharmaceutically acceptable salt, solvate or hydrate thereof wherein A, B, c, d, X, $R^1$, $R^3$, n, $R^{10}$, $R^{11}$, m, Y, p and $R^{12}$ are as previously defined.

In another preferred embodiment, the invention provides compounds having the structural formula (III):

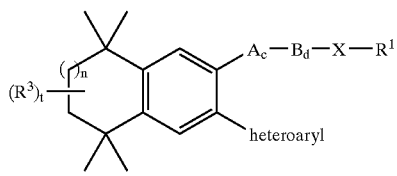

III or a pharmaceutically acceptable salt, solvate or hydrate thereof wherein A, B, c, d, X, $R^1$, $R^3$ and n are as previously defined.

In still another embodiment, the invention provides compounds having the structural formula (IV):

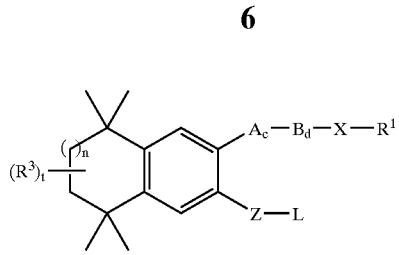

IV or a pharmaceutically acceptable salt, solvate or hydrate thereof wherein A, B, c, d, X, $R^1$, $R^3$, n, Z and L are as previously defined.

In still another embodiment of generic formula (I), c is 0, d is 1, B is —CR$^7$=CR$^8$— and n, $R^1$, $R^2$ $R^3$, $R^7$, $R^8$ and X are as previously defined. Preferably, $R^7$ and $R^8$ are hydrogen.

In a more specific embodiment, X is aryl. In a preferred embodiment, the invention provides compounds having the structural formula (V):

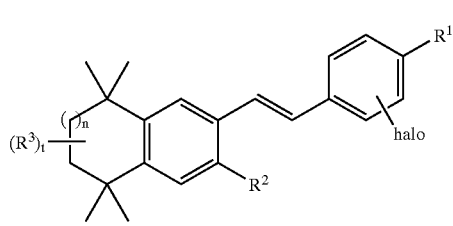

V or a pharmaceutically acceptable salt, solvate or hydrate thereof wherein n, $R^1$, $R^2$ and $R^3$ are as previously defined. In another preferred embodiment, the invention provides compounds having the structural formula (VI):

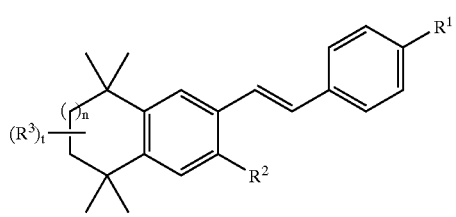

VI or a pharmaceutically acceptable salt, solvate or hydrate thereof wherein n, $R^1$, $R^2$ and $R^3$ are as previously defined.

In another specific embodiment, X is heteroaryl. In this embodiment, the invention provides compounds having the structural formula (VII):

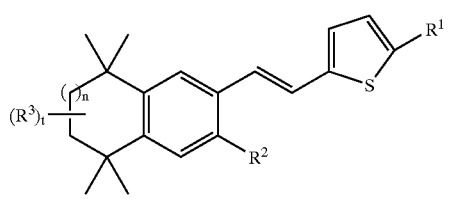

VII or a pharmaceutically acceptable salt, solvate or hydrate, thereof wherein n, $R^1$, $R^2$ and $R^3$ are as previously defined. In all of the embodiments hitherto described, also preferred are those where $R^1$ is —CO$_2$H or —CO$_2$-alkyl, particularly —CO$_2$H. Furthermore, also preferred are those embodiments where $R^3$ is hydrogen and n and t are 1.

Another embodiment of the invention is represented by compounds of structural formula VIII,

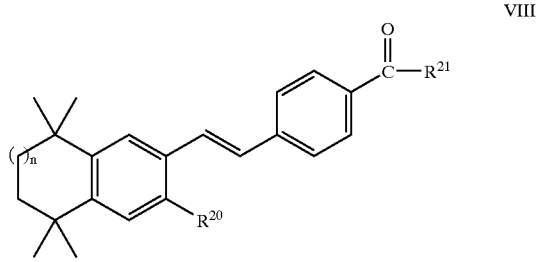

VIII wherein:
$R^{20}$ is alkyl;
$R^{21}$ is: (a) heteroalkyloxy, heteroalkylamino, or heteroalkylthio; or
(b) Q—$R^{22}$ where Q is —O—, —$NR^{23}$— or —S— (where $R^{23}$ is hydrogen or alkyl) and
$R^{22}$ is carboxyalkyl;
and n is an integer from 0 to 2.

The present invention also encompasses the use of the compounds of the invention to treat or prevent certain chronic obstructive airway disorders, particularly chronic obstructive pulmonary disease including chronic bronchitis, emphysema and asthma in mammals, especially humans that smoke or smoked cigarettes. In a preferred embodiment, the invention encompasses the treatment or prevention of panlobar emphysema, centrilobular emphysema or distal lobular emphysema in mammals using therapeutically effective doses of the compounds of the invention.

In one embodiment, the present invention encompasses the use of the compounds of the invention for treating or preventing emphysema. Further, the instant invention encompasses the use of pharmaceutical compositions of the compounds of the invention to treat or prevent emphysema. Moreover, the invention encompasses the use of electrohydrodynamic aerosol devices, aerosol devices and nebulizers to deliver formulations of compounds of the invention into the lung of a mammal suffering from or at risk of emphysema.

The invention encompasses the systemic use as well as the local use of the compounds of the invention or both in combination. Either or both can be achieved by the oral, mucosal or parenteral modes of administration. As mentioned above, means of delivering compounds of the invention directly into the lung by nebulizer, inhaler or other known delivery devices are encompassed by the invention.

A method for treating emphysema by combining compounds of the invention with one or more additional therapies such as smoking cessation (where appropriate) bronchodilators, antibiotics, oxygen therapy and the like is also encompassed by the invention.

In another aspect, the current invention encompasses methods for preventing emphysema in a human at risk of emphysema through administration of an amount of a compound of the invention, or pro-drug thereof, that is sufficient to prevent emphysema. In a another aspect, the current invention encompasses pharmaceutical compositions for preventing emphysema in a human at risk of emphysema through administration of a amount of a compound of the invention or pro-drug thereof, in a pharmaceutically acceptable carrier, that is sufficient to prevent emphysema.

In another aspect, the present invention encompasses the use of compounds of the invention for treating or preventing cancer. Further, the instant invention encompasses the use of pharmaceutical compositions of compounds of the invention to treat or prevent cancer. Moreover, the current invention encompasses the use of electrohydrodynamic aerosol devices, aerosol devices and nebulizers to deliver formulations of compounds of the invention into the lung of a mammal suffering from or at risk of cancer. Cancers include solid tumours such as breast, lung, prostate and liver cancer, promyelocytary leukaemias, precancerous changes of the mucosa in the mouth, tongue, larynx, oesophagus, bladder, cervix and colon.

A method for treating cancer by combining compounds of the invention with one or more additional therapies is also encompassed by the invention. Additional therapies include DNA intercalating agents such as cis-platin and immunotherapeutic agents such as gamma interferons and other cytokines.

In another aspect, the current invention encompasses methods for preventing cancer in a human at risk of cancer through administration of an amount of a compound of the invention, or a pro-drug thereof, that is sufficient to prevent cancer. In another aspect, the current invention encompasses pharmaceutical compositions for preventing cancer in a human at risk of cancer through administration of a amount of a compound of the invention or pro-drug thereof, in a pharmaceutically acceptable carrier, that is sufficient to prevent cancer.

In another aspect, the present invention encompasses the use of compounds of the invention for treating or preventing dermatological disorders. Further, the instant invention encompasses the use of pharmaceutical compositions of compounds of the invention to treat or prevent dermatological disorders. Dermatological disorders include acne, psoriasis, photodamaged skin and other dermatoses accompanied by cornification. Also included are wound healing, e.g., cuts, burns, operation wounds and other wounds associated with cutaneous trauma.

A method for treating dermatological disorders by combining compounds of the invention with one or more additional therapies and the like is also encompassed by the invention.

In another aspect, the current invention encompasses methods for preventing dermatological disorders in a human at risk from dermatological disorders through administration of an amount of a compound of the invention, or a pro-drug thereof, that is sufficient to prevent dermatological disorders. In a final aspect, the current invention encompasses pharmaceutical compositions for preventing emphysema in a human at risk from dermatological disorders through administration of a amount of a compound of the invention or pro-drug thereof, in a pharmaceutically acceptable carrier, that is sufficient to prevent dermatological disorders.

Definitions

As used herein the term "compounds of the invention" means the compounds of generic formula (I–VII) including but not limited to specific compounds within those formulas disclosed herein. The compounds of the invention are identified herein by their chemical structure and/or chemical name. Where a compound is referred to by both a chemical structure and a chemical name and the chemical structure and chemical name conflict, the chemical structure is determinative of the compound's identity. The compounds of the invention may contain one or more chiral centers and/or double bonds and therefore, may exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers using either separation techniques or chiral synthesis techniques known in the art.

"Acyl" means a radical —C(O)R, where R is hydrogen, alkyl, cycloalkyl, cycloalkyl-alkyl, aryl or arylalkyl wherein alkyl, cycloalkyl, cycloalkyl-alkyl, aryl and arylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where R' is hydrogen or alkyl, and R is hydrogen, alkyl, cycloalkyl, cycloalkyl-alkyl, aryl or arylalkyl wherein alkyl, cycloalkyl, cycloalkyl-alkyl, aryl and arylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R is an alkyl group as defined herein e.g., methoxy, ethoxy, propoxy, butoxy, and the like.

"Alkoxycarbonyl" means a radical —C(O)—R where R is alkoxy is as defined herein.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, n-butyl, iso-butyl, tert-butyl, pentyl, and the like.

"Alkylamino" means a radical —NHR where R represents an alkyl, cycloalkyl or cycloalkyl-alkyl group as defined herein. Representative examples include, but are not limited to methylamino, ethylamino, 1-methylethylamino, cyclohexylamino, and the like.

"Alkylene" means a linear saturated divalent hydrocarbon radical of one to ten carbon atoms or a branched saturated divalent hydrocarbon radical of three to ten carbon atoms, e.g., methylene, ethylene, 2,2-dimethylethylene, propylene, 2-methylpropylene, butylene, pentylene, and the like.

"Alkylsulfonyl" means a radical —S(O)$_2$R where R is an alkyl, cycloalkyl or cycloalkyl-alkyl group as defined herein, e.g., methylsulfonyl, ethylsulfonyl, propylsulfonyl, butylsulfonyl, cyclohexylsulfonyl and the like.

"Alkylsulfinyl" means a radical —S(O)R where R is an alkyl, cycloalkyl or cycloalkyl-alkyl group as defined herein e.g., methylsulfinyl, ethylsulfinyl, propylsulfinyl, butylsulfinyl, cyclohexylsulfinyl and the like.

"Alkylthio" means a radical —SR where R is an alkyl, cycloalkyl or cycloalkyl-alkyl group as defined herein e.g., methylthio, ethylthio, propylthio, butylthio, cyclohexylthio and the like.

"Aryl" means a monocyclic or bicyclic aromatic hydrocarbon radical which is optionally substituted with one or more substituents, preferably one, two or three, substituents preferably selected from the group consisting of alkyl, acyl, acylamino, alkoxycarbonyl, alkylamino, alkylsulfinyl, alkylsulfonyl, —SO$_2$NR'R" (where R' and R" are independently hydrogen or alkyl), alkylthio, alkoxy, amino, aryloxy, carbamoyl, cyano, dialkylamino, halo, haloalkyl, heteroalkyl, heterocyclyl, hydroxy, hydroxyalkyl, methylenedioxy, ethylenedioxy, nitro and thio. More specifically the term aryl includes, but is not limited to, phenyl, chlorophenyl, fluorophenyl, methoxyphenyl, 1-naphthyl, 2-naphthyl,and the derivatives thereof.

"Arylalkyl" refers to an alkyl radical as defined herein in which one of the hydrogen atoms of the alkyl group is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like.

"Aryloxy" means a radical —O—R where R is an aryl group as defined herein.

"Arylalkyloxy" means a radical —O—R where R is arylalkyl as defined herein.

"Carbamoyl" means the radical —C(O)N(R)$_2$ where each R group is independently hydrogen, alkyl or aryl as defined herein.

"Carboxy" means the radical —C(O)OH.

"Cyano" means the radical —CN.

"Cycloalkyl" refers to a saturated monovalent cyclic hydrocarbon radical of three to seven ring carbons e.g., cyclopropyl, cyclobutyl, cyclohexyl, 4-methylcyclohexyl and the like.

"Cycloalkyl-alkyl" means a radical —R$^a$R$^b$ where R$^a$ is an alkylene group and R$^b$ is a cycloalkyl group as defined herein, e.g., cyclohexylmethyl and the like.

"Cycloalkoxy" refers to a radical —OR wherein R is a saturated monovalent cyclic hydrocarbon radical of three to seven ring carbons e.g., cyclopropyl, cyclobutyl, cyclohexyl, 4-methylcyclohexyl and the like.

"Cycloalkyl-alkyloxy" means a radical —R$^a$OR$^b$ where R$^a$ is an alkylene group and R$^b$ is a saturated monovalent cyclic hydrocarbon radical of three to seven ring carbons.

"Substituted cycloalkyl" means a cycloalkyl radical as defined herein with one, two or three (preferably one) hydrogen atoms replaced by —Y—C(O)R (where, Y is absent or an alkylene group and R is hydrogen, acyl, acylamino, alkyl, alkoxycarbonyl, alkyamino, alkylsulfinyl, alkylsulfonyl, alkylthio, alkoxy, amino, aryloxy, arylalkyloxy, carbamoyl, cyano, dialkylamino, halo, haloalkyl, heteroalkyl, hydroxy, hydroxyalkyl, nitro or thio)

"Dialkylamino" means a radical —NRR' where R and R' independently represent an alkyl, cycloalkyl or cycloalkyl-alkyl group as defined herein. Representative examples include, but are not limited to dimethylamino, methylethylamino, di-(1-methylethyl)amino, (cyclohexyl) (methyl)amino, (cyclohexyl)(ethyl)amino, (cyclohexyl) (propyl)amino, (cyclohexylmethyl)(methyl)amino, (cyclohexylmethyl)(ethyl)amino and the like.

"Halo" means fluoro, chloro, bromo, or iodo, preferably fluoro and chloro.

"Haloalkyl" means an alkyl group substituted with one or more same or different halo atoms, e.g., —CH$_2$Cl, —CF$_3$, —CH$_2$CF$_3$, —CH$_2$CCl$_3$ and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from acyl, acylamino, alkyl, alkoxycarbonyl, alkyamino, alkylsulfinyl, alkylsulfonyl, —SO$_2$NR'R" (where R' and R" are independently hydrogen or alkyl), alkylthio, alkoxy, amino, aryloxy, carbamoyl, cyano, dialkylamino, ethylenedioxy, halo, haloalkyl, heteroalkyl, heterocyclyl, hydroxy, hydroxyalkyl, methylenedioxy, nitro and thio. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl and derivatives thereof.

"Heteroarylalkyl means an alkyl radical as defined herein in which one of the hydrogen atoms of the alkyl group is replaced with a heteroaryl group.

"Heteroalkyl" means an alkyl radical as defined herein wherein one or more hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkyl-alkyl; $R^b$ and $R^c$ are independently of each other hydrogen, acyl, alkyl, cycloalkyl, or cycloalkyl-alkyl; and when n is 0, $R^d$ is hydrogen, alkyl, cycloalkyl, or cycloalkyl-alkyl, and when n is 1 or 2, $R^d$ is alkyl, cycloalkyl, cycloalkyl-alkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroalkylamino" means a radical —NHR where R is a heteroalkyl group as defined herein.

"Heteroalkyloxy" means a radical —O—R where R is a heteroalkyl group as defined herein.

"Heteroalkylthio" means a radical —S—R where R is a heteroalkyl group as defined herein.

"Heteroalkylsubsituted cycloalkyl" means a cycloalkyl radical as defined herein wherein one, two or three hydrogen atoms in the cycloalkyl radical have been independently replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethylcyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo (C=O), imino, hydroximino (=NOH), $NR'SO_2R^d$ (where R' is hydrogen or alkyl and $R^d$ is alkyl, cycloalkyl, amino, monoalkylamino or dialkylamino), —X—C(O)R (where X is O or NR', R is hydrogen, alkyl, haloalkyl, hydroxy, alkoxy, amino, monoalkylamino, dialkylamino, or optionally substituted phenyl, and R' is H or alkyl) or —$S(O)_nR$ (where n is an integer from 0 to 2) such that when n is 0, R is hydrogen, alkyl, cycloalkyl, or cycloalkyl-alkyl, and when n is 1 or 2, R is alkyl, cycloalkyl, cycloalkyl-alkyl, amino, acylamino, monoalkylamino or dialkylamino. Representative examples include, but are not limited to, 2-, 3- or 4-hydroxycyclohexyl, 2-, 3- or 4-aminocyclohexyl, 2-, 3- or 4-sulfonamidocyclohexyl, and the like, preferably 4-hydroxycyclohexyl, 2-aminocyclohexyl, 4-sulfonamidocyclohexyl.

"Heterosubstituted cycloalkyl-alkyl" means a radical $R^aR^b$— where $R^a$ is a heterosubstituted cycloalkyl radical and $R^b$ is an alkylene radical.

"Heterocyclyl" means a saturated or unsaturated non-aromatic cyclic radical of 3 to 8 ring atoms in which one or two ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino, dialkylamino, arylalkyl, —$(X)_n$—C(O)R (where, X is O or NR', n is 0 or 1, R is hydrogen, alkyl, haloalkyl, hydroxy, alkoxy, amino, monoalkylamino, dialkylaamino, or optionally substituted phenyl and R' is H or alkyl), -alkylene-C(O)R (where R is hydrogen, alkyl, haloalkyl, hydroxy, alkoxy, amino, monoalkylamino, dialkylamino or optionally substituted phenyl) or —$S(O)_nR^d$ (where n is an integer from 0 to 2, and $R^d$ is hydrogen (provided that n is 0), alkyl, haloalkyl, cycloalkyl, cycloalkyl-alkyl, amino, monoalkylamino, dialkylamino, or hydroxyalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, and the derivatives thereof.

"Heterocyclylalkyl" means a radical —$R^aR^b$ where $R^a$ is an alkylene group and $R^b$ is a heterocyclyl group as defined above, e.g., tetrahydropyran-2-ylmethyl, 1,2-, or 3-piperidinylmethyl, 1-piperazinylmethyl, 4-methyl-piperazin-1-ylmethyl, and the like.

"Hydroxyalkyl" means an alkyl radical as defined herein, substituted with one or more hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Oxo" means divalent radical (C=O).

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to structural formula (I–VII) in vivo when such prodrug is administered to a mammalian subject. Prodrugs of a compound of structural formula (I–VII) are prepared by modifying one or more functional group(s) present in the compound of structural formula (I–VII) in such a way that the modification(s) may be cleaved in vivo to release the parent compound. Prodrugs include compounds of structural formula (I–VII) wherein a hydroxy, amino, or sulfhydryl group in a compound of structural formula (I–VII) is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of structural formula (I–VIII), N-acyl derivatives (e.g. N-acetyl) N-Mannich bases, Schiff bases and enaminones of amino functional groups, oximes, acetals, ketals and enol esters of ketone and aldehyde functional groups in compounds of Formula I–VII, and the like, see Bundegaard, H. "Design of Prodrugs" p1–92, Elesevier, New York-Oxford (1985), and the like.

"Protecting group" refers to a grouping of atoms that when attached to a reactive group in a molecule masks, reduces or prevents that reactivity. Examples of protecting groups can be found in T. W. Green and P. G. Futs, "Protective Groups in Organic Chemistry", (Wiley, $2^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include but are not limited to, those where the hydroxy group is either acylated or alkylated such as benzyl, and trityl ethers as well as alkyl ethers, tetrahydropyranyl ethers, trialkylsilyl ethers and allyl ethers.

As used herein, the term "mammal" includes human. The terms "human" and "patient" are used interchangeably herein.

"Treating" or "treatment" of emphysema, cancer or a dermatological disorder includes preventing the disease, (i.e., causing at least one of the clinical symptoms of the disease not to develop in a mammal that may be exposed to or predisposed to the disease but does not yet experience or display symptoms of the disease) inhibiting the disease (i.e., arresting or reducing the development of the disease or at least one of the clinical symptoms) or relieving the disease, (i.e., causing regression of the disease or at least one of the clinical symptoms). Preventing or prevention encompasses administration administration prior to manifestation of the disease or disorder.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Reference will now be made in detail to preferred embodiments of the invention. While the invention will be described in conjunction with preferred embodiments, it should be understood that it is not intended to limit the invention to these preferred embodiments. To the contrary, it is intended to cover alternatives, modifications, and equivalents as may be included within the spirit and scope of the invention as defined by the appended claims.

DETAILED DESCRIPTION OF THE INVENTION

The present invention encompasses novel retinoid compounds and their uses to effectively treat emphysema, cancer and dermatological disorders. The invention encompasses treating emphysema and related disorders, cancer and dermatological disorders, preferably while reducing or avoiding adverse effects associated with natural and synthetic retinoids when used at therapeutic levels. Adverse effects associated with retinoids at therapeutic levels include, but are not limited to, the toxic effects of hypervitaminosis A, such as headache, fever, skin and membrane dryness, bone pain, nausea and vomiting, psychiatric disorders and gastrointestinal disorders.

In one embodiment, the present invention provides compounds having the structural formula (I):

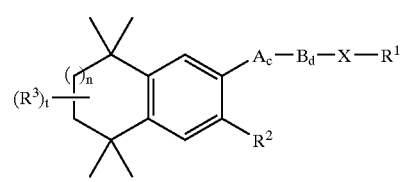

I or a pharmaceutically acceptable salt, solvate or hydrate thereof wherein:
  n is an integer from 0 to 2;
  c is 0 or 1;
  d is 0 or 1;
  A is —C(=O)—, —C(=CH$_2$)—, —C(=NR$^4$)— or —CR$^5$R$^6$—;

R$^4$ is hydrogen, alkyl, hydroxy, alkoxy or amino; and
R$^5$ and R$^6$ are independently hydrogen, alkyl or together, along with the carbon to which they are both attached, are cycloalkyl;

B is —C(O)O—, —OC(O)—, —C(O)NH—, —NHC(O)—, —NHC(O)NH—, —CR$^7$=CR$^8$—, —R$^7$C=CR$^8$—C(O)—, —C≡C—, —C≡C—C(O)—, —CH$_2$O—, —CH$_2$S—, —OCH$_2$—, —SCH$_2$—, —COCH$_2$—, or —CH$_2$CO—;

R$^7$ and R$^8$ are independently hydrogen or alkyl;
with the provisos that:
when A is —C(=O)—, or —C(=NR$^4$)—, then B is not —OC(O)—; and
when A is —C(=CH$_2$)—, then B is not —OC(O)—;

X is aryl or heteroaryl;
R$^1$ is —C(=O)—R$^9$;
R$^9$ is alkyl, cycloalkyl, cycloalkyl-alkyl, hydroxy, alkoxy, aryloxy, cycloalkyloxy, cycloalkyl-alklyloxy, arylalkyloxy, amino, alkylamino, dialkylamino, heteroalkyloxy, heteroalkylamino, heteoalkylthio, heterocyclyl or heterocyclylalkyl; and R$^2$ is:
(a) —(CR$^{10}$R$^{11}$)$_m$—Y$_p$—R$^{12}$;
m is an integer from 1 to 10;
p is 0 or 1;
R$^{10}$ and R$^{11}$ are independently hydrogen, alkyl, hydroxy or hydroxyalkyl;
Y is —O—, —S(O)$_q$— or —NR$^{13}$—; and
q is an integer from 0 to 2; and
R$^{13}$ is hydrogen or alkyl;
R$^{12}$ is hydrogen, alkyl, cycloalkyl, cycloalkyl-alkyl, aryl, arylalkyl, heteroaryl, heteroarylalkyl, acyl, alkoxycarbonyl, carbamoyl, substituted cycloalkyl, heteroalkyl, heteroalkylsubstituted cycloalkyl, heterosubstituted cycloalkyl, heterosubstituted cycloalkyl-alkyl, heterocyclyl or heterocyclylalkyl;
with the proviso that when p=0, then R$^{12}$ is not hydrogen or alkyl;
(b) heteroaryl;
(c) —Z—L; where:
Z is —CR$^{14}$=CR$^{15}$—, —C≡C—, —O—, —NR$^{16}$—, C(=O) or —S(O)$_q$—;
R$^{14}$, R$^{15}$ and R$^{16}$ are independently hydrogen or alkyl; and
L is heteroaryl, heteroarylalkyl or heteroalkyl;
with the proviso that when A$_c$—B$_d$ is —C(=O)—CR$^7$=CR$^8$—, then L is not heteroalkyl; or
(d) —CR$^{14}$=CR$^{15}$—L$_1$ where L$_1$ is S(O)$_2$R$^{17}$ or SO$_2$NR$^{18}$R$^{19}$ where R$^{17}$ is alkyl and R$^{18}$ and R$^{19}$ are independently hydrogen or alkyl;

each R$^3$ is independently hydrogen, alkyl, hydroxy or oxo; and
t is 1 or 2.

Preferred compounds of the invention are RAR agonists, particularly RAR-gamma selective agonists and bind to the RAR-gamma receptor at least five fold better than they bind to the RAR-alpha receptor. Binding affinities for RAR agonists are typically less than 10 micromolar, preferably less than 1 micromolar.

In one embodiment, n is 1. In another embodiment, A is —C(=O)—. In yet another embodiment, c is 0.

Preferably, B is —NHC(O)NH—, —CR$^7$=CR$^8$—, —R$^7$C=CR$^8$—C(O)—, —C≡C—, —C≡C—C(O)— or —CH$_2$O—, most preferably —CR$^7$=CR$^8$—, and particularly R$^7$ and R$^8$ are hydrogen where B is trans —CH=CH—, i.e., the alkene moiety has the E-stereochemistry.

In one embodiment, X is phenyl. In another embodiment, X is thienyl. In one embodiment, R$^3$ is hydrogen. In another embodiment, R$^3$ is hydroxy or oxo. In one embodiment, R$^9$ is alkoxy, aryloxy or arylalkyloxy. In another embodiment, R$^9$ is hydroxy.

In one preferred embodiment, the invention provides compounds having structural formula (II):

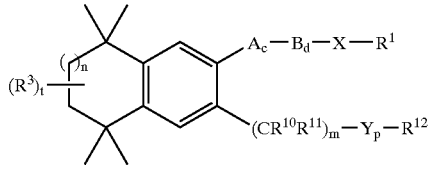

II or a pharmaceutically acceptable salt, solvate or hydrate thereof, wherein A, B, c, d, X, R$^1$, R$^3$, n, R$^{10}$, R$^{11}$, m, Y, p and R$^{12}$ are as previously defined. Preferably, m is 1 to 4. In one embodiment, p is 1. In another embodiment, p is 0.

In a preferred embodiment of compounds having structural formula (II), m is 1, p is 1 and Y is —O—. Preferably, R$^{12}$ is hydrogen, acyl, alkyl, carbamoyl, cycloalkyl, aryl, heteroaryl, or heteroalkyl. Compounds 1, 5 and 15 in Table 10 exemplify this embodiment.

In another preferred embodiment of compounds having structural formula (II), m is 1, p is 1 and Y is —S(O)$_q$—. In one embodiment, R$^{12}$ is alkyl, cycloalkyl or heteroalkyl. Compounds 2, 3, 4, 9, 17 and 18 in Table 1 exemplify this embodiment. In another embodiment, R$^{12}$ is heteroaryl, heteroarylalkyl, heterocyclyl or heterocyclylalkyl. Compounds 8, 19, 22, 23, 25, 32, 34 and 35 in Table 1 exemplify this embodiment.

In still another preferred embodiment of compounds having structural formula (II), m is 3, p is 1 and Y is —O—. Preferably, R$^{12}$ is hydrogen, acyl, alkyl, carbamoyl, cycloalkyl, aryl, heteroaryl, or heteroalkyl. Compounds 10, 11 and 12 in Table 1 exemplify this embodiment.

In still another preferred embodiment of compounds having structural formula (II), m is 3, p is 1 and Y is —NR$^{13}$—. Preferably, R$^{12}$ is acyl, alkyl, cycloalkyl, aryl, heteroaryl, or heterocyclyl. Compound 33 in Table 1 exemplifies this embodiment.

In still another preferred embodiment of compounds having structural formula (II), m is 3, p is 1 and Y is —S(O)$_q$—. Preferably, R$^{12}$ is aryl, arylalkyl, heteroaryl, heteroalkyl, heterocyclyl or heterocyclylalkyl. Compounds 24 and 28 in Table 1 exemplify this embodiment.

In still another preferred embodiment of compounds having structural formula (II), m is 2, p is 1 and Y is —O—. Preferably, R$^{12}$ is hydrogen, acyl, alkyl, carbamoyl, cycloalkyl, aryl, heteroaryl, or heteroalkyl. Compound 31 in Table 1 exemplifies this embodiment.

In still another preferred embodiment of compounds having structural formula (II), m is 2, p is 1 and Y is —S(O)$_q$—. Preferably, R$^{12}$ is aryl, arylalkyl, heteroaryl, heteroalkyl, heterocyclyl or heterocyclylalkyl. Compounds 26 and 27 in Table 1 exemplify this embodiment.

In still another preferred embodiment of compounds having structural formula (II), m is 4, p is 1 and Y is —(O)—. Preferably, R$^{12}$ is hydrogen, acyl, alkyl, carbamoyl, cycloalkyl, aryl, heteroaryl, or heteroalkyl. Compound 51 in Table 1 exemplifies this embodiment.

In still another preferred embodiment of compounds having structural formula (II), m is 1 and p is 0. In one embodiment, $R^{12}$ is heteroaryl, heteroarylalkyl, heterocyclyl or heterocyclylalkyl. Compounds 6, 7, 44, 45, 47, 50, 53, 54, 55, 138, 139, 143, 146,149 and 150 in Table 1 exemplify this embodiment. Compound 6 is a particularly preferred member of the above group of compounds. In another embodiment, $R^{12}$ is aryl, arylalkyl, cycloalkyl or substituted cycloalkyl. Compounds 42 and 54 in Table 1 exemplify this embodiment.

In still another preferred embodiment of compounds having structural formula (II), m is 2 and p is 0. Preferably, $R^{12}$ is aryl, arylalkyl, heteroaryl, heteroarylalkyl, heteroalkyl, heterocyclyl or heterocyclylalkyl. Compounds 29, 37, 38, 40, 41, 132, 134, 140, 147 and 152 in Table 1 exemplify this embodiment.

In still another preferred embodiment of compounds having structural formula (II), m is 3 and p is 0. Preferably, $R^{12}$ is aryl, arylalkyl, heteroaryl, heteroarylalkyl, heterocyclyl or heterocyclylalkyl. Compounds 30, 36, 46, 52, 130, 131, 135, 141 and 142 in Table 1 exemplify this embodiment.

In another preferred embodiment, the invention provides compounds having the structural formula (III):

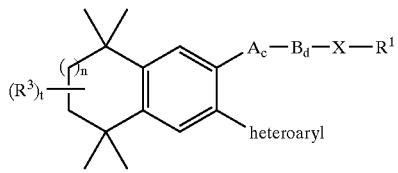

III or a pharmaceutically acceptable salt, solvate or hydrate thereof, wherein A, B, c, d, X, $R^1$, $R^3$ and n are as previously defined. Compounds 48, 49, 156 and 157 in Table 1 exemplify the preceding embodiment.

In another embodiment, the invention provides compounds having structural formula (IV):

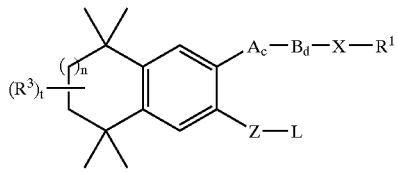

IV or a pharmaceutically acceptable salt, solvate or hydrate thereof, wherein A, B, c, d, X, $R^1$, $R^3$, n, Z and L are as previously defined. In one embodiment, L is heteroaryl or heteroarylalkyl. In another embodiment, Z is —O— or —S(O)$_q$—. Compounds 154, 155, 159 and 160 in Table 1 exemplify this embodiment.

In another embodiment of generic formula (I), c is 0, d is 1 and B is —CR$^7$═CR$^8$— and n, $R^1$, $R^2$ $R^3$ and X are as previously defined. Preferably, $R^7$ and $R^8$ are both hydrogen. In one embodiment, X is aryl. In a more specific embodiment, the invention provides compounds having the structural formula (V):

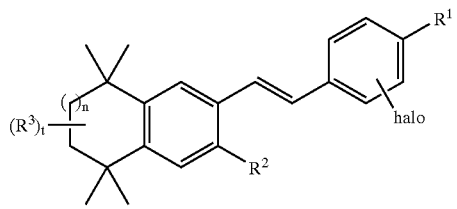

V or a pharmaceutically acceptable salt, solvate or hydrate thereof, wherein n, $R^1$, $R^2$ and $R^3$ are as previously defined. In another embodiment, the invention provides compounds having the structural formula (VI):

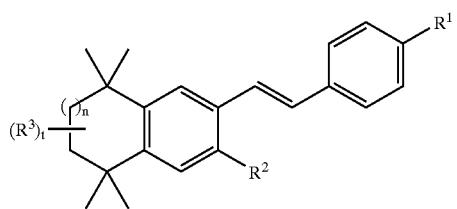

VI or a pharmaceutically acceptable salt, solvate or hydrate thereof, wherein n, $R^1$, $R^2$ and $R^3$ are as previously defined.

In another embodiment, X is heteroaryl. In this embodiment, the invention provides compounds having the structural formula (VII):

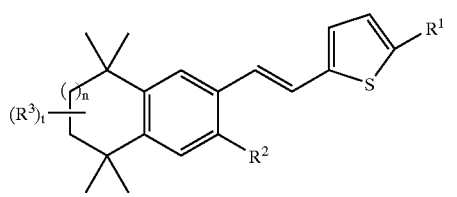

VII or a pharmaceutically acceptable salt, solvate or hydrate, thereof, wherein n, $R^1$, $R^2$ and $R^3$ are as previously defined.

Another embodiment of this invention is represented by compounds of structural formula VIII,

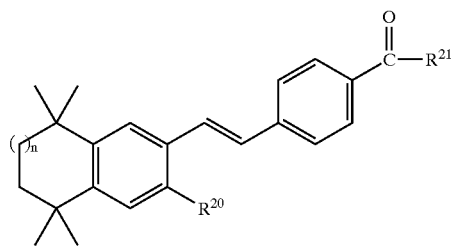

VIII wherein:
$R^{20}$ is alkyl;
$R^{21}$ is: (a) heteroalkyloxy, heteroalkylamino, or heteroalkylthio; or
(b) Q—$R^{22}$ where Q is —O—, —NR$^{23}$— or —S— (where $R^{23}$ is hydrogen or alkyl) and
$R^{22}$ is carboxyalkyl;
and n is an integer from 0 to 2.

These compounds are prodrugs of compounds of Formula VIII where $R^{21}$ is hydroxy and are converted in vivo to compounds where R²¹ is hydroxy. Compounds 56, 57, 58 and 59 exemplify this embodiment.

Preferred compounds of the invention include those depicted in Table 1 below.

TABLE 1

| CMP # | MOLECULAR STRUCTURE | Mp (° C.) | Mol. Ion. M+ |
|---|---|---|---|
| 1 | 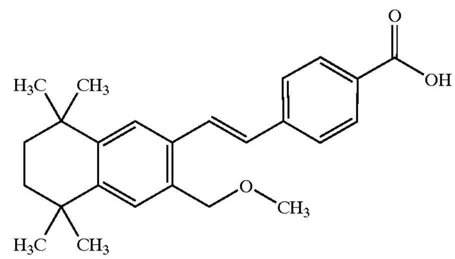 | 184.2–187.9 | |
| 2 | 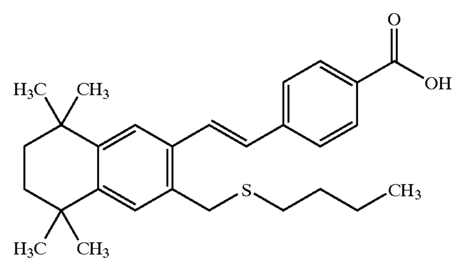 | | 436 |
| 3 | 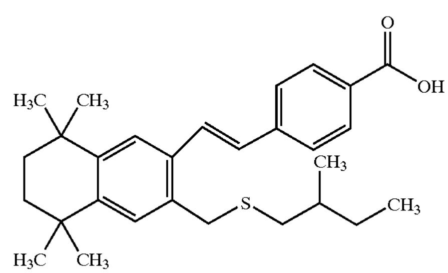 | 66.1–68.5 | |
| 4 | 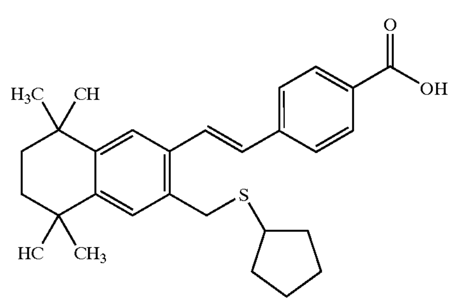 | 209.4–211.3 | |
| 5 | 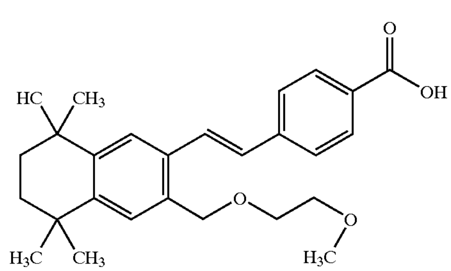 | 55.9–58.2 | |

TABLE 1-continued

| CMP # | MOLECULAR STRUCTURE | Mp (° C.) | Mol. Ion. M+ |
|---|---|---|---|
| 6 | 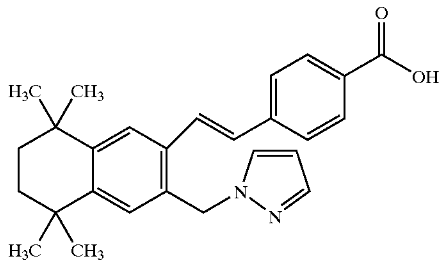 | 246.5–248 | |
| 7 | 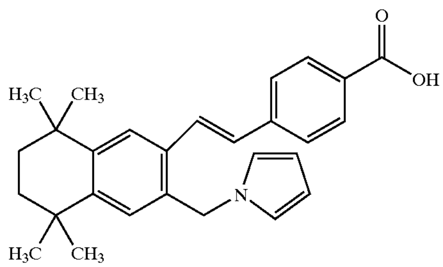 | 255.6–257.4 | |
| 8 | 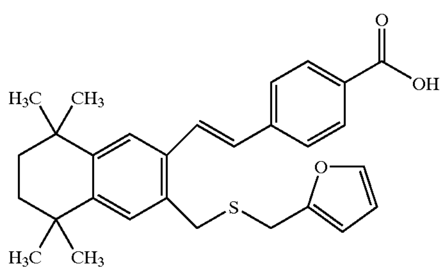 | 169.7–171 | |
| 9 | 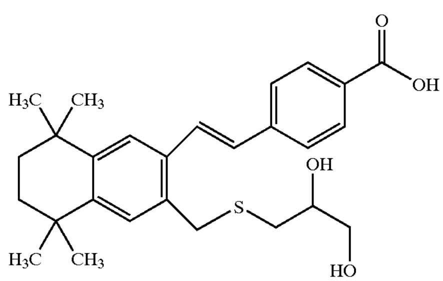 | 174.8–175.9 | |
| 10 | 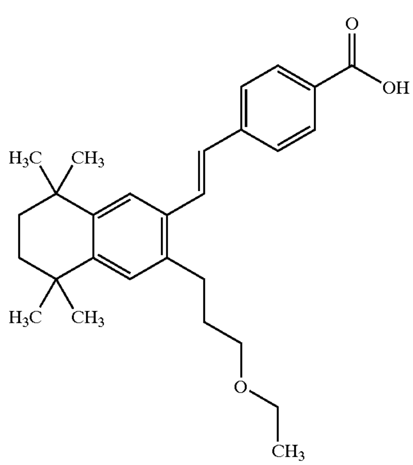 | 169.4–173.3 | 420 |

TABLE 1-continued

| CMP # | MOLECULAR STRUCTURE | Mp (° C.) | Mol. Ion. M+ |
|---|---|---|---|
| 11 | 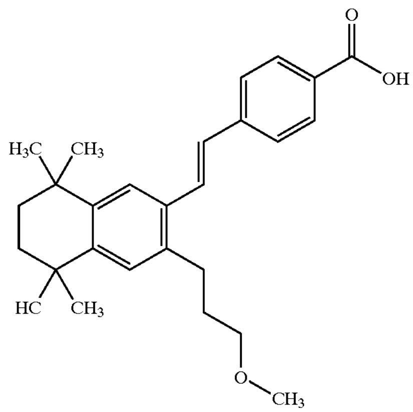 | 164.7–166 | |
| 12 | 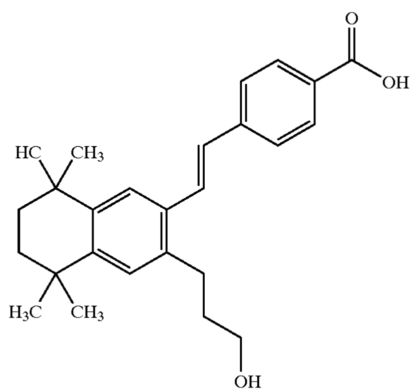 | 212.8–213.2 | |
| 13 | 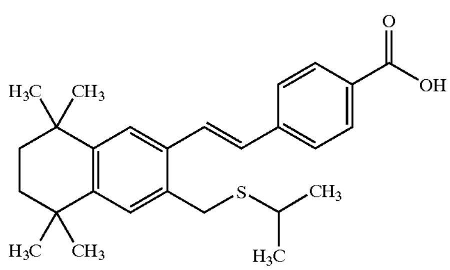 | 208.6–210.8 | |
| 14 | 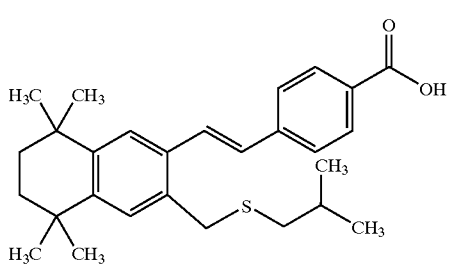 | | 436 |

TABLE 1-continued

| CMP # | MOLECULAR STRUCTURE | Mp (° C.) | Mol. Ion. M+ |
|---|---|---|---|
| 15 | 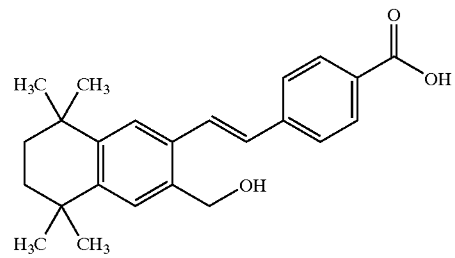 | | 364 |
| 16 | 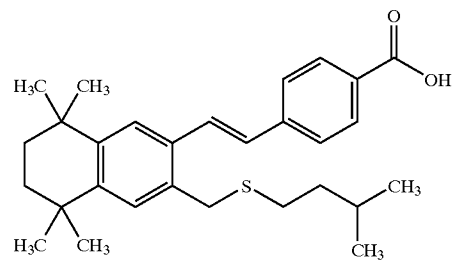 | | 450 |
| 17 | 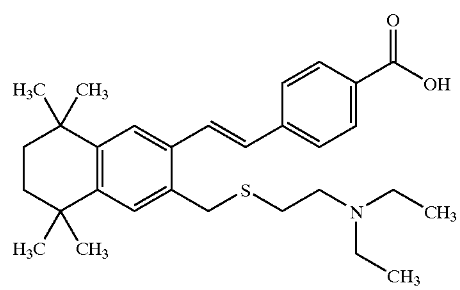 | | 479 |
| 18 | 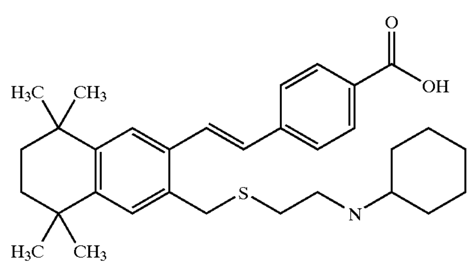 | | 505 |
| 19 | 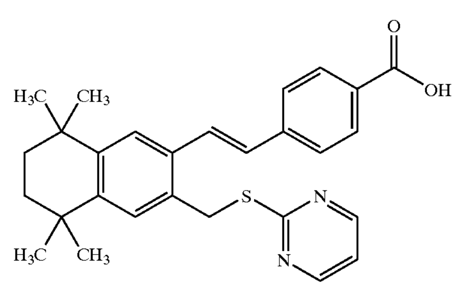 | | 458 |

TABLE 1-continued

| CMP # | MOLECULAR STRUCTURE | Mp (° C.) | Mol. Ion. M+ |
|---|---|---|---|
| 20 | 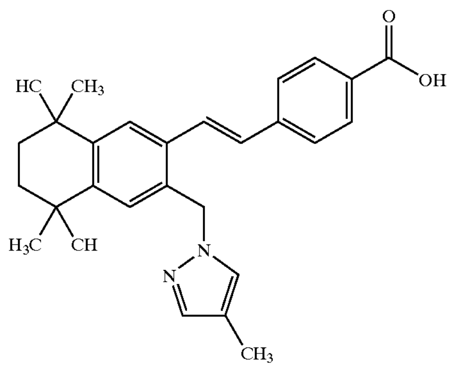 | | 428 |
| 21 | 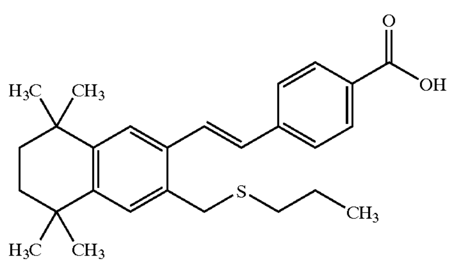 | | 422 |
| 22 | 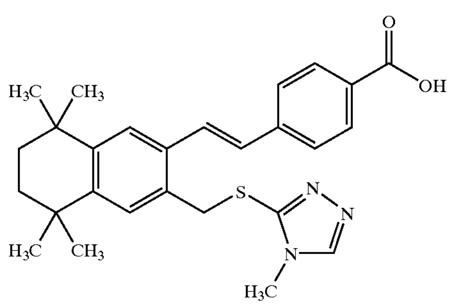 | 251.6–252.6 | |
| 23 | 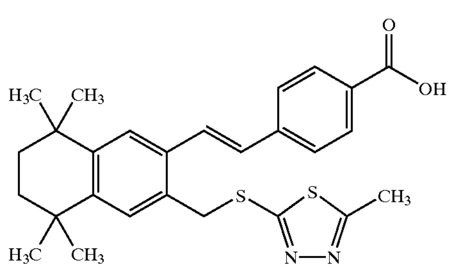 | 218.1–218.5 | |
| 24 | 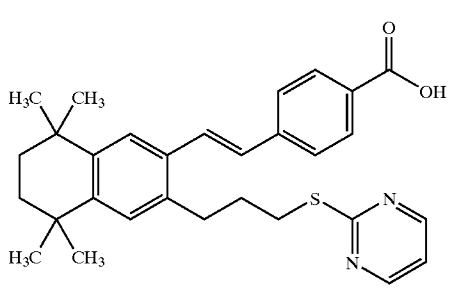 | 177–177.5 | |

TABLE 1-continued

| CMP # | MOLECULAR STRUCTURE | Mp (° C.) | Mol. Ion. M+ |
|---|---|---|---|
| 25 | 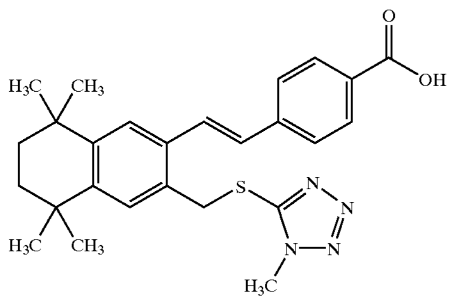 | | 462 |
| 26 | 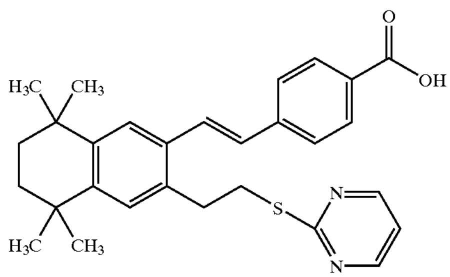 | 224.3–228.6 | |
| 27 | 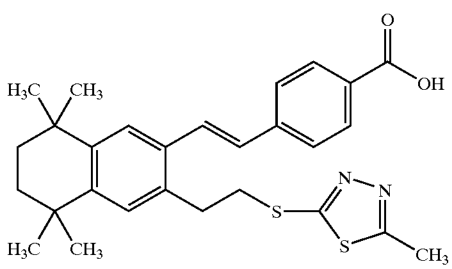 | 244.7–245.2 | |
| 28 | 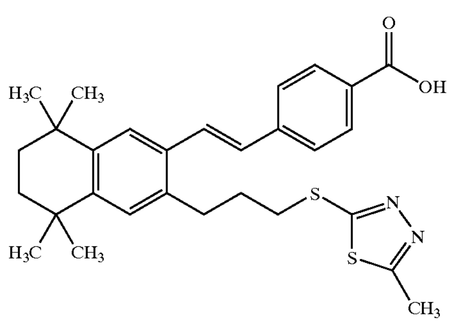 | 144–145.3 | |
| 29 | 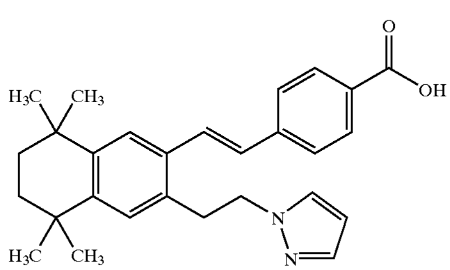 | 235.3–235.9 | |

TABLE 1-continued

| CMP # | MOLECULAR STRUCTURE | Mp (° C.) | Mol. Ion. M+ |
|---|---|---|---|
| 30 | 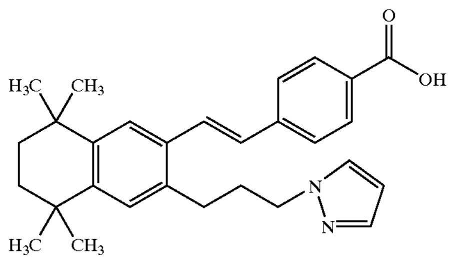 | 181.5–182.5 | |
| 31 | 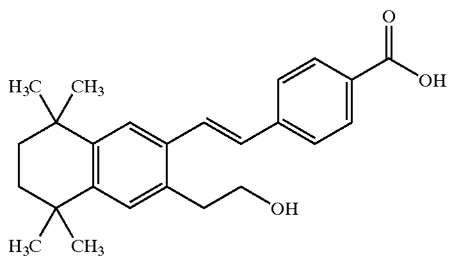 | | MH+ = 379 |
| 32 | 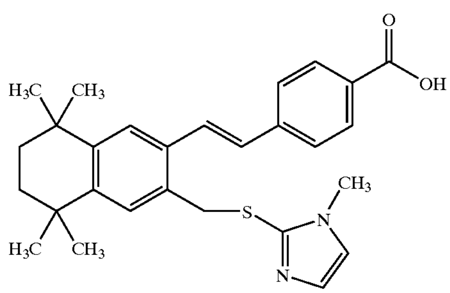 | | 460 |
| 33 | 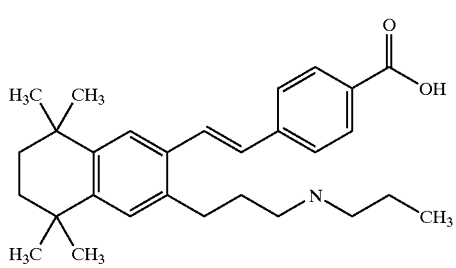 | | 433 |
| 34 | 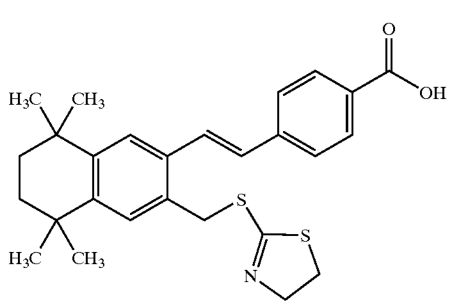 | | 465 |

TABLE 1-continued
| CMP # | MOLECULAR STRUCTURE | Mp (° C.) | Mol. Ion. M+ |
|---|---|---|---|
| 35 | 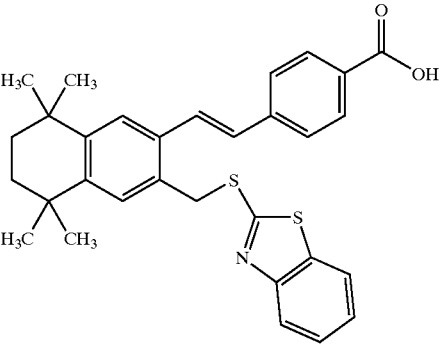 | | 513 |
| 36 | 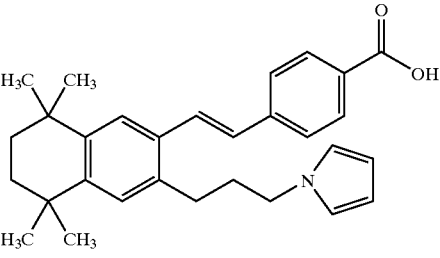 | | MH+ = 442 |
| 37 | 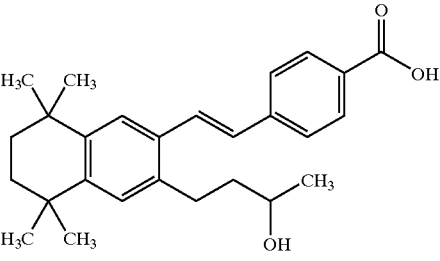 | | MH+ = 407 |
| 38 | 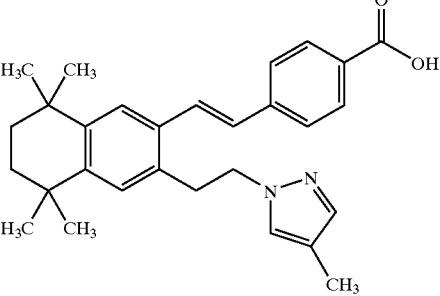 | | MH+ = 443 |
| 39 | 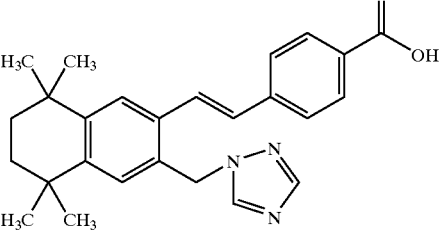 | | 415 |

TABLE 1-continued
| CMP # | MOLECULAR STRUCTURE | Mp (° C.) | Mol. Ion. M+ |
|---|---|---|---|
| 40 | 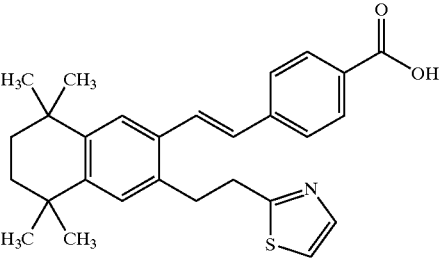 | 215.8–217.5 | |
| 41 | 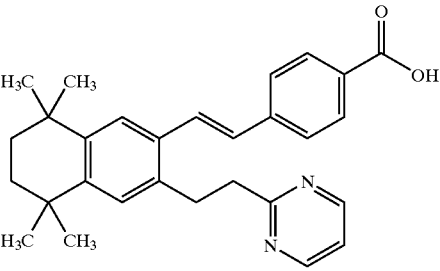 | 228–228.9 | |
| 42 | 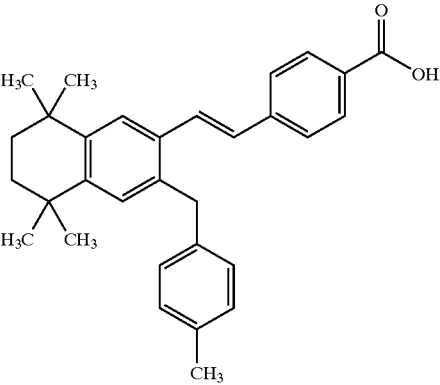 | 216.3–217.3 | |
| 43 | 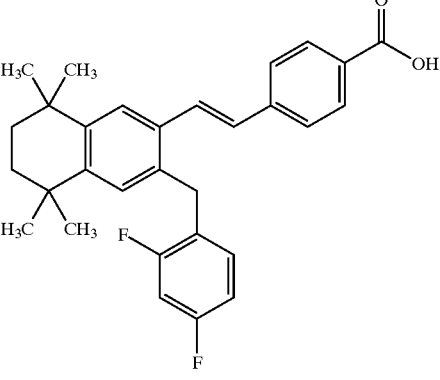 | 204.3–205.7 | |

TABLE 1-continued

| CMP # | MOLECULAR STRUCTURE | Mp (° C.) | Mol. Ion. M+ |
|---|---|---|---|
| 44 | 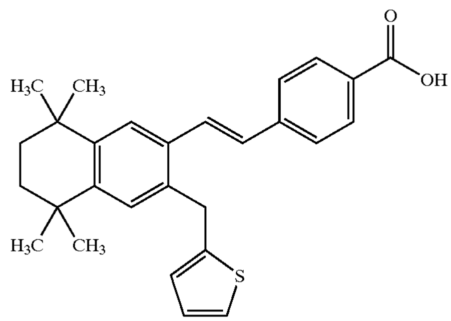 | 229.1–229.6 | |
| 45 | 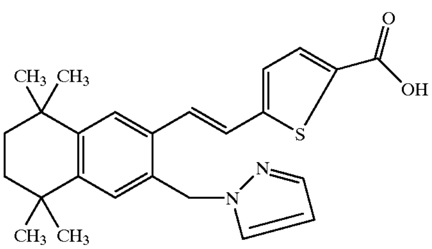 | 168–174 | M − H = 419 |
| 46 | 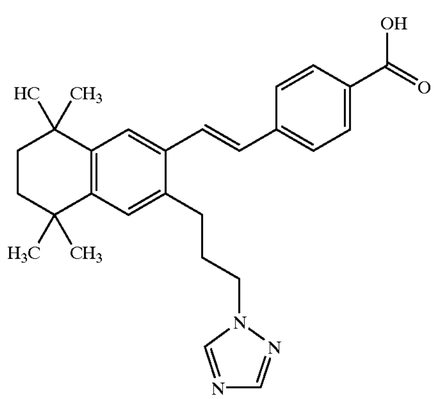 | | |
| 47 | 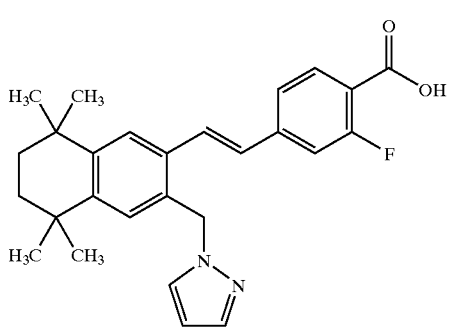 | 177–179 | |

TABLE 1-continued

| CMP # | MOLECULAR STRUCTURE | Mp (° C.) | Mol. Ion. M+ |
|---|---|---|---|
| 48 | 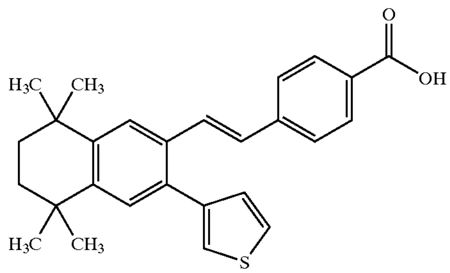 | 244.5–245.8 | |
| 49 | 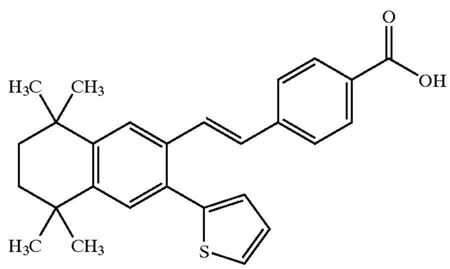 | 242.5–243.6 | |
| 50 | 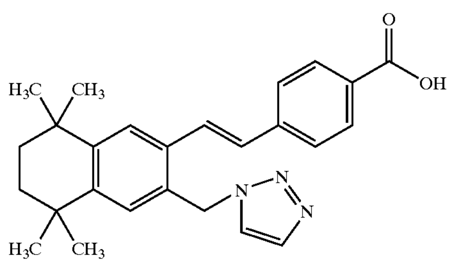 | | M − H = 414 |
| 51 | 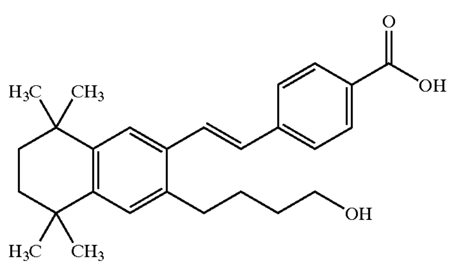 | | M − H = 405 |
| 52 | 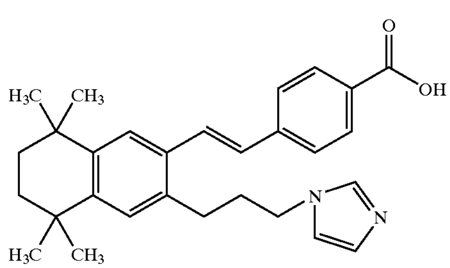 | | 443 |

TABLE 1-continued

| CMP # | MOLECULAR STRUCTURE | Mp (° C.) | Mol. Ion. M+ |
|---|---|---|---|
| 53 | 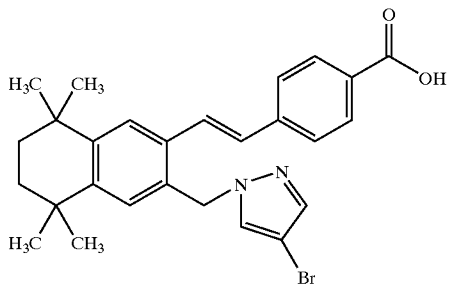 | | 521 |
| 54 | 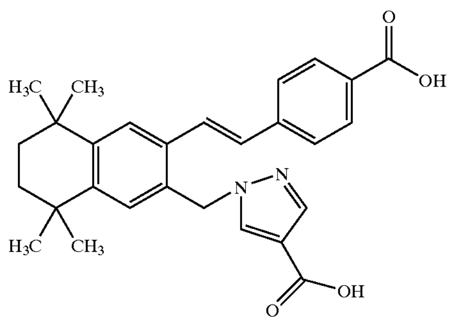 | | 459 |
| 55 | 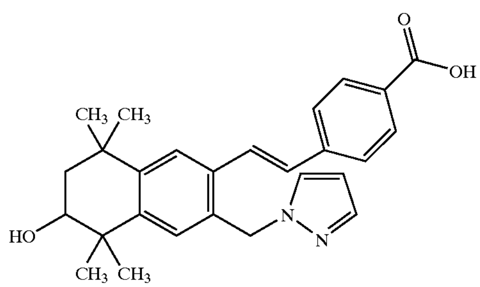 | 241.6–242 | |
| 56 | 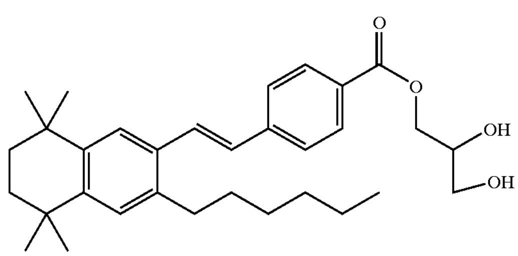 | | 492 |
| 57 | 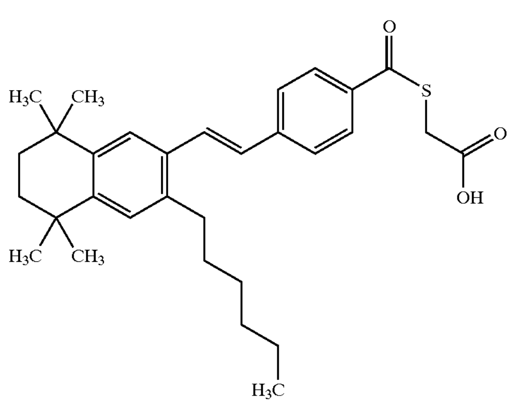 | | |

TABLE 1-continued

| CMP # | MOLECULAR STRUCTURE | Mp (° C.) | Mol. Ion. M+ |
|---|---|---|---|
| 58 | 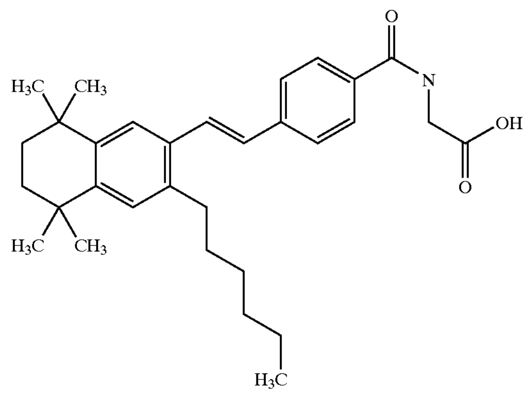 | | |
| 59 | 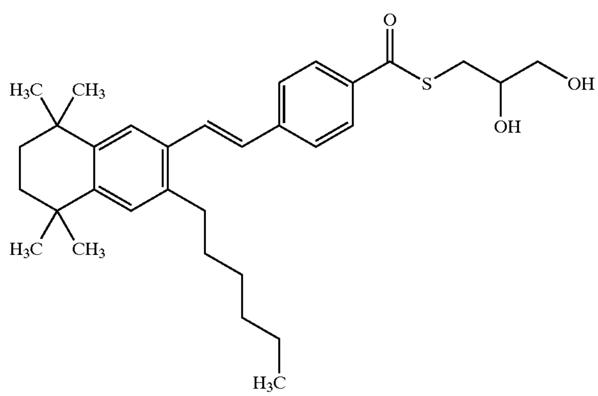 | | |
| 130 | 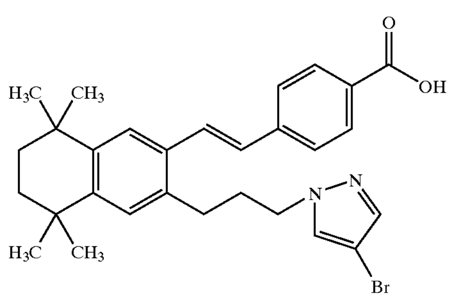 | | 521 (MH+) |
| 131 | 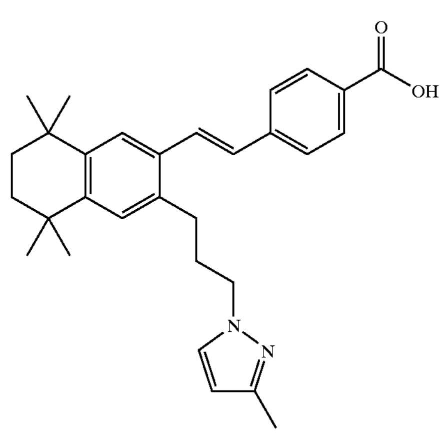 | | 457 (MH+) |

TABLE 1-continued
| CMP # | MOLECULAR STRUCTURE | Mp (° C.) | Mol. Ion. M+ |
|---|---|---|---|
| 132 | 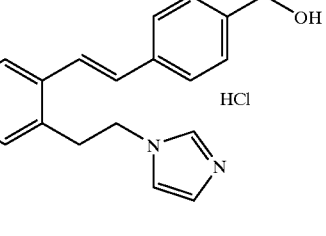 | | 429 (MH⁺) |
| 133 | 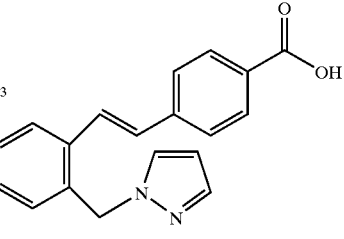 | 233–233.5 | |
| 134 | 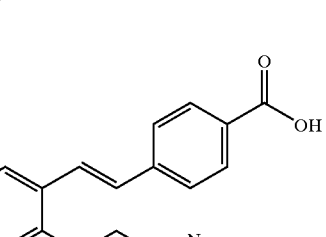 | | 506 (M − H⁺) |
| 135 | 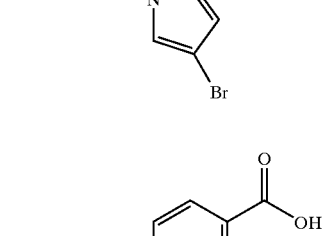 | | 457 (MH⁺) |
| 136 | 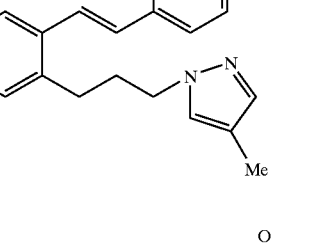 | | 430 (MH⁺) |

TABLE 1-continued
| CMP # | MOLECULAR STRUCTURE | Mp (° C.) | Mol. Ion. M+ |
|---|---|---|---|
| 137 | 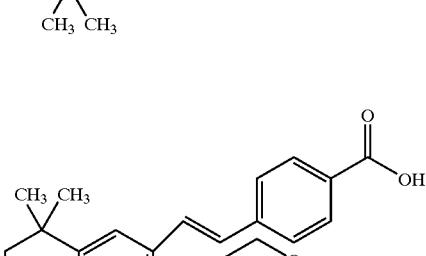 | 247.6–248.4 | |
| 138 | 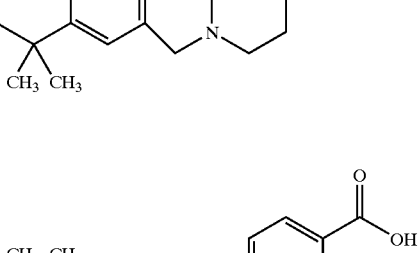 | | 434 (MH+) |
| 139 | 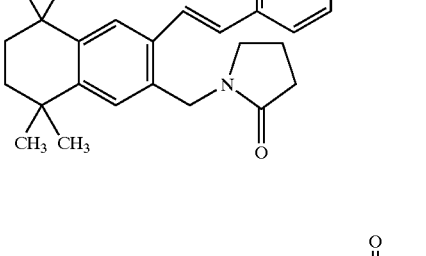 | | 432 (MH+) |
| 140 | 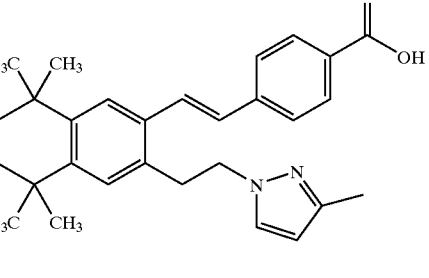 | | 443 (MH+) |
| 141 | 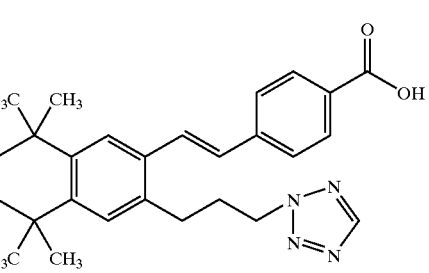 | | 443 (M − H) |

TABLE 1-continued

| CMP # | MOLECULAR STRUCTURE | Mp (° C.) | Mol. Ion. M+ |
|---|---|---|---|
| 142 | 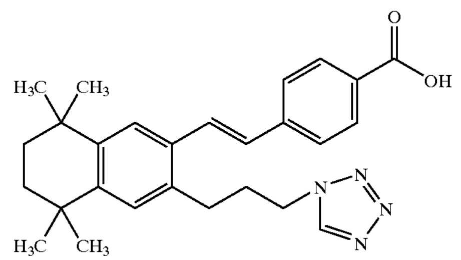 | | 445 (MH+) |
| 143 | 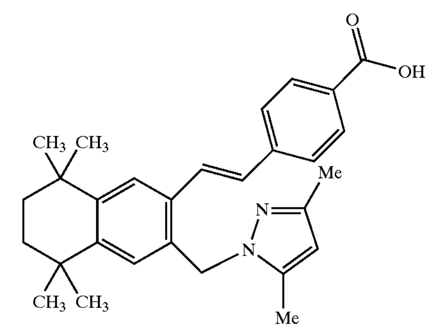 | | 443 (MH+) |
| 144 | 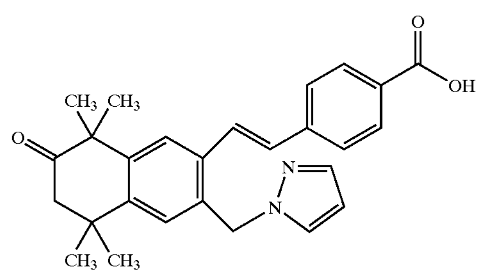 | 264.8–265.9 | |
| 145 | 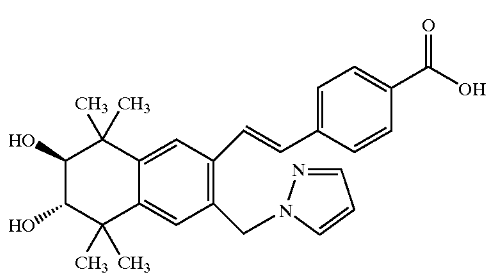 | | 447 (MH+) |
| 146 | 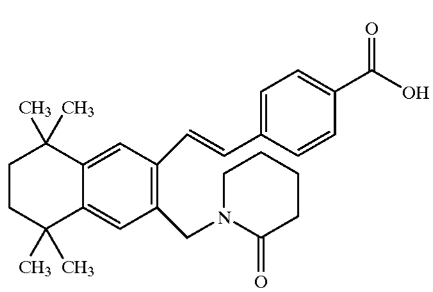 | | 444 (M − H)+ |

TABLE 1-continued

| CMP # | MOLECULAR STRUCTURE | Mp (° C.) | Mol. Ion. M+ |
|---|---|---|---|
| 147 | 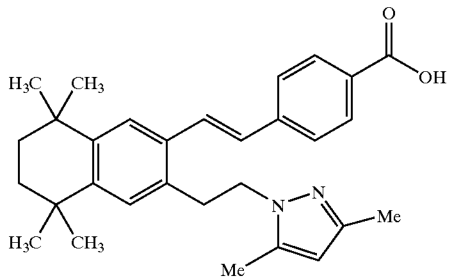 | | 457 (MH+) |
| 148 | 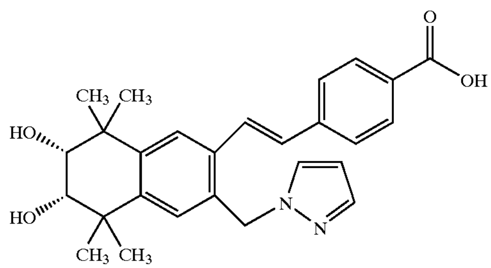 | 238.5–241.5 | |
| 149 | 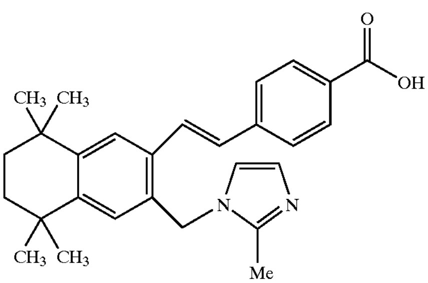 | | 429 (MH+) |
| 150 | 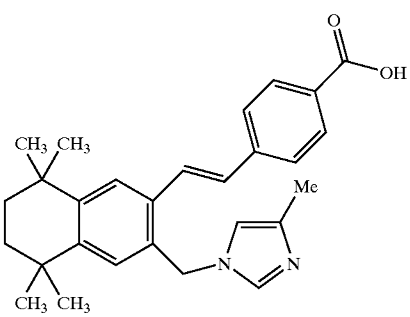 | | 428 |
| 151 | 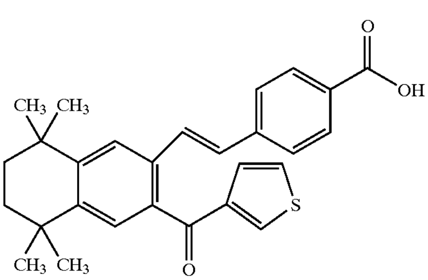 | | 444 (MH+) |

TABLE 1-continued
| CMP # | MOLECULAR STRUCTURE | Mp (° C.) | Mol. Ion. M+ |
|---|---|---|---|
| 152 | 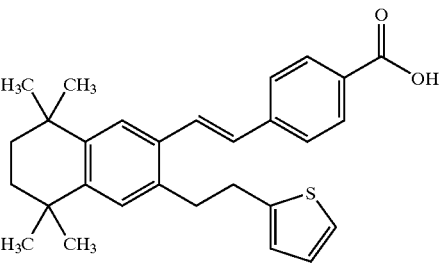 | | 444 |
| 154 | 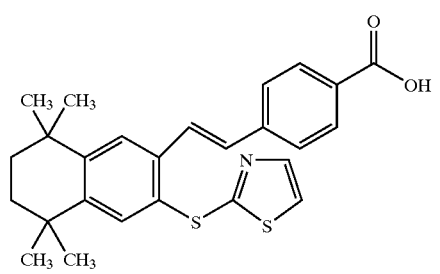 | | 450 (MH+) |
| 155 | 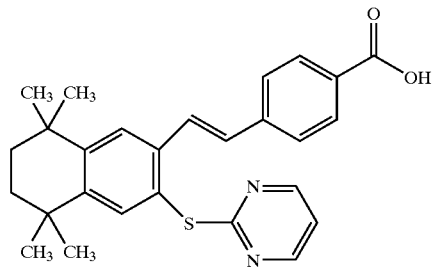 | 283–283.5 | |
| 156 | 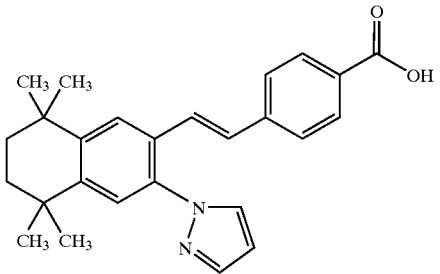 | | 401 (MH+) |
| 157 | 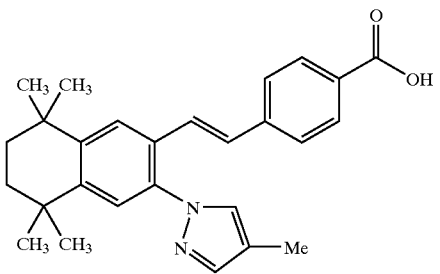 | | 415 (MH+) |

TABLE 1-continued

| CMP # | MOLECULAR STRUCTURE | Mp (° C.) | Mol. Ion. M+ |
|---|---|---|---|
| 158 | 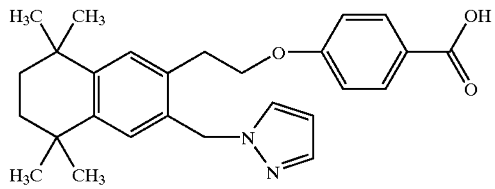 | | 433 (MH+) |
| 159 | 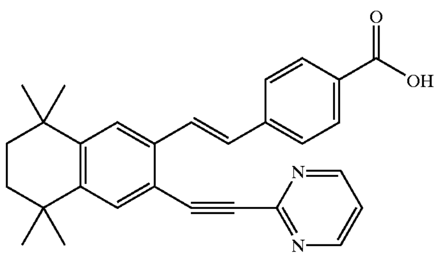 | | 436 (M+) |
| 160 | 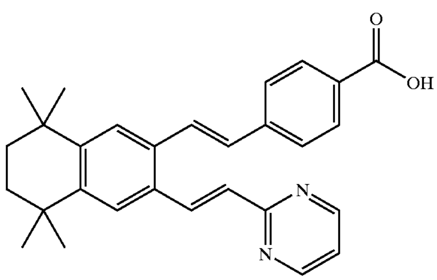 | | 437 (M-1) |
| 161 | 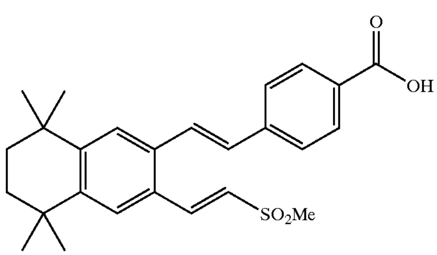 | | 437 (M-1) |
| 162 | 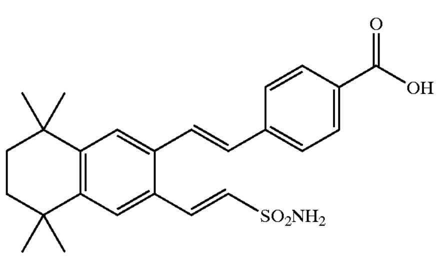 | | 437 (M-1) |
| 163 | 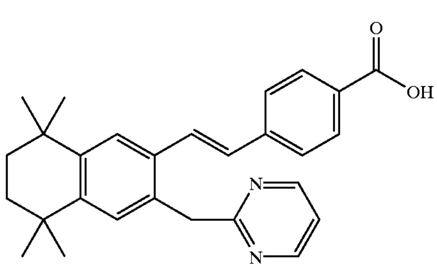 | | 427 |

TABLE 1-continued

| CMP # | MOLECULAR STRUCTURE | Mp (° C.) | Mol. Ion. M+ |
|---|---|---|---|
| 164 | 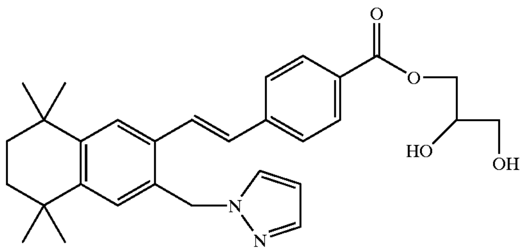 | | 489 (MH$^+$) |
| 165 | 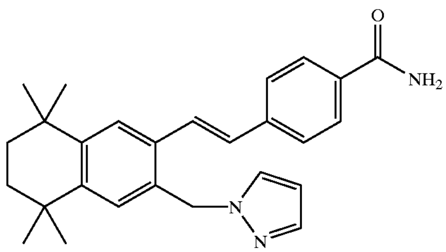 | 248–249 | |
| 166 | 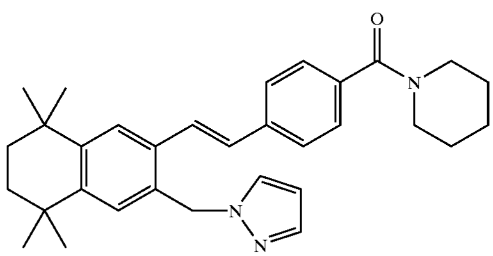 | 171.6–172.5 | |

Another aspect of the invention encompasses a method of treating emphysema in a mammal which comprises administering to a mammal in need of such treatment a therapeutically effective amount of a compound of the invention, or pro-drug thereof. In one embodiment, the emphysema is panlobar emphysema, centrilobular emphysema or distal emphysema.

Preferably, the therapeutically effective amount of a compound of the invention or pro-drug thereof, for treating emphysema, is between about 0.1 μg/qd and about 30.0 mg/qd, more preferably between about 1.0 μg/qd and about 1.0 mg/qd. In one embodiment, especially for oral administration, the therapeutically effective amount of a compound of the invention or pro-drug thereof is between about 10.0 μg/qd and about 30 mg/qd, preferably 30.0 μg/qd to about 300.0 μg/qd. In another embodiment, especially for administration by inhalation, the therapeutically effective amount of a compound of the invention or pro-drug thereof, is between about 0.1 μg/qd and about 100.0 μg/qd, more preferably between about 10.0 μg/qd and about 100.0 μg/qd, most preferably between about 1.0 μg/qd and about 30.0 μg/qd.

This aspect of the invention encompasses a method of treating emphysema in a mammal by repairing alveoli in a mammal. In a preferred embodiment, the mammal is human. Preferably, the human was or is a cigarette smoker. In another preferred embodiment, an electrohydrodynamic aerosol device or a nebulizer device or an aerosol device is used to administer the therapeutically effective amount of a compound of the invention, or pro-drug thereof.

Another aspect of the invention encompasses a pharmaceutical composition for the treatment of a mammal suffering from emphysema comprising an amount of a compound of the invention or pro-drug thereof in a pharmaceutically acceptable carrier, with the amount of the compound being sufficient to alleviate one symptom of emphysema. In one embodiment, the emphysema is panlobar emphysema, centrilobular emphysema or distal emphysema. In a preferred embodiment, the mammal is human. Preferably, the human was or is a cigarette smoker.

The major symptoms of emphysema include but are not limited to chronic shortness of breath, chronic cough, coloration of the skin caused by lack of oxygen, shortness of breath with minimal physical activity and wheezing. Additional symptoms that may be associated with emphysema include, but are not limited to vision abnormalities, dizziness, temporary cessation of respiration, anxiety, swelling, fatigue, insomnia and memory loss.

Preferably, the amount of a compound of the invention or pro-drug thereof, in the pharmaceutical composition, is between about 0.1 μg and about 30.0 mg, more preferably between about 1.0 μg and about 1.0 mg, most preferably between about 100.0 μg and about 300.0 μg.

In one embodiment, the pharmaceutically acceptable carrier is suitable for an electrohydrodynamic aerosol device, a nebulizer device or a aerosol device. In one preferred embodiment, the pharmaceutically acceptable carrier is a liquid such as water, alcohol, polyethylene glycol or perfluorocarbon. The amount of a compound of the invention, or pro-drug thereof in the pharmaceutical composition in this preferred embodiment is between about 0.1 μg and about 1.0 mg, more preferably between about 1.0 μg and about 100.0 μg, most preferably between about 50.0 μg and about 150.0 μg.

Another aspect of the invention encompasses a method for treating emphysema and related disorders by delivering a formulation of a compound of the invention or pro-drug thereof, into the lungs of a mammal. Preferably, the mammal is a human, more preferably, the human was or is a cigarette smoker. In one embodiment, the formulation is delivered into the lungs of the mammal with a nebulizer device. In a second embodiment, the formulation is delivered into the lungs of the mammal with an aerosol device. In a third embodiment, the formulation is delivered into the lungs of the mammal with an electrohydrodynamic aerosol device.

In an exemplary embodiment, the formulation is a pharmaceutical composition of a compound of the invention. Preferably, the amount of a compound of the invention, or pharmaceutically acceptable salt, hydrate, solvate, or pro-drug thereof in the pharmaceutical composition is between about 1.0 μg and about 10.0 mg, more preferably between about 10.0 μg and about 1.0 mg, most preferably between about 50.0 μg and about 150.0 μg. In one preferred embodiment, the pharmaceutically acceptable vehicle is a liquid such as water, alcohol, polyethylene glycol or perfluorocarbon. In another preferred embodiment, a material that alters the aerosol properties of the formulation is added to the formulation. Preferably, the material is an alcohol, glycol, polyglycol or fatty acid.

In still another aspect, the present invention encompasses a method for treating emphysema that combines use of a compound of the invention with one or more additional therapies. The additional therapies include, but are not limited to, smoking cessation, antibiotics, bronchodilators and oxygen therapy. In a preferred embodiment, a pharmaceutical composition of a compound of the invention is used in combination with other therapies.

In a still another aspect, the current invention provides a method for preventing emphysema in a human at risk of emphysema by administering a amount of a compound of the invention or pro-drug thereof, sufficient to prevent emphysema. In a preferred embodiment, the human was or is a cigarette smoker.

In another aspect, the present invention provides a pharmaceutical composition that prevents emphysema in a human at risk of emphysema. The composition comprises an amount of a compound of the invention or pro-drug thereof, and a pharmaceutically acceptable carrier that is sufficient to prevent emphysema.

Another aspect of the invention encompasses a method of treating cancer in a mammal which comprises administering to a mammal in need of such treatment a therapeutically effective amount of a compound of the invention or pro-drug thereof. Preferably, the cancer is of epithelial origin and includes, but is not limited to breast cancer, skin cancer, colon cancer, stomach tumors, laryngeal cancer and lung cancer.

Preferably, the therapeutically effective amount of a compound of the invention or pro-drug thereof for treating cancer, is between about 50 μg/qd and about 500 mg/qd, more preferably between about 300 μg/qd and about 30 mg/qd. In one embodiment, especially for oral administration, the therapeutically effective amount of a compound of the invention or pro-drug thereof is between about 3 mg/qd and about 120 mg/qd. In another embodiment, especially for administration by inhalation, the therapeutically effective amount of a compound of the invention or pro-drug thereof, is between about 50 μg/qd and about 500 μg/qd, more preferably between about 50 μg/qd and 150 μg/qd.

In a preferred embodiment, the mammal is human. In another preferred embodiment, a electrohydrodynamic aerosol device or a nebulizer device or a aerosol device is used to administer the therapeutically effective amount of a compound of the invention or pro-drug thereof.

Another aspect of the invention encompasses a pharmaceutical composition for the treatment of a mammal suffering from cancer comprising an amount of a compound of the invention or pro-drug thereof in a pharmaceutically acceptable carrier, with the amount of the compound being sufficient to alleviate one symptom of cancer. Preferably, the cancer is of epithelial origin and includes, but is not limited to breast cancer, skin cancer, colon cancer, stomach tumors, laryngeal cancer and lung cancer. In a preferred embodiment, the mammal is human.

Preferably, the amount of a compound of the invention or pro-drug thereof, in the pharmaceutical composition, is between about 250 μg and about 500 mg, more preferably between about 2.5 mg and about 100 mg, most preferably between about 10 mg and about 50 mg.

In one embodiment, the pharmaceutically acceptable carrier is suitable for a electrohydrodynamic aerosol device, a nebulizer device or a aerosol device. In one preferred embodiment, the pharmaceutically acceptable carrier is a liquid such as water, alcohol, polyethylene glycol or perfluorocarbon. The amount of a compound of the invention or pro-drug thereof, in the pharmaceutical composition in this preferred embodiment is between about 50 μg and about 1.5 mg, more preferably between about 150 μg and about 1.5 mg, most preferably between about 150 μg and about 300 μg.

Another aspect of the invention encompasses a method for treating cancer by delivering a formulation of a compound of the invention or pro-drug thereof, into the lungs of a mammal. Preferably, the mammal is a human, more preferably, the human has lung cancer. In one embodiment, the formulation is delivered into the lungs of the mammal with a nebulizer device. In a second embodiment, the formulation is delivered into the lungs of the mammal with an aerosol device. In a third embodiment, the formulation is delivered into the lungs of the mammal with an electrohydrodynamic aerosol device.

In an exemplary embodiment, the formulation is a pharmaceutical composition of a compound of the invention. Preferably, the amount of a compound of the invention or pro-drug thereof, in the pharmaceutical composition is between about 50 μg and about 1.5 mg, more preferably between about 50 μg and about 1.5 μg, most preferably between about 100 μg and about 300 μg. In one preferred embodiment, the pharmaceutically acceptable vehicle is a liquid such as water, alcohol, polyethylene glycol or perfluorocarbon. In another preferred embodiment, a material that alters the aerosol properties of the formulation is added to the formulation. Preferably, the material is an alcohol, glycol, polyglycol or fatty acid.

In still another aspect, the present invention encompasses a method for treating cancer that combines use of a compound of the invention with one or more additional therapies. The additional therapies include, but are not limited to, chemotherapy, radiation or surgery. In a preferred embodiment, a pharmaceutical composition of a compound of the invention is used in combination with other therapies.

In a still another aspect, the current invention provides a method for preventing cancer in a human at risk of cancer (e.g., smokers, asbestos workers and uranium workers) by administering a amount of a compound of the invention or pro-drug thereof, sufficient to prevent cancer. Examples of premalignant and precancerous lesions or tumors which may be prevented by compounds of the invention include, but are not limited to, actinic and arsenic keratoses, dysplasias and papillomas of mucous membranes and precancerous changes of the bladder.

Another aspect of the present invention provides a pharmaceutical composition that prevents cancer in a human at risk of cancer. The composition comprises an amount of a compound of the invention or pro-drug thereof, and a pharmaceutically acceptable carrier that is sufficient to prevent cancer.

Another aspect of the invention encompasses a method of treating dermatological disorders in a mammal which comprises administering to a mammal in need of such treatment a therapeutically effective amount of a compound of the invention or pro-drug thereof. Preferably, the dermatological disorders include, but are not limited to, damage to the skin caused by light and age, surgical wounds, burn wounds, wounds caused by cutaneous trauma, acne and psoriasis.

Preferably, the therapeutically effective amount of a compound of the invention or pro-drug thereof for treating dermatological disorders, is between about 5 μg/qd and about 50 mg/qd, more preferably between about 50 μg/qd and about 5 mg/qd. Topical (skin) emollients typically are creams, lotions or ointments containing from about 1% to 0.005%, preferably 0.5% to 0.01%, most preferably 0.05% to 0.01%.

Synthesis of the Compounds of the Invention

The compounds of the invention having formulas (I–VII) may be obtained via the synthetic methodology illustrated in Schemes 1–7 and methods described in the art (Douget et al., *Quant. Struct. Act. Relat.*, 18, 107, (1999) and references disclosed therein, which are herein incorporated by reference). Starting materials useful for preparing compounds of the invention and intermediates thereof are commercially available or can be prepared by well known synthetic methods.

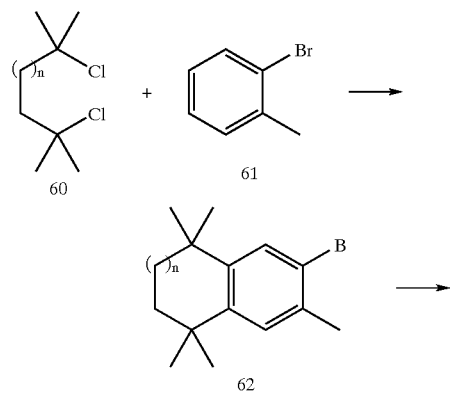

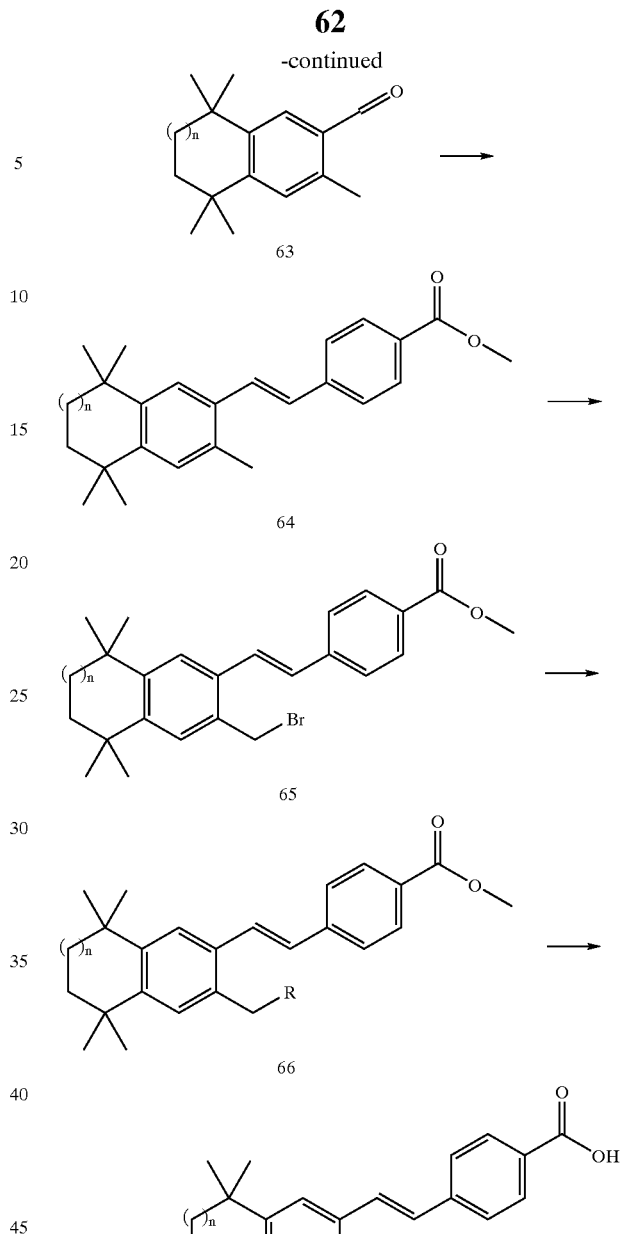

Compounds 67 of formula (I) where n=0, 1 or 2, m is 1 and R is alkoxy, alkylthio, heteroaryl, heterocyclyl, amino, alkylamino etc. may be prepared as described in Scheme 1. Bromo substituted 5,5,8,8-tetramethyl-5,6,7,8 tetrahydronapthalenes 62 and the corresponding five and seven member ring analogues may be synthesized by a number of methods known to the skilled artisan. In a preferred embodiment, Friedel-Crafts alkylation of 2-bromotoluene 61 with 2,4-dichloro-2,4-dimethylpentane, 2,5-dichloro-2,5-dimethylhexane or 2,6-dichloro-2,6-dimethylheptane 60 provides compounds 62. Aryl bromides 62 may be homologated to aldehydes 64 by halogen-metal exchange (i.e., n-butyl lithium) to form an intermediate organolithium compound, which is then quenched with N-formylpiperidine. Alternatively, aldehydes 63 may be made by homologation of bromides 62 (i.e., Cu(I)CN) to a cyano compound which may reduced (i.e., diisobutyl aluminum hydride). Other synthetic methods for effecting conversion of bromides 62 to aldehydes 63 will be apparent to the skilled artisan.

Horner-Emmons olefination of aldehydes 63 with an appropriate phosphonate ester may be used to provide E olefins 64. Corresponding Z olefins may be prepared by conventional Wittig reactions followed by separation if necessary. Bromination of compounds 64 (i.e., N-bromosuccinimide, benzoyl peroxide and light) affords the benzyl bromides 65. The bromides may be displaced with nitrogen, sulfur or oxygen nucleophiles to yield the corresponding substituted esters 66 which may be hydrolyzed (acid or base) to provide the acids 67. Acids 67 may be esterified using well known methods to provide a large number of esters.

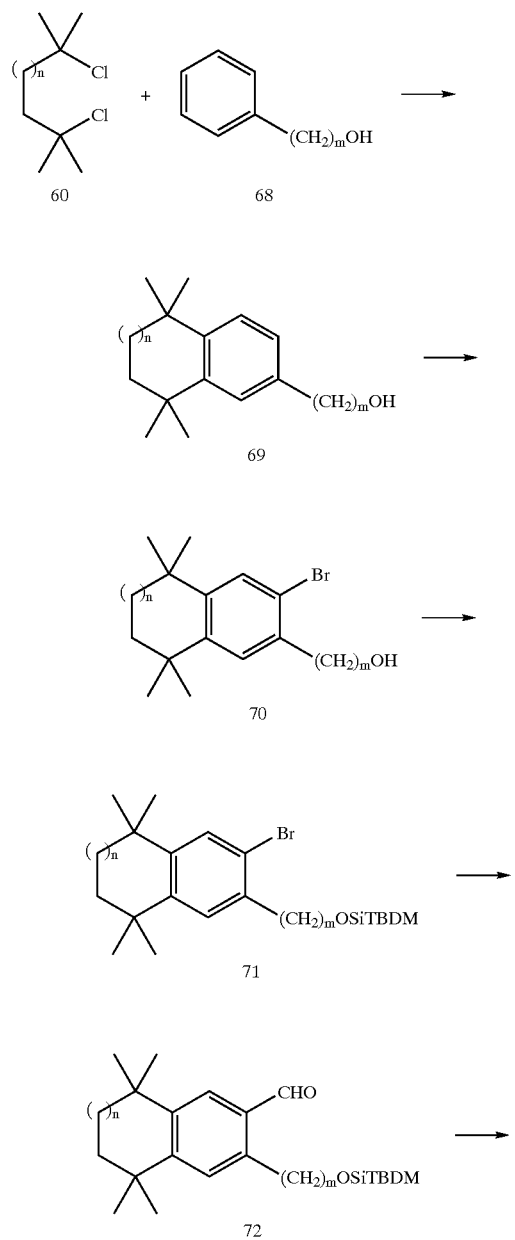

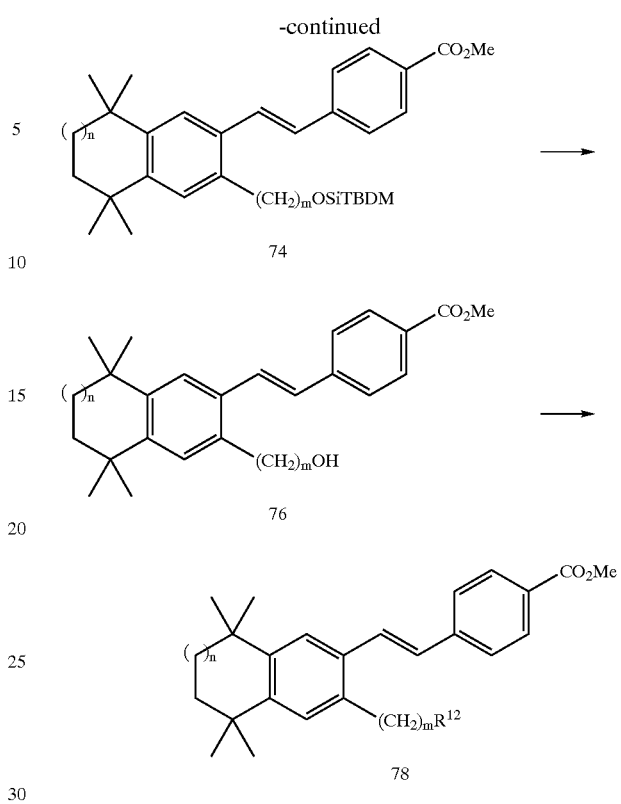

Compounds 78 of formula (I) where n=0, 1 or 2, m is 2–10 and $R^{12}$ is alkoxy, alkylthio, heteroaryl, heterocyclyl, amino, alkylamino etc. may be prepared as described in Scheme 2. Hydroxyalkyl substituted 5,5,8,8–5,6,7,8 tetrahydronapthalenes 69 are readily accessible by Friedel-Crafts reaction of 2,4-dichloro-2,4-dimethylpentane, 2,5-dichloro-2,5-dimethylhexane or 2,6-dichloro-2,6-dimethylheptane 60 with hydroxyalkylbenzenes 68. Bromination of hydroxyalkyl-5,5,8,8–5,6,7,8 tetrahydronapthalenes 69 affords aryl bromides 70. The hydroxyl group of 70 can be protected (i.e., t-butyldimethylsilyl chloride and imidazole) to provide compounds 71. Bromides 71 can be converted to aldehydes 72 in one step (i.e., halogen-metal exchange with n-butyl lithium, followed by treatment with N-formylpiperidine). Alternatively, aldehydes 72 may be made from bromides 70 by a two step procedure (i.e., Cu(I)CN to provide a nitrile and reduction with di-isobutyl aluminum hydride). Other methods for effecting conversion of bromides 70 to aldehydes 72 are within the capability of those of skill in the art.

Horner-Emmons olefination of aldehydes 72 with an appropriate phosphonate ester may be used to provide E olefins 74. The protecting group may be removed from compounds 74 (i.e., aqueous tetrabutyl ammonium fluoride) to provide alcohols 76. In a preferred embodiment, alcohols 76 may be converted by Mitsonobu reaction, (i.e., alkylthiols, triphenylphosphine and diisopropyl azodicarboxylate) to thiol analogs 78 (R=alkylthio). Alternatively, the hydroxyl functionality of compounds 76 may be activated by conversion to the mesylate (MsCl, $Et_3N$) followed by displacement reactions with nitrogen or oxygen nucleophiles to provide compounds 78 (R=alkoxy, amino, alkylamino, dialkyamino etc.). Other methods for effecting conversion of alcohols 76 to compounds of the invention are known to the skilled artisan. Ester hydrolysis may be used to provide the free acids of compounds 78.

SCHEME 3a

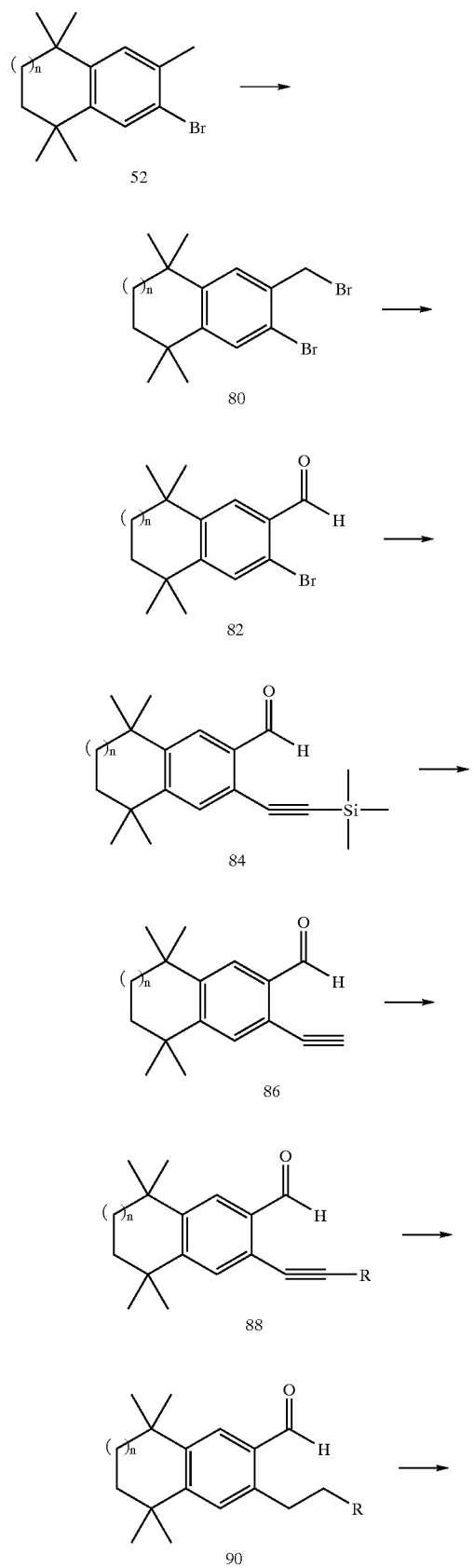

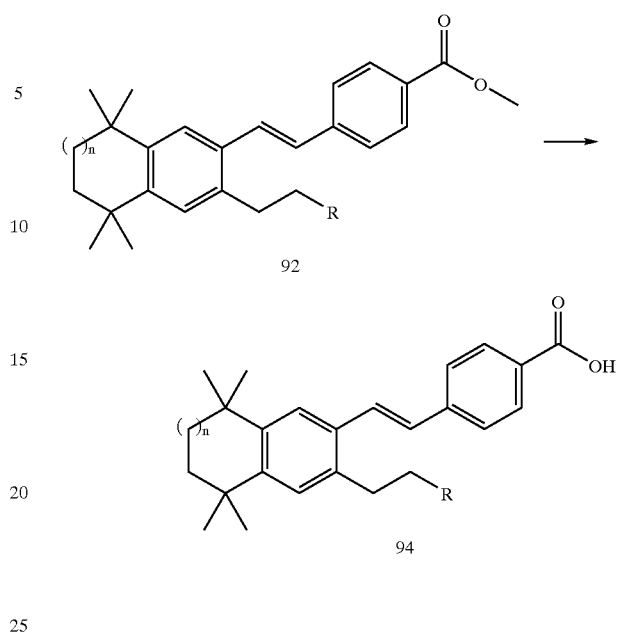

For compounds of formula I, where m=2, an alternative method is depicted in Scheme 3. Bromo substituted 5,5,8,8-tetramethyl-5,6,7,8 tetrahydronapthalenes 62 described in Scheme 1 may converted to bromoaldehydes 82 by benzylic bromination with N-bromosuccinimide and benzoyl peroxide to afford 80, followed by treatment with 2-nitropropane and sodium hydride. Treatment of bromoaldehyde 82 with trimethylsilylacetylene, dichlorobis(triphenylphosphine) palladium (II), cuprous iodide and triethylamine afforded silyated acetylene compounds 84. Removal of the trimethylsilyl group with base provides 86 which is followed by reaction with halogenatedheteroaromatics, dichlorobis(triphenylphosphine) palladium (II), cuprous iodide and triethylamine to yield acetylenic heteroaromatic intermediates 88. Catalytic hydrogenation of acetylenes 88 afforded the saturated heteroaromatic intermediates 90. Horner-Emmons olefination of 90 with the appropriate phosphonate ester yields E olefins 92. The ester may then be hydrolyzed to provide retinoid analogs 94.

SCHEME 3b

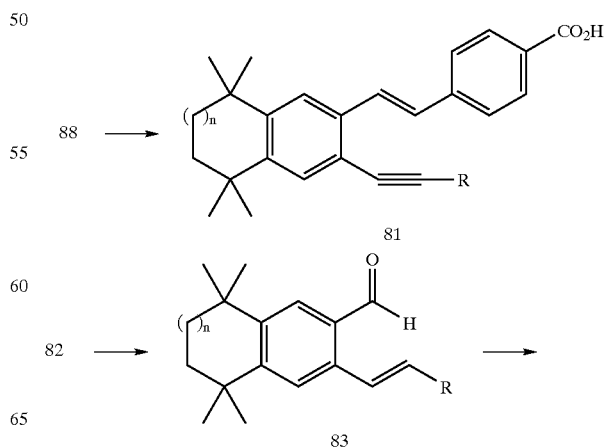

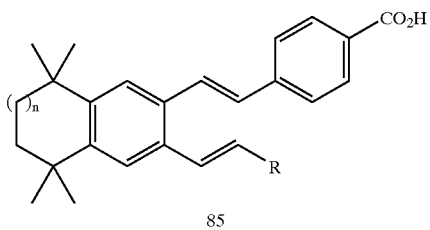

85

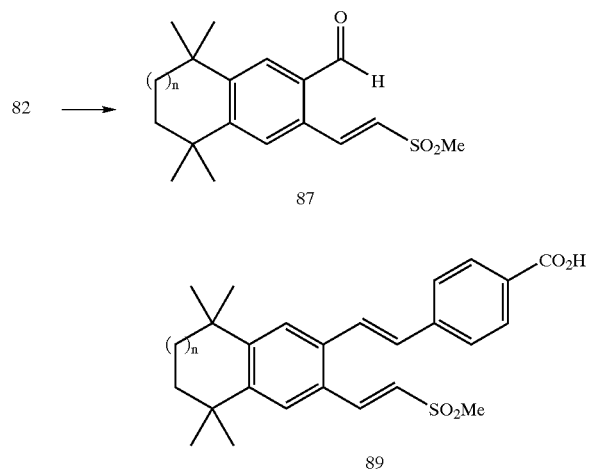

87

89

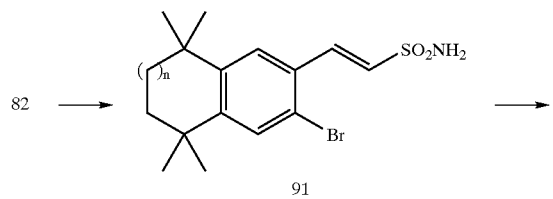

91

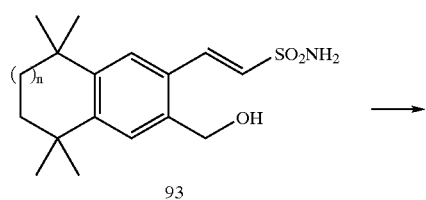

93

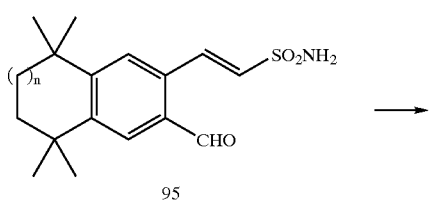

95

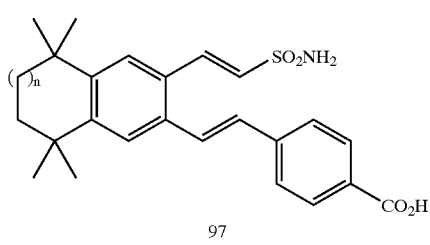

97

For compounds of Formula 1 where Z=acetylene and L=heteroaryl, as shown in Scheme 3b, intermediate 88 may be treated under Horner-Emmons olefination conditions with the appropriate phosphonate to give E olefins and subsequently hydrolyzed to provide retinoid analogs 81.

For compounds of Formula 1 where Z=olefin and L=heteroaryl, intermediate 82 may be treated with trans-1,2-bis(tri-n-butylstannyl)ethylene and tetrakis(triphenylphosphine)palladium in toluene under reflux, followed by addition of halo heteroaromatics to afford olefin 83. Horner-Emmons olefination of 83 with the appropriate phosphonate ester followed by hydrolysis provides retinoid analogs 85. Alternatively for $R^2$=vinylsulfone, treatment of intermediate 82 with methyl vinyl sulfone, tetrakis (triphenylphosphine)palladium and TEA in DMF affords vinyl sulfone intermediate 87. Olefination, followed by hydrolysis provides retinoid analogs 89. Alternatively for $R^2$=vinylsulfonamide, treatment of intermediate 82 with tert-butyl[diphenylphosphoryl)methyl]sulfonylcarbamate and NaH in DMF affords vinylsulfonamide intermediate 91. Treatment of 91 with tributylstannylmethane and tetrakis (triphenyl phosphine) palladium in dioxane gave hydroxymethyl intermediate 93. Oxidation of 93 with 1,1,1-triacetoxy-1,1,1-1,1-dihydro-1,2-benziiodoxol-3(1H)-one, affords aldehyde 95 and olefination, followed by hydrolysis gives retinoid analog 97.

SCHEME 4

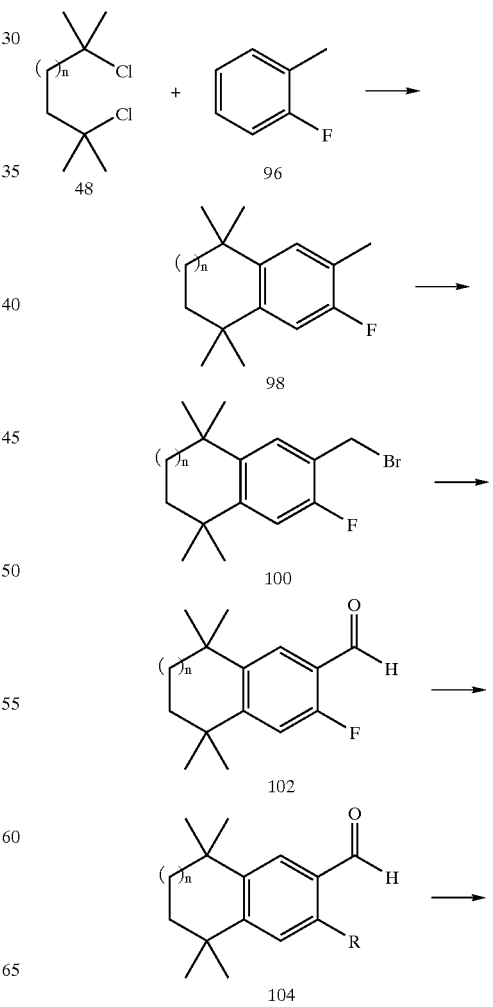

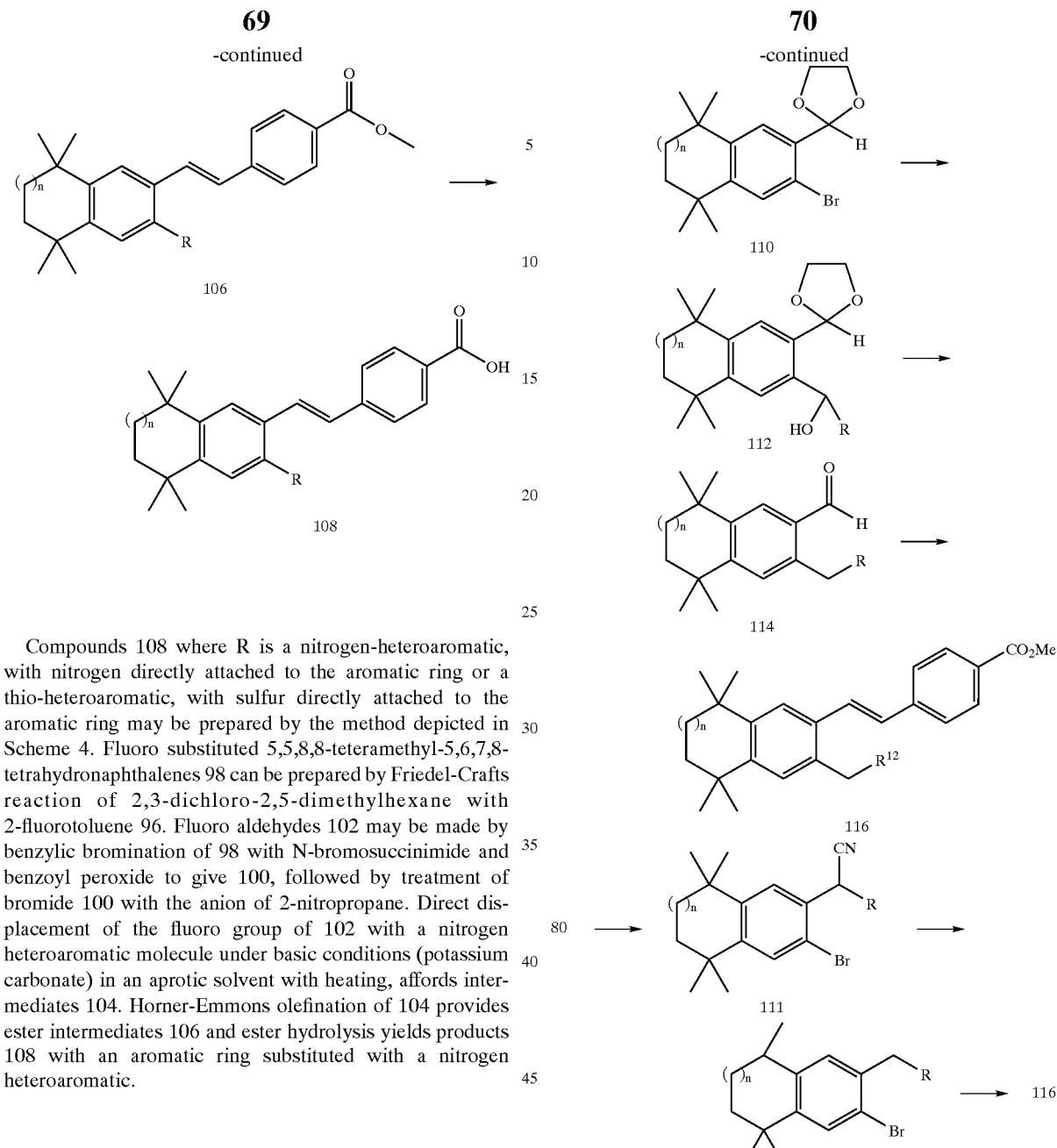

Compounds 108 where R is a nitrogen-heteroaromatic, with nitrogen directly attached to the aromatic ring or a thio-heteroaromatic, with sulfur directly attached to the aromatic ring may be prepared by the method depicted in Scheme 4. Fluoro substituted 5,5,8,8-teteramethyl-5,6,7,8-tetrahydronaphthalenes 98 can be prepared by Friedel-Crafts reaction of 2,3-dichloro-2,5-dimethylhexane with 2-fluorotoluene 96. Fluoro aldehydes 102 may be made by benzylic bromination of 98 with N-bromosuccinimide and benzoyl peroxide to give 100, followed by treatment of bromide 100 with the anion of 2-nitropropane. Direct displacement of the fluoro group of 102 with a nitrogen heteroaromatic molecule under basic conditions (potassium carbonate) in an aprotic solvent with heating, affords intermediates 104. Horner-Emmons olefination of 104 provides ester intermediates 106 and ester hydrolysis yields products 108 with an aromatic ring substituted with a nitrogen heteroaromatic.

Alternatively, treatment of thio-heteroaromatics with sodium hydride in a polar aprotic solvent followed by addition of fluoroaldehyde 102 afforded intermediates 104 with a thioheteroaromatic group directly attached to the aromatic ring. As before, Horner-Emmons olefination of 104 provided ester intermediate 106 followed by ester hydrolysis to afford products 108 with an aromatic ring substituted with a sulfur heteroaromatic.

SCHEME 5

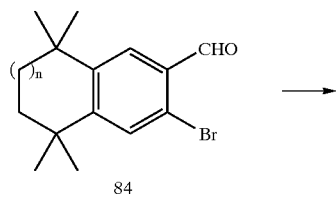

84

Compounds 116 where m is 1 and $R^{12}$ is a heteroaryl group linked through carbon or an aryl group can be prepared according to the method depicted in Scheme 5. Bromoaldehyde intermediates 84, previously described, can be protected as acetals 110. Treatment of 110 with an organometallic reagent such as n-BuLi, followed by addition of heteroaryl aldehydes affords alcohols 112. Catalytic hydrogenolysis with noble metal catalysts in the presence of hydrogen removes both the hydroxyl group and the acetal protecting group to provide aldehyde 114. Horner-Emmons olefination with an appropriate phosphonate ester followed by ester hydrolysis provides compound 116.

Alternatively, treatment of 84 with an aryl zinc reagent under palladium catalysis affords aldehyde 114 where R is substituted aryl, after removal of the acetal under acidic conditions. Horner-Emmons olefination of 114 with an appropriate phosphonate ester followed by ester hydrolysis provides compound 116.

Alternatively, dibromo intermediate 80 may be treated with NaCN, followed by reaction with an organometallic heteroaromatic reagent to give 111. Hydrolysis of 111 to the corresponding acid, followed by decarboxylation gives intermediate 113. Double Heck reaction, first with trimethoxyvinlysilane and then with methyl-4-bromobenzoate, followed by hydrolysis gives retinoid analogs 116.

SCHEME 6

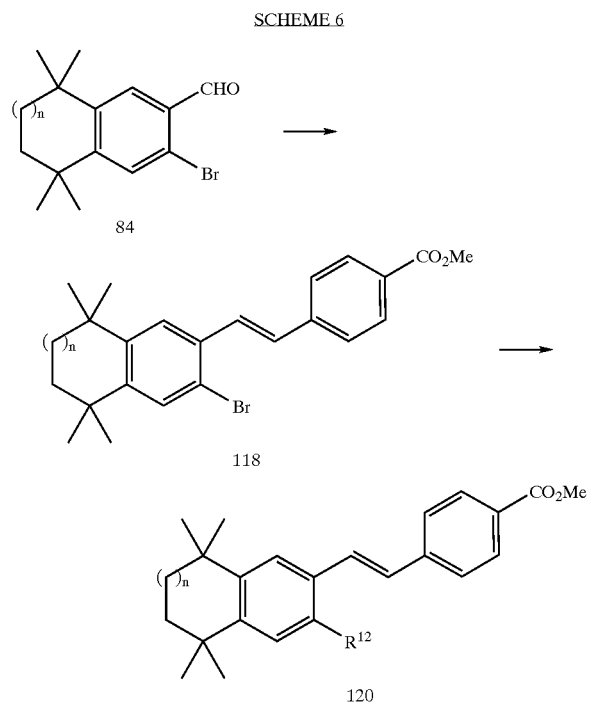

Compounds 120 where $R^{12}$ is a heteroaryl group or an aryl group directly attached to the aromatic ring of the tetrahydronapthalene can be prepared according to the method depicted in Scheme 6. Horner-Emmons olefination of 84 with an appropriate phosphonate ester provides bromide 118. Treatment of 118 with heteroaryl boronates or aryl boronates in the presence of palladium catalyst affords the respective heteroaryl substituted analogs or aryl substituted analogues, which upon ester hydrolysis gives compounds 120 with an heteroaryl group or an aryl group directly attached to the aromatic ring.

SCHEME 7

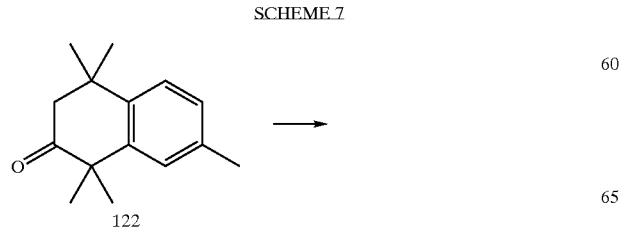

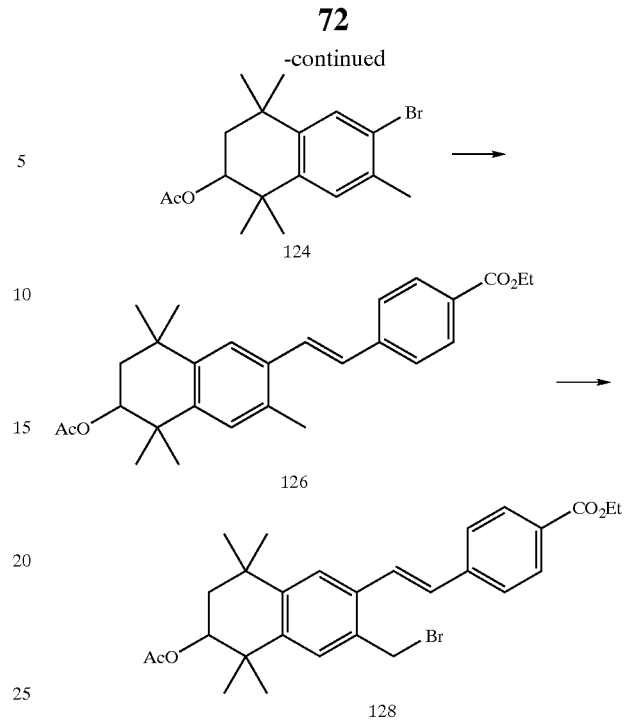

Compounds of formula I where $R^3$ is hydroxy may be prepared as exemplified in Schemes 7 and 8. Tetralone 122 may be prepared by condensation of dihydro-2,2,5,5 tetramethyl-3(2H) furanone with toluene. Reduction and protection using standard reagents provides acteate 124. Bis-palladium cross coupling using 4-bromo-ethyl-benzoate and trimethoxyvinylsilane provides compound 126, which may be converted to bromide 128 by free radical bromination. Bromide 128 may be directly displaced with an appropriate nucleophile to provide compounds where m=1 or may be homologated with appropriate carbon nucleophiles to provide compounds where m is greater than 1.

SCHEME 8

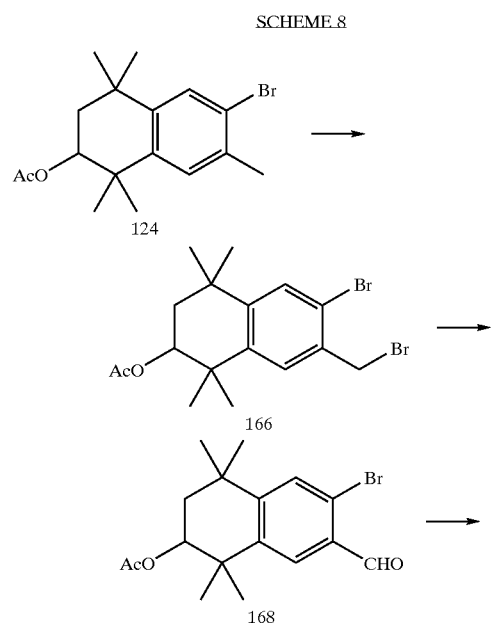

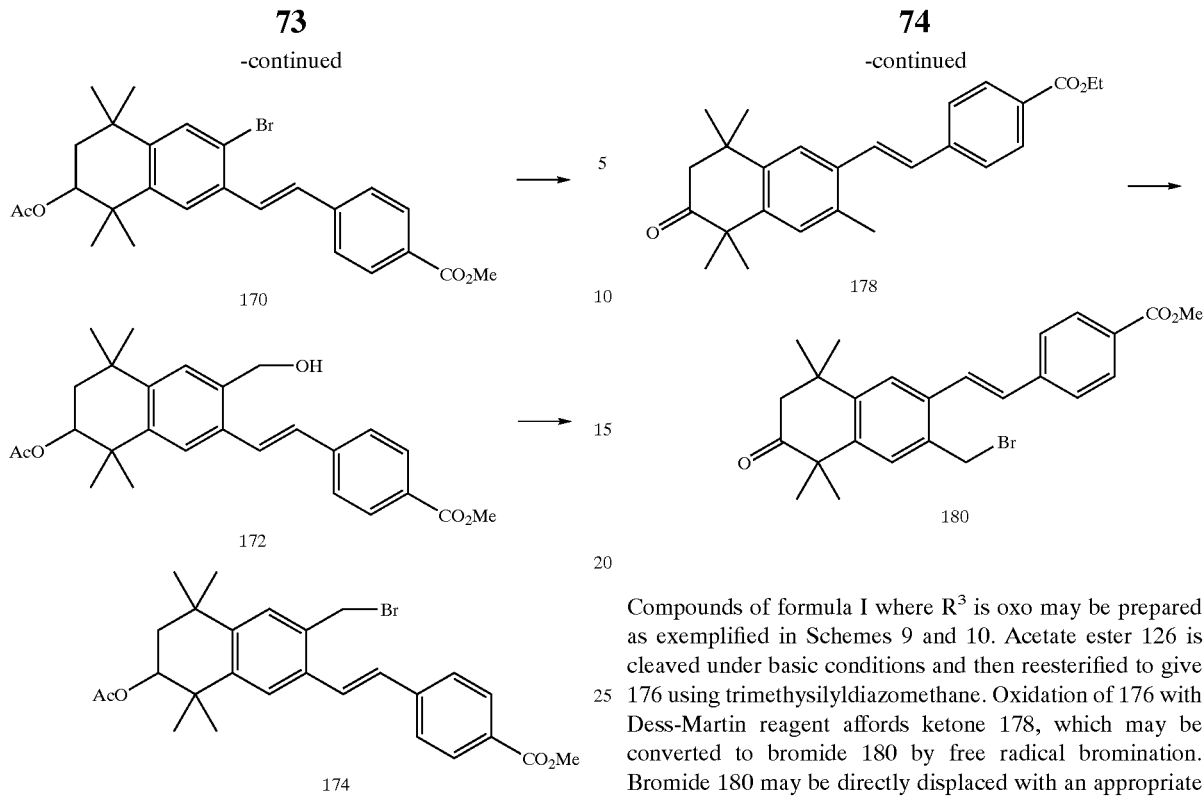

Alternatively, compounds of formula I where $R^3$ is hydroxy may be prepared as exemplified in Scheme 8. Intermediate acetate 124 can be brominated to prepare 166, followed by treatment with the anion prepared from 2-nitropropane to afford aldehyde 168. Horner-Emmons olefination provides compound 170 and Stille coupling with hydroxymethyl-tributyltin affords 172. NBS bromination of 172 affords bromide 174. Bromide 174 may be directly displaced with an appropriate nucleophile to provide compounds where m=1 or may be homologated with appropriate carbon nucleophiles to provide compounds where m is greater than 1.

Compounds of formula I where $R^3$ is oxo may be prepared as exemplified in Schemes 9 and 10. Acetate ester 126 is cleaved under basic conditions and then reesterified to give 176 using trimethysilyldiazomethane. Oxidation of 176 with Dess-Martin reagent affords ketone 178, which may be converted to bromide 180 by free radical bromination. Bromide 180 may be directly displaced with an appropriate nucleophile to provide compounds where m=1 or may be homologated with appropriate carbon nucleophiles where m is greater than 1.

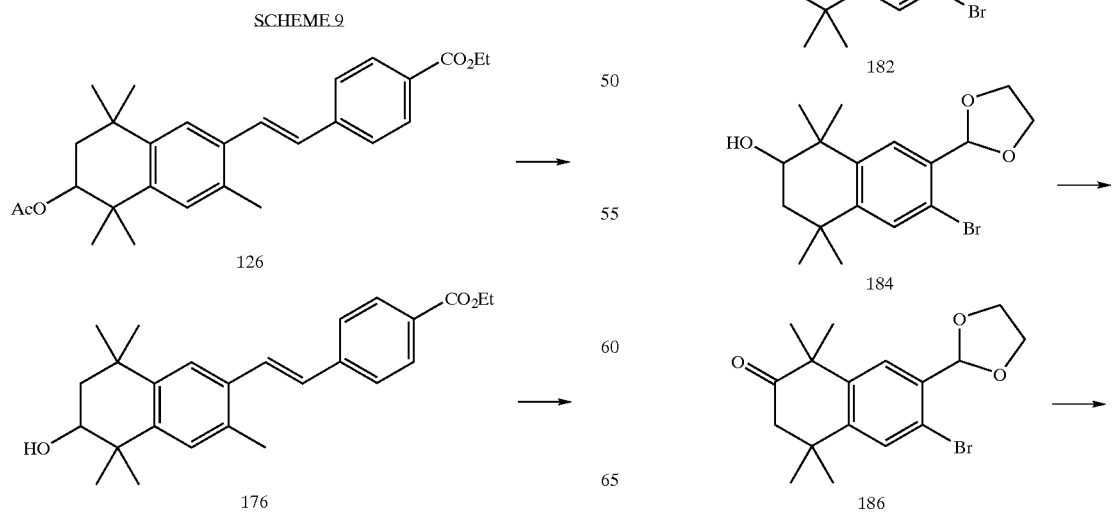

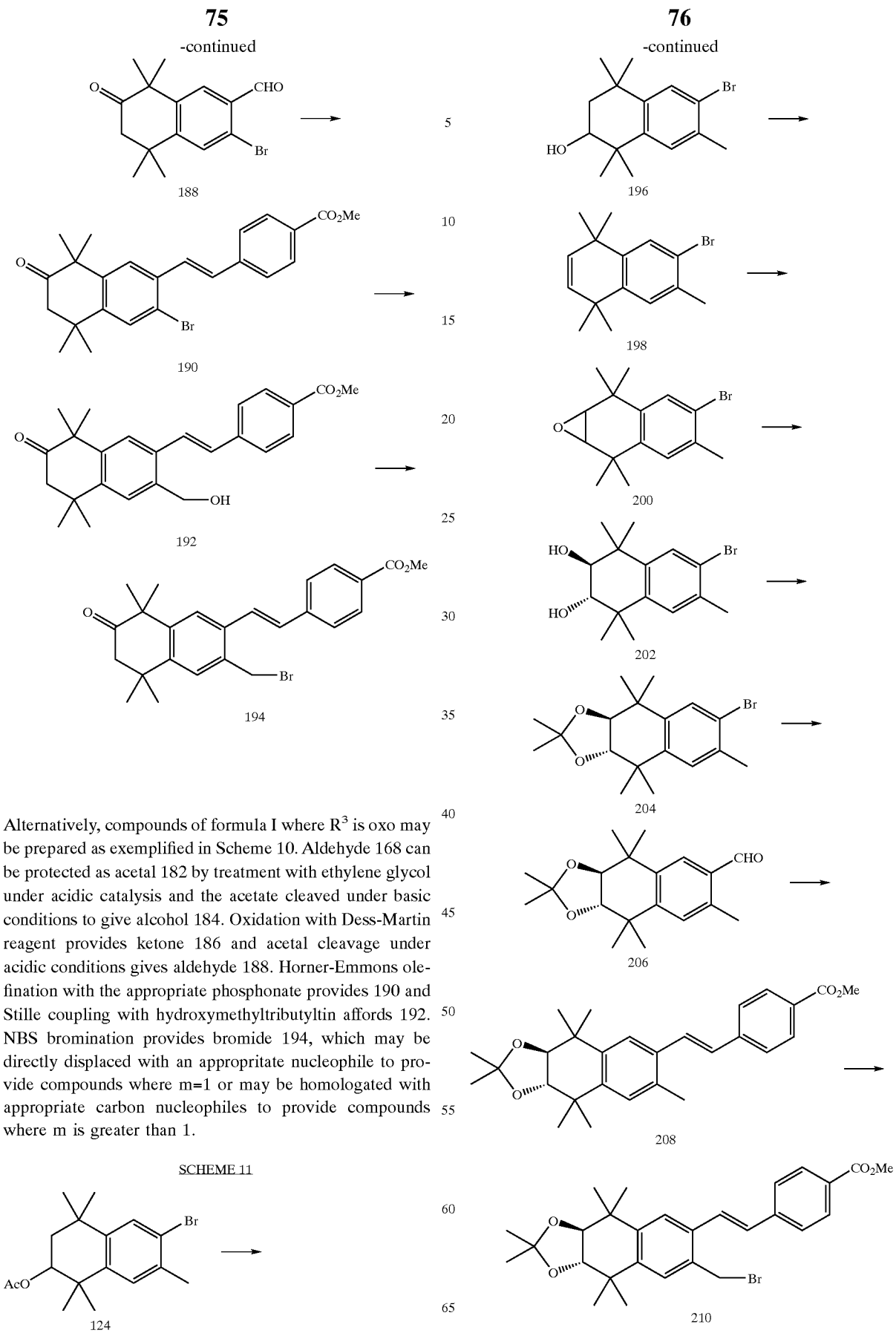

Alternatively, compounds of formula I where $R^3$ is oxo may be prepared as exemplified in Scheme 10. Aldehyde 168 can be protected as acetal 182 by treatment with ethylene glycol under acidic catalysis and the acetate cleaved under basic conditions to give alcohol 184. Oxidation with Dess-Martin reagent provides ketone 186 and acetal cleavage under acidic conditions gives aldehyde 188. Horner-Emmons olefination with the appropriate phosphonate provides 190 and Stille coupling with hydroxymethyltributyltin affords 192. NBS bromination provides bromide 194, which may be directly displaced with an appropritate nucleophile to provide compounds where m=1 or may be homologated with appropriate carbon nucleophiles to provide compounds where m is greater than 1.

SCHEME 11

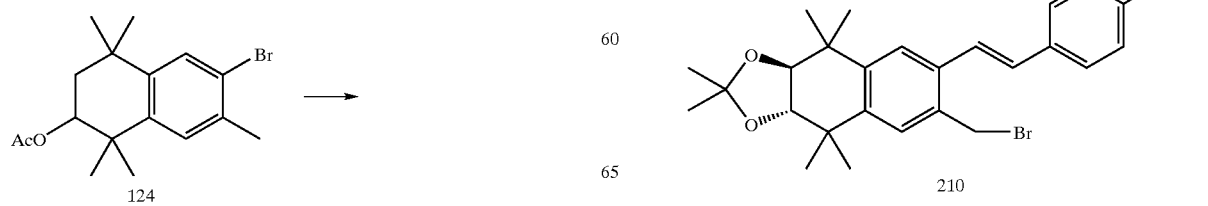

Compounds of formula I where $R^3$ is a diol may be prepared as exemplified in Schemes 11 and 12. Saponification of acetate intermediate 124 under basic conditions gives alcohol 196 and dehydration upon treatment with $POCl_3$ and pyridine provides olefin 198. Epoxidation of 198 with MCPBA affords 200. The epoxide can be open opened under acidic conditions to give the trans acetate diols which can then be hydrolysed under basic conditions to give the trans diol 202. Protection of the diol as the dimethyl ketal 204 using 2,2 dimethoxypropame under acidic conditions is followed by conversion to aldehyde 206 by treatment with n-butyl lithium and N-formyl piperidine. Horner-Emmons olefination of aldehyde 206 with the appropriate phosphonate gives 208, which may be converted to bromide 210 by free radical bromination. Bromide 210 may be directly displaced with an appropriate nucleophile to provide compounds where m=1 or may be homologated with appropriated carbon nucleophiles to provide compounds where m is greater than 1.

SCHEME 12

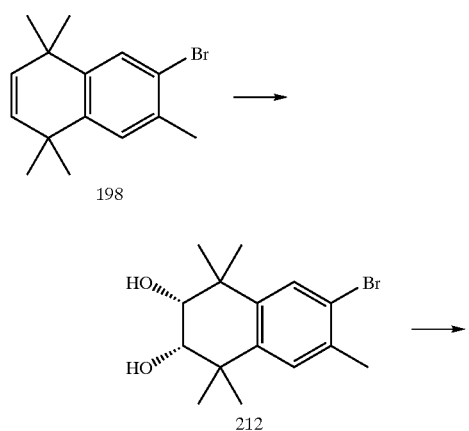

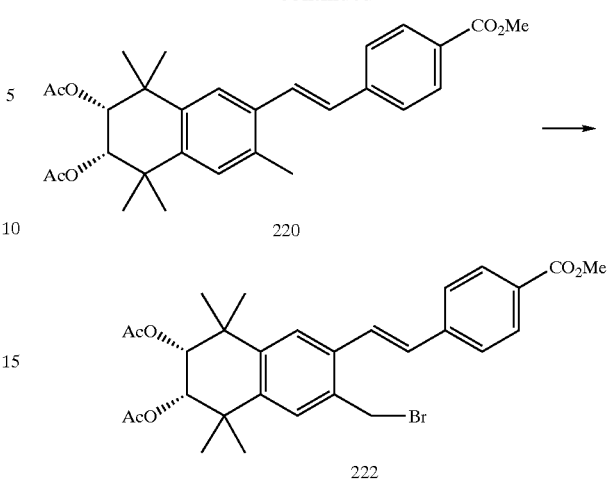

Alternatively, compounds of formula I where $R^3$ is a diol may be prepared as exemplified in Scheme 12. Olefin 198 can be treated with osmium tetroxide to afford the cis diol 212. Protection of 212 as ketal 214 was followed by conversion to aldehyde 216 by sequential treatment with n-butyl lithium and N-formylpiperidine. Horner-Emmons olefination with the appropriated phosphonate provided 218 and deprotection was followed by reprotection to the bis-acetate 220 with acetic anhydride in pyridine. Free radical bromination of 220 gives bromide 222 which may be directly displaced with an appropriate nucleophile to provide compounds where m=1 or may be homologated with appropriate carbon nucleophiles to provide compounds where m is greater than 1.

SCHEME 13

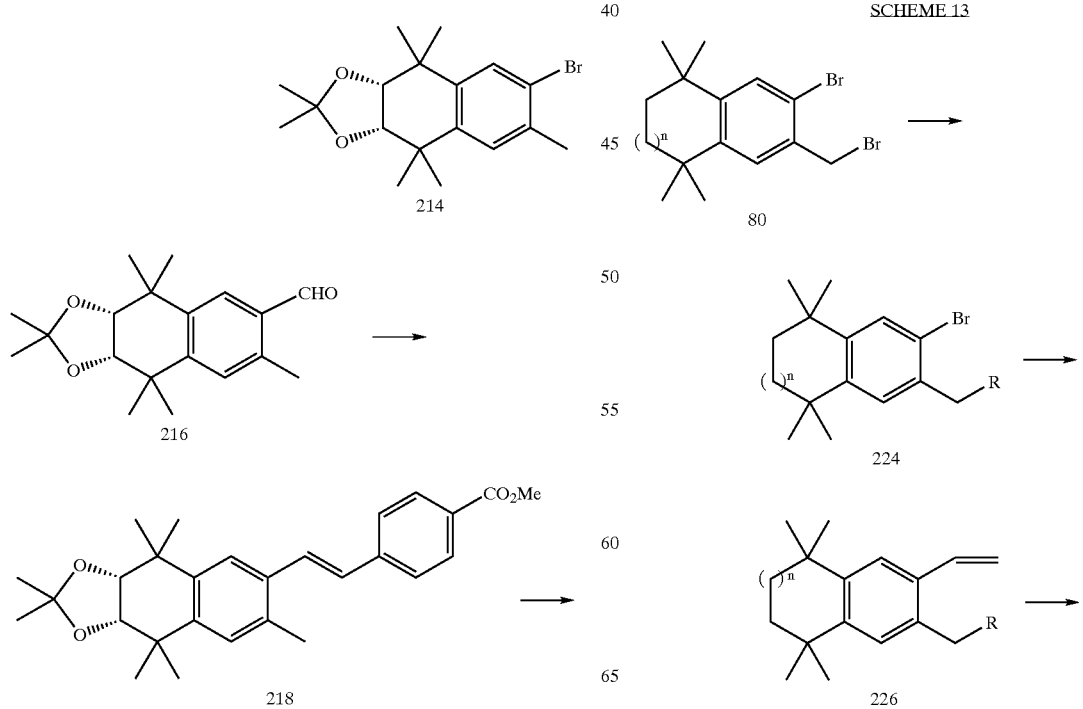

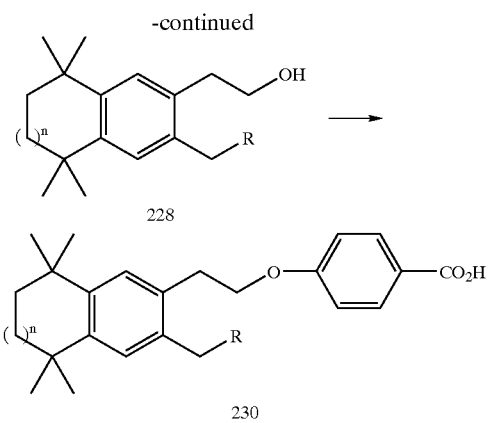

Compounds of Formula 1 where A=CH$_2$ and B=CH$_2$O may be prepared as described in Scheme 13. Treatment of intermediate 80 with an appropriate heteroaromatic nucleophile under basic conditions (e.g. pyrazole, and potassium tert-butoxide in THF) affords 224. Treatment of 224 with trimethoxyvinylsilane, palladium acetate, tri-o-tolulyphopsine in NMP gives vinyl intermediates 226. Hydroboration-oxidation of 226 with 9BBN in THF, followed by oxidation with 30% hydrogen peroxide gave hydroxyethyl intermediate 228. Mitsonobu coupling of 228 with methyl 4-hydroxybenxoate with triphenylphosphine and diethylazodicarboxylate in THF, followed by ester saponication affords retinoid analogs 230.

Also provided is method of preparing a compound of Formula VI, where n and t are 1, $R^1$ is CO$_2$H or CO$_2$-alkyl, $R^2$ is —(CR$^{10}$R$^{11}$)$_m$—R$^{12}$ and $R^3$ is H and $R^{12}$ is heteroaryl.

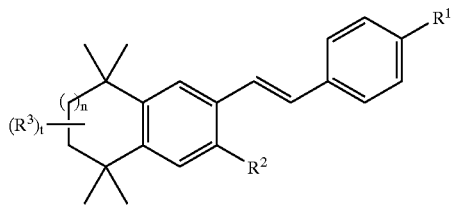

VI comprising: treating a compound of Formula VII

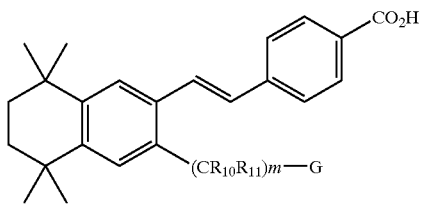

where G is a leaving group with a nucleophile $R^{12}$—H; and when R is CO$_2$-alkyl, hydrolysis with a base.

Assays, Pharmaceutical Compositions and Modes of Administration

Compounds of the invention disclosed herein are useful for promoting the repair of damaged alveoli and septation of alveoli. Thus, methods of the invention may be employed to treat pulmonary diseases such as emphysema. The methods of treatment using a compound of the invention disclosed herein also may be used to treat cancer and dermatological disorders.

The retinoic acid receptor agonist selectivity of a compound of the invention may be determined by using ligand binding assays known to the skilled artisan (Apfel et al., *Proc. Natl. Acad. Sci.*, (1992), 89, 7129; Teng et al., *J. Med. Chem.*, (1997), 40, 2445; Bryce et al., U.S. Pat. No. 5,807, 900 which are herein incorporated by reference). Treatment with RAR agonists, particularly RAR γ agonists may promote repair of alveolar matrix and septation, which are in important in treating emphysema. Preferably, compounds of the invention are γ selective agonists that bind to the γ receptor with affinities between about 25 nm and about 1000 nm and show a five to ten fold selectivity over binding to the RAR α receptor. It should be noted that RAR agonists that are not γ selective may be effective in treating emphysema. Transactivation, which is the ability of a retinoid to activate gene transcription when gene transcription is initiated by the binding of a ligand to the particular retinoic acid receptor being tested, may be determined by using methods described in the art (Apfel et al., *Proc. Natl. Acad. Sci.*, (1992), 89, 7129; Bernard et al., *Biochem. And Biophys. Res. Comm.*, (1992), 186, 977 which is herein incorporated by reference.

The suitability of the compounds of the invention in treating dermatological disorders caused by light or age and wound healing may be determined by methods described in the art (Mustoe et al., *Science* 237, 1333 (1987); Sprugel et al., *J. Pathol.*, 129, 601, (1987), which are herein incorporated by reference). Methods described in the art may be used to determine the usefulness of the compounds of the invention to treating dermatological disorders such as acne or psoriasis (Boyd, *Am. J. Med.*, 86, 568, (1989) and references therein; Doran et al., *Methods in Enzymology*, 190, 34, (1990), which are herein incorporated by reference). Finally, the ability of the compounds of the invention to treat cancer may also be determined by methods described in the art (Sporn et al., *Fed. Proc.* (1976), 1332; Hong et al., "Retinoids and Human Cancer" in *The Retinoids: Biology, Chemistry and Medicine*, M. B. Sporn, A. B. Roberts and D. S. Goodman (eds.) Raven Press, New York, 1994, 597–630, which are herein incorporated by reference).

When used to treat or prevent emphysema or related diseases, cancer or dermatological disorders, compounds of the invention may be administered or applied singly, in combination with other agents. The compounds of the invention may also be administered or applied singly, in combination with other pharmaceutically active agents including other compounds of the invention. A compound of the invention can be administered or applied per se or as pharmaceutical compositions. The specific pharmaceutical formulation will depend upon the desired mode of administration, and will be apparent to those having skill in the art. Numerous compositions for the topical or systemic administration of retinoid agonists are known in the art. Any of these compositions may be formulated with a compound of the invention.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

For topical administration a compound of the invention may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include but are not limited to sodium channel blockers, antibiotics, N-acetyl cysteine, homocysteine and phospholipids.

For injection, a compound of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, compounds of the invention may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a compound of the invention can be readily formulated by combination with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. Methods for formulating retinoid agonists for oral administration have been described in the art (See, e.g., the formulation of Accutane®, *Physicians' Desk Reference* 54$^{th}$ Ed., p. 2610, 2000).

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the compositions may take the form of tablets, lozenges, etc. formulated in conventional manner.

A compounds of the invention may also be administered directly to the lung by inhalation for the treatment of emphysema (see e.g., Tong et al., PCT Application, WO 97/39745; Clark et al., PCT Application, WO 99/47196, which are herein incorporated by reference). For administration by inhalation, a compound of the invention may be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver compounds of the invention directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device may be used to administer a compound of the invention to the lung (See, e.g.,. Raleigh et al., *Proc. Amer. Assoc. Cancer Research Annual Meeting*, (1999), 40, 397, which is herein incorporated by reference). DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of a compound of the invention and a suitable powder base such as lactose or starch for these systems.

Another type of device that may be used to deliver a compound of the invention to the lung is a liquid spray device supplied, for example, by Aradigm Corporation. Liquid spray systems use extremely small nozzle holes to aerosolize liquid drug formulations that may then be directly inhaled into the lung.

In one preferred embodiment, a nebulizer device is used to deliver a compound of the invention to the lung. Nebulizers create aerosols from liquid drug formulations by using, for example, ultrasonic energy to form fine particles that may be readily inhaled (see e.g., Verschoyle et al., *British J. Cancer*, (1999), u, Suppl. 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In another preferred embodiment, an electrohydrodynamic ("EHD") aerosol device is used to deliver a compound of the invention to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of a compound of the invention formulation may be important parameters to optimize when delivering this compound to the lung with an EHD aerosol device and such optimization is routinely performed by one of skill in the art. EHD aerosol devices may more efficiently deliver drugs to the lung than existing pulmonary delivery technologies. Other methods of intra-pulmonary delivery of a compound of the invention will be known to the skilled artisan and are within the scope of the invention.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611, which are herein incorporated by reference).

A compound of the invention may also be formulated in rectal or vaginal compositions such as suppositories or retention enemas, e.g., containing conventional suppository bases such as cocoa butter or other glycerides.

In addition to the formulations described previously, a compound of the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver a compound of the invention. Certain organic solvents such as dimethylsulfoxide also may be employed, although usually at the cost of greater toxicity. A compound of the invention may also be delivered in a controlled release system. In one embodiment, a pump may be used (Sefton, *CRC Crit. Ref. Biomed. Eng.*, (1987), u, 201; Buchwald et al., *Surgery*, (1980), u, 507; Saudek et al., *N. Engl. J. Med.*, (1989), 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, *J. Macromol. Sci. Rev. Macromol. Chem.*, (1983), 23, 61; see also Levy et al., *Science* (1985), 228, 190; During et al., *Ann. Neurol.*, (1989), 25, 351; Howard et al., (1989), *J. Neurosurg.* 71, 105). In yet another embodiment, a controlled-release system can be placed in proximity of the target of a compound of the invention, e.g., the lung, thus requiring only a fraction of the systemic dose (see, e.g., Goodson, in Medical Applications of Controlled Release, supra, vol. 2, pp. 115 (1984)). Other controlled-release system may be used (see e.g., Langer, *Science*, (1990), 249, 1527).

When a compound of the invention is acidic, it may be included in any of the above-described formulations as the free acid, a pharmaceutically acceptable salt, a pro-drug, solvate or hydrate. Pharmaceutically acceptable salts substantially retain the activity of the free acid and may be prepared by reaction with bases. Pharmaceutically acceptable salts include any known suitable salts of retinoic acids known in the art for administration to mammals. Pharmaceutical salts tend to be more soluble in aqueous and other protic solvents than the corresponding free acid form. Similarly, a compound of the invention may be included in any of the above-described formulations as a solvate, hydrate or pro-drug. Preferred pro-drugs include hydrolyzable ester derivatives such as aromatic esters, benzyl esters and lower alkyl esters such as ethyl, cyclopentyl etc. Other pro-drugs are known to those of skill in the pharmaceutical arts.

Methods of use, Dosage and Doses

A compound of the invention, or compositions thereof, will generally be used in an amount effective to achieve the intended purpose. Of course, it is to be understood that the amount used will depend on the method of administration.

For use to treat or prevent emphysema, cancer or dermatological disorders, compounds of the invention or compositions thereof, are administered or applied in a therapeutically effective amount. Therapeutically effective amounts of compounds of the invention for systemic administration may be found in the detailed disclosure provided herein.

The pharmacokinetic profile of the compounds of the invention is predictable and can be described by using linear pharmacokinetic theory. Importantly, the pharmacokinetics of compounds of the invention in humans may be readily determined by one of skill in the art. The skilled artisan may determine a range of standard pharmacokinetic parameters after single oral dosing with a compound of the invention using procedures described in the art (see e.g., Khoo et al., *J. Clin. Pharm*, (1982), 22, 395; Colburn et al., *J. Clin. Pharm*, (1983), 23, 534; Colburn et al., *Eur. J. Clin. Pharm.*, (19), 23, 689). The skilled artisan may also measure values of these pharmacokinetic parameters after multiple dosing, following procedures described in the art, to determine whether induction or accumulation of the compound of the invention occurs under these circumstances (Brazzel et al., *Eur. J. Clin. Pharm.*, (1983), 24, 695; Lucek et al., *Clin. Pharmacokinetics*, (1985), 10, 38). Those of skill in the art may estimate the appropriate systemic dosage levels of compounds of the invention necessary to treat emphysema, cancer or dermatological disorders in mammals (preferably, humans) using the pharmacokinetic parameters determined by the above procedures in conjunction with animal model dosage data.

Dosage amounts and intervals may be adjusted individually to provide plasma levels of a compound of the invention which are sufficient to maintain therapeutic effect. Usual patient dosages for administration by injection range from 0.1 μg and about 10.0 mg, preferably, between about 1.0 μg and about 1.0 mg, more preferably, between about 100.0 μg and about 300.0 μg. Therapeutically effective serum levels may be achieved by administering a single daily dose or multiple doses each day.

The amount of a compound of the invention administered will, of course, be dependent on, among other factors, the subject being treated, the subject's weight, the severity of the affliction, the manner of administration and the judgment of the prescribing physician. For example, the dosage may be delivered in a pharmaceutical composition by a single administration, by multiple applications or controlled release. Dosing may be repeated intermittently, may be provided alone or in combination with other drugs and will continue as long as required for effective treatment of emphysema.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating emphysema, cancer or dermatological disorders when compared to other retinoid agonists. The dosage of a compound of the inventions described herein will preferably be within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, In: *The Pharmacological Basis of Therapeutics*, Ch. 1, p. 1). For example, a therapeutically effective dose of a compound of the invention may be administered either orally or directly into the lung.

EXAMPLES

The invention is further defined by reference to the following examples describing in detail the preparation of the compound and compositions of the invention. It will be apparent to those skilled in the art that many modifications, both to materials and methods, may be practiced without departing from the scope of the invention.

Example 1

Oral Formulation of a Compound of the Invention

Table 2 provides the ingredients for a tablet dosage form of a compound of the invention:

TABLE 2

| Component | Quantity per Tablet (mg) |
|---|---|
| Compound of the invention | 0.1–10.0 |
| Lactose | 125.0 |
| Corn Starch | 50 |
| Magnesium Stearate | 0.5 |
| Croscarmellose Sodium | 25 |

The active ingredient (i.e., a compound of the invention) is blended with the lactose until a uniform mixture is formed. The remaining ingredients are mixed intimately with the lactose mixture and are then pressed into single scored tablets.

Example 2

Oral Formulation of a Compound of the Invention

Capsules of a compound of the invention suitable for the treatment of emphysema may be made using the ingredients provided in Table 3:

TABLE 3

| Component | Quantity per capsule (mg) |
|---|---|
| Compound of the invention | 0.1–5.0 |
| Lactose | 148 |
| Magnesium Stearate | 2 |

The above ingredients are mixed intimately and loaded into a hard-shell gelatin capsule.

Example 3

Suspension Formulation of a Compound of the Invention

TABLE 4

| Component | Amount |
|---|---|
| Compound of the invention | 0.1 g–1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavorings | 0.035 ml |
| Colorings | 0.5 mg |
| Distilled water | q.s. to 100 ml |

The above ingredients listed in Table 4 are mixed to form a suspension for oral administration.

Example 4

Injectable Formulation of a Compound of the Invention

TABLE 5

| Component | Amount |
|---|---|
| Compound of the invention | 0.02 g–0.2 g |
| Sodium acetate buffer solution, 0.4M | 2.0 ml |
| HCl (1N) or NaOH (1N) | q.s. to suitable pH |
| Distilled water | q.s. to 20 ml |

The above ingredients listed in Table 5 are mixed to form an injectable formulation.

Example 5

Injectable Formulation of a Compound of the Invention

TABLE 6

| Component | Amount (mg/ml) |
|---|---|
| Compound of the invention | 2.0–20 |
| Citric acid | 0.2 |
| Sodium citrate | 2.6 |
| Benzalkonium chloride | 0.2 |
| Sorbitol | 35 |
| Sodium taurocholate or glycholate | 10 |

The above ingredients are mixed to form an injectable formulation.

Example 6

Nasal Formulation of a Compound of the Invention

TABLE 7

| Component | Amount |
|---|---|
| Compound of the invention | 0.2 g |
| Sodium acetate buffer solution, 0.4M | 2.0 ml |

TABLE 7-continued

| Component | Amount |
|---|---|
| HCl (1N) or NaOH (1N) | q.s. to suitable pH |
| Distilled or sterile water | q.s to 20 ml |

The above ingredients are mixed to form a suspension for nasal administration.

Example 7

Inhalation Formulation of a Compound of the Invention

TABLE 8

| Component | Percentage by weight |
|---|---|
| Compound of the invention (stabilized with ☐ - tocopherol) | 1.0 |
| 1,1,2-tricholoro-trifluoroethane | 26.1 |
| 40% by weight dichlorodifluoromethane and 60% by weight 1,2-dichloro-1,1,2,2 tetraflouroethane | 72.0 |

A compound of the invention is dissolved carefully in 1,1,2-tricholoro-1,2,2 trifluoroethane without evaporation of any solvent and the resultant solution is filtered and stored in a sealed container. The resultant solution and the propellant gas may be introduced into aerosol cans for dispensation in the percentages shown in Table 8 using methods known to the skilled artisan. A metering valve which is designed for a discharge of between 100 µg and 300 µg per spray shot may be employed to deliver the correct dosage of the compound of the invention.

Example 8

Inhalation Formulation of a Compound of the Invention

TABLE 9

| Component | Percentage by weight |
|---|---|
| Compound of the invention (stabilized with ☐ - tocopherol) | 0.5 |
| Emulsifier (i.e., Cremophor RH 40) | 22.0 |
| 1,2 propylene glycol | 2.0 |
| Water and carrier gas | ad 100% by weight |

Cremaphor RH 40 may be purchased from BASF corporation. Other emulsifiers or solutizers are known to those of skill in the art and may be added to the aqueous solvent instead of Cremaphor RH 40. A compound of the invention, emulsifier, 1,2 propylene glycol and water are mixed together to form a solution. The above liquid formulation may be used, for example, in a pressurized gas aerosol with an appropriate carrier gas (e.g., nitrogen or carbon dioxide).

Example 9

EHD Formulation of a Compound of the Invention

TABLE 10

| Component | Percentage by weight |
|---|---|
| Compound of the invention (stabilized with ☐ - tocopherol) | 0.1 |
| Emulsifier (i.e., Cremophor RH 40) | 10.0 |
| Polyethylene glycol | 3.0 |
| Water | 86.9 |

A compound of the invention, emulsifier, polyethylene glycol and water are mixed together to form a solution. The above liquid formulation may be used in typical EHD devices known in the art.

Example 10

Measurement of Alveolar Repair in Rat Lung with a Compound of the Invention

Compounds of the invention may be evaluated for their effects on alveolar repair in the rat model of elastase-induced emphysema (Massaro et al., Nature, 1997, Vol. 3, No. 6: 675; Massaro et al., U.S. Pat. No. 5,998,486). Preferably, animals are divided into treatment groups of approximately eight. Lung inflammation and alveolar damage may be induced in male Sprague Dawley rats by a single instillation of about 2 U/gram body mass of pancreatic elastase (porcine derived, Calbiochem).

Animals may be treated with a compound of the invention prepared in Capmul at convenient oral dosage ranges (preferably, between about 10.0 mg/kg and 0.0001 mg/kg) and will be dosed orally once per day starting 21 days post injury. Control groups are challenged with elastase and 21 days later are treated with vehicle (Capmul solution) for 14 days. Animals are sacrificed 24 hours after the last dose by exsanguination under deep anesthesia. Blood was collected at time of exsanguination for analysis.

The lungs are inflated with 10% neutral buffered formalin by intratracheal instillation at a constant rate (1 ml/gram body mass/min). The lung is excised and immersed in fixative for 24 hours prior to processing. Alveolar measurements are made in four regions of the lung/rat. The mean value/treatment group may be determined by summing the average area/rat for all eight rats relative to the elastase+ vehicle treated group. In some cases, the variability between rats within a treatment group was too large for the group average to be statistically significant. Standard methods may be used to prepare 5 µm paraffin sections. Sections are stained with Hematoxylin and Eosin. Computerized Morphometric analysis was performed to determine the average alveolar size and alveolar number.

Quantitation of triglycerides contained in rat plasma may be performed using established procedures. Briefly, plasma triglycerides may be converted to dihdroxyacetone and hydrogen peroxide by sequential treatment of plasma with lipase and glycerokinase according directions described by the manufacturer of triglycerides/GPO kit (Boehringer Mannheim #1488872). Hydrogen peroxide may be quantitated calorimetrically in a Hitachi 911 Chemistry Analyzer. In rats normal triglyceride levels are between about 75 mg/dl and about 175 mg/dl. Triglyceride values are a convenient measure of toxicity.

The following examples describe synthesis of particular compounds of the invention, including many compounds illustrated in Table 1.

Example 11

Preparation of (E)-methyl-4-[2-(3-bromomethyl-5,5,8,8-tetramethyl-5,6,7,8-tetrahydro-naphthalen-2-yl)vinyl]benzoate

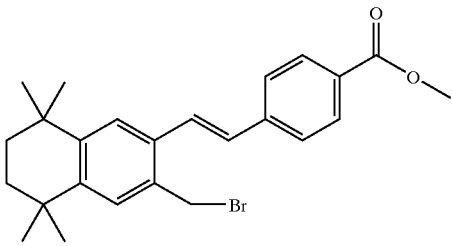

Step A: Preparation of 2,5-dichloro-2,5-dimethylhexane

HCl gas was added by bubbling through a gas dispersion tube to a solution of 100 g (684 mmol) of 2,5-dimethyl-2,5-hexanediol in 300 mL of ethanol. The reaction mixture slowly warmed from room temperature to 60° C. over 3 hours. The reaction mixture was cooled in a wet ice bath and a white solid was filtered off. The solid was washed with water and cold ethanol, then dried to give 65.2 g (65%) of 2,5-dichloro-2,5-dimethylhexane ($M^+$=181).

Step B: Preparation of 2-bromo-3-methyl-5,5,8,8-tetramethyl-5,5,7,8-tetrahydronaphthalene

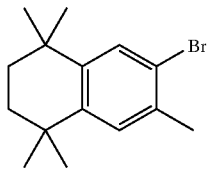

To a solution of 20 g (117 mmol) of 2-bromotoluene and 14.4 g (97.4 mmol) of 2,5-dichloro-2,5-dimethylhexane in 100 mL of dichloromethane was added 1.56 g (16.9 mmol) of aluminum chloride and the mixture heated at reflux. After 16 hours, the mixture was cooled to room temperature, diluted with 150 mL of hexane and 100 mL of 1 N HCl was added. The organic layer was separated and the aqueous layer was extracted with hexane. The combined organic layers were washed with saturated NaCl solution, dried over sodium sulfate and concentrated under reduced pressure. The product was purified by filtration through a pad of silica gel with elution with hexane and afforded 23.9 g (87%) of 2-bromo-3-methyl-5,5,8,8-tetramethyl-5,6,7,8-tetrahydronaphthalene as a solid. (m.p.: 81.1–85° C.).

Step C: Preparation of 2-formyl-3-methyl-5,5,8,8-tetramethyl-5,6,7,8-tetrahydronaphthalene

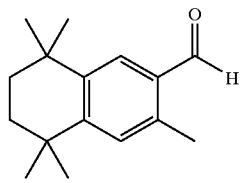

22.2 mL (35.2 mmol) of n-butyl lithium (1.6 M in hexanes) was added. After 1 hours, a solution of 3.95 mL (35.5 mmol) of N-formylpiperidine was added to a solution of 5 g (17.8 mmol) of 2-bromo-3-methyl-5,5,8,8-tetramethyl-5,6,7,8-tetrahydronaphthalene in 50 mL of tetrahydrofuran, cooled in a dry ice/acetone bath. After 30 minutes 30 mL of saturated aqueous ammonium chloride was added to the reaction mixture. The reaction mixture was warmed to room temperature and extracted with ethyl acetate. The organic phase was separated, washed with brine, dried over sodium sulfate and concentrated under reduced pressure. The residue was purified by flash chromatography on silica gel with gradient elution (hexane-10% ethyl acetate/hexane) to provide 3.5 g (85%) of 2-formyl-3-methyl-5,5,8,8-tetramethyl-5,6,7,8-tetrahydronaphthalene (m.p.: 82.4–84.1° C.).

An Alternative Preparation of 2-formyl-3-methyl-5,5,8,8-tetramethyl-5,6,7,8-tetrahydronaphthalene 28.9 g (322 mmol) of copper(I) cyanide was added to 22.7 g (80.7 mmol) of 2-bromo-3-methyl-5,5,8,8-tetramethyl-5,6,7,8-tetrahydronaphthalene in 270 mL of N-methyl pyrrolidine. The reaction mixture was heated at 175° C. After 16 hours, the mixture was cooled to room temperature and treated with 400 mL of 10% aqueous ammonium hydroxide. The reaction mixture was filtered to remove salts and the solids were extracted with hot ethyl acetate. The combined organic fractions were washed with brine, dried over sodium sulfate and concentrated under reduced pressure. The product was purified by gradient elution through a pad of silica gel (hexane-5% ethyl acetate/hexane) to give 18 g (95%) of 2-cyano-3-methyl-5,5,8,8-tetramethyl-5,6,7,8-tetrahydronaphthalene ($M^+$=227).

To a solution of 18.7 g (82.3 mmol) of 2-cyano-3-methyl-5,5,8,8-tetramethyl-5,6,7,8-tetrahydronaphthalene in 280 mL of dichloromethane, cooled at −78°, was added 123 mL (123 mmol) of diisobutyl aluminum hydride (1.0 M in toluene). The reaction mixture was stirred and allowed to gradually warm to room temperature. After 16 hours, the reaction mixture was treated with 30 mL of acetic acid added dropwise, followed by 150 mL of water. The organic layer was separated, diluted with 200 mL of hexane, washed with brine, dried over sodium sulfate and concentrated under reduced pressure. The residue was purified by flash chromatography (gradient elution 5–10% ethyl acetate/hexane) on silica gel to afford 11.8 g (63%) of 2-formyl-3-methyl-5,5,8,8-tetramethyl-5,6,7,8-tetrahydronaphthalene.

Step D:

Preparation of Methyl-4-[(E)-2-(3,5,5,8,8-pentamethyl-5,6,7,8-tetrahydro-naphtalen-2yl)vinyl]benzoate

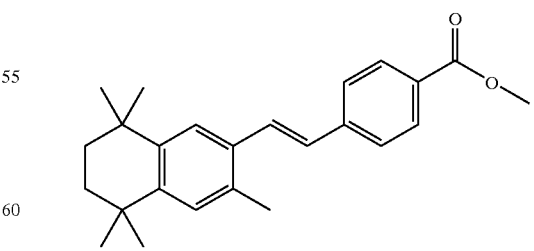

To a solution of 3.5 g (13.5 mmol) of dimethyl-4-methylcarboxylbenzylphosphonate in 80 mL of toluene at 0°, was added 7.6 mL (23 mmol) of potassium tert-pentylate (Fluka Chemical Co.). After 15 minutes a solution of 2.3 g (10 mmol) of 2-formyl-3-methyl-5,5,8,8-tetramethyl-5,6,7,8-tetrahydronaphthalene in 20 mL of toluene was added and the reaction was allowed to stir and warm to room temperature. After 16 hours, the reaction mixture was poured into 50 mL 2 N HCl, extracted with ethyl acetate, washed with brine, dried over sodium sulfate and concentrated under reduced pressure. The residue was stirred with 100 mL of hexane, filtered and the filtrate concentrated under reduced pressure. The residue was stirred with 100 mL of methyl alcohol and the product filtered off to give 2.32 g (64%) of methyl-4-[(E)-2-(3,5,5,8,8-pentamethyl-5,6,7,8-tetrahydro-naphthalen-2-yl)vinyl]benzoate ($M^+$=362).

Step E:

Preparation of Methyl-4-[(E)-2-(3-bromomrethyl-5,5,8,8-tetramethyl-5,6,7,8-tetrahydro-naphthalene-2-yl)vinyl]benzoate

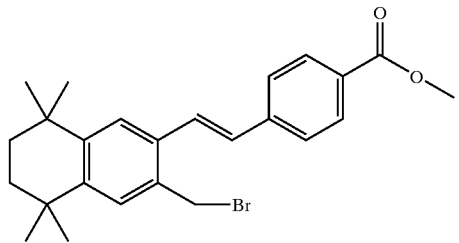

A mixture of 1.0 g (2.76 mmol) of (E)-methyl-4-[2-(3-methyl-5,5,8,8-tetramethyl-5,6,7,8-tetrahydro-naphthalen-2-yl)vinyl]benzoate, 0.64 g (3.6 mmol) of N-bromosuccinimide and 0.033 g (0.13 mmol) of benzoyl peroxide in 20 mL of carbon tetrachloride was heated under reflux, under a high intensity lamp. After 2 hours, the reaction was cooled to room temperature and poured into 10% aqueous sodium bisulfite solution. The organic layer was separated, washed with brine, dried over sodium sulfate and concentrated under reduced pressure. The residue was stirred with methyl alcohol to afford 0.88 g of Methyl-4-[2-(3-bromomethyl-5,5,8,8-tetramethyl-5,6,7,8-tetrahydro-naphthalen-2-yl)vinyl]benzoate (72%) ($M^+$=440).

Example 12

Preparation of 4-[(E)-2-(5,5,8,8-tetramethyl-3-pyrazol-1-ylmethyl-5,6,7,8-tetrahydro-naphthalen-2-yl)vinyl]benzoic acid (6)

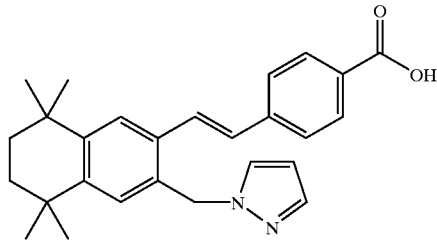

A mixture of 2.0 g (4.5 mmol) of (E)-methyl-4-[2-(3-bromomethyl-5,5,8,8-tetramethyl-5,6,7,8-tetrahydro-naphthalen-2-yl)vinyl]benzoate and 0.65 g (9.5 mmol) of pyrazole in 15 mL of N-methyl pyrrolidine was heated at 100°. After 2 hours, the reaction mixture was cooled to room temperature, poured into brine and extracted with ethyl acetate. The organic extracts were washed with brine, dried over sodium sulfate and concentrated under reduced pressure. The residue was stirred with hexane and the product was filtered off, washed with hexane and dried to give 1.6 g (83%) of methyl-4-[2-(5,5,8,8-Tetramethyl-3-pyrazol-1-ylmethyl-5,6,7,8-tetrahydro-naphthalen-2-yl)vinyl]benzoate ($M^+$=429).

A mixture of 27.6 g (64.4 mmol) of methyl-4-[2-(5,5,8,8-tetramethyl-3-pyrazol-1-ylmethyl-5,6,7,8-tetrahydro-naphthalen-2-yl)vinyl]benzoate and 97 mL (193 mmol) of 2 N sodium hydroxide in 300 mL of ethyl alcohol was heated at reflux. After 1 hour, the reaction mixture was cooled to room temperature and diluted with 900 mL of water. The reaction mixture was acidified with 2 N HCl and the product was isolated by filtration, washed with water and pentane and dried to give 25.9 g (97%) of 4-[(E)-2-(5,5,8,8-tetramethyl-3-pyrazol-1-ylmethyl-5,6,7,8-tetrahydro-naphthalen-2-yl)vinyl]benzoic acid (m.p.=246.5–248° C.) 6.

Proceeding as described in the example above but substituting pyrazole with pyrrole, 4-methylpyrazole, 1,2,4-triazole, morpholine, 2-pyrrolidone, 3,5-dimethylpyrzole, δ-valerolactone, 2-methylimidazole and 4-methylimidzole gave 4-[(E)-2-(5,5,8,8-tetramethyl-3-pyrrol-1-ylmethyl-5,6,7,8-tetrahydro-naphthalen-2-yl)vinyl]benzoic acid 7,4-{(E)-2-[5,5,8,8-Tetramethyl-3-(4-methylpyrazol-1-ylmethyl-5,6,7,8-tetrahydro-naphthalen-2-yl)vinyl]benzoic acid 20, 4-[(E)-2-(5,5,8,8-Tetramethyl-3-[1,2,4]triazol-1-ylmethyl-5,6,7,8-tetrahydro-naphthalen-2-yl]vinyl}benzoic acid 39, 4-[(E)-2-(5,5,8,8-tetramethyl-3-morpholin-4-ylmethyl-5,6,7,8-tetrahydro-naphthalen-2-yl)vinyl]benzoic acid 138, 4-[(E)-2-(5,5,8,8-tetramethyl-3-(2-oxo-pyrrolidin-1-yl-methyl-5,6,7,8-tetrahydro-naphthalen-2-yl)vinyl]benzoic acid 139, 4-{(E)-2-[5,5,8,8-Tetramethyl-3-(3,5-dimethylpyrazol-1-ylmethyl-5,6,7,8-tetrahydro-naphthalen-2-yl)vinyl]benzoic acid 143, 4-[(E)-2-(5,5,8,8-tetramethyl-3-(2-oxo-piperidin-1-yl-methyl-5,6,7,8-tetrahydro-naphthalen-2-yl)vinyl]benzoic acid 146 4-{(E)-2-[5,5,8,8-Tetramethyl-3-(2-methylimidazol-1-ylmethyl-5,6,7,8-tetrahydro-naphthalen-2-yl)vinyl]benzoic acid 149 and 4-{(E)-2-[5,5,8,8-Tetramethyl-3-(4-methylimidazol-1-ylmethyl-5,6,7,8-tetrahydro-naphthalen-2-yl)vinyl]benzoic acid 150 respectively.

Example 13

Preparation of 4-[(E)-2-(3-butylthiomethyl-5,5,8,8-tetramethyl-5,6,7,8-tetrahydro-naphthalen-2-yl)vinyl]benzoic acid

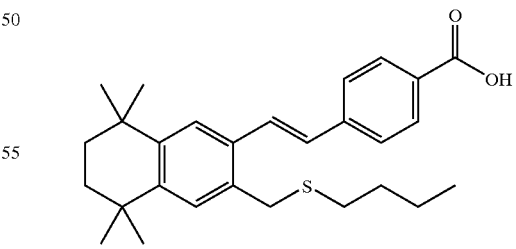

A solution of 445 mg (1 mmol) of Methyl-4-[(E)-2-(3-Bromomethyl-5,5,8,8-tetramethyl-5,6,7,8-tetrahydro-naphthalen-2-yl)vinyl]benzoate, 418 mg (3 mmol) of potassium carbonate and 180 mg (2 mmol) of 1-butanethiol in 10 mL dimethylformamide was heated to reflux. After 40 minutes, the reaction mixture was cooled to room temperature, then diluted with water. The mixture was extracted with ethyl acetate, the organic extracts washed with brine, dried over sodium sulfate, then concentrated under reduced pressure. The residue was purified by flash chromatography on silica gel (5% ethyl acetate/hexane) to give 263 mg (58%) of Methyl-4-[(E)-2-(3-Butylthiomethyl-5,5,8,8-tetramethyl-5,6,7,8-tetrahydro-naphthalen-2-yl)vinyl]benzoate.

This above compound was taken up in 10 mL methyl alcohol and 5 mL 1 N LiOH and heated to reflux. After 2 hours the reaction mixture was cooled to room temperature, diluted with brine and acidified with concentrated HCl. The mixture was extracted with ethyl ether and the organic fraction was dried over sodium sulfate. The solution was concentrated under reduced pressure to give 200 mg (78%) of 4-[(E)-2-(3-Butylthiomethyl-5,5,8,8-tetramethyl-5,6,7,8-tetrahydro-naphthalen-2-yl)vinyl]benzoic acid (M$^+$=456).

Proceeding as described in the example above but substituting 1-butanethiol with, furfuryl mercaptan, 1-mercapto-2,3-propanediol, 1-mercapto-2-methylbutane, cyclopentylmercaptan, isopropylmercaptan, isobutylmercaptan, 3-methylbutylmercaptan, 2-diethylaminoethylmercaptan, 2-cyclohexylaminoethylmercaptan, 2-mercaptopyrimidine, propylmercaptan, 4-methyl-4H-1,2,4-triazole-3-thiol, 5-methyl-1,3,4-thiadiazole-2-thiol, 5-mercapto-1-methyltetrazole, 2-mercapto-1-methylimidazole, 2-mercaptothiazoline and 2-mercaptobenzothiazole gave 8, 9, 3, 4, 13, 14, 16, 17, 18, 19, 21, 22, 23, 25, 32, 34 and 35 respectively.

Example 14

Preparation of 2-fluoro-4-[(E)-2-(5,5,8,8-tetramethyl-3-pyrazol-1-ylmethyl-5,6,7,8-tetrahydro naphthalen-2-yl]vinyl}benzoic acid

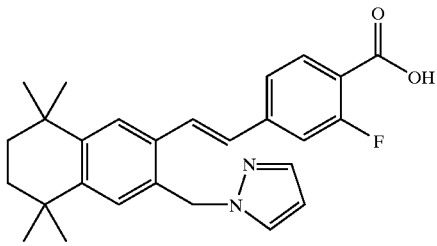

A 0° C., 3M tetrahydrofuran solution of 350 mg (1.62 mmol) of 2-formyl-3,5,5,8,8-pentamethyl-5,6,7,8-tetrahydro-naphthalene and 541 mg (1.78 mmol) of diethyl 2-fluoro-4-carbomethoxybenzylphosphonate was treated with 84 mg (2.10 mmol, 60% wt. in mineral oil) NaH in 10 mg portions over 10 minutes. The reaction mixture was stirred at room temperature for 2 hours before diluting with ethyl acetate and washing with brine. The organic extracts were dried over magnesium sulfate, concentrated in vacuo and triturated with methanol to provide 330 mg (54%) Methyl 2-fluoro-4-[(E)-2-(3,5,5,8,8-pentamethyl-5,6,7,8-tetrahydro-naphthalen-2-yl)vinyl]benzoate.

A slurry of 315 mg (0.828 mmol) of Methyl 2-fluoro-4-[(E)-2-(3,5,5,8,8-pentamethyl-5,6,7,8-tetrahydro-naphthalen-2-yl)vinyl]benzoate, 147 mg of N-bromosuccinimide, and 10 mg of benzoyl peroxide in 6 mL of carbon tetrachloride was heated to reflux and exposed to the radiation from a tungsten filament sun lamp for 1.5 hours. The reaction mixture was then filtered and concentrated in vacuo. The resulting residue was purified by flash chromatography on silica gel (2% ethyl acetate in hexane) to provide 247 mg (65%) of Methyl 2-fluoro-4-[(E)-2-(3-Bromomethyl-5,5,8,8-tetramethyl-5,6,7,8-tetrahydro-naphthylen-2-yl)vinyl]benzoate.

A mixture of 231 mg (0.503 mmol) of Methyl 2-fluoro-4-[(E)-2-(3-Bromomethyl-5,5,8,8-tetramethyl-5,6,7,8-tetrahydro-naphthylen-2-yl)vinyl]benzoate, 120 mg (1.76 mmol) of pyrazole and 1.5 mL of N-methyl pyrrolidine was heated to 125° C. for 6 hours. The resulting slurry was partitioned between ethyl acetate and water. The organic layer was washed with brine, dried over magnesium sulfate, and concentrated under reduced pressure yielding 207 mg (92%) of Methyl 2-fluoro-4-[(E)-2-[5,5,8,8-tetramethyl-3-pyrazol-1ylmethyl-5,6,7,8-tetrahydro naphthalen-2-yl]vinyl}benzoate.

A slurry of 199 mg (0.446 mmol) of Methyl 2-fluoro-4-[(E)-2-[5,5,8,8-tetramethyl-3-pyrazol-1-ylmethyl-5,6,7,8-tetrahydro-naphthalen-2-yl)vinyl]benzoate, 1.5 mL ethanol and 1 mL of 2M aqueous sodium hydroxide was stirred for 16 hours. The mixture was neutralized with aqueous ammonium chloride and extracted with ethyl acetate. The organic layer was then washed with brine, dried over magnesium sulfate and concentrated in vacuo. The resulting 145 mg of residue was triturated in methanol to provide 85 mg (44%) of 2-Fluoro-4-[(E)-2-[5,5,8,8-tetramethyl-3-pyrazol-1-ylmethyl-5,6,7,8-tetrahydro naphthalen-2-yl)vinyl]benzoic acid 47.

Example 15

Preparation of 5-[(E)-2-(5,5,8,8-tetramethyl-3-pyrazol-1-ylmethyl-5,6,7,8-tetrahydro-naphthalen-2-yl)vinyl]-thiophene-2-carboxylic acid

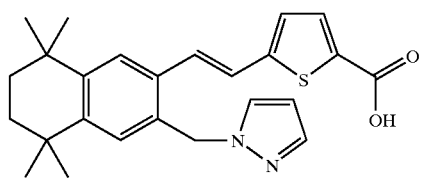

A 3M tetrahydrofuran solution of 434 mg (1.46 mmol) of 2-formyl-5,5,8,8-tetramethyl-3-pyrazol-1-ylmethyl-5,6,7,8-tetrahydro-naphthalene and 494 mg (1.61 mmol) of diethyl (5-carboethoxythiophen-2-yl) methylphosphonate at 0° C. was treated with 76 mg (1.91 mmol, 60% wt. in mineral oil) NaH in 5 mg portions over 10 minutes. The slurry was then stirred at room temperature for 2 hours. The reaction mixture was then diluted with ethyl acetate and washed with water and brine. The organic layer was then dried over magnesium sulfate and concentrated in vacuo. The resulting residue was triturated with methanol yielding 45.

Example 16

Preparation of 4-{(E)-2-[3-(2-methoxy-ethoxymethy)L-5,5,8,8-tetramethyl-5,6,7,8-tetrahydro-naphthalen-2-yl]vinyl}benzoic acid

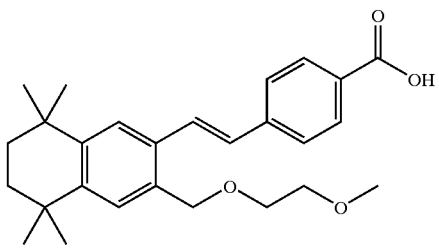

To a mixture of 63 mg (1.57 mmol) of sodium hydride in 5 mL of tetrahydrofuran was added 110 mg (1.47 mmol) of 2-methoxyethanol, followed by 16 mg (0.098 mmol) of potassium iodide. The reaction mixture was cooled to −30° and a solution of 434 mg (0.98 mmol) of Methyl-4-[(E)-2-(3-bromomethyl-5,5,8,8-tetramethyl-5,6,7,8-tetrahydro-naphthalen-2-yl)vinyl]benzoate in 5 mL of tetrahydrofuran was added. The reaction mixture was allowed to slowly warm to room temperature. After 5 hours the reaction mixture was diluted with water and extracted with ethyl acetate. The organic fraction was washed with brine, dried over sodium sulfate and concentrated under reduced pressure. The residue was purified by flash chromatography on silica gel (13% ethyl acetate/hexane).

The above product was taken up in 10 mL methyl alcohol and 5 mL of 1N LiOH. The reaction mixture was heated to reflux. After 4 hours, the reaction mixture was cooled to room temperature, diluted with water and ethyl ether and then acidified with concentrated HCl. The mixture was extracted with ethyl acetate, the organic extracts washed with brine, dried over sodium sulfate and concentrated under reduced pressure. The residue was recrystallized (ethyl acetate/hexane) to give 50 mg (12%) of 4-{(E)-2-[3-(2-methoxy-ethoxymethyl-5,5,8,8-tetramethyl-5,6,7,8-tetrahydro-naphthalen-2-yl]vinyl}benzoic acid (m.p.= 55.9–58.2° C.) 5.

Example 17

Preparation of 4-{(E)-2-[3-(3-hydroxypropyl)-5,5,8,8-tetramethyl-5,6,7,8-tetrahydro-naphthalen-2-yl]vinyl}benzoic acid

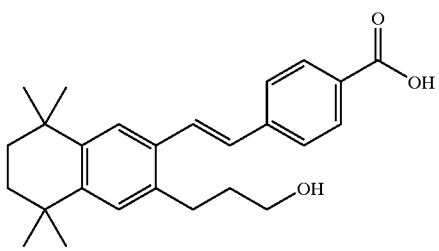

Step A

Preparation of 2-(3-hydroxypropyl)-5,5,8,8-tetramethyl-5,6,7,8-tetrahydro-naphthalene

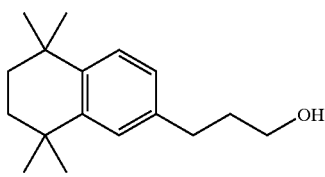

To a solution of 14 g (103 mmol) of 3-phenyl-1-propanol and 18.2 g (123 mmol) of 2,5-dichloro-2,5-dimethylhexane in 100 mL of dichloromethane was added 15 g (113 mmol) of aluminum chloride. After the addition of aluminum chloride was complete, the reaction was heated to reflux. After 16 hours, the reaction mixture was cooled to room temperature and 100 mL of water was added, followed by 100 mL of 1N HCl. The reaction mixture was stirred for 2 hours, filtered through a Celite pad and the layers were separated. The aqueous layer was extracted with diethyl ether and the combined organic fractions were washed with brine, dried over sodium sulfate and concentrated under reduced pressure. The residue was purified by flash chromatography on silica gel (30% ethyl acetate/hexane) to afford 13.45 g (53%) of 2-(3-hydroxypropyl)-5,5,8,8-tetramethyl-5,6,7,8-tetrahydro-naphthalene.

Step B

Preparation of 2-bromo-3-(3-hydroxypropyl)-5,5,8,8-tetramethyl-5,5,7,8-tetrahydro-naphthalene

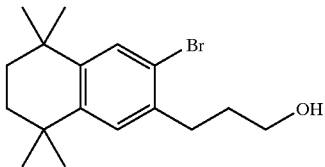

To a solution of 12.3 g (49.8 mmol) of 2-(3-hydroxypropyl)-5,5,8,8-tetramethyl-5,6,7,8-tetrahydro-naphthalene in 100 mL of carbon tetrachloride at 0° C. was added a trace of iron powder followed by a solution of 8.76 g (54.8 mmol) of bromine in 80 mL of carbon tetrachloride. After 4.5 hours at 0° C. the reaction mixture was warmed to room temperature. After 3 hours at room temperature, the reaction mixture was poured into ice water and the mixture was extracted with dichloromethane. The organic fraction was washed with brine, dried over sodium sulfate and concentrated under reduced pressure. The residue was purified by flash chromatography on silica gel (30% ethyl acetate/hexane) to give 10.2 g (63%) of 2-bromo-3-(3-hydroxypropyl)-5,5,8,8-tetramethyl-5,6,7,8-tetrahydro-naphthalene. ($M^+$=324).

Step C

Preparation of 2-bromo-3-(3-t-butyldimethylsiloxypropyl)-5,5,8,8-tetremethyl-5,5,7,8-tetrahydro-naphthalene

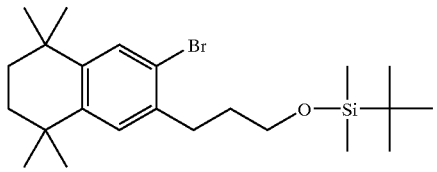

To a solution of 10.2 g (31.55 mmol) of 2-bromo-3-(3-hydroxypropyl)-5,5,8,8-tetramethyl-5,6,7,8-tetrahydro-naphthalene in 80 mL of dimethlformamide was added 9.46 g (138.8 mmol) of imidazole and 10.46 g (69.4 mmol) of tert-butyldimethylsilyl chloride. After 4 hours the reaction mixture was diluted with diethyl ether and washed with 1 N aqueous ammonium chloride and brine. The organic fraction was dried over sodium sulfate and then concentrated under reduced pressure. The residue was purified by flash chromatography on silica gel (gradient elution: 1–2% ethyl acetate/hexane) to afford 9.17 g (66%) of 2-bromo-3-(3-t-butyldimethylsiloxypropyl)-5,5,8,8-tetramethyl-5,6,7,8-tetrahydro-naphthalene.

Step D

Preparation of 2-cyano-3-(3-t-butyldimethylsiloxypropyl)-5,5,8,8-tetramethyl-5,5,7,8-tetrahydro-naphthalene

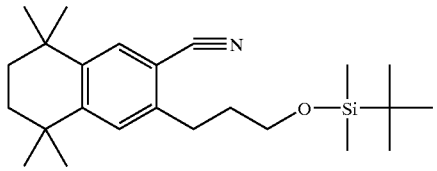

To a solution of 9.0 g (20.5 mmol) of 2-bromo-3-(3-t-butyldimethylsiloxypropyl)-5,5,8,8-tetramethyl-5,6,7,8-tetrahydro-naphthalene in 70 mL of N-methyl pyrollidine was added 7.36 g (82 mmol) of copper (I) cyanide and the reaction mixture was heated to 175° C. After 16 hours the reaction mixture was cooled to room temperature and diluted with 10% aqueous ammonium hydroxide. The resulting salts were removed by filtration and washed with hot ethyl acetate. The filtrate was extracted with ethyl acetate and the combined organic fractions were washed with brine, dried over sodium sulfate and concentrated under reduced pressure. The residue was purified by flash chromatography on silica gel (gradient elution: 3-25% ethyl acetate/hexane) to give 4.8 g (61%) of 2-cyano-3-(3-t-butyldimethylsiloxypropyl)-5,5,8,8-tetramethyl-5,6,7,8-tetrahydro-naphthalene.

Step E

Preparation of 2-formyl-3-(3-t-butyldimethylsiloxypropyl)-5,5,8,8-tetramethyl-5,5,7,8-tetrahydro-naphthalene

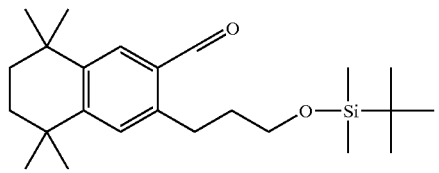

To a solution of 4.6 g (11.9 mmol) of 2-cyano-3-(3-t-butyldimethylsiloxypropyl)-5,5,8,8-tetramethyl-5,6,7,8-tetrahydro-naphthalene.in 40 mL of dichloromethane at −78° C. was added 17.9 mL (17.9 mmol) of diisobutylaluminum hydride (1.0 M in toluene). The reaction mixture was stirred and allowed to slowly warm to room temperature. After 16 hours, acetic acid was added dropwise, followed by addition of water and dichloromethane. The organic fraction was separated, washed with brine, dried over sodium sulfate and concentrated under reduced pressure. The residue was purified by flash chromatography on silica gel (gradient elution: 4–25% ethyl acetate/hexane) to afford 2.48 g (53%) of 2-formyl-3-(3-t-butyldimethylsiloxypropyl)-5,5,8,8-tetramethyl-5,6,7,8-tetrahydro-naphthalene. M$^+$=389).

An Alternative Preparation of 2-formyl-3-(3-t-butyldimethylsiloxypropyl)-5,5,8,8-tetramethyl-5,6.7,8-tetrahydro-naphthalene To a solution of 14 g (32 mmol) of 2-bromo-3-(3-t-butyldimethylsiloxypropyl)-5,5,8,8-tetramethyl-5,6,7,8-tetrahydro-naphthalene in 200 mL of dry tetrahydrofuran at −78° C. was added 24.9 mL (64 mmol) of n-BuLi (2.5 M in hexane) via syringe under N$_2$ atmosphere. The reaction mixture was stirred at this condition for 1 hour. Then it was quenched with a solution of 7 mL (64 mmol) of N-formyl piperidine in 10 mL of dry tetrahydrofuran. The resulting solution was stirred for an additional 30 minutes, when it was quenched with 100 mL of NH$_4$Cl solution. The reaction mixture was extracted with 3×100 mL of ethyl acetate. The organic layers were combined, dried over MgSO$_4$ and the solvent was removed under reduced pressure. The residue was purified by flash chromatography on silica gel (gradient elution: 30% ethyl acetate/hexanes) to afford 11.1 g (90%) of 2-formyl-3-(3-t-butyldimethylsiloxypropyl)-5,5,8,8-tetramethyl-5,6,7,8-tetrahydro-naphthalene. (M$^+$=386).

Step F: Preparation of Methyl-4-{(E)-2-[3-(3-t-butyldimethylsiloxypropyl)-5,5,8,8-tetramethyl-5,5,7,8-tetrahydro-naphthalen-2-yl]vinyl}benzoate

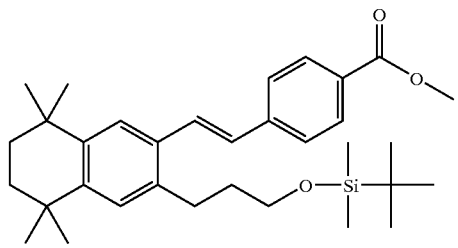

To a suspension of 0.85 g (21.3 mmol) of 2-formyl-3-(3-t-butyldimethylsiloxypropyl)-5,5,8,8-tetramethyl-5,6,7,8- tetrahydro-naphthalene in 20 mL dimethyl sulfoxide at 0° C. was added a solution of 6.25 g (21.8 mmol) of dimethyl-4-methylcarboxylbenzylphosphonate in 20 mL of dimethyl sulfoxide. After 2 hours a solution of 4 g (10.4 mmol) in 10 mL dimethyl sulfoxide was added. After 3.5 hours, the reaction mixture was poured into ice. The aqueous solution was acidified with 1 N HCl and extracted with ethyl acetate. The organic fraction was washed with brine, dried over sodium sulfate and concentrated under reduced pressure. The residue was purified by chromatography through a short plug of silica gel (4% ethyl acetate/hexane) to afford 4.22 g (78%) of Methyl-4-{(E)-2-[3-(3-t-butyldimethylsiloxy-propyl)-5,5,8,8-tetramethyl-5,6,7,8-tetrahydro-naphthalen-2-yl]vinyl}benzoate (m.p.:73.2–76.5° C.).

Step G

Preparation of Methyl-4-{(E)-2-[3-(3-hydroxypropyl)-5,5,8,8-tetramethyl-5,5,7,8-tetrahydro-naphthalen-2-yl]vinyl}benzoate

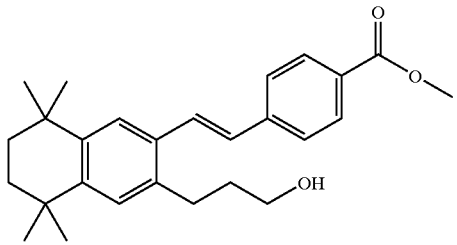

To a solution of 4.0 g (7.7 mmol) of Methyl-4-{(E)-2-[3-(3-t-butyldimethylsiloxypropyl)-5,5,8,8-tetramethyl-5,6,7,8-tetrahydro-naphthalen-2-yl]vinyl}benzoate in 20 mL tetrahydrofuran was added a solution of 8 mL (8.08 mmol) tetrabutylammonium fluoride (1.0 M in tetrahydrofuran). After 30 min the reaction mixture was diluted with water and extracted with ethyl acetate. The organic fraction was washed with brine, dried over sodium sulfate and concentrated under reduced pressure. The residue was purified by flash chromatography on silica gel (ethyl acetate) to give 2.67 g (85%) of Methyl-4-{(E)-2-[3-(3-hydroxypropyl)-5,5,8,8-tetramethyl-5,6,7,8-tetrahydro-naphthalen-2-yl]vinyl}benzoate (m.p.=109–115.5° C.).

Step H

Preparation of 4-{(E)-2-[3-(3-hydroxypropyl)-5,5,8,8-tetramethyl-5,5,7,8-tetrahydro-naphthalen-2-yl]vinyl}benzoic acid

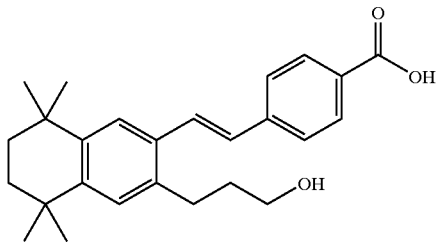

To a solution of 27.0 g (0.66 mmol) of Methyl-4-{(E)-2-[3-(3-hydroxypropyl)-5,5,8,8-tetramethyl-5,6,7,8-tetrahydro-naphthalen-2-yl]vinyl}benzoate in 10 mL of methyl alcohol was added 5 mL of 1 N LiOH. The reaction mixture was heated to reflux. After 4 hours, the reaction mixture was cooled to room temperature, diluted with diethyl ether and acidified with concentrated HCl. The organic layer was separated, washed with brine, dried over sodium sulfate and concentrated under reduced pressure. The residue was purified by crystallization (hexane/ethyl acetate) to give 200 mg (76%) of 4-{(E)-2-[3-(3-hydroxypropyl)-5,5,8,8-tetramethyl-5,6,7,8-tetrahydro-naphthalen-2-yl]vinyl}benzoic acid (m.p.: 212.8–213.2° C.) 12.

Proceeding as described in the Example above but substituting 3-hydroxypropylbenzene with 2-hydroxyethylbenzene gave 4-{(E)-2-[3-(2-hydroxyethyl)-5,5,8,8-tetramethyl-5,6,7,8-tetrahydro-naphthalen-2-yl]vinyl}benzoic acid 31.

Example 18

Preparation of 4-{(E)-2-[3-(3-methoxy-propyl})5,8,8-tetramethyl-5,6,7,8-tetrahydro-naphthalen-2-yl]vinyl}benzoic acid

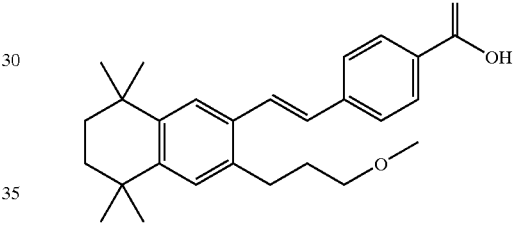

To 390 mg (0.96 mmol) of Methyl-4-[(E)-2-[3-(3-hydroxypropyl)-5,5,8,8-tetramethyl-5,6,7,8-tetrahydro-naphthalen-2-yl]vinyl}benzo ate in 5 mL of dimethylformamide was added 480 mg (4.78 mmol) of methyl iodide at 0° C. was added 38 mg (0.96 mmol) of sodium hydride (60% oil dispersion). After 4 hours, the reaction mixture was diluted with saturated aqueous ammonium chloride and extracted with dichloromethane. The organic fraction was washed with brine, dried over sodium sulfate and concentrated under reduced pressure. The residue was purified by flash chromatography on silica gel (6% ethyl acetate/hexane) to give 200 mg of product. This material was taken up in 10 mL methyl alcohol and 5 mL of 1 N LiOH and heated to reflux. After 2 hours, the reaction was cooled to room temperature, diluted with water and acidified with concentrated HCl. The reaction was extracted with ethyl acetate, the organic fractions were washed with brine, dried over sodium sulfate and concentrated under reduced pressure. The residue was purified by flash chromatography on silica gel (40% ethyl acetate/hexane/0.5% acetic acid) to 100 mg of 4-{(E)-2-[3-(3-methoxypropyl}-5,8,8-tetramethyl-5,6,7,8-tetrahydro-naphthalen-2-yl]vinyl}benzoic acid 11.

Proceeding as in the Example above but substituting methyl iodide with ethyl iodide gave 4-{(E)-2-[3-(3-ethoxypropyl)-5,8,8-tetramethyl-5,6,7,8-tetrahydro-naphthalen-2-yl]vinyl}benzoic acid 10.

Example 19

Preparation of 4-{(E)-2-[5,5,8,8-tetramethyl-3-(pyrimidin-2-ylthiopropyl)-5,6,7,8-tetrahydro-naphthalen-2-yl]vinyl}benzoic acid

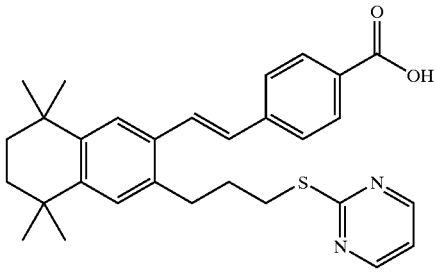

A mixture of 250 mg (0.62 mmol) of methyl-4-{(E)-2-[3-(3-hydroxypropyl)-5,5,8.8-tetramethyl-5,6,7,8-tetrahydro-naphthalen-2-yl]vinyl}benzoate, 1 mL (4.9 mmol) of diisopropyl azodicarboxylate, 1.3 g (4.9 mmol) of triphenylphosphine and 550 mg (4.9 mmol) of 2-mercaptopyrimidine in 10 mL tetrahydrofuran was stirred at room temperature. After 48 hours, the reaction mixture was poured into brine and extracted with ethyl acetate, the organic extracts were washed with brine, dried over sodium sulfate and concentrated under reduced pressure. The residue was purified by flash chromatography on silica gel (10% ethyl acetate/hexane).

The purified material was taken up in 20 mL of methyl alcohol and 10 ML of 1 N LiOH and heated to reflux. After 1 hour the reaction mixture was cooled and methanol was removed under reduced pressure. The solution was acidified with acetic acid, extracted with ethyl acetate, washed with brine, dried over sodium sulfate and concentrated under reduced pressure. The residue was purified by flash chromatography on silica gel (gradient elution: 10–20% ethyl acetate/hexane) and the product was recrystallized (ethyl acetate/hexane) to give 160 mg (55%) of 4-{(E)-2-[5,5,8,8-tetramethyl-3-(pyrimidin-1-ylthiopropyl)-5,6,7,8-tetrahydro-naphthalen-2-yl]vinyl}benzoic acid 24 (m.p.= 177–177.5° C.).

Proceeding as above but substituting 2-mercaptopyrimidine with 5-methyl-1,3,4-thiadiazole2-thiol gave 4-((E)-2-{5,5,8,8-Tetramethyl-3-[3-(5-methyl-[1,3,4]thiadiazol-2-ylsulfanyl)-propyl]-5,6,7,8-tetrahydro-naphthalen-2-yl}vinyl)benzoic acid 28.

Proceeding as above but substituting (E)-methyl-4-[2-(3-{3-hydroxypropyl}-5,5,8,8-tetramethyl-5,6,7,8-tetrahydro-naphthalen-2-yl)vinyl]benzoate with (E)-methyl-4-[2-(3-{2-hydroxyethyl}-5,5,8,8-tetramethyl-5,6,7,8-tetrahydro-naphthalen-2-yl)vinyl]benzoate gave 4-{(E)-2-[5,5,8,8-tetramethyl-3-(pyrimidin-2-ylthiomethyl)-5,6,7,8-tetrahydro-naphthalen-2-yl]vinyl}benzoic acid 26 and 4-((E)-2-{5,5,8,8-tetramethyl-3-[3-(5-methyl-[1,3,4]thiadizol-2ylsulfanyl)-ethyl]-5,6,7,8-tetrahydro-naphthalen-2-yl}vinyl)benzoic acid 27.

Example 20

Preparation of 4-{(E)-2-[5,5,8,8-tetramethyl-3-(3-pyrazol-1-ylpropyl)-5,6,7,8-tetrahydro-naphthalen-2-yl]vinyl}benzoic acid

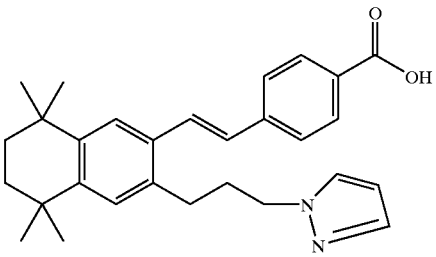

To a solution of 210 mg (0.54 mmol) of methyl-4-{(E)-2-[3-(3-hydroxypropyl)-5,5,8,8-tetramethyl-5,6,7,8-tetrahydro-naphthalen-2-yl]vinyl}benzoate in 20 mL of dichloromethane at 0° C. was added 0.22 mL (1.62 mmol) of triethylamine and 0.083 mL (1.1 mmol) of methanesulfonyl chloride. After 3 hours at 0° C. the reaction mixture was diluted with water and extracted with dichloromethane. The organic fraction was separated, washed with brine, dried over sodium sulfate and concentrated under reduced pressure. The residue was purified by chromatography through a short plug of silica gel. To a mixture of the product in 5 mL of tetrahydrofuran was added a mixture of 65 mg (0.25 mmol) of 18-crown-6 and 28 mg (0.27 mmol) of potassium-tert-butoxide in 5 mL of tetrahydrofuran at 0° C. The reaction mixture was stirred and allowed to warm to room temperature overnight. After 16 hours the reaction mixture was diluted with water and extracted with ethyl acetate. The organic fraction was separated, washed with brine and concentrated under reduced pressure. The residue was purified by flash chromatography on silica gel (25% ethyl acetate/hexane). The purified product was dissolved in 10 mL of methyl alcohol and 5 mL of 1 N LiOH. The reaction mixture was heated at reflux. After 1.5 hours, the reaction was cooled to room temperature, diluted with water and acidified with 1 N HCl. The reaction mixture was extracted with ethyl acetate, washed with brine, dried over sodium sulfate and concentrated under reduced pressure. The residue was purified by flash chromatography on silica gel (10% methyl alcohol/dichloromethane) to give 84 mg (24%) of 4-{(E)-2-[5,5,8,8-tetramethyl-3-(3-pyrazol-1-ylpropyl)-5,6,7,8-tetrahydro-naphthalen-2-yl]vinyl}benzoic acid 30 (m.p.=181.5–182.5° C.).

Proceeding as in the above example but substituting pyrazole with pyrrole, 3-aminopropane, 4-bromopyrazole, 3-methylpyrazole, 4-methylpyrazole and tetrazole gave 4-{(E)-2-[5,5,8,8-tetramethyl-3-(3-pyrrol-1-ylpropyl)-5,6,7,8-tetrahydro-naphthalen-2-yl]vinyl}benzoic acid 36, 4-{(E)-2-[5,5,8,8-tetramethyl-3-(3-propylaminopropyl)-5,6,7,8-tetrahydro-naphthalen-2-yl)vinyl]benzoic acid 33, 4-{(E)-2-[5,5,8,8-tetramethyl-3-[3-(4-bromopyrazol-1-yl)-propyl]-5,6,7,8-tetrahydro-naphthalen-2-yl]vinyl}benzoic acid 130, 4-{(E)-2-[5,5,8,8-tetramethyl-3-[3-(3-methylpyrazol-1-yl)-propyl]-5,6,7,8-tetrahydro-naphthalen-2-yl]vinyl}benzoic acid 131, 4-{(E)-2-[5,5,8,8-tetramethyl-3-[3-(4-methylpyrazol-1yl)-propyl]-5,6,7,8-tetrahydro-naphthalen-2-yl]vinyl}benzoic acid 135, 4-{(E)-2-[5,5,8,8-tetramethyl-3-(3-tetrazol-3-yl)-propyl)-5,6,7,8-tetrahydro-naphthalen-2-yl]vinyl}benzoic acid 141, and 4-{(E)-2-[5,5,8,8-tetramethyl-3-(3-tetrazol-1-yl)-propyl)-5,6,7,8-tetrahydro-naphthalen-2-yl]vinyl}benzoic acid 142 respectively.

Proceeding as in the above example but substituting Methyl-4-{(E)-2-[3-(3-hydroxypropyl)-5,5,8,8-tetramethyl-5,6,7,8-tetrahydro-naphthalen-2-yl]vinyl}benzoate with (Methyl-4-{(E)-2-[3-(2-hydroxyethyl)-5,5,8,8-tetramethyl-5,6,7,8-tetrahydro-naphthalen-2-yl]vinyl}benzoate utilizing pyrazole, 4-methylpyrazole, 4-bromopyrazole, imidazole, triazole, 3-methylpyrazole and 3,5-dimethylpyrzole gave 4-{(E)-2-[5,5,8,8-tetramethyl-3-(2-pyrazol-1-ylethyl)-5,6,7,8-tetrahydro-naphthalen-2-yl]vinyl}benzoic acid 29, 4-{(E)-2-[5,5,8,8-tetramethyl-3-[2-(4-methyl-pyrazol-1-yl)ethyl]-5,6,7,8-tetrahydro-naphthalen-2-yl]vinyl}benzoic acid 38, 4-{(E)-2-[5,5,8,8-tetramethyl-3-[2-(4-bromopyrazol-1-yl)ethyl]-5,6,7,8-tetrahydro-naphthalen-2-yl]vinyl}benzoic acid 134, 4-{(E)-2-[5,5,8,8-tetramethyl-3-[2-(imdazol-1-yl)ethyl]-5,6,7,8-tetrahydro-naphthalen-2-yl]vinyl}benzoic acid 132, 4-{(E)-2-[5,5,8,8-tetramethyl-3-(2-[1,2,4]triazol-1-ylethyl)-5,6,7,8-tetrahydro-naphthalen-2-yl]vinyl}benzoic acid 136, 4-{(E)-2-[5,5,8,8-tetramethyl-3-[2-(3-methyl-pyrazol-1yl)ethyl]-5,6,7,8-tetrahydro-naphthalen-2-yl]vinyl}benzoic acid 140 and -4-{(E)-2-[5,5,8,8-tetramethyl-3-[2-(3,5-dimethyl-pyrazol-1-yl)ethyl]-5,6,7,8-tetrahydro-naphthalen-2-yl]vinyl}benzoic acid 147 respectively.

Example 21

Preparation of 3-bromo-5,5,8,8-tetramethyl-5,6,7,8-tetrahydro-2-naphthaldehyde

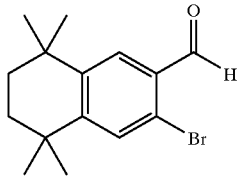

Step A

To a solution of 12.0 g (281 mmol) of 2-bromo-3-methyl-5,5,8,8-tetramethyl-5,6,7,8-tetrahydronaphthalene in 84 mL carbon tetrachloride was added 7.59 g (42.7 mmol) of N-bromosuccinimide and 0.310 g (1.28 mmol) of benzoyl peroxide. This was heated to reflux for 40 minutes and then cooled to room temperature. To the cooled solution was added 170 mL petroleum ether and the solution was filtered and concentrated in vacuo to give 17.3 g of 2-bromo-3-bromomethyl-5,5,8,8-tetramethyl-5,6,7,8-tetrahydronaphthalene which was used without further purification.

Step B 0.981 g (42.7 mmol) of sodium was dissolved in 50 mL of ethanol. To this solution was added 4.94 g (55.5 mmol) of 2-nitropropane followed by 17.3 g (42.7 mmol) of crude 2-bromo-3-bromomethyl-5,5,8,8-tetramethyl-5,6,7,8-tetrahydronaphthalene in 75 mL ethanol. After 8 hours, this mixture was concentrated in vacuo and then partitioned between ethyl acetate and water. The organic layer was sequentially washed with 1M aqueous sodium hydroxide, water, brine, dried over anhydrous sodium sulfate and concentrated in vacuo. The product was purified by flash chromatography on silica gel with gradient elution (1–2% ethyl acetate/hexane) to afford 7.63 g (61%) of 3-bromo-5,5,8,8-tetramethyl-5,6,7,8-tetrahydro-2-naphthaldehyde (m.p.=113.9–114.3° C.).

Example 22

Preparation of 3-(2-trimethylsilyethynyl)-5,5,8,8-tetramethyl-5,6,7,8-tetrahydro-2-naphthaldehyde

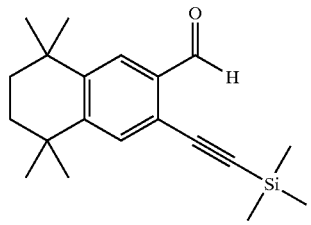

A solution of 6.97 g (23.6 mmol) of 3-bromo-5,5,8,8-tetramethyl-5,6,7,8-tetrahydro-2-naphthaldehyde, 4.66 g (47.4 mmol) of trimethylsilyacetylene, 700 mg (0.997 mmol) of dichlorobis(triphenylphosphine) palladium(II), 350 mg (1.84 mmol) of cuprous iodide, and 3.60 g (35.5 mmol) of triethylamine in 95 mL dimethylformamide was heated to 45□ C. for 2.5 hours, cooled and partitioned between ethyl acetate and water. The organic phase was washed with brine, dried over anhydrous sodium sulfate and concentrated in vacuo. The product was purified by filtration through a pad of silica gel with elution with 10% ethyl acetate/hexane and afforded 7.23 g (98%) of 3-(2-trimethylsilyl-ethynyl)-5,5,8,8-tetramethyl-5,6,7,8-tetrahydro-2-naphthaldehyde (m.p.=78.4–82.0° C.).

Example 23

Preparation of 3-ethynyl-5,5,8,8-tetramethyl-5.6,7,8-tetrahydro-2-naphthaldehyde

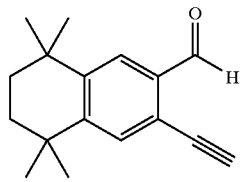

To a solution of 7.21 g (23.1 mmol) of 3-(2-trimethylsilyl-ethynyl)-5,5,8,8-tetramethyl-5,6,7,8-tetrahydro-2-naphthaldehyde in 150 mL of methanol was added 6.38 g (46.2 mmol) of potassium carbonate. After 1 hour, the reaction mixture was poured into water and extracted with ethyl acetate. The organic phase was washed with brine, dried over anhydrous sodium sulfate, and concentrated in vacuo. The product was purified by flash chromatography on silica gel (3% ethyl acetate/hexane) to afford 4.04 g (73%) of 3-ethynyl-5,5,8,8-tetramethyl-5,6,7,8-tetrahydro-2-naphthaldehyde (m.p.=94.0–94.6° C.).

Example 24

4-[(E)-2-(5,5,8,8-tetramethyl-3-((pyrimidin-2-yl)ethynyl)-5,6,7,8-tetrahydro-2-naphthalen-2-yl)vinyl]benzoic acid

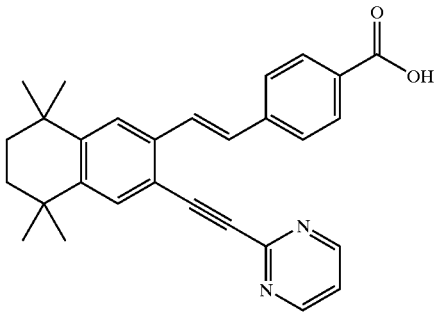

Step A

Preparation of 5,5,8,8-tetramethyl-3-pyrimindin-2-ylethynyl-5,6,7,8-tetrahydro-2naphthaldehyde

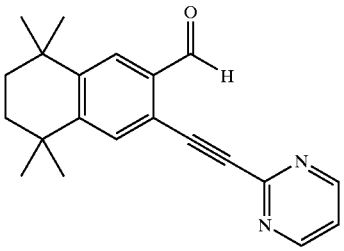

A solution of 0.400 g (1.66 mmol) of 3-ethynyl-5,5,8,8-tetramethyl-5,6,7,8-tetrahydro-2-naphthaldehyde, 0.278 g (1.75 mmol) of 2-bromopyrimidine, 0.053 g (0.075 mmol) of dichlorobis(triphenylphosphine)palladium(II), 0.026 g (0.14 mmol) of cuprous iodide, and 0.253 g (2.50 mmol) of triethylamine in 12 mL of dimethylformamide was heated to 45° C. for 3 hours, cooled to room temperature and partitioned between ethyl acetate and water. The organic layer was washed with brine, dried over anhydrous sodium sulfate, and concentrated in vacuo. The product was purified by flash chromatography on silica gel (25% ethyl acetate/hexane) to afford 0.372 g (70%) of 5,5,8,8-tetramethyl-3-pyrimidin-2-ylethynyl-5,6,7,8-tetrahydro-2-naphthaldehyde.(M+=318).

Step B

Preparation of Methyl 4-[(E)-2-(5,5,8,8-tetramethyl-3-((pyramidin-2-yl)ethynyl)-5,6,7,8-tetrahydro-2-naphthalen-2-yl)vinyl]benzoate

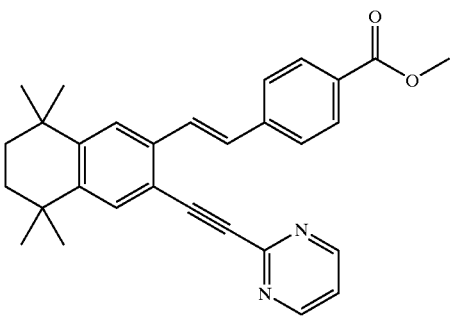

To a suspension of 0.057 g (1.43 mmol) of 60% NaH in 1.5 ml tetrahydrofuran was added 0.180 g (0.70 mmol) of 4-(dimethoxyphosphorylmethyl)-benzoic acid methyl ester in 2.5 ml THF and the reaction was stirred at room temperature. After 20 minutes 0.182 g (0.57 mmol) of 3-((pyrimidin-2-yl)ethynyl)-5,5,8,8,-tetramethyl-5,6,7,8-tetrahydro-2-naphthaldehyde in 3 ml THF was added slowly and the reaction was stirred at room temperature. After 1 hour 20 minutes the reaction was quenched with 6 ml 1M hydrochloric acid and extracted with ethyl ether. The organic layer was washed with water, brine, dried over anhydrous sodium sulfate, and concentrated in vacuo. The crude material was purified by flash chromatography (elution with 40% ethyl acetate/hexane) to afford 0.055 g (21%) of Methyl-4-[(E)-2-(5,5,8,8-tetramethyl-3-((pyrimidin-2yl)ethynyl)-5,6,7,8-tetrahydro-2naphthalen-2-yl)vinyl]benzoate (M+1=451).

Step C

Preparation of 4-[(E)-2-(5,5,8,8-tetramethyl-3-((pyramidin-2-yl)ethynyl)-5,6,7,8-tetrahydro-2-naphthalen-2-yl)vinyl]benzoic acid

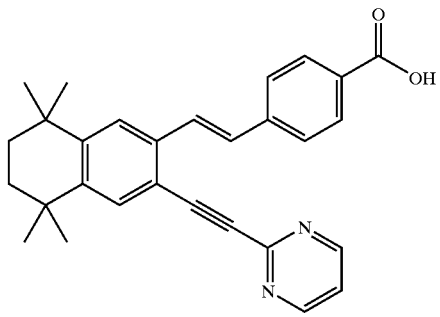

A solution of 0.055 g (0.123 mmol) of Methyl-4-[(E)-2-(5,5,8,8-tetramethyl-3-((pyrimidin-2-yl)ethynyl)-5,6,7,8-tetrahydro-2-naphthalen-2-yl)vinyl]benzoate in 2.5 ml 1M LiOH and 5 ml ethyl alcohol was heated to reflux. After 55 minutes the reaction was cooled to room temperature and acidified with 4 ml 1M hydrochloric acid. The aqueous was extracted with ethyl ether, washed with water, brine, dried over anhydrous magnesium sulfate and stripped in vacuo to afford 0.054 g (99%) of 4-[(E)-2-(5,5,8,8-tetramethyl-3-((pyrimidin-2-yl)ethynyl)-5,6,7,8-tetrahydro-2-naphthalen-2-yl)vinyl]benzoic acid 159 (M+=436).

Example 25

Preparation of 5,5,8,8-tetramethyl-3-(2-pyrimidin-2-ylethyl)-5,6,7,8-tetrahydro-2-naphthaldehyde

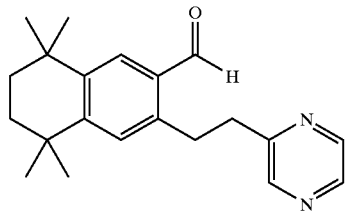

To a solution of 0.362 g (1.14 mmol) of 3-(2-(2-pyrimidyl)ethynyl)-5,5,8,8-tetramethyl-5,6,7,8-tetrahydro-2-naphthaldehyde in 20 mL of ethanol was added 0.060 g of 10% palladium on carbon and the suspension was shaken under 40 psi hydrogen gas for 3 hours. The resulting solution was filtered and concentrated in vacuo. The product was purified by flash chromatography on silica gel (30% ethyl acetate/hexane) to afford 0.251 g (68%) of 3-(2-(2-pyrimidyl)ethyl)-5,5,8,8-tetramethyl-5,6,7,8-tetrahydro-2-naphthaldehyde (m.p.=78.0–84.5° C.).

Replacement of 2-bromo-pyridine with 2-bromo-thiazole gave 2-formyl-3-[2-(thiazol-2-yl)ethyl]-5,5,8,8-tetramethyl-5,6,7,8-tetrahydro-naphthalene.

Example 26

Preparation of 4-{(E)-2-[5,5,8,8-tetramethyl-3-(2-thiazol-2-yl-ethyl)-5,6,7,8-tetrahydro-naphthalen-2-yl]vinyl}benzoic acid

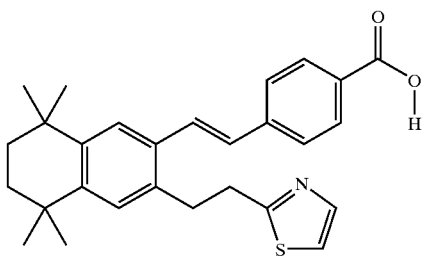

Step A

Preparation of Ethyl-4-{(E)-2-[5,5,8,8-tetramethyl-3-(2-thiazol-2-yl-ethyl)-5,6,7,8-tetrahydro-naphthalen-2-yl]vinyl}benzyl ester A 0° C., 0.3 M tetrahydrofuran solution of 229 mg (0.699 mmol) of 2-formyl-3-[2-(thiazol-2-yl)ethyl]-5,5,8,8-tetramethyl-5,6,7,8-tetrahydro-naphthalene and 202 mg (0.706 mmol) of diethyl 4-carboethoxybenzyl phosphonate was treated with 30 mg (0.768 mmol, 60% wt. in mineral oil) NaH in 5 mg portions over ten minutes. The solution was allowed to warm to room temperature and stirred for 2 hours. The reaction mixture was diluted with ethyl acetate and washed with water and brine. The organic layer was then dried over magnesium sulfate, concentrated under reduced pressure and the resulting residue triturated with methanol to provide 278 mg (86%) of Ethyl-4-{(E)-2-[5,5,8,8-tetramethyl-3-(2-thiazol-2-yl-ethyl)-5,6,7,8-tetrahydro-naphthalen-2-yl]vinyl}benzoate.

Step B

Preparation of 4-{(E)-2-[5,5,8,8-tetramethyl-3-(2-thiazol-2-yl-ethyl)-5,6,7,8-tetrahydro-naphthalen-2-yl]vinyl}benzyl acid A slurry containing 278 mg (0.604 mmol) of ethyl-4-{(E)-2-[5,5,8,8-tetramethyl-3-(2-thiazol-2-yl-ethyl)-5,6,7,8-tetrahydro-naphthalen-2-yl]vinyl}benzoate in 2.3 mL of ethanol and 1.7 mL of 2M aqueous sodium hydroxide was stirred for 7 hours. The reaction mixture was neutralized and washed with a saturated solution of aqueous ammonium chloride. The resulting precipitate was extracted several times with ethyl acetate. The organic layers were combined, washed with brine and dried over magnesium sulfate before being concentrated in vacuo. The residue (95 mg) obtained was then dissolved in dichloromethane and precipitated out by adding excess hexane resulting in 25 mg (10%) of 4-{(E)-2-[5,5,8,8-tetramethyl-3-(2-thiazol-2-yl-ethyl)-5,6,7,8-tetrahydro-naphthalen-2-yl)vinyl]benzoic acid 40 (m.p.= 215.8–217.5° C., M$^+$=446).

Example 27

Preparation of 2-fluoro-3-methyl-5,5,8,8-tetramethyl-5,6,7,8-tetrahydronaphthalene

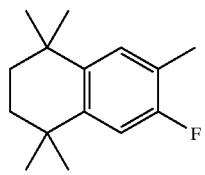

To a solution of 15 g (136 mmol) of 2-fluorotoluene and 24.9 g (136 mmol) of 2,5-dichloro-2,5-dimethylhexane in 120 mL dichloromethane was added 1.82 g (13.6 mmol) of aluminum chloride and the solution heated at reflux. After 18 hours the reaction mixture was cooled to room temperature and 5% aqueous HCl was added. This was partitioned between hexane and water. The aqueous phase was washed once with hexane. The combined organic layers were washed with brine, dried over anhydrous sodium sulfate, and concentrated in vacuo to afford 25.8 g (86%) of 2-fluoro-3-methyl-5,5,8,8-tetramethyl-5,6,7,8-tetrahydronaphthalene (m.p.=90.0–91.8° C.).

Example 28

Preparation of 3-fluoro-5,5,8,8-tetramethyl-5,6,7,8-tetrahydro-2-naphthaldehyde

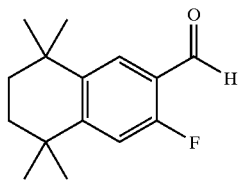

Step A

To a solution of 10.0 g (45.4 mmol) of 2-fluoro-3-methyl-5,5,8,8-tetramethyl-5,6,7,8-tetrahydronaphthalene in 91 mL of carbon tetrachloride was added 8.48 g (47.7 mmol) of N-bromosuccinimide and 0.330 g (1.36 mmol) of benzoyl peroxide. The solution was heated at reflux for 35 minutes and then cooled to room temperature. 200 mL petroleum ether was added and the solution filtered and concentrated in vacuo to afford 16.9 g of 2-fluoro-3-bromomethyl-5,5,8,8-tetramethyl-5,6,7,8-tetrahydronaphthalene which was used without further purification.

Step B 5.26 g (59.0 mmol) of 2-nitropropane was added to a solution prepared by dissolving 1.04 g (45.4 mmol) of sodium in 60 mL of ethanol. The resulting solution was added to a solution of 16.9 g (45.4 mmol) of crude 2-fluoro-3-bromomethyl-5,5,8,8-tetramethyl-5,6,7,8-tetrahydronaphthalene in 60 mL of ethanol. After 5 hours the reaction mixture was partitioned between ethyl acetate and water. The organic layer was washed with 1M aqueous sodium hydroxide, water, brine, dried over anhydrous sodium sulfate and concentrated in vacuo. The product was purified by flash chromatography on silica gel (1% ethyl acetate/hexane) to afford 6.17 g (58%) of 3-fluoro-5,5,8,8-tetramethyl-5,6,7,8-tetrahydro-2-naphthaldehyde (m.p.= 119.4–120.0° C.).

Example 29

Preparation of 5,5,8,8-tetramethyl-3-pyrazol-1-yl-5,6,7,8-tetrahydro-2-naphthaldehyde

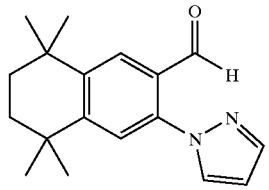

A solution of 0.200 g (0.845 mmol) of 3-fluoro-5,5,8,8-tetramethyl-5,6,7,8-tetrahydro-2-naphthaldehyde, 0.058 g (0.854 mmol) of pyrazole, and 0.130 g (0.939 mmol) of potassium carbonate in 2 mL dimethylsulfoxide was heated to 95° C. for 18 hours. The reaction mixture was cooled to room temperature and partitioned between ethyl acetate and water. The organic layer was washed with brine, dried over anhydrous sodium sulfate, and concentrated in vacuo. The product was purified on flash chromatography on silica gel (5% ethyl acetate/hexane) to afford 0.101 g (42%) of 5,5,8,8-tetramethyl-3-pyrazol-1-yl-5,6,7,8-tetrahydro-2-naphthaldehyde. (mp=95.7–97.6).
Horner-Emmons olefination, followed by ester saponification gave 4-{(E)-2-[5,5,8,8-Tetramethyl-3-(pyrazol-1-yl)-5,6,7,8-tetrahydro-naphthalen-2-yl)vinyl]benzoic acid 156 (MH+=401).
Substitution of pyrazole with 3-methylpyrazole gave 4-{(E)-2-[5,5,8,8-Tetramethyl-3-(3-methylpyrazol-1-yl)-5,6,7,8-tetrahydro-naphthalen-2-yl)vinyl]benzoic acid 157 (MH+=415).

Example 30

Preparation of 5,5,8,8-tetramethyl-3-(pyrimidin-2-yl-thio)-5,6,7,8-tetrahydro-2-naphthaldehyde

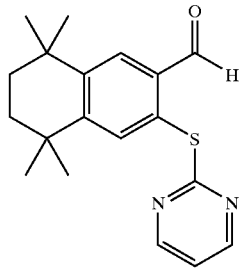

To a solution of 0.479 g (4.27 mmol) of 2-mercaptopyrimidine in 11 mL dimethylformamide was added 0.108 g (4.27 mmol) of 95% sodium hydride. After 20 minutes, 1.00 g (4.27 mmol) of 3-fluoro-5,5,8,8-tetramethyl-5,6,7,8-tetrahydro-2-naphthaldehyde was added and the resulting solution was heated at reflux. After 18 hours, the reaction mixture was cooled to room temperature and partitioned between ethyl acetate and water. The organic phase was washed with water, brine, dried over anhydrous sodium sulfate and concentrated in vacuo. The product was purified by flash chromatography on silica (15% ethyl acetate/hexane) to afford 0.219 g (16%) of 5,5,8,8-tetramethyl-3-(pyrimidin-2-yl-thio)-5,6,7,8-tetrahydro-2-naphthaldehyde (mp=143.2–145.8). Horner-Emmons olefination, followed by ester saponification gave 4-{(E)-2-[5,5,8,8-Tetramethyl-3-(mercaptopyrmidin-2-yl)-5,6,7,8-tetrahydro-naphthalen-2-yl)vinyl]benzoic acid 155 (mp= 283–283.5). Substitution of 2-mercaptopyrimidine with 2-mercaptothiazole gave 4-{(E)-2-[5,5,8,8-Tetramethyl-3-(mercaptothiazol-2-yl)-5,6,7,8-tetrahydro-naphthalen-2-yl) vinyl]benzoic acid 154 (MH+=450).

Example 31

Preparation of 2-(1,3-dioxolan-2-yl)-3-bromo-5,5,8,8-tetramethyl-5,6,7,8-tetrahydronaphthalene

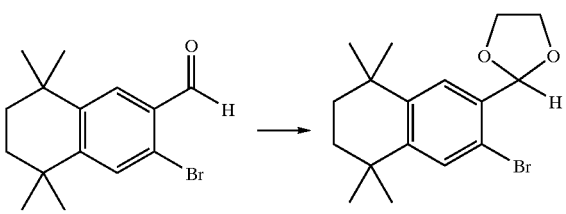

To a solution of 1.8 g (6.3 mmol) of 2-formyl-3-bromo-5,5,8,8-tetramethyl-5,6,7,8-tetrahydronaphthalene in 70 mL of benzene was added 3.5 mL of ethylene glycol (63 mmol) followed by p-toluenesulfonic acid monohydrate (180 mg, 0.9 mmol). The reaction mixture was heated at reflux for about 3 hours and is then concentrated under reduced pressure. The residue was partitioned between ether and saturated sodium bicarbonate solution. The ether layer was washed with brine, dried over MgSO$_4$ and concentrated under reduced pressure. The residue was purified by flash chromatography 1.4% ethyl acetate/) on a Biotage 40M SiO$_2$ cartridge to afford 1.5 g (72%) of 2-(1,3-dioxolan-2-yl)-3-bromo-5,5,8,8-tetramethyl-5,6,7,8-tetrahydronaphthalene as a crystalline solid.

Example 32

Preparation of 2-formyl-3-[(thiophene-2-yl)methyl]-5,5,8,8-tetramethyl-5,6,7,8-tetrahydronaphthalene To a −78° C. tetrahydrofuran (3.0 mL) solution of 2-(1,3-dioxolan-2-yl)-3-bromo-5,5,8,8-tetramethyl-5,6,7,8-tetrahydronaphthalene (253 mg, 0.75 mmol) was added n-BuLi (1.6 M in hexane, 0.49 mL). The reaction mixture gradually thickened over 45 min. A solution of thiophene-2-carboxaldehyde (0.09 mL, 0.94 mmol) in tetrahydrofuran (0.75 mL) was added dropwise to the above slurry. The reaction mixture rapidly became homogeneous and was stirred at −78° C. for 45 minutes. Saturated ammonium chloride and ethyl acetate were added and the layers were separated. The organic layer was washed with brine, dried over magnesium sulfate and concentrated to give a yellow oil which was purified by preparative thin layer chromatography (15% ethyl acetate/hexane) to give 2-(1,3-dioxolan-2-yl)-3-[1-hydroxy-1-(thiophene-2-yl)methyl]-5,5,8,8-tetramethyl-5,6,7,8-tetrahydronaphthalene as a waxy solid (190 mg, 67%).
The alcohol prepared above was dissolved in 7 mL of ethyl acetate and 75 mg of 10% Pd/C was added and the reaction mixture stirred under a hydrogen atmosphere for about 4 hours. The reaction mixture was filtered through Celite and concentrated in vacuo. The resulting residue was purified by preparative thin layer chromatography (10% ethyl acetate/hexane) to give 2-formyl-3-[(thiophene-2-yl) methyl]-5,5,8,8-tetramethyl-5,6,7,8-tetrahydronaphthalene (94 mg, 62%) directly.

Example 33

Preparation of 4-[(E)-2-(5,5,8,8-tetramethyl-3-thiophen-2-ylmethyl-5,6,7,8-tetrahydro-naphthalen-2-yl)vinyl]benzoic acid

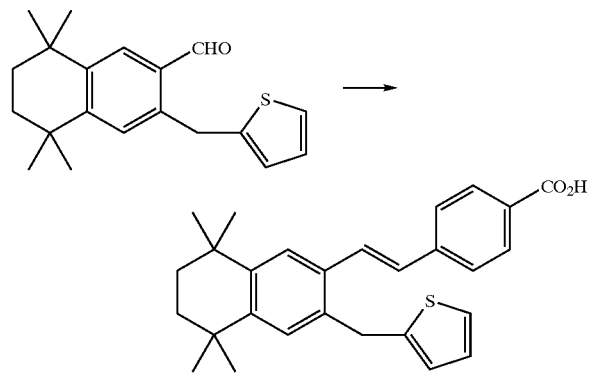

Horner-Emmons olefination (following the procedure of Example) of 2-formyl-3-[(thiophene-2-yl)methyl]-5,5,8,8-tetramethyl-5,6,7,8-tetrahydronaphthalene (94 mg, 0.3 mmol) followed by ester hydrolysis (following the procedure of Example) of ethyl (E)-4-{2-[3-((thiophene-2-yl) methyl)-5,5,8,8-tetramethyl-5,6,7,8-tetrahydro-naphthalen-2-yl]vinyl}benzoate (53 mg, 0.11 mmol) provides 4-[(E)-2-(5,5,8,8-tetramethyl-3-thiophen-2ylmethyl-5,6,7,8-tetrahydro-naphthalen-2-yl)vinyl]benzoic acid (30 mg, 63%) as a white crystalline solid 44 (m.p. 229.1–229.6° C.).

Example 34

Preparation of 4-{(E)-2-[5,5,8,8-tetramethyl-3-(4-methylbenzyl)-5,6,7,8-tetrahydro-naphthalen-2-yl] vinyl}benzoic acid

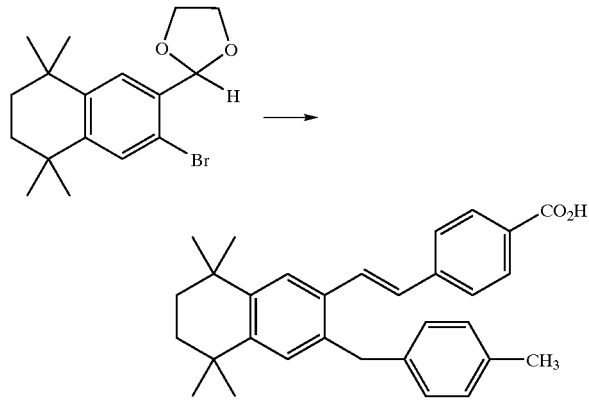

To a mixture of 2-(1,3-dioxolan-2-yl)-3-bromo-5,5,8,8-tetramethyl-5,6,7,8-tetrahydronaphthalene (250 mg, 0.74 mmol) and tetrakis(triphenylphospine)palladium(0) (21 mg, 0.018 mmol) under an argon atmosphere was added a 0.5 M tetrahydrofuran solution of 4-methylbenzylzinc chloride (7.3 mL, 3.68 mmol). The reaction mixture was stirred at reflux overnight and partitioned between saturated ammonium chloride solution and ethyl acetate. The organic layer was washed with brine, dried over $MgSO_4$, and concentrated in vacuo. The residue was purified by preparative thin layer chromatography on silica gel (5% ethyl acetate/hexane) to give 2-(1,3-dioxolan-2-yl)-3-(4-methylbenzyl)-5,5,8,8-tetramethyl-5,6,7,8-tetrahydronaphthalene as a white crystalline solid (240 mg, 89%).

A solution of the acetal prepared above (240 mg, 0.66 mmol) in 3 mL of tetrahydrofuran was treated with 2 mL of 1 M HCl. The reaction was stirred at room temperature for 1.5 hours and then partitioned between saturated ammonium chloride solution and ethyl acetate. The organic layer was washed with brine, dried over $MgSO_4$ and concentrated to give 2-formyl-3-(4-methylbenzyl)-5,5,8,8-tetramethyl-5,6,7,8-tetrahydronaphthalene as a clear oil which slowly crystallized on standing (210 mg, 99%).

Horner-Emmons olefination (following the procedure of Example) of 2-formyl-3-(4-methylbenzyl)-5,5,8,8-tetramethyl-5,6,7,8-tetrahydronaphthalene (210 mg, 0.65 mmol) followed by ester hydrolysis (following the procedure of Example) of ethyl 4-{(E)-2-[5,5,8,8-tetramethyl-3-(4-methylbenzyl)-5,6,7,8-tetrahydro-naphthalen-2-yl] vinyl}benzoate gave 4-{(E)-2-[5,5,8,8-tetramethyl-3-(4-methylbenzyl)-5,6,7,8-tetrahydro-naphthalen-2-yl] vinyl}benzoic acid (185 mg, 64%) as a white crystalline solid (m.p. 216.3–217.3° C. ($CH_2CL_2$/hexane) 42.

Example 35

Preparation of 4-{(E)-2-[5,5,8,8-tetramethyl-3-(2,4-difluorobenzyl)-5,6,7,8-tetrahydro-naphthalen-2-yl] vinyl}benzoic acid

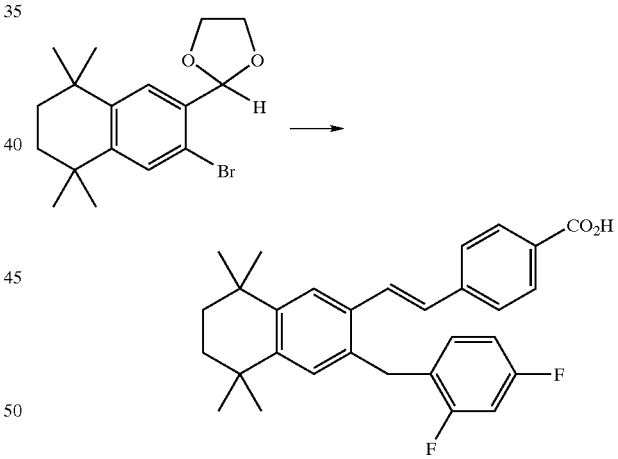

To a mixture of 2-(1,3-dioxolan-2-yl)-3-bromo-5,5,8,8-tetramethyl-5,6,7,8-tetrahydronaphthalene (250 mg, 0.74 mmol) and tetrakis(triphenylphospine)palladium(0) (21 mg, 0.018 mmol) under an argon atmosphere was added a 0.5 M tetrahydrofuran solution of 2,4-difluorobenzylzinc chloride (7.3 mL, 3.68 mmol). The reaction was stirred at reflux overnight and partitioned between saturated ammonium chloride solution and ethyl acetate. The organic layer was washed with brine, dried over $MgSO_4$, and concentrated. The residue was purified by preparative thin layer chromatography on silica gel (5% ethyl acetate/hexane) to give 2-(1,3-dioxolan-2-yl)-3-(2,4-difluorobenzyl)-5,5,8,8-tetramethyl-5,6,7,8-tetrahydronaphthalene as a white crystalline solid (245 mg, 96%).

A solution of the above acetal (245 mg, 0.71 mmol) in 3 mL of tetrahydrofuran was treated with 2 mL of 1 M HCl. The reaction was stirred at room temperature for 1.5 hours and then partitioned between saturated ammonium chloride solution and ethyl acetate. The organic layer was washed with brine, dried over magnesium sulfate and concentrated to give 2-formyl-3-(2,4-difluorobenzyl)-5,5,8,8-tetramethyl-5,6,7,8-tetrahydronaphthalene as a clear oil (239 mg, 97%).

Horner-Emmons olefination (following the procedure of Example) of 2-formyl-3-(4-methylbenzyl)-5,5,8,8-tetramethyl-5,6,7,8-tetrahydronaphthalene (239 mg, 0.69 mmol) followed by ester hydrolysis (following the procedure of Example) of ethyl 4-{(E)-2-[5,5,8,8-tetramethyl-3-(2,4-difluorobenzyl)-5,6,7,8-tetrahydro-naphthalen-2-yl]vinyl}benzoate gave 4-{(E)-2-[5,5,8,8-tetramethyl-3-(2,4-difluorobenzyl)-5,6,7,8-tetrahydro-naphthalen-2-yl]vinyl}benzoic acid (230 mg, 72%) as a white crystalline solid (m.p. 204.3–205.7° C.) recrystallized from (CH$_2$Cl$_2$/hexane) 43.

Example 36

Preparation of 4-{(E)-2-[5,5,8,8-tetramethyl-3-(thiophen-3-yl)-5,6,7,8-tetrahydro-naphthalen-2-yl]vinyl}benzoic acid

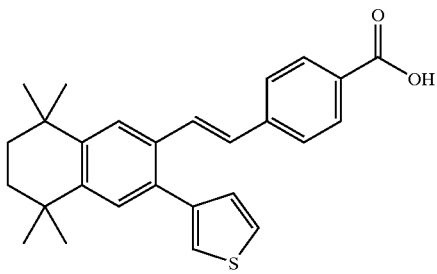

A 0° C., 0.3M tetrahydrofuran solution of 1.832 g (6.21 mmol) of 2-formyl-3-bromo-5,5,8,8-tetramethyl-5,6,7,8-tetrahydro-naphthylene and diethyl 4-carboethoxybenzyl phosphonate was treated with 301 mg (7.51 mmol, 60% wt. in mineral oil) NaH in 30 mg portions over ten minutes. The mixture was then stirred at room temperature for 2 hours before diluting with ethyl acetate and washing with water. The organic layer was washed with brine, dried over magnesium sulfate, and concentrated in vacuo. The resulting residue was triturated with methanol yielding 1.334 g (50%) Ethyl 4-[(E)-2-(3-bromo-5,5,8,8-tetramethyl-5,6,7,8-tetrahydro-naphthylen-2-yl)vinyl]benzoate.

To a solution of 375 mg (0.825 mmol) of Ethyl 4-[(E)-2-(3-bromo-5,5,8,8-tetramethyl-5,6,7,8-tetrahydro-naphthylen-2-yl)vinyl]benzoate and 48 mg (0.0413 mmol) of tetrakis(triphenylphosphine)palladium(0) in 17 mL of toluene were added 158 mg of 3-thiophene boronic acid (Aldrich) in 5 mL of ethanol followed by 8.5 mL of a saturated aqueous sodium bicarbonate. The mixture was refluxed for 16 hours before diluting with ethyl acetate and washing with water. The organic layer was washed with brine, dried over magnesium sulfate and concentrated in vacuo yielding 504 mg of crude residue. The crude mixture was purified by preparatory thin layer chromatography on silica gel (2% ethyl acetate in hexane) yielding 160 mg (44%) of Ethyl 4-{(E)-2-[5,5,8,8-tetramethyl-3-(thiophen-3-yl)-5,6,7,8-tetrahydro-naphthylen-2-yl]vinyl}benzoate.

A slurry of 160 mg (0.359 mmol) of Ethyl 4-{(E)-2-[5,5,8,8-tetramethyl-3-(thiophen-3-yl)-5,6,7,8-tetrahydro-naphthylen-2-yl]vinyl}benzoate, 1.5 mL ethanol, and 1 mL of 2M aqueous NaOH was stirred for 16 hours before neutralizing with ammonium chloride and extracting with ethyl acetate. The organic layer was washed with brine, dried over magnesium sulfate, and concentrated in vacuo yielding 115 mg of crude residue. The residue was purified by preparatory thin layer chromatography on silica gel (10% MeOH-dichloromethane) to provide 42 mg of 4-{(E)-2-[5,5,8,8-tetramethyl-3-(thiophen-3-yl)-5,6,7,8-tetrahydro-naphthalen-2-yl]vinyl}benzoic acid 48.

Example 37

Preparation of 4-[(E)-2-(5,5,8,8-tetramethyl-3-pyrazol-1-ylmethyl-6-hydroxy-5,6,7,8-tetrahydro-naphthalen-2-yl)-vinyl]-benzoic acid

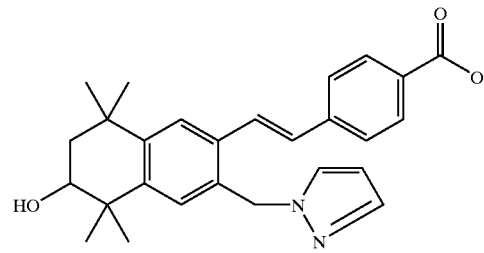

Step A

Preparation of 1,1,4,4,7-pantamenthyl-2-tetralone

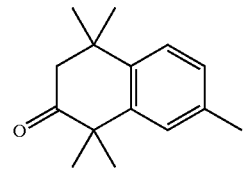

To a solution of 20 g (140.6 mmol) of dihyrdo-2,2,5,5-tetramethyl-3(2H)-furanone in 240 mL of toluene, cooled in a wet ice bath, was added 38.4 g (288 mmol) of aluminum chloride portionwise over 15 minutes. After the addition was complete the reaction mixture was allowed to warm to room temperature. After 16 hours the reaction was carefully poured onto ice and the resulting aqueous solution was extracted with ethyl acetate. The organic fraction was washed with brine, dried over sodium sulfate and concentrated under reduced pressure. The residue was purified by flash chromatography (elution with hexane) to afford 26 g (86%) of 1,1,4,4,7-pentamenthyl-2-tetralone (M$^+$=216).

Step B

Preparation of 3-methyl-6-hydroxy-5,5,8,8-tetramethyl-5,6,7,8-tetrahydronaphthalene

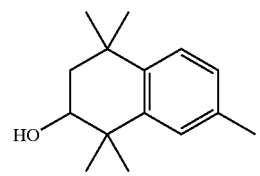

To a solution of 10 g (46.2 mmol) of 1,1,4,4,7-pentamenthyl-2-tetralone in 100 mL of ethyl alcohol was added 7 g (185 mmol) of sodium borohydride portionwise over 15 minutes. After the addition was complete the reaction was stirred at room temperature. After 16 hours the reaction mixture was concentrated under reduced pressure and the residue was partitioned between water and ethyl acetate. The organic extracts were washed with brine, dried over sodium sulfate and concentrated under reduced pressure. The residue was purified by flash chromatography (gradient elution with 5–10% ethyl acetate/hexane), followed by crystallization from hexane to afford 4 g (40%) of 3-methyl-6-hydroxy-5,5,8,8-tetramethyl-5,6,7,8-tetrahydronaphthalene.(M$^+$=218).

Step C

Preparation of 2-bromo-3-methyl-6-acetoxy-5,5,8,8-tetramethyl-5,6,7,8-tetrahydronaphthalene

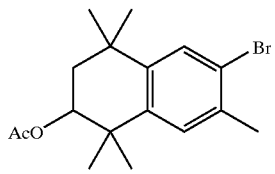

To a solution of 4 g (18.3 mmol) of 3-methyl-6-hydroxy-5,5,8,8-tetramethyl-5,6,7,8-tetrahydronaphthalene in 20 mL of acetic acid was added 3.25 g (20.15 mmol) of bromine dropwise and the reaction was stirred at room temperature. After 16 hours, the reaction mixture was poured into brine and extracted with ethyl acetate. The organic extracts were washed with brine, dried over sodium sulfate and concentrated under reduced pressure. The residue was purified by flash chromatography (gradient elution with hexane-15% ethyl acetate/hexane) to give 6 g (97%) of 2-bromo-3-methyl-6-acetoxy-5,5,8,8-tetramethyl-5,6,7,8-tetrahydronaphthalene.(M$^+$=338).

Step D

Preparation of Ethyl-4-[(E)-2-(5,5,8,8tetramethyl-3-methyl-6-acetoxy-5,6,7,8-tetrahydro-naphthalen-2-yl)vinyl]benzoate

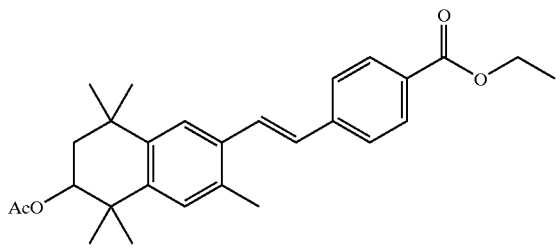

A mixture of 1 g (3 mmol) of 2-bromo-3-methyl-6-acetoxy-5,5,8,8-tetramethyl-5,6,7,8-tetrahydronaphthalene, 0.68 ml (4.42 mmol) of trimethoxyvinyl silane, 0.12 g (0.53 mmol), 0.36 g of Tri-o-tolylphosphine (1.2 mmol) and 0.82 mL of triethylamine (5.9 mmol) in 10 mL of N-methyl pyrollidine was heated at 90° C. After 3 hours, the reaction was cooled to room temperature and 0.57 mL (3.5 mmol) of ethyl4-bromobenzoate, 0.82 mL of triethylamine (5.9 mmol) and 5 mL (5 mmol) of tetrabutylammonium fluoride were added. The reaction mixture was heated to 90° C again. After 2.5 hours, the reaction was cooled to room temperature, poured into brine and extracted with ethyl acetate. The organic extracts were washed with brine, dried over sodium sulfate and concentrated under reduced pressure. The residue was purified by flash chromatography (gradient elution 2–5% ethyl acetate/hexane) to afford 0.2 g (20%) of Ethyl-4-[(E)-2-(5,5,8,8-Tetramethyl-3-methyl-6-acetoxy-5,6,7,8-tetrahydro-naphthalen-2-yl)vinyl]benzoate (M$^+$=434).

Step E

Preparation of Ethyl-4-[(E)-2-(5,5,8,8tetramethyl-3-bromomethyl-6-acetoxy-5,6,7,8-tetrahydro-naphthalen-2-yl)vinyl]benzoate

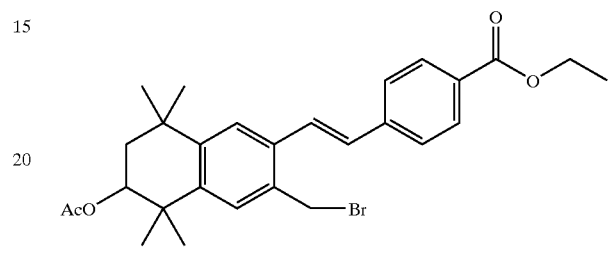

A solution of 0.68 g (1.57 mmol) of Ethyl-4-[(E)-2-(5,5,8,8-Tetramethyl-3-methyl-6-acetoxy-5,6,7,8-tetrahydro-naphthalen-2-yl)vinyl]benzoate, 0.36 g (2.03 mmol) of N-bromosuccinimide and 0.019 g (0.078 mmol) of benzoyl peroxide in 15 mL of carbon tetrachloride was heated at reflux. After 3 hours the reaction was cooled to room temperature, washed with 10% aqueous sodium bisulfite and brine, dried over sodium sulfate and concentrated under reduced pressure. The residue was purified by flash chromatography (gradient elution, hexane-5% ethyl acetate/hexane) to give 0.45 g (56%) of Ethyl-4-[(E)-2-(5,5,8,8-Tetramethyl-3-bromomethyl-6-acetoxy-5,6,7,8-tetrahydro-naphthalen-2-yl)vinyl]benzoate (M$^+$=512).

Step F

Preparation of Ethyl-4-[(E)-2-(5,5,8,8tetramethyl-3pyrazol-1-ylmethyl-6-acetoxy-5,6,7,8-tetrahydro-naphthalen-2-yl)vinyl]benzoate

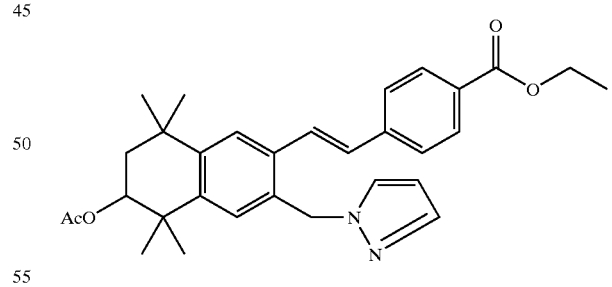

A solution of 0.45 g (0.88 mmol) of ethyl-4-[(E)-2-(5,5,8,8-tetramethyl-3-bromomethyl-6-acetoxy-5,6,7,8-tetrahydro-naphthalen-2-yl)vinyl]benzoate and 0.24 g (3.5 mmol) of pyrazole in 15 mL of N-methyl pyrrolidine was heated to 100° C. After 2 hours the reaction was cooled to room temperature, poured into brine and extracted with ethyl acetate. The organic extracts were washed with brine, dried over sodium sulfate and concentrated under reduced pressure. The residue was purified by flash chromatography (gradient elution, hexane-16% ethyl acetate/hexane) to afford 32 g (73%) of ethyl-4-[(E)-2-(5,5,8,8-tetramethyl- 3pyrazol-1-ylmethyl-6-acetoxy-5,6,7,8-tetrahydro-naphthalen-2-yl)vinyl]benzoate (M+=500).

Step G

Preparation of 4-[(E)-2-(5,5,8,8tetramethyl-3pyrazol-1-ylmethyl-6-hydroxy-5,6,7,8-tetrahydro-naphthalen-2-yl)vinyl]benzoic acid

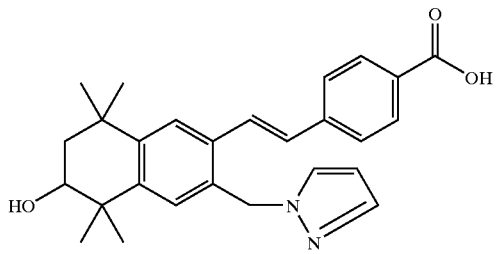

A mixture of 0.32 g (0.64 mmol) of ethyl-4-[(E)-2-(5,5,8,8-tetramethyl-3pyrazol-1-ylmethyl-6-acetoxy-5,6,7,8-tetrahydro-naphthalen-2-yl)vinyl]benzoate in 10 mL of 1 N LiOH solution and 20 mL of ethyl alcohol was heated to reflux. After 1 hour the reaction was cooled to room temperature, concentrated under reduced pressure and acidified with 2 N HCl. The aqueous solution was extracted with ethyl acetate, washed with brine, dried over sodium sulfate and concentrated under reduced pressure. The residue was recrystallized from ethyl acetate/hexane to afford 0.22 g (82%) of 4-[(E)-2-(5,5,8,8-tetramethyl-3pyrazol-1-ylmethyl-6-hydroxy-5,6,7,8-tetrahydro-naphthalen-2-yl)vinyl]benzoic acid 55 (mp=241.6–242.0°).

Example 38

Preparation of 4-[(E)-2-(5,5,8,8-tetramethyl-3pyrazol-1-ylmethyl-7-hydroxy-5,6,7,8-tetrahydro-naphthalen-2-yl)vinyl]benzoic acid

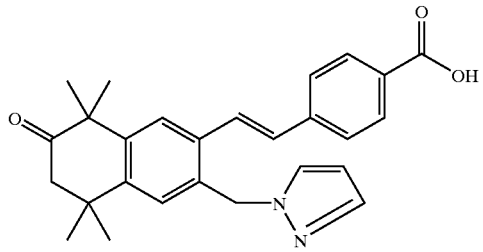

Step A

Preparation of 7-acetoxy-3-bromo-2-bromomethyl-5,5,8,8-tetramethyl-5,6,7,8-tetrahydronaphthalene.

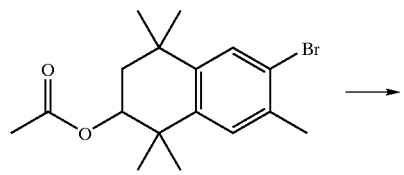

-continued

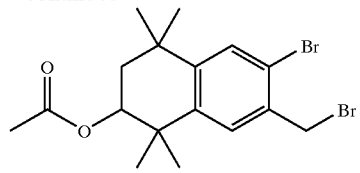

A mixture of 7-acetoxy-3bromo-2,5,5,8,8-pentamethyl-5,6,7,8-tetrahydronaphthalene containing a small amount of the 2-des-bromo derivative (10 g, 29.5 mmol) was dissolved in carbon tetrachloride. N-bromosuccinimide (5.25 g, 29.5 mmol, recrystallized from water) was added and the solution was warmed to 50° C. Benzoyl peroxide (0.36 g, 1.47 mmol) was added and the solution was brought to reflux while being irradiated with a tungsten lamp. The reaction was monitored by TLC ($SiO_2$, 5% ethyl acetate/hexanes) and a total of 0.15 g of additional N-bromosuccinimide was added over 3 hours. The reaction was cooled to room temperature, filtered, and evaporated to give a semi-solid residue. Chromatography ($SiO_2$, 5% ethyl acetate/hexanes) gave an oil (9.85 g) consisting of an inseparable mixture of 7-acetoxy-3-bromo-2-bromomethyl-5,5,8,8-tetramethyl-5,6,7,8-tetrahydronaphthalene and the corresponding 3-des-bromo derivative which was taken directly into the next reaction.

Step B

Preparation of 7-acetoxy-3-bromo-2-formyl-5,5,8,8-tetramethyl-5,6,7,8-tetrahydronaphthalene.

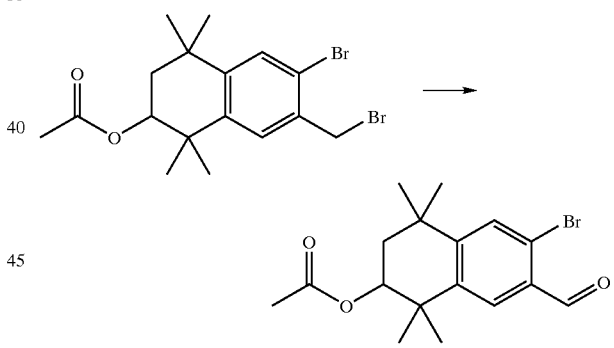

To a solution of sodium methoxide (7 mL, 30.6 mmol, 25 wt % solution in methanol) diluted with 7 mL of additional methanol was added a solution of 2-nitropropane (3.63 mL, 35.33 mmol) in 3 mL of methanol. The reaction was stirred for 10 minutes and a solution of the product mixture (9.85 g) from the preceding reaction in 84 mL of methanol and added slowly with stirring. The reaction was followed by TLC ($SiO_2$, 5% ethyl acetate/hexanes) and was judged to be complete after 5 hours at rt. The reaction mixture was concentrated and partitioned between ethyl acetate and saturated $NaHCO_3$ solution. The organic layer was washed with brine, dried over sodium sulfate, and evaporated to give a thick oil which was purified by chromatography ($SiO_2$, 2–5% ethyl acetate/hexane) to yield 7-acetoxy-3-bromo-2-formyl-5,5,8,8-tetramethyl-5,6,7,8-tetrahydronaphthalene (3 g, 36%) as a clear oil which slowly solidifies on standing.

119

Step C

Preparation of 7-acetoxy-3-bromo-2-(1,3-dioxolane-2-yl)-5,5,8,8-tetramethyl-5,6,7,8-tetrahydronaphthalene.

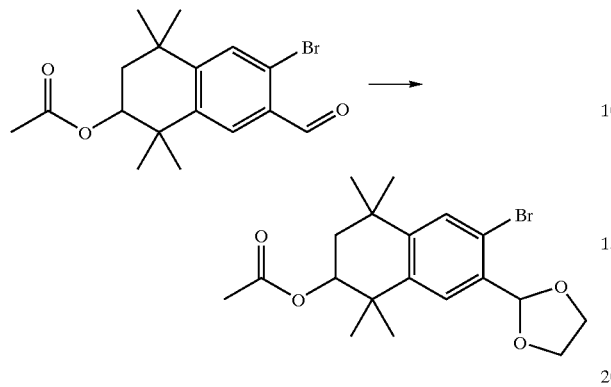

7-Acetoxy-3-bromo-2-formyl-5,5,8,8-tetramethyl-5,6,7,8-tetrahydronaphthalene (0.3 g, 0.849 mmol) from the preceding reaction was dissolved in 2 mL of benzene. Ethylene glycol (0.104 mL, 1.87 mmol) and p-toluenesulfonic acid monohydrate (0.024 g, 0.127 mmol) were added. A Dean-Stark apparatus was attached to the reaction flask and the reaction was brought to reflux for several hours. When the reaction was judged complete by TLC (SiO$_2$, 20% ethyl acetate/hexanes), dichloromethane (25 mL) and sodium bicarbonate solution (50 mL) were added and the layers were separated. The aqueous layer was extracted one more time with dichloromethane. The combined organic layers were washed with brine, dried over sodium sulfate and concentrated to give 7-Acetoxy-3-bromo-2-(1,3-dioxolane-2-yl)-5,5,8,8-tetramethyl-5,6,7,8-tetrahydronaphthalene as an oily residue that was used directly in the next step.

Step D: Preparation of 3-bromo-2-(1,3-dioxolane-2-yl)-7-hydroxy-5,5,8,8-tetramethyl-5,6,7,8-tetrahydronaphthalene.

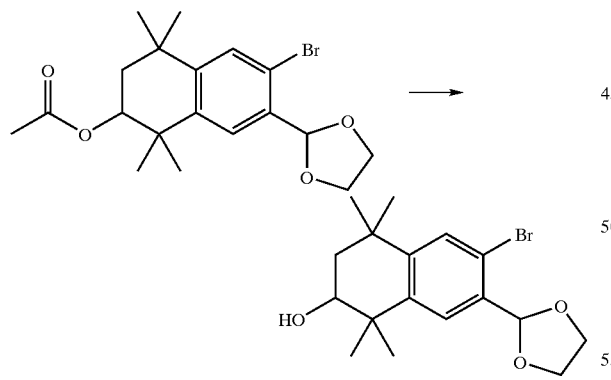

The crude acetal from the proceeding step was dissolved in 8 mL of 1:1 tetrahydrofuran/methanol and a solution of LiOH (0.17 g, 4 mmol) in 2 mL of water was added slowly. The reaction was stirred for 2 hours and then partitioned between ethyl acetate and water. The aqueous phase was adjusted to pH 6 with 1 $\underline{M}$HCl. The organic layer was washed with brine, dried over sodium sulfate, and concentrated to give 3-bromo-2-(1,3-dioxolane-2-yl)-7-hydroxy-5,5,8,8-tetramethyl-5,6,7,8-tetrahydronaphthalene (0.29 g, 96%) as a foamy residue.

120

Step E

Preparation of 3-bromo-2-(1,3-dioxolane-2-yl)-7-oxo-5,5,8,8-tetramethyl-5,6,7,8-tetrahydronaphthalene.

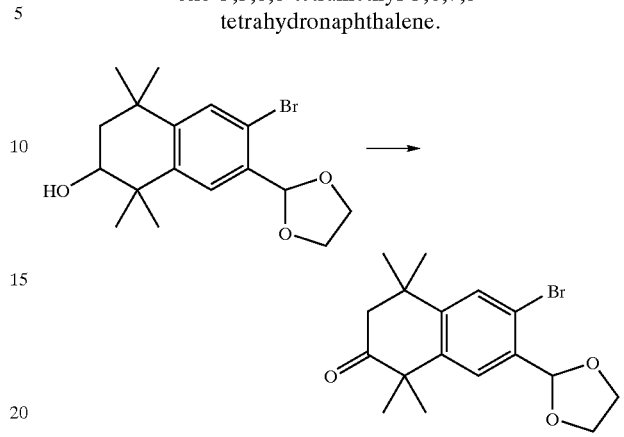

The above alcohol (0.29 g, 0.816 mmol) was dissolved in 16 mL dichloromethane. Dess-Martin periodinane (0.38 g, 0.9 mmol, Lancaster) was added. The reaction was stirred for 1 h and was worked up by pouring into a saturated solution of sodium bicarbonate and 1 $\underline{M}$sodium thiosulfate. This mixture was extracted twice with dichloromethane and the combined organic layers were washed with water, sodium bicarbonate solution, and dried over sodium sulfate. The solvent was evaporated and the residue was chromatographed (SiO$_2$, 20% ethyl acetate/hexanes) to give 3-bromo-2-(1,3-dioxolane-2-yl)-7-oxo-5,5,8,8-tetramethyl-5,6,7,8-tetrahydronaphthalene (200 mg, 69%) as a clear oil.

Step F

Preparation of 3-bromo-2-formyl-7-oxo-5,5,8,8-tetramethyl-5,6,7,8-tetrahydronaphthalene.

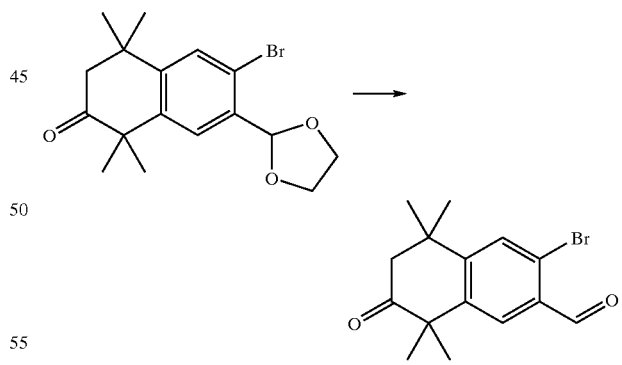

The above ketone was dissolved in approximately 5 mL of tetrahydrofuran and 0.75 mL of 3 M HCl was added. The mixture was stirred for 3 h at room temperature followed by 1 h at 40° C. The reaction was partitioned between ethyl acetate and saturated sodium bicarbonate solution. The organic layer was washed with brine, dried over sodium sulfate, and concentrated to give 3-bromo-2-formyl-7-oxo-5,5,8,8-tetramethyl-5,6,7,8-tetrahydronaphthalene as a solid that was carried directly into the next reaction.

Step G

Preparation of Ethyl (E)-4-[2-(3-bromo-7-oxo-5,5,8,8-tetramethyl-5,6,7,8-tetrahydronaphthalene-2-yl)vinyl]benzoate.

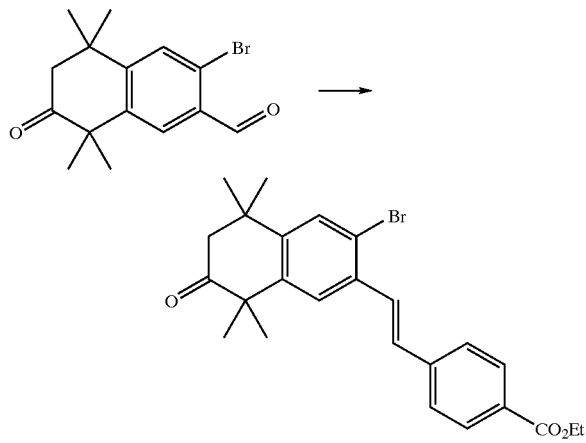

To the above aldehyde (0.19 g, 0.612 mmol) in 3 mL tetrahydrofuran was added ethyl 4-(diethoxyphosphorylmethyl)benzoate (0.275 g, 0.919 mmol). The resulting solution was cooled in ice/water and NaH (0.029 g, 0.73 mmol, 60% disp. in oil) was added. The reaction was stirred while allowing to warm to rt over 2.5 h. The reaction was judged complete by TLC (SiO$_2$, 20% ethyl acetate/hexanes) and partitioned between 1M HCl and ethyl acetate. The organic layer was dried over sodium sulfate, evaporated to a foam and purified by silica gel chomatography (20% ethyl acetate/hexanes) to give ethyl (E)-4-[2-(3-bromo-7-oxo-5,5,8,8-tetramethyl-5,6,7,8-tetrahydronaphthalene-2-yl)vinyl]benzoate (230 mg, 82%).

Step H

Preparation of Ethyl (E)-4-[2-(3-hydroxymethyl-7-oxo-5,5,8,8-tetramethyl-5,6,7,8-tetrahydronaphthalene-2-yl)vinyl]benzoate.

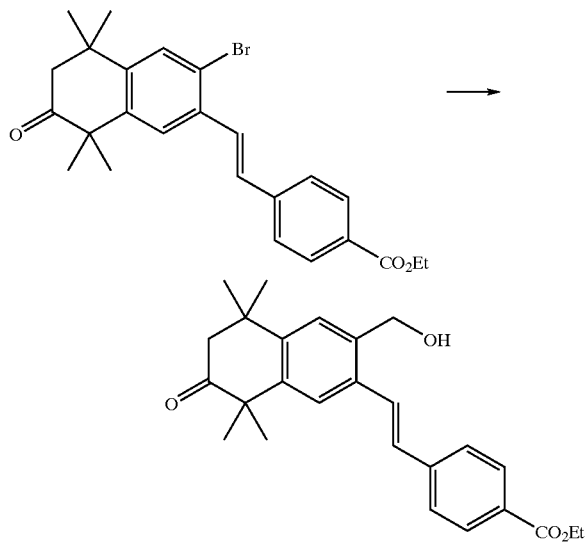

The above bromo-ester (0.23 g, 0.5 mmol) was dissolved in 2 mL of anhydrous 1,4-dioxane and hydroxymethyltributyltin (241 mg, 0.75 mmol, ref.: Seitz, D. E. et. al., *Synth. Comm.* 1983, 13(2), 129; Kosugi, M. et. al., *Chem. Lett.* 1985, 997) was added while the reaction solution was degassed with argon. Tetrakis(triphenylphosphine)palladium(0) (0.043 g, 0.038 mmol) was added and the reaction was stirred at reflux overnight. The reaction was cooled to room temperature and partitioned between ethyl acetate and saturated sodium bicarbonate. The layers were separated and the aqueous layer was extracted one time more with ethyl acetate. The combined organic layers were washed with brine, dried over sodium sulfate, and concentrated. The residue was purified by silica gel chromatography (25% ethyl acetate/hexane) to give ethyl (E)-4-[2-(3-hydroxymethyl-7-oxo-5,5,8,8-tetramethyl-5,6,7,8-tetrahydronaphthalene-2-yl)vinyl]benzoate (150 mg, 73%).

Step I

Preparation of Ethyl 4-[2-(3-bromomethyl-7-oxo-5,5,8,8-tetramethyl-5,6,7,8-tetrahydronaphthalene-2-yl)vinyl]benzoate.

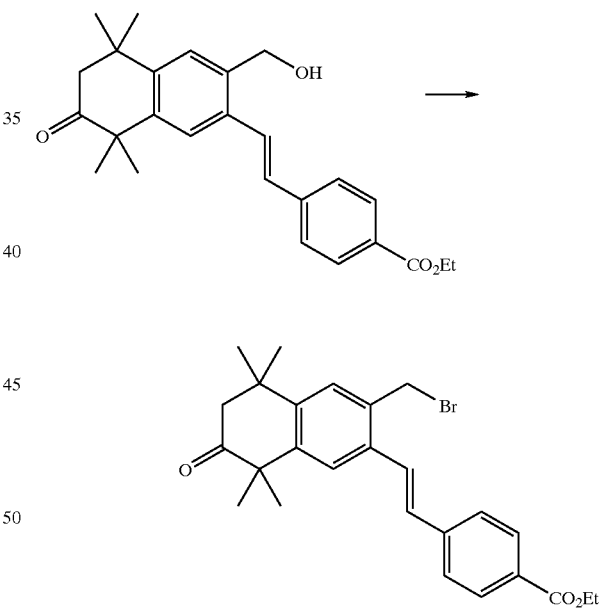

The above hydroxymethyl material (0.15 g, 0.368 mmol) was dissolved in 4 mL of dichloromethane and treated with triphenylphosphine (0.11 g, 0.42 mmol) and N-bromosuccinimide (0.076 g, 0.42 mmol). The reaction was stirred at rt for 30 min and then concentrated to give a foamy residue which was chromatographed (SiO$_2$, 25% ethyl acetate/hexanes) to give ethyl 4-[2-(3-bromomethyl-7-oxo-5,5,8,8-tetramethyl-5,6,7,8-tetrahydronaphthalene-2-yl)vinyl]benzoate (130 mg, 75%) as an oil.

Step J

Preparation of Ethyl (E)-4-[2-(3-(pyrazole-1-ylmethyl)-7-oxo-5,5,8,8-tetramethyl-5,6,7,8-tetrahydronaphthalene-2-yl)vinyl]benzoate.

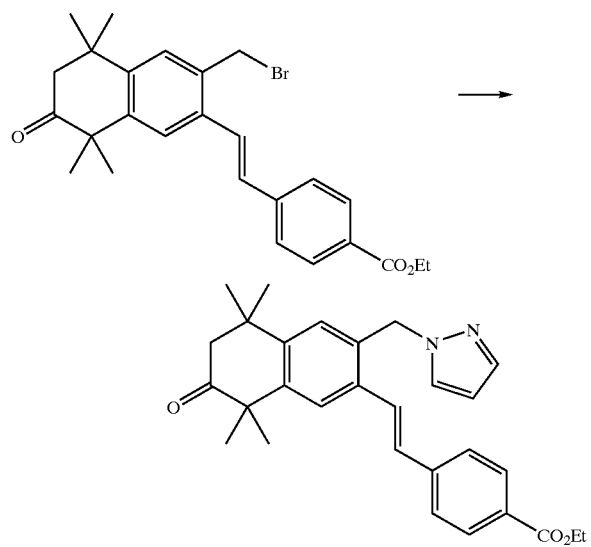

To a solution of 18-crown-6 (0.092 g, 0.35 mmol) and potassium tert-butoxide (0.04 g, 0.36 mmol) in 2 mL of tetrahydrofuran was added Pyrazole (0.024 g, 0.346 mmol). The reaction mixture stirred for 10 minutes and a solution of the above bromomethyl material (0.13 g, 0.277 mmol) in 1 mL of tetrahydrofuran was added dropwise over 5 minutes. The reaction was stirred for 45 minutes at rt and then partitioned between ethyl acetate and ammonium chloride solution. The ethyl acetate layer was dried over sodium sulfate, concentrated, and the residue chromatographed (SiO$_2$, 30% ethyl acetate/hexanes) to give ethyl (E)-4-[2-(3-(pyrazole-1-ylmethyl)-7-oxo-5,5,8,8-tetramethyl-5,6,7,8-tetrahydronaphthalene-2-yl)vinyl]benzoate (120 mg, 94%).

Step K

Preparation of Ethyl (E)-4-[2-(3-(pyrazole-1-ylmethyl)-7-oxo-5,5,8,8-tetramethyl-5,6,7,8-tetrahydronaphthalene-2-yl)vinyl]benzoic acid.

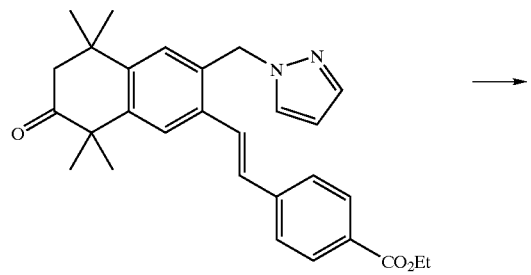

-continued

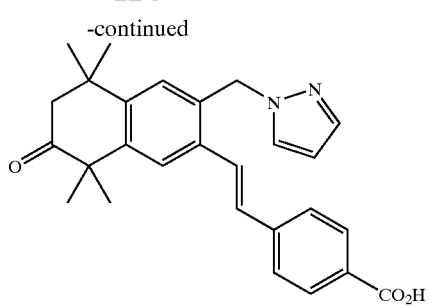

To a solution of the above ester (0.12 g, 0.262 mmol) in 4 mL of ethanol was slowly added a solution of LiOH (0.055 g, 1.3 mmol) in 0.65 mL of water. The cloudy reaction mixture was heated to 50° C., at which point the reaction became homogeneous. The reaction was stirred at 50° C. for 2 h and then cooled to room temperature and treated with 1.1 mL of 1 M HCl solution was added. A white solid separated and stirring was continued for 30 minutes. The solid was filtered, rinsed with 20% ethanol/water, and dried under vacuum to give (E)-4-[2-(3-(pyrazole-1-ylmethyl)-7-oxo-5,5,8,8-tetramethyl-5,6,7,8-tetrahydronaphthalene-2-yl)vinyl] benzoic acid (71 mg, 63%) 144 as a white solid: M−H=427; mp 264.8–265.9° C.

Example 39

Preparation of (E)-4-[2-(3-(pyrazole-1-ylmethyl)-7-hydroxy-5,5,8,8-tetramethyl-5,6,7,8-tetrahydronaphthalene-2-yl)vinyl]benzoic acid

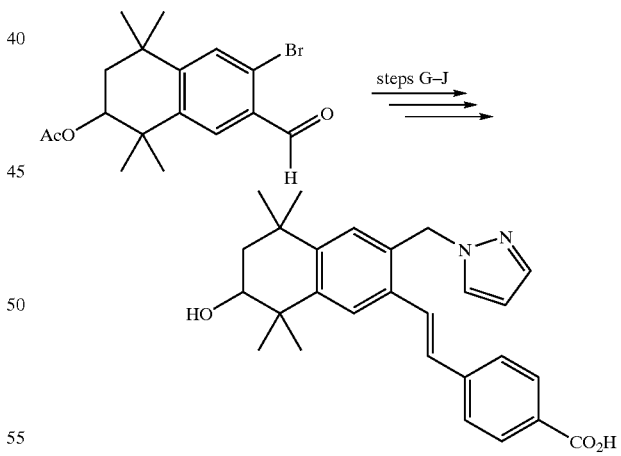

Proceeding as in steps 7–11 above except replacing 3-bromo-2-formyl-7-oxo-5,5,8,8-tetramethyl-5,6,7,8-tetrahydronaphthalene at the beginning of step 7 with 7-acetoxy-3-bromo-2-formyl-5,5,8,8-tetramethyl-5,6,7,8-tetrahydronaphthalene leads to (E)-4-[2-(3-(pyrazole-1-ylmethyl)-7-hydroxy-5,5,8,8-tetramethyl-5,6,7,8-tetrahydronaphthalene-2-yl)vinyl]benzoic acid (158 mg, 81%) 137 as a white solid: M−H=429; mp 247.6–248.4° C.

Example 40

Preparation of 4-[(E)-2-(5,5,8,8-tetramethyl-3-pyrazol-1-ylmethyl-6-keto-5,6,7,8-tetrahydro-naphthalen-2-yl)vinyl]-benzoic acid

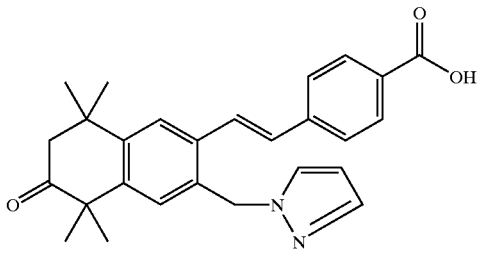

Step A

Preparation of 4-[(E)-2-(5,5,8,8-Tetramethyl-3-Methyl-6-Hydroxy-5,6,7,8-Tetrahydro-Naphthalen-2-yl)vinyl]-benzoic acid

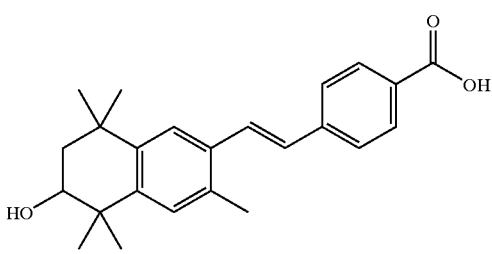

A suspension of 6 g (13.8 mmol) of ethyl-4-[(E)-2-(5,5,8,8-tetramethyl-3-methyl-6-acetoxy-55,6,7,8-tetrahydro-naphthalen-2yl)vinyl]benzoate obtained from Example 37, Step D was stirred with 30 ml of 1 N LiOH and 30 mL of MeOH at reflux temperature. After 1.5 h, the reaction mixture was cooled to room temperature, acidified with 2 N HCl and extracted with ethyl acetate. The organic fraction was washed with brine, dried over sodium sulfate and concentrated under reduced pressure to afford 3.5 g (70%) of 4-[(E)-2-(5,5,8,8-tetramethyl-3-methyl-6-hydroxy-5,5,6,7,8-tetrahydro-naphthalen-2yl)vinyl]-benzoic acid.

Step B

Preparation of Mehyl-4-[(E)-2-(5,5,8,8-Tetramethyl-3-Methyl-6-Hydroxy-5,6,7,8-Tetrahydro-Naphthalen-2-yl)vinyl]-benzoic acid

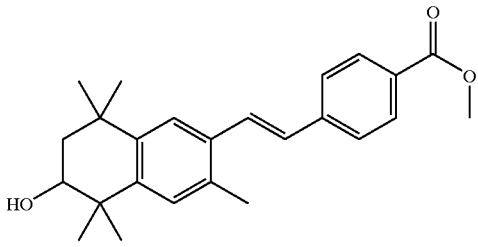

To a mixture of 3.4 g (9.3 mmol) of 4-[(E)-2-(5,5,8,8-tetramethyl-3-methyl-6-hydroxy-5,5,6,7,8-tetrahydro-naphthalen-2yl)vinyl]-benzoic acid in 100 ml of 1:1MeOH/CH$_2$Cl$_2$ was added 5.4 ml of 2M (11.2 mmol) trimethylsilyldiazomethane at room termperature. After 0.5 h, added additional 5.4 ml of trimethylsilyldiazomethane. After 16 h, added 0.5 ml of acetic acid and the reaction mixture was concentrated under reduced pressure. The residue was partitioned between water and ethyl acetate and the organic fraction was separated, washed with aqueous sodium bicarbonate and brine, dried over sodium sulfate and adsorbed onto silica gel. Purification by flash chromatography (gradient elution, hexane-15% ethyl acetate/hexane) to provide 1.8 g (51%) of methyl-4-[(E)-2-(5,5,8,8-tetramethyl-3-methyl-6-hydroxy-5,6,7,8-tetrahydro-naphthalen-2-yl)vinyl]-benzoic acid.(M$^+$=378).

Step C

Preparation of Mehyl-4-[(E)-2-(5,5,8,8-tetramethyl-3-methyl-6-oxo-5,6,7,8-tetrahydro-naphthalen-2-yl)vinyl]-benzoic acid

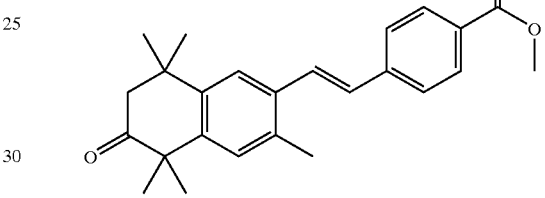

To a solution of 1.6 g (4.2 mmol) of methyl-4-[(E)-2-(5,5,8,8-tetramethyl-3-methyl-6-hydroxy-5,6,7,8-tetrahydro-naphthalen-2-yl)vinyl]-benzoic acid in 50 ml of methylene chloride at room temperature was added 1.97 g (4.65 mmol) of Dess-Martin periodinane. After 1 h, the reaction mixture was poured into brine and extracted with methylene chloride. The organic fraction was dried over sodium sulfate, adsorbed onto silica gel and purified by flash chromatography (gradient elution: hexane-8% ethyl acetate/hexane) to afford 1.45 g (92%) of methyl-4-[(E)-2-(5,5,8,8-tetramethyl-3-methyl-6-oxo-5,6,7,8-tetrahydro-naphthalen-2-yl)vinyl]-benzoic acid (M$^+$=376).

Step D

Preparation of Mehyl-4-[(E)-2-(5,5,8,8-tetramethyl-3-bromomethyl-6-oxo-5,6,7,8-tetrahydro-naphthalen-2-yl)vinyl]-benzoic acid

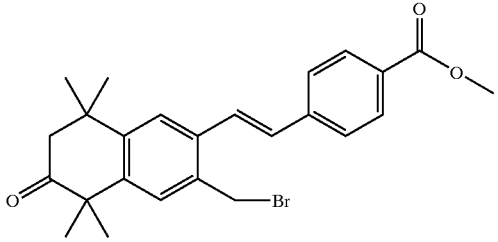

To a solution of 1.4 g (3.7 mmol) of methyl-4-[(E)-2-(5,5,8,8-tetramethyl-3-methyl-6-oxo-5,6,7,8-tetrahydro-naphthalen-2-yl)vinyl]-benzoic acid and 0.86 g (4.8 mmol) of N-bromosuccinimide in 50 ml carbon tetrachloride was added 45 mg (0.19 mmol) of benzoyl peroxide and the reaction was heated to reflux temperature. After 1 h, added additional 45 mg of benzoyl peroxide and 25 ml carbon tetrachloride. After 3 h total added 0.2 g N-bromosuccinimide. After 6 h total, cooled to room temperature, washed with 10% aqueous sodium bisulfite and brine, dried over sodium sulfate and adsorbed onto silica gel. Purified by flash chromatography (hexane-8% ethyl acetate/hexane) to give 1.0 g (59%) of methyl-4-[(E)-2-(5,5,8,8-tetramethyl-3-bromomethyl-6-oxo-5,6,7,8-tetrahydro-naphthalen-2-yl)vinyl]-benzoic acid.

Step E

Preparation of 4-[(E)-2-(5,5,8,8-tetramethyl-3-pyrazol-1-ylmethyl-6-oxo-5,6,7,8-tetrahydro-naphthalen-2-yl)vinyl]-benzoic acid

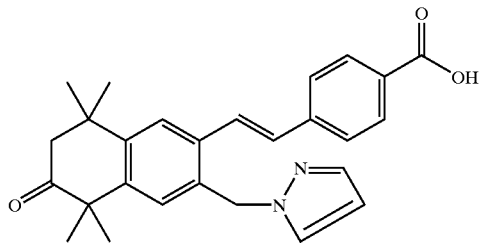

A solution of 1.0 g (2.2 mmol) of methyl-4-[(E)-2-(5,5,8,8-tetramethyl-3-bromomethyl-6-oxo-5,6,7,8-tetrahydro-naphthalen-2-yl)vinyl]-benzoic acid and 0.6 g (8.8 mmol) of pyrazole in 15 ml of N-methylpyrrolidine was heated at 100°. After 2 h, the reaction mixture was cooled to room temperature, poured into brine, extracted with ethyl acetate, washed with brine and dried over sodium sulfate. The organic solution was adsorbed onto silica gel and purified by flash chromatography (gradient elution: hexane-18% ethyl acetate/hexane) to afford 0.71 g (73%) of Methyl-4-[(E)-2-(5,5,8,8-tetramethyl-3-pyrazol-1-ylmethyl-6-oxo-5,6,7,8-tetrahydro-naphthalen-2-yl)vinyl]-benzoic acid (MH$^+$= 443).

A mixture of 0.7 g (1.58 mmol) of methyl-4-[(E)-2-(5,5,8,8-tetramethyl-3-pyrazol-1-ylmethyl-6-oxo-5,6,7,8-tetrahydro-naphthalen-2-yl)vinyl]-benzoic acid in 40 ml of MeOH and 20 ml of 1 N LiOH was heated to reflux temperature. After 1 h, the reaction was cooled to room temperature and the MeOH removed under reduced pressure. The aqueous solution was acidified with 2 N HCl, extracted with ethyl acetate, washed with brine, dried over sodium sulfate and adsorbed onto silica gel. The product was purified by flash chromatography (gradient elution: 10–30% ethyl acetate/hexane with 0.2% acetic acid) and by recrystallization (ethyl acetate/hexane) to afford 100 mg (15%) of 4-[(E)-2-(5,5,8,8-tetramethyl-3-pyrazol-1-ylmethyl-6-oxo-5,6,7,8-tetrahydro-naphthalen-2-yl)vinyl]-benzoic acid (mp=233–233.5) 133.

Example 41

Preparation of 4-[(E)-2-(5,5,8,8-tetramethyl-3-pyrazol-1-ylmethyl-6,7-trans-dihydroxy-5,6,7,8-tetrahydro-naphthalen-2-yl)vinyl]-benzoic acid

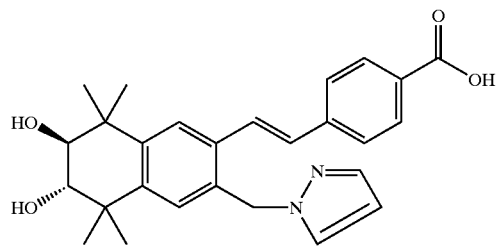

Step A

Preparation of 2-bromo-3-methyl-6-hydroxy-5,5,8,8-tetramethyl-5,6,7,8-tetrahydronaphthalene

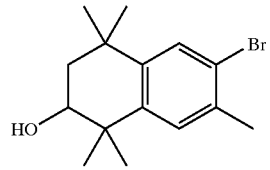

A mixture of 20 g (59 mmol) of 2-bromo-3-methyl-6-acetoxy-5,5,8,8-tetramethyl-5,6,7,8-tetrahydronaphthalene and 177 m 1 N LiOH and 350 ml of methyl alcohol was heated at reflux temperature. After 1 h, the reaction mixture was cooled to room temperature, concentrated under reduced pressure, acidified with 2 N HCl, extracted with ethyl acetate, dried over sodium sulfate and adsorbed onto silica gel. The product was purified by flash chromatography (gradient elution 5–20% ethyl acetate/hexane) to afford 15.3 g (87%) of 2-bromo-3-methyl-6-5,5,8,8-tetramethyl-5,6,7,8-tetrahydronaphthalene.

Step B

Preparation of 2-bromo-3,5,5,8,8-pentamethyl-5,8-dihydronaphthalene

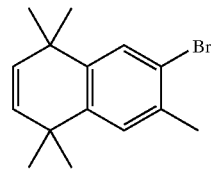

To a solution of 15.3 g (51.5 mmol) of 2-bromo-3-methyl-6-hydroxy-5,5,8,8-tetramethyl-5,6,7,8-tetrahydronaphthalene in 120 ml of pyridine was added 17.9 ml (192 mmol) of phosphorus oxychloride. The reaction mixture was heated to 100°. After 6 h, cooled to room temperature and carefully poured onto ice with stirring. After 1 h, extracted with ethyl acetate, washed with 2 N HCl and brine, dried over sodium sulfate and concentrated under reduced pressure. The residue was purified by gravity chromatography (gradient elution: hexane-10% ethyl acetate/hexane) to afford 12.5 g (87%) of 2-bromo-3,5,5,8,8-pentamethyl-5,8-dihydronaphthalene.

Step C

Preparation of 4-bromo-2,2,5,7,7-pentamethyl-1A,2,7,7A-tetrahydro-1-oxa-cyclopropa[b[napththalene

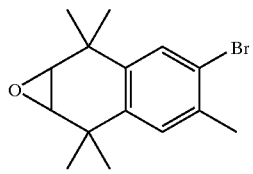

To a solution of 10 g (35.8 mmol) of 2-bromo-3,5,5,8,8-pentamethyl-5,8-dihydronaphthalene in 300 ml of dichloromethane at 0° was added 12.4 g (35.8 mmol) of metachloroperbenzoic acid portionwise over 20 minutes. One hour after the addition was complete, the reaction mixture was washed with 10% aqueous sodium bisulfite and brine, dried over sodium sulfate and adsorbed onto silica gel. Purified by flash chromatography (gradient elution: hexane-10% ethyl acetate/hexane) to afford 9 g (8 5%) of 4-bromo-2,2,5,7,7-pentamethyl-1a,2,7,7a-tetrahydro-1-oxa-cyclopropa[b]napththalene.

Step D

Preparation of 2-bromo-3-methyl-6,7-dihydroxy-5,5,8,8-tetramethyl-5,6,7,8-tetrahydronaphthalene.

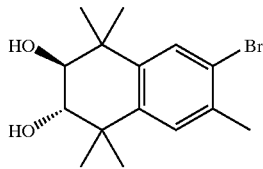

A solution of 2.0 g (6.8 mmol) of 4-bromo-2,2,5,7,7-pentamethyl-1a,2,7,7a-tetrahydro-1-oxa-cyclopropa[b]napththalene in 20 ml of acetic acid with 0.2 ml $H_2SO_4$ was heated to reflux temperatures. After 0.5 h, the reaction mixture was cooled to room temperature and concentrated under reduced pressure. The residue was dissolved in toluene and reconcentrated under reduced pressure. The product was dissolved in 40 ml of methyl alcohol and 20 ml of 1 N LiOH was added. The reaction solution was heated at reflux temperature. After 1 h, the reaction was cooled to room temperature and the concentrated under reduced pressure. The reaction mixture was acidified with 2 N HCl, extracted with ethyl acetate, washed with brine, dried over sodium sulfate, then adsorbed onto silica gel. The product was purified by flash chromatography (gradient elution: hexane-20% ethyl acetate/hexane) to give 1.2 g (56%) of 2-bromo-3-methyl-6,7-dihydroxy-5,5,8,8-tetramethyl-5,6,7,8-tetrahydronaphthalene.

Step E

Preparation of 6-bromo-2,2,4,4,7,9,9-heptamethyl-3a,4,9,9a-tetrahydro-naptao[2,3-d][1,3]-trans-dioxole

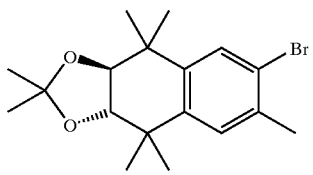

To a suspension of 1.0 g (3.2 mmol) of 2-bromo-3-methyl-6,7-dihydroxy-5,5,8,8-tetramethyl-5,6,7,8-tetrahydronaphthalene in 30 ml of 2,2-dimethoxypropane was added 100 mg of p-toluene sulphonic acid. The reaction was stirred at room temperature. After 1 h, the reaction was poured into aqueous sodium bicarbonate and extracted with ethyl acetate. The organic extracts were washed with brine, dried over sodium sulfate, concentrated under reduced pressure and purified by flash chromatography (gradient elution: hexane-5% ethyl acetate) to give 1.2 g (97%) of 6-bromo-2,2,4,4,7,9,9-heptamethyl-3a,4,9,9a-tetrahydro-naphtao[2,3-d][1,3]-trans-dioxole.

Step F

Preparation of 2,2,4,4,7,9,9-heptamethyl-3a,4,9,9a-tetrahydro-naphtho[2,3-d][1,3]-trans-dioxole-6-carbaldehyde

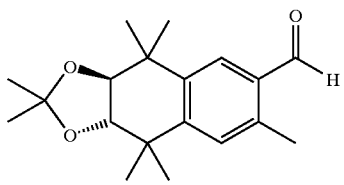

To a solution of 3.8 g (10.8 mmol) of 6-bromo-2,2,4,4,7,9,9-heptamethyl-3a,4,9,9a-tetrahydro-naphtao[2,3-d][1,3]-trans-dioxole in 50 ml of THF at −78° was added 13.5 ml of 1.6 M (21.5 mmol) of n-BuLi. After 1 h, added a solution of 2.4 ml (21.5 mmol) of N-formyl piperidine in 10 ml THF. After 1.5 h, added saturated aqueous ammonium chloride solution, warmed to room temperature, extracted with ethyl acetate, washed with brine, dried over sodium sulfate and adsorbed onto silica gel. Purified by flash chromatography (gradient elution: hexane-3% ethyl acetate/hexane). Isolated 2.1 g (64%) of 2,2,4,4,7,9,9-heptamethyl-3a,4,9,9a-tetrahydro-naphtho[2,3-d][1,3]-trans-dioxole-6-carbaldehyde ($M^+$=302).

Step G

Preparation of 4-[(E)-2-(2,2,4,4,7,9,9)-heptamethyl-3a,4,9,9a-tetrahydro-naphtho[2,3d][1,3]-trans-dioxol-6-yl)-vinyl]-benzoic acid methyl ester

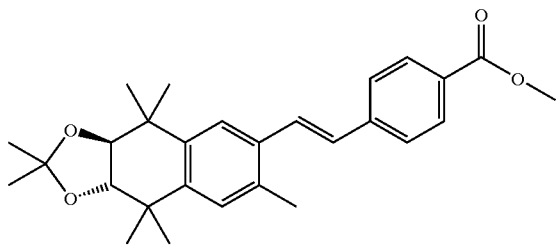

To a solution of 2.0 g (6.6 mmol) of 2,2,4,4,7,9,9-heptamethyl-3a,4,9,9a-tetrahydro-naphtho[2,3-d][1,3]-trans-dioxole-6-carbaldehyde and 2.2 g (8.6 mmol) of 4-(Dimethoxy-phosphorylmethyl)-benzoic acid methyl ester in 50 ml of toluene at 0° was added 5.6 ml of 1.7 M (8.6 mmol) of potassium tert-pentylate in toluene. After 1.5 h, poured into brine, extracted with ethyl acetate, dried over sodium sulfate and adsorbed onto silica gel. Purified by flash chromatography (gradient elution: hexane-2% ethyl acetae/hexane) to give 2.5 g (87%) of 4-[(E)-2-(2,2,4,4,7,9,9)-heptamethyl-3a,4,9,9a-tetrahydro-naphtho[2,3d][1,3]-trans-dioxol-6-yl)-vinyl]-benzoic acid methyl ester.

Step H

Preparation of 4-[(E)-2-(7-bromomethyl-2,2,4,4,7,9,9)-hexamethyl-3a,4,9,9a-tetrahydro-naphtho[2,3d][1,3]-trans-dioxol-6-yl)-vinyl]-benzoic acid methyl ester

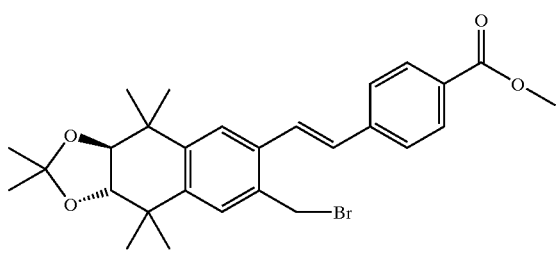

A solution of 2.4 g (5.5 mmol) of 4-[2-(2,2,4,4,7,9,9)-heptamethyl-3a,4,9,9a-tetrahydro-naphtho[2,3d][1,3]-trans-dioxol-6-yl)-vinyl]-benzoic acid methyl ester, 1.47 g (8.28 mmol) of N-bromosuccinimide and 67 mg (0.28 mmol) of benzoyl peroxide in 50 ml of $CCl_4$ was heated at reflux temperatures. After 2 h, added additional 34 mg (0.14 mmol) of benzoyl peroxide. After 3 h total the reaction was filtered and the filtrate was washed with aqueous sodium bisulfite, dried over sodium sulfate and adsorbed onto silica gel. The product was purified by flash chromatography (gradient eluion: hexane-3% ethyl acetae/hexane) to afford 1.7 g of 4-[(E)-2-(7-bromomethyl-2,2,4,4,7,9,9)-hexamethyl-3a,4,9,9a-tetrahydro-naphtho[2,3d][1,3]-trans-dioxol-6-yl)-vinyl]-benzoic acid methyl ester.

Step I

Preparation of 4-[(E)-2-(2,2,4,4,7,9,9)-hexamethyl-7-pyrazol-1-ylmethyl-3a,4,9,9a-tetrahydro-naphtho[2,3d][1,3]-trans-dioxol-6-yl)-vinyl]-benzoic acid methyl ester

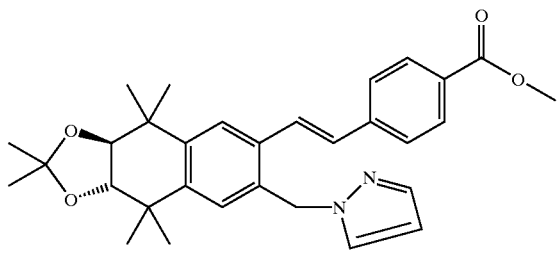

A solution of 170 mg (0.33 mmol) of 4-[(E)-2-(7-bromomethyl-2,2,4,4,7,9,9)-hexamethyl-3a,4,9,9a-tetrahydro-naphtho[2,3d][1,3]-trans-dioxol-6-yl)-vinyl]-benzoic acid methyl ester. and 47 mg (0.7 mmol) of pyrazole in 10 ml of NMP was heated at 100. After 2 h, the reaction mixture was cooled to room temperature, poured into brine, extracted with ethyl acetate, washed with brine, dried over sodium sulfate and adsorbed onto silica gel. The product was purified by flash chromatography (gradient elution: hexane-15% ethyl acetate/hexane) to give 75 mg (45) of 4-[(E)-2-(2,2,4,4,7,9,9)-hexamethyl-7-pyrazol-1-ylmethyl-3a,4,9,9a-tetrahydro-naphtho[2,3d][1,3]-trans-dioxol-6-yl)-vinyl]-benzoic acid methyl ester.

Step J

Preparation of 4-[(E)-2-(5,5,8,8-tetramethyl-3-pyrazol-1-ylmethyl-6,7-trans-dihydroxy-5,6,7,8-tetrahydro-naphthalen-2-yl)vinyl]-benzoic acid

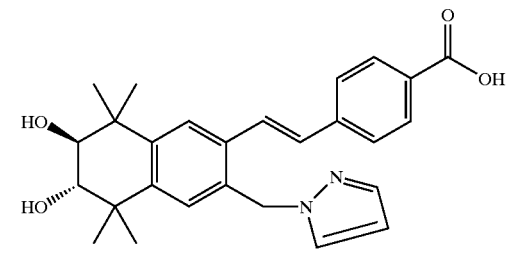

A mixture of 75 mg (0.15 mmol) of 4-[(E)-2-(2,2,4,4,7,9,9)-hexamethyl-7-pyrazol-1-ylmethyl-3a,4,9,9a-tetrahydro-naphtho[2,3d][1,3]-trans-dioxol-6-yl)-vinyl]-benzoic acid methyl ester. in 10 ml 1 N HCl and 10 ml of THF was stirred at room temperature. After 1 h the reaction mixture was concentrated under reduced pressure, extracted with ethyl acetate, concentrated under reduced pressure and taken up in 20 ml of methyl alcohol and 10 ml of LiOH. The reaction mixture was heated to reflux. After 1 h the reaction was cooled to room temperature and concentrated under reduced pressure. The reaction mixture was acidified with 2 N HCl, extracted with ethyl acetate, washed with brine, dried over sodium sulfate and concentrated under reduced pressure to afford 60 mg (90%) of 4-[(E)-2-(5,5,8,8-tetramethyl-3-pyrazol-1-ylmethyl-6,7-trans-dihydroxy-5,6,7,8-tetrahydro-naphthalen-2-yl)vinyl]-benzoic acid (MH+= 447) 145.

Example 42

Preparation of 4-[(E)-2-(5,5,8,8-tetramethyl-3-pyrazol-1-ylmethyl-6,7-cis-dihydroxy-5,6,7,8-tetrahydro-naphthalen-2-yl)vinyl]-benzoic acid

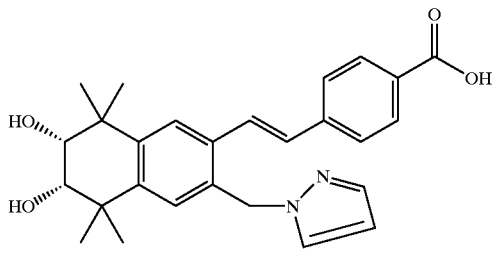

Step A

Preparation of 2-bromo-cis-6,7-dihydroxy-3,5,5,8,8-pentamethyl-5,6,7,8-tetrahydronaphthalene

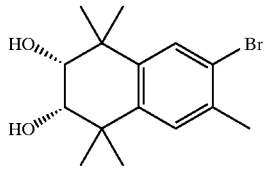

To a solution of 9.41 g (33.7 mmol) of 2-bromo-3,5,5,8,8-pentamethyl-5,8-dihydronaphthalene in 110 ml pyridine was added 8.65 g (34.0 mmol) osmium tetroxide under an atmosphere of nitrogen. After stirring at room temperature for 18 hours, 17.3 g (166 mmol) of sodium bisulfite in 110 ml water was added. After 2 hours the resulting solution was partitioned between ethyl acetate and aqueous hydrochloric acid. The organic layer was washed with water, washed with brine, dried over anhydrous sodium sulfate, and concentrated in vacuo. The crude material was purified by flash chromatography with elution with 30% ethyl acetate/hexane to yield 7.97 g (75%) of 2-bromo-cis-6,7-dihydroxy-3,5,5,8,8-pentamethyl-5,6,7,8-tetrahydronaphthalene as a white solid ($M^+$=312).

Step B

Preparation of 2-bromo-cis-6,7-dihydroxy-3,5,5,8,8-pentamethyl-5,6,7,8-tetrahydronaphthalene acetonide

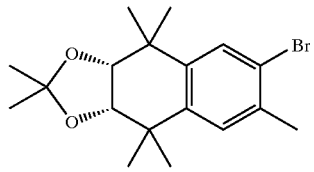

A solution of 7.73 g (24.7 mmol) of 2-bromo-cis-6,7-dihydroxy-3,5,5,8,8-pentamethyl-5,6,7,8-tetrahydronaphthalene and 445 mg (2.39 mmol) of p-toluenesulfonic acid monohydrate in 100 ml 2,2-dimethoxypropane was heated to reflux for 90 minutes. Upon cooling the resulting solution was partitioned between ethyl acetate and dilute aqueous sodium bicarbonate. The organic layer was washed with brine, dried over anhydrous sodium bicarbonate, and concentrated in vacuo to yield 9.10 g of 2-bromo-cis-6,7-dihydroxy-3,5,5,8,8-pentamethyl-5,6,7,8-tetrahydronaphthalene acetonide ($M^+$=352) which was used without further purification.

Step C

Preparation of 3-methyl-cis-6,7-dihydroxy-5,5,8,8-tetramethyl-5,6,7,8-tetrahydro-2-naphthaldehyde acetonide

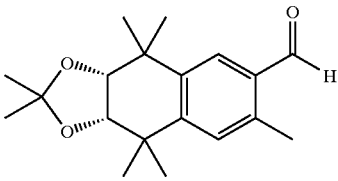

To a −78° C. solution of 9.04 g (25.6 mmol) 2-bromo-cis-6,7-dihydroxy-3,5,5,8,8-pentamethyl-5,6,7,8-tetrahydronaphthalene acetonide in 110 ml tetrahydrofuran was added 32.0 ml (51.1 mmol) of a 1.6M solution of n-butyllithium in hexanes. After 1 hour at −78° C., 5.79 g (51.1 mmol) of 1-formylpiperidine was added. After 20 minutes at −78° C., the resulting mixture was quenched with water. Upon warming to room temperature, the mixture was partitioned between ethyl acetate and water. The organic layer was washed with brine, dried over anhydrous sodium sulfate, and concentrated in vacuo. The crude material was purified by flash chromatography with elution with 5% ethyl acetate/hexane to yield 5.65 g (73%) of 3-bromo-cis-6,7-dihydroxy-5,5,8,8-tetramethyl-5,6,7,8-tetrahydro-2-naphthaldehyde acetonide($MH^+$=303).

Step D

Preparation of 4-[(E)-2(2,2,4,4,7,9,9)-heptamethyl-3a,4,9,9a-tetrahydro-naphtho[2,3d][1,3]-cis-dioxol-6-yl)-vinyl]-benzoic acid methyl ester

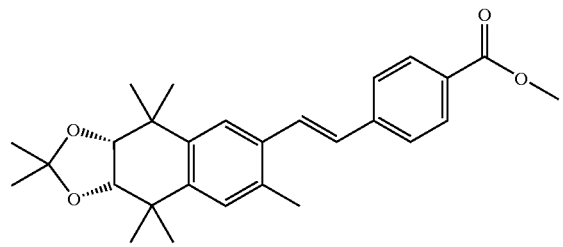

To a solution of 5.3 g (17.5 mmol) of 2,2,4,4,7,9,9-heptamethyl-3a,4,9,9a-tetrahydro-naphtho[2,3-d][1,3]-cis-dioxole-6-carbaldehyde and 5.9 g (22.8 mmol) of 4-(Dimethoxy-phosphorylmethyl)-benzoic acid methyl ester in 50 ml of toluene at 0° was added 13.4 ml of 1.7 M (22.2 mmol) potassium-tert-pentyl ate. After 1 h, the reaction was poured into brine, extracted with ethyl acetate, washed with brine, dried over sodium sulfate and adsorbed onto silica gel. The product was purified by flash chromatography (gradient elution: hexane-15% ethyl acetate/hexane) to afford 6.0 g (79%) of 4-[(E)-2-(2,2,4,4,7,9,9)-heptamethyl-3a,4,9,9a-tetrahydro-naphtho[2,3d][1,3]-cis-dioxol-6-yl)-vinyl]-benzoic acid methyl ester.

Step E

Preparation of 4-(E)-2-(5,5,8,8-tetramethyl-3-methyl-6,7-cis-diacetoxy-5,6,7,8-tetrahydro-naphthalen-2-yl)vinyl]-benxoic acid methyl ester

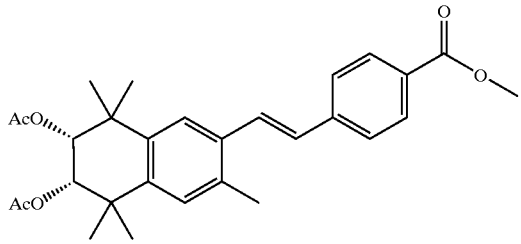

A mixture of 4.7 g (10.8 mmol) of 4-[(E)-2-(2,2,4,4,7,9,9)-heptamethyl-3a,4,9,9a-tetrahydro-naphtho[2,3d][1,3]-cis-dioxol-6-yl)-vinyl]-benzoic acid methyl ester in 50 ml of THF and 50 ml 1 N HCl was stirred at room temperature. After 3 h, concentrated under reduced pressure, extracted with ethyl acetate, washed with brine, dried over sodium sulfate and concentrated under reduced pressure. The residue was taken up in 50 ml of pyridine and 5 ml (53 mmol) of acetic anhydride was added. The reaction was heated to 60°. After 2 h, the reaction mixture was cooled to room temperature, diluted with water and extracted with ethyl acetate. The organic fraction was washed with 2 N HCl and brine, dried over sodium sulfate and purified by flash chromatography (gradient elution: hexane-10% ethyl acetate/hexane) to provide 5.2 g (100%) of 4-[(E)-2-(5,5,8,8-tetramethyl-3-methyl-6,7-cis-diacetoxy-5,6,7,8-tetrahydro-naphthalen-2-yl)vinyl]-benzoic acid methyl ester.

Step F

Preparation of 4-(E)-2-(5,5,8,8-tetramethyl-3-bromomethyl-6,7-cis-diacetoxy-5,6,7,8-tetrahydro-naphthalen-2-yl)vinyl]-benzoic acid methyl ester

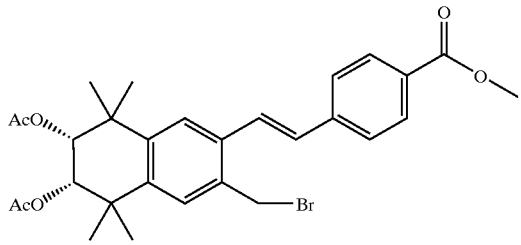

A solution of 5.2 g (10.8 mmol) of 4-[(E)-2-(5,5,8,8-tetramethyl-3-methyl-6,7-cis-diacetoxy-5,6,7,8-tetrahydro-naphthalen-2-yl)vinyl]-benzoic acid methyl ester and 2.4 g (13.3 mmol) of N-bromosuccinimide with 124 mg (0.5 mmol) of benzoyl peroxide in 50 ml of carbon tetrachloride was heated to reflux temperature. After 5 h, cooled to room temperature, filtered and washed filtrate with 10% aqueous bisulfite and brine, dried over sodium sulfate and purified by flash chromatography (gradient elution: hexane-10% ethyl acetate/hexane) to give 4.0 g (66%) of 4-[(E)-2-(5,5,8,8-tetramethyl-3-bromomethyl-6,7-cis-diacetoxy-5,6,7,8-tetrahydro-naphthalen-2-yl)vinyl]-benzoic acid methyl ester.

Step G

Preparation of 4-(E)-2-(5,5,8,8-tetramethyl-3-pyrazol-1-ylmethyl-6,7-cis-diacetoxy-5,6,7,8-tetrahydro-naphthalen-2-yl)vinyl]benxoic acid methyl ester

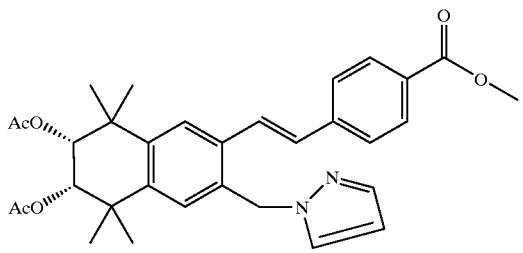

To a solution of 730 mg (2.76 mmol) of 18-crown-6 and 338 mg (3 mmol) of potassium-tert-butoxide in 3o ml of THF was added 205 mg (3 mmol) of pyrazole. After 20 minutes, the reaction was cooled to 0 and a solution of 1.4 g (2.5 mmol) of 4-[(E)-2-(5,5,8,8-tetramethyl-3-bromomethyl-6,7-cis-diacetoxy-5,6,7,8-tetrahydro-naphthalen-2-yl)vinyl]-benzoic acid methyl ester in 20 ml of THF was added dropwise. After 3 h, the reaction mixture was poured into brine, extracted with ethyl acetate, washed with brine, dried over sodium sulfate and adsorbed onto silica gel. The product was purified by flash chromatography (gradient elution: hexane-30% ethyl acetate/hexane) to give 1.05 g (77%) of 4-[(E)-2-(5,5,8,8-tetramethyl-3-pyrazol-1-ylmethyl-6,7-cis-diacetoxy-5,6,7,8-tetrahydro-naphthalen-2-yl)vinyl]benzoic acid methyl ester.

Step H

Preparation of 4-(E)-2-(5,5,8,8-tetramethyl-3-pyrazol-1-ylmethyl-6,7-cis-dihydroxy-5,6,7,8-tetrahydro-naphthalen-2-yl)vinyl]benzoic acid

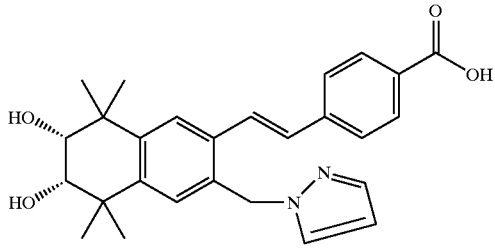

A mixture of 1.0 g (2.2 mmol) of 4-[(E)-2-(5,5,8,8-tetramethyl-3-pyrazol-1-ylmethyl-6,7-cis-diacetoxy-5,6,7,8-tetrahydro-naphthalen-2-yl)vinyl]benzoic acid methyl ester. in 20 ml of methyl alcohol and 10 ml of 1 N LiOH was heated at reflux. After 1 h, cooled to room temperature concentrated under reduced pressure, acidified with 2 N HCl, extracted with ethyl acetate, washed with brine, dried over sodium sulfate and adsorbed onto silica gel. The product was purified by flash chromatography (gradient elution: 20–60% ethyl acetate/hexane with 0.2% acetic acid) to give 560 mg of 4-[(E)-2-(5,5,8,8-tetramethyl-3-pyrazol-1-ylmethyl-6,7-cis-dihydroxy-5,6,7,8-tetrahydro-naphthalen-2-yl)vinyl]-benzoic acid.(mp 238.3–241.5) 148.

Example 43

Preparation of 4-[(E)-2-(5,5,8,8-tetramethyl-3-((E)-2-(pyrimidin-2-yl)vinyl)-5,6,7,8-tetrahydro-2-naphthalen-2-yl)vinyl]benzoic acid

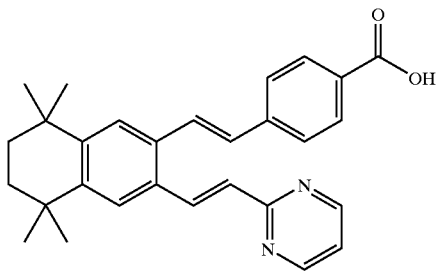

Step A

Preparation of 3-(E)-2-(pyrimidin-2-yl)vinyl)-5,5,8,8-tetramethyl-5,6,7,8-tetrahydro-2-naphthaldehyde

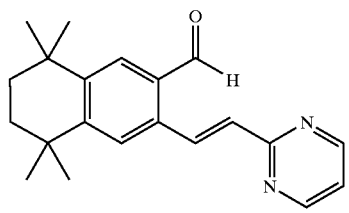

A solution of 0.874 g (2.96 mmol) of 3-bromo-5,5,8,8-tetramethyl-5,6,7,8-tetrahydro-2-naphthaldehyde, 1.886 g (3.11 mmol) of trans-1,2-bis(tri-n-butylstannyl)ethylene and 0.068 g (0.059 mmol) of tetrakis(triphenylphosphine) palladium in 20 ml toluene was heated to reflux under argon for 1.75 hour. The reaction was cooled slightly and 0.518 g (3.26 mmol) of 2-bromopyrimidine and 0.068 g (0.059 mmol) of tetrakis(triphenylphosphine)palladium was added in 3.5 ml toluene. The reaction was heated at reflux for 3 hours. The reaction was cooled to room temperature, quenched with 5% potassium fluoride and diluted with ethyl acetate. The two phases were stirred vigorously for 16 hours. The mixture was filtered through celite and the organic layer was washed with brine, dried over anhydrous sodium sulfate, and concentrated in vacuo. The crude material was purified by flash chromatography (gradient elution with 20% ethyl acetate/hexane-25% ethyl acetate/hexane) to afford 0.254 g (27%) of 3-((E)-2-(pyrimidin-2-yl)vinyl)-5,5,8,8,-tetramethyl-5,6,7,8-tetrahydro-2-naphthaldehyde (M+1=321).

Step B

Preparation of Methyl-4-[(E)-2-(5,5,8,8-tetramethyl-3-((E)-2-(pyrimidin-2-yl)vinyl)-5,6,7,8-tetrahydro-2-naphthalen-2-yl)vinyl]benzoate

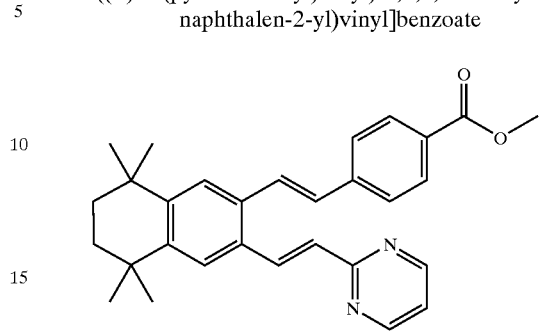

To a suspension of 0.079 g (1.98 mmol) of 60% NaH in 1.5 ml tetrahydrofuran was added 0.248 g (0.96 mmol) of 4-(dimethoxyphosphorylmethyl)-benzoic acid methyl ester in 2.5 ml THF and the reaction was stirred at room temperature for 1 hour 20 minutes. 0.254 g (0.79 mmol) of 3-((E)-2-(pyrimidin-2yl)vinyl)-5,5,8,8,-tetramethyl-5,6,7,8-tetrahydro-2-naphthaldehyde in 3 ml THF was added and the reaction was stirred at room temperature. After 17 hours the reaction was quenched with 5 ml 1M hydrochloric acid and extracted with ethyl ether. The organic layer was washed with water, brine, dried over anhydrous magnesium sulfate and concentrated in vacuo. The crude material was purified by flash chromatography (elution with 30% ethyl acetate/hexane) to afford 0.180 g (50%) of Methyl-4-[(E)-2-(5,5,8,8-tetramethyl-3-((E)-2-(pyramidin-2-yl)-5,6,7,8-tetrahydro-2-naphthalen-2-yl)vinyl]benzoate (M+1=453).

Step C

Preparation of 4-[(E)-2-(5,5,8,8-tetramethyl-3-((E)-2-(pyrimidin-2-yl)vinyl)-5,6,7,8-tetrahydro-2-naphthalen-2-yl)vinyl]benzoic acid

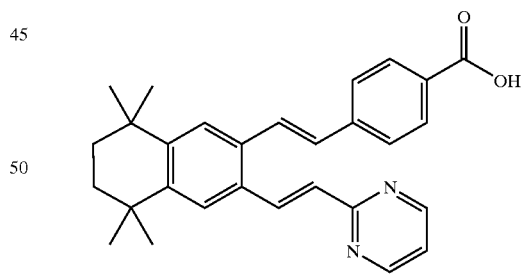

A solution of 0.180 g (0.40 mmol) of Methyl-4-[(E)-2-(5,5,8,8-tetramethyl-3-((E)-2-(pyrimidin-2-yl)vinyl)-5,6,7,8-tetrahydro-2-naphthalen-2-yl)vinyl]benzoate in 5 ml 1M LiOH and 10 ml ethyl alcohol was heated to reflux. After 50 minutes the reaction was cooled to room temperature and acidified with IM hydrochloric acid. The aqueous was extracted with ethyl ether, washed with water, brine, dried over anhydrous magnesium sulfate and stripped in vacuo to afford 0.160 g (91%) of 4-[(E)-2-(5,5,8,8-tetramethyl-3-((E)-2-(pyrimidin-2-yl)vinyl)-5,6,7,8-tetrahydro-2-naphthalen-2-yl)vinyl]benzoic acid 160 (M−1=437).

Example 44

Preparation of 5,5,8,8,-tetramethyl-3-((E)-2-thiazol-2-yl-vinyl)-5,6,7,8-tetrahydro-2-naphthaldehyde

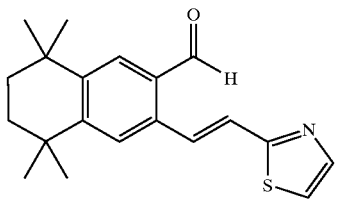

A solution of 0.147 g (0.498 mmol) of 3-bromo-5,5,8,8-tetramethyl-5,6,7,8-tetrahydro-2-naphthaldehyde, 0.302 g (0.498 mmol) of trans-1,2-bis(tri-n-butylstannyl)ethylene, and 0.012 g (0.00996 mmol) of tetrakis(triphenylphosphine)palladium(0) in 5 ml toluene was heated to reflux under an atmosphere of argon for 1 hour. This was cooled. 0.082 g (0.498 mmol) of 2-bromothiazole and 0.012 g (0.00996 mmol) of tetrakis(triphenylphosphine)palladium(0) were added. This was stirred at reflux for 2 hours and at room temperature for 16 hours. 20 ml of 5% aqueous potassium fluoride and 15 ml of ethyl acetate were added. The resulting mixture was stirred vigorously for 2 hours and was filtered through celite. The organic layer was washed with brine, dried over anhydrous sodium sulfate, and was concentrated in vacuo. The product was purified by flash chromatography with elution with 15% ethyl acetate/hexane to afford 0.065 g (40%) of 5,5,8,8,-tetramethyl-3-((E)-2-thiazol-2-yl-vinyl)-5,6,7,8-tetrahydro-2-naphthaldehyde (M+H=326).

Example 45

Preparation of (E)-4-{2-[3-((thiophen-3-yl)oxomethyl)-5,5,8,8-tetramethyl-5,6,7,8-tetrahydronaphthalen-2-yl]vinyl}benzoic acid

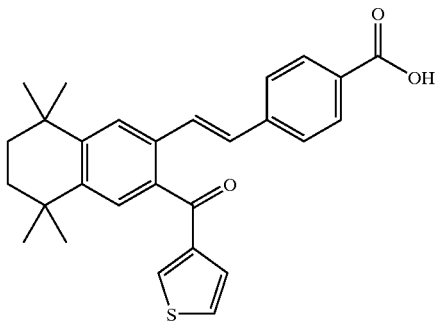

A solution of 2-(1,3-dioxolane-2-yl)-3-[(thiophen-3-yl)hydroxymethyl]-5,5,8,8-tetramethyl-5,6,7,8-tetrahydronaphthalene (1.31 g, 3.86 mmol) [prepared from 3-bromo-2-(1,3-dioxolane-2-yl)-5,5,8,8-tetramethyl-5,6,7,8-tetrahydronaphthalene and 3-thiophenecarboxaldehyde as previously described for the preparation of 2-(1,3-dioxolane-2-yl)-3-[(thiophene-2-yl)hydroxymethyl)-5,5,8,8-tetramethyl-5,6,7,8-tetrahydronaphthalene] in 13 ml of anhydrous dichloromethane was cooled to 0° C. and Des-Martin periodinane (1.80 g, 4.25 mmol) was added over 3 minutes. The reaction was warmed to rt and stirred for 4 hours. The cloudy solution was diluted with 200 ml of dichloromethane and washed with sodium bicarbonate solution. The organic layer was washed with brine, dried over magnesium sulfate and concentrated in vacuo. This residue was then dissolved in 10 ml of tetrahydrofuran and stirred vigorously while adding 10 ml of an aqueous 1N HCl solution. Mixture was stirred for two hours and partitioned between ethyl acetate and water. The resulting organic layer was washed with brine, dried over magnesium sulfate and dried in vacuo. Chromatographic separation was achieved using a silica gel column eluting with a gradient starting with 2% ethyl acetate/hexanes to 8% ethyl acetate/hexanes to give 2-formyl-[3-((thiophen-3-yl)oxomethyl)-5,5,8,8-tetramethyl-5,6,7,8-tetrahydronaphthalene (386 mg).

Following the standard Horner-Emmons/hydrolysis procedures 2-formyl-[3-((thiophen-3-yl)oxomethyl)-5,5,8,8-tetramethyl-5,6,7,8-tetrahydronaphthalene was converted to (E)-4-{2-[3-((thiophen-3-yl)oxomethyl)-5,5,8,8-tetramethyl-5,6,7,8-tetrahydronaphthalen-2-yl]vinyl}benzoic acid as a white solid: M+=444 151.

Example 46

Preparation of 4-[(E)-2-( 5,5,8,8-tetramethyl-3-((E)-2-methylsulfonylvinyl)-5,6,7,8-tetrahydro-2-naphthalen-2-yl)vinyl]benzoic acid Step A Preparation of 3-((E)-2-methylsulfonylvinyl)-5,5,8,8-tetramethyl-5,6,7,8-tetrahydro-2-naphthaldehyde

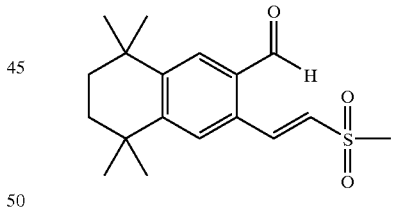

A solution of 0.537 g (1.82 mmol) of 3-bromo-5,5,8,8-tetramethyl-5,6,7,8-tetrahydro-2-naphthaldehyde, 0.579 g (5.46 mmol) of methyl vinyl sulfone, 0.191 g (0.27 mmol) of tetrakis(triphenylphosphine) palladium and 5.23 g (51.7 mmol) of triethylamine in 12 ml dimethylformamide was heated to 100° C. under argon for 5 hours. The reaction mixture was poured into water and extracted with ethyl acetate. The organic layer was washed with brine, dried over anhydrous sodium sulfate, and concentrated in vacuo. The crude material was purified by flash chromatography (elution with 25% ethyl acetate/hexane) to afford 0.359 g (62%) of 3-(2-methylsulfonylvinyl)-5,5,8,8-tetramethyl-5,6,7,8-tetrahydro-2-naphthaldehyde (M+1=321).

141

Step B

Preparation of Methyl-4-[(E)-2-( 5,5,8,8-tetramethyl-3-((E)-2-methylsulfonylvinyl)-5,6,7,8-tetrahydro-2-naphthalen-2-yl)vinyl]benzoate

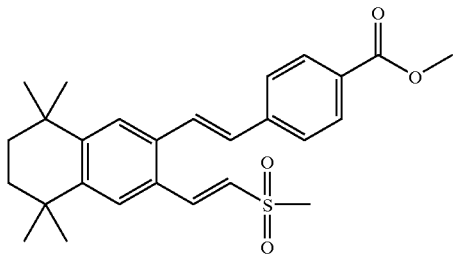

To a suspension of 0.065 g (1.63 mmol) of 60% NaH in 1.5 ml tetrahydrofuran was added 0.205 g (0.79 mmol) of 4-(dimethoxyphosphorylmethyl)-benzoic acid methyl ester in 2.5 ml THF and the reaction was stirred at room temperature for 35 minutes. 0.209 g (0.65 mmol) of 3-(2-methylsulfonylvinyl)-5,5,8,8,-tetramethyl-5,6,7,8-tetrahydro-2-naphthaldehyde in 2 ml THF was added and the reaction mixture was stirred at room temperature. After 16 hours the reaction was quenched with 4 ml 1M hydrochloric acid and extracted with ethyl ether. The organic layer was washed with water, brine, dried over anhydrous sodium sulfate, and concentrated in vacuo. The crude material was purified by flash chromatography (elution with 30% ethyl acetate/hexane) to afford 0.085 g (29%) of Methyl-4-[(E)-2-(5,5,8,8-tetramethyl-3-((E)-2-methylsulfonylvinyl)-5,6,7,8-tetrahydro-2-naphthalen-2-yl)vinyl]benzoate (M+1=453).

Step C

Preparation of 4-[(E)-2-(5,5,8,8-tetramethyl-3-((E)-2-methylsulfonylvinyl)-5,6,7,8-tetrahydro-2-naphthalene-2-yl)vinyl]benzoic acid

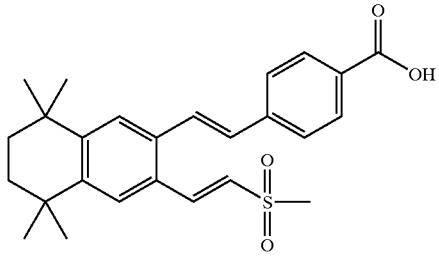

A solution of 0.085 g (0.18 mmol) of Methyl-4-[(E)-2-(5,5,8,8-tetramethyl-3-((E)-2-methylsulfonylvinyl)-5,6,7,8-tetrahydro-2-naphthalen-2-yl)vinyl]benzoate in 5 ml 1M LiOH and 10 ml ethyl alcohol was heated to reflux. After 30 minutes the reaction was cooled to room temperature and acidified with 1M hydrochloric acid. The aqueous was extracted with ethyl ether, washed with water, brine, dried over anhydrous sodium sulfate and concentrated in vacuo. The residue was purified by flash chromatography (elution with 50% ethyl acetate/hexane with 0.5% acetic acid) to afford 0.013 g (15%) of 4-[(E)-2-(5,5,8,8-tetramethyl-3-((E)-2-methylsulfonylvinyl)-5,6,7,8-tetrahydro-2-naphthalen-2-yl)vinyl-benzoic acid (M−1=437) 161.

142

Example 47

Preparation of 4-[(E)-2-(5,5,8,8-tetramethyl-3-((E)-2-sulfonamidylvinyl)-5,6,7,8-tetrahydro-2-naphthalen-2-yl)vinyl]benzoic acid

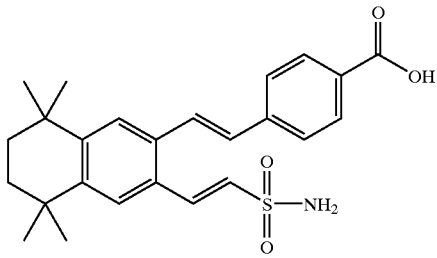

Step A

Preparation of 2-bromo-3-((E)-2-sulfonamidylvinyl)-5,5,8,8-tetramethyl-5,6,7,8-tetrahydronaphthalene

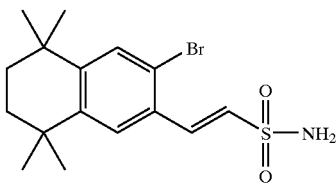

To a solution of 0.943 g (2.39 mmol) tert-butyl [(diphenylphosphoryl)methyl]sulfonylcarbamate in 6 ml dimethylformamide at 0° C. was added 0.133 g (5.25 mmol) of 95% sodium hydride. The mixture was warmed to room temperature. After 15 minutes, 0.704 g (2.39 mmol) of 3-bromo-5,5,8,8-tetramethyl-5,6,7,8-tetrahdro-2-naphthaldehyde was added in 5 ml dimethylformamide. After stirring for 18 hours, the resulting solution was partitioned between 5% aqueous hydrochloric acid and ethyl acetate. The organic layer was washed with water, brine, dried over anhydrous sodium sulfate, and concentrated in vacuo. The residue was taken up in 10 ml dichloromethane and 5 ml trifluoroacetic acid and stirred at room temperature for 3 hours. The reaction was concentrated in vacuo and coevaporated once with toluene. The residue was purified by flash chromatography (elution with 25% ethyl acetate/hexane) to yield 0.417 g (47%) of 2-bromo-3-((E)-2-sulfonamidylvinyl)-5,5,8,8-tetramethyl-5,6,7,8-tetrahydronaphthalene (M+Na=396).

Step B

Preparation of 2-hydroxymethyl-3-((E)-2-sulfonamidylvinyl)-5,5,8,8-tetramethyl-5,6,7,8-tetrahydronaphthalene

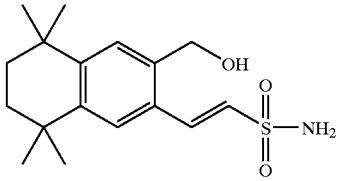

A solution of 0.412 g (1.11 mmol) of 2-bromo-3-((E)-2-sulfonamidylvinyl)-5,5,8,8-tetramethyl-5,6,7,8-tetrahydronaphthalene, 0.533 g (1.66 mmol) of tributylstannylmethanol and 0.060 g of tetrakis(triphenylphosphine) palladium in 10 ml 1,4-dioxane was heated to reflux for 3.5 hours under an atmosphere of argon. The reaction was cooled and stirred for 18 hours at room temperature. The resulting solution was partitioned between ethyl acetate and water. The organic layer was washed with brine, dried over anhydrous sodium sulfate, and concentrated in vacuo. The crude material was purified by flash chromatography (elution with 45% ethyl acetate/hexane) to yield 0.162 g (45%) of 2-hydroxymethyl-3-((E)-2-sulfonamidylvinyl)-5,5,8,8-tetramethyl-5,6,7,8-tetrahydronaphthalene (M−H= 322).

Step C

Preparation of 3-((E)-2-sulfonamidylvinyl)-5,5,8,8-tetramethyl-5,6,7,8-tetrahydro-2naphthaldehyde

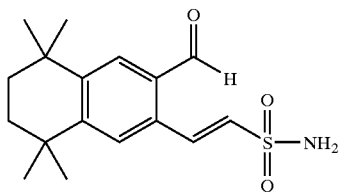

To a suspension of 0.155 g (0.479 mmol) of 2-hydroxymethyl-3-((E)-2-sulfonamidylvinyl)-5,5,8,8-tetramethyl-5,6,7,8-tetrahydronaphthalene in 4 ml dichloromethane was added 0.225 g (0.527 mmol) of 1,1,1-triacetoxy-1,1-dihydro-1,2-benziodoxol-3(1H)-one. The reaction was stirred at room temperature. After 3.5 hours the solution was partitioned between ethyl acetate and saturated aqueous ammonium chloride. The organic layer was washed with brine, dried over anhydrous sodium sulfate, and concentrated in vacuo. The residue was purified by flash chromatography (elution with 30% ethyl acetate/hexane) to yield 0.117 g (76%) of 3-((E)-2-sulfonamidylvinyl)-5,5,8,8-tetramethyl-5,6,7,8-tetrahydro-2-naphthaldehyde M+H= 322).

Step D

Preparation of Methyl-4-[(E)-2-5,5,8,8-tetramethyl-3-((E)-2-sulfonamidylvinyl)-5,6,7,8-tetrahydro-2-naphthalene-2-yl)vinyl]benzoate

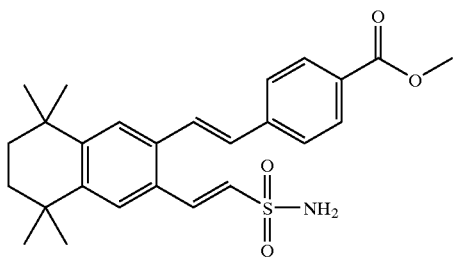

To a suspension of 0.036 g (0.90 mmol) of 60% NaH in 1.5 ml tetrahydrofuran was added 0.114 g (0.44 mmol) of 4-(dimethoxyphosphorylmethyl)-benzoic acid methyl ester in 2.5 ml THF and the reaction was stirred at room temperature for 35 minutes. 0.117 g (0.36 mmol) of 3-((E)-2-sulfonamidylvinyl)-5,5,8,8,-tetramethyl-5,6,7,8-tetrahydro-2-naphthaldehyde in 2 ml THF was added and the reaction was stirred at room temperature. After 17 hours the reaction was quenched with 2 ml 1M hydrochloric acid, adjusted to pH 7 with saturated sodium bicarbonate and extracted with ethyl ether. The organic layer was washed with water, brine, dried over anhydrous sodium sulfate, and concentrated in vacuo. The crude material was purified by flash chromatography (elution with 35% ethyl acetate/hexane) to afford 0.015 g (9%) of Methyl-4-[(E)-2-(5,5,8,8-tetramethyl-3-((E)-2-sulfonamidylvinyl)-5,6,7,8-tetrahydro-2-naphthalen-2-yl)vinyl]benzoate (M−1=452).

Step E

Preparation of 4-[(E)-2-5,5,8,8-tetramethyl-3-((E)-2-sulfonamidylvinyl)-5,6,7,8-tetrahydro-2-naphthalene-2-yl)vinyl]benzoic acid

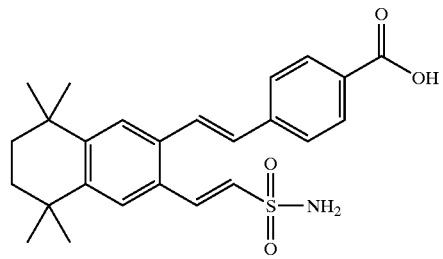

A solution of 0.015 g (0.034 mmol) of Methyl-4-[(E)-2-(5,5,8,8-tetramethyl-3-((E)-2-sulfonamidylvinyl)-5,6,7,8-tetrahydro-2-naphthalen-2-yl)vinyl]benzoate in 0.5 ml 1M LiOH and 1 ml ethyl alcohol was heated to 60° C. After 15 minutes the reaction was cooled to room temperature and acidified with 1M hydrochloric acid. The aqueous was extracted with ethyl ether, washed with brine, dried over anhydrous sodium sulfate and concentrated in vacuo. The residue was taken up in ethyl acetate and passed through a 4 micron filter. The filtrate was stripped in vacuo to afford 0.012 g (82%) of 4-[(E)-2-(5,5,8,8-tetramethyl-3-((E)-2-sulfonamidylvinyl)-5,6,7,8-tetrahydro-2-naphthalen-2-yl)vinyl]benzoic acid (M−1=438) 162.

EXAMPLE 48

Preparation of 4-[2-(5,5,8,8-tetramethyl-3-((pyrazol-1-yl)methyl)-5,6,7,8-tetrahydronaphthalen-2-yl)ethyl]phenoxy benzoic acid

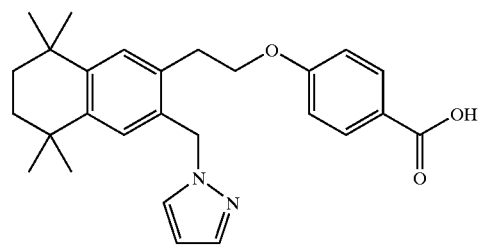

Step A

Preparation of 2bromo-5,5,8,8-tetramethyl-3-((pyrazol-1-yl)methyl)-5,6,7,8-tetrahydronaphthalene

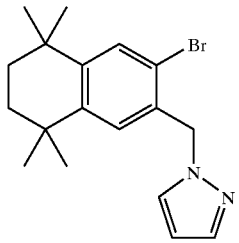

To a suspension of 0.955 g (8.52 mmol) of potassium tert-butoxide and 1.877 g (7.10 mmol) 18-crown-6 ether in 35 ml tetrahydrofuran was added 0.580 g (8.52 mmol) pyrazole. After 10 minutes 2.557 g (7.10 mmol) 2-bromo-5,5,8,8-tetramethyl-3-bromomethyl-5,6,7,8-tetrahydronaphthalene was added in 15 ml THF. After 17 hours the reaction was concentrated under reduced pressure and acidified with 1M hydrochloric acid. The aqueous solution was extracted with ethyl ether, washed with saturated sodium bicarbonate, water, brine, dried over anhydrous sodium sulfate and concentrated in vacuo. The crude material was purified by flash chromatography (gradient elution with hexane-25% ethyl acetate/hexane) to afford 1.185 g (48%) of 2-bromo-5,5,8,8,-tetramethyl-3-((pyrazol-1-yl)methyl)-5,6,7,8-tetrahydronaphthalene (M+1=348).

Step B

Preparation of 2vinyl-3-((pyrazol-1-yl)methyl)-5,5,8,8-tetramethyl-5,6,7,8-tetrahydronaphthalene

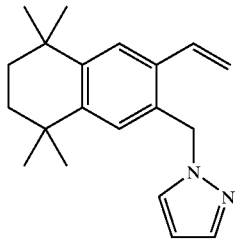

To a suspension of 2.076 g (3.99 mmol) 2-bromo-5,5,8,8,-tetramethyl-3-((pyrazol-1-yl)methyl)-5,6,7,8-tetrahydronaphthalene p-toluenesulfonate, 0.045 g (0.20 mmol) of palladium acetate, 0.122 g (0.40 mmol) of tri-o-tolulylphosphine) and 1.22 ml (7.97 mmol) trimethoxyvinylsilane in 8 ml N-methylpyrrolidinone was added 1.80 ml (12.90 mmol) triethylamine. The reaction vessel was evacuated and filled with nitrogen three times then heated to 90° C. for 1.5 hours. The reaction was cooled and stirred for 17 hours at room temperature. The resulting suspension was quenched with 1M hydrochloric acid and extracted with ethyl ether. The organic layer was washed with 1M HCl, water, brine, dried over anhydrous sodium sulfate and concentrated in vacuo. The residue was purified by flash chromatography (elution with 20% ethyl acetate/hexane) to yield 0.249 g (21%) of 2-vinyl-5,5,8,8,-tetramethyl-3-((pyrazol-1-yl)methyl)-5,6,7,8-tetrahydronaphthalene (M+1=295).

Step C

Preparation of 2-(2-hydroxy)ethyl-3-(pyrazol-1-ylmethyl)-5,5,8,8-tetramethyl-5,6,7,8-tetrahydronaphthalene

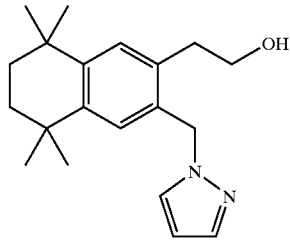

To a solution of 0.249 g (0.85 mmol) of 2-vinyl-5,5,8,8,-tetramethyl-3-(pyrazol-1-ylmethyl)-5,6,7,8-tetrahydronaphthalene in 3 ml tetrahydrofuran was added 1.86 ml (0.93 mmol) of 9-borabicyclo[3.3.1]nonane as a 0.5M solution in THF. The reaction was stirred at room temperature. After 7 hours the solution was quenched with 2 ml water and 4 ml 1M sodium hydroxide. After 15 minutes 10 ml 30% hydrogen peroxide was added and the reaction was stirred at room temperature. After 30 minutes the solution was extracted with ethyl acetate. The organic phase was washed with 10% sodium sulfite, water, brine, dried over anhydrous sodium sulfate and concentrated in vacuo. The residue was purified by flash chromatography (elution with 50% ethyl acetate/hexane) to yield 0.106 g (40%) of 2-(2-hydroxy)ethyl-3-((pyrazol-1-yl)methyl)-5,5,8,8,-tetramethyl-5,6,7,8-tetrahydronaphthalene (M+1=313).

Step D

Preparation of Methyl-4-[2-(5,5,8,8-tetramethyl-3-(pyrazol-1-ylmethyl)-5,6,7,8-tetrahydronaphthalene-2-yl)ethyl]phenoxybenzoate

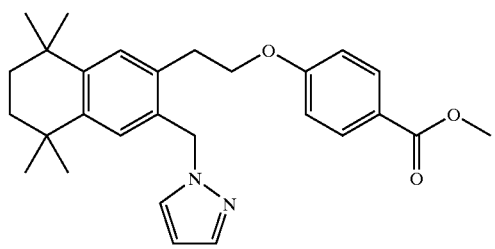

To a solution of 0.106 g (0.34 mmol) of 2-(2-hydroxy) ethyl-3-(pyrazol-1-ylmethyl)-5,5,8,8,-tetramethyl-5,6,7,8-tetrahydronaphthalene, 0.057 g (0.37 mmol) of methyl 4-hydroxybenzoate and 0.097 g (0.37 mmol) triphenylphosphine in 5 ml tetrahydrofuran was added 0.066 g (0.38 mmol) of diethyl azodicarboxylate and the reaction was heated at 70° C. After 2 hours the reaction was cooled to room temperature and quenched with water. The aqueous solution was extracted with ethyl ether, washed with water, brine, dried over anhydrous sodium sulfate and concentrated in vacuo. The crude material was purified by flash chromatography (elution with 30% ethyl acetate/hexane) to afford 0.131 g (86%) of Methyl-4-[2-(5,5,8,8-tetramethyl-3-(pyrazol-1-ylmethyl)-5,6,7,8-tetrahydronaphthalen-2-yl) ethyl]phenoxybenzoate (M+1=447).

Step E

Preparation of 4-[2-(5,5,8,8-tetramethyl-3-(pyrazol-1-ylmethyl)-5,6,7,8-tetrahydronaphthalene-2-yl)ethyl]phenoxy benzoic acid

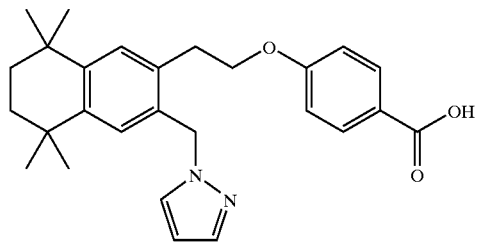

A solution of 0.131 g (0.293 mmol) of Methyl-4-[2-(5,5,8,8-tetramethyl-3-(pyrazol-1-ylmethyl)-5,6,7,8-tetrahydronaphthalen-2-yl)ethyl]phenoxybenzoate in 3 ml 1M LiOH and 10 ml ethyl alcohol was heated to reflux. After 2 hours the reaction was cooled to room temperature and acidified with 1M hydrochloric acid. The aqueous layer was extracted with ethyl ether, washed with brine, dried over anhydrous sodium sulfate and concentrated in vacuo. The crude material was purified by flash chromatography (gradient elution with 10% methanol/dichloromethane-10% methanol/dichloromethane with 5% acetic acid) to afford 0.101 g (79%) of 4-[2-(5,5,8,8-tetramethyl-3-((pyrazol-1-yl)methyl)-5,6,7,8-tetrahydronaphthalen-2-yl)ethyl]phenoxy benzoic acid (M+1=433).

Example 49

Preparation of Methyl-4-[2-5,5,8,8-tetramethyl-3-pyrimidin-2-ylmethyl-5,6,7,8-tetrahydro-naphalen-2-yl)-vinyl]benzoate

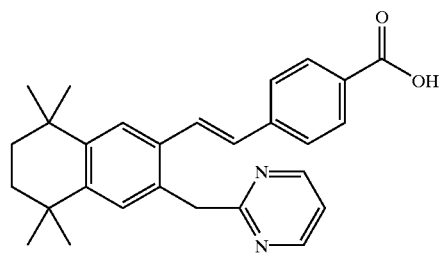

Step A

Preparation of 2-bromo-3-cyanomethylmethyl-5,5,8,8-tetramethyl-5,6,7,8-tetrahydronaphthalene.

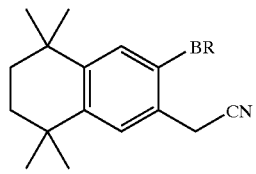

A mixture of 14.2 g (39.4 mmol) of 2-bromo-3-bromomethyl-5,5,8,8-tetramethyl-5,6,7,8-tetrahydronaphthalene (cf Example 5.21, Step A for preparation), 6.15 g (39.4 mmol) of tetraethyl ammonium cyanide in 50 ml of DMF was stirred at room temperature. After 48 h, the reaction was poured into brine and 50 ml of 2 N HCl was added. The mixture was extracted with ethyl acetate, dried (MgSO$_4$), concentrated to dryness and purified by flash chromatography (10% ethyl acetate/hexane) to give 9.2 g (75%) of 2-bromo-3-cyanomethylmethyl-5,5,8,8-tetramethyl-5,6,7,8-tetrahydronaphthalene.

Step B

Preparation of 2-bromo-3-[1,1-(2-pyrimidinyl)-cyano]methyl-5,5,8,8-tetramethyl-5,6,7,8-tetrahydronaphthalene.

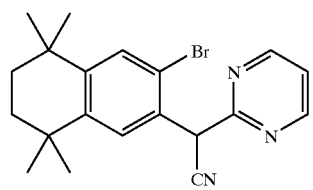

To a slurry of 1.5 g (65.6 mmol) of sodium hydride in 80 ml of DMF in a wet ice bath was added a solution of 9.2 g (29.1 mmol) of 2-bromo-3-cyanomethylmethyl-5,5,8,8-tetramethyl-5,6,7,8-tetrahydronaphthalene in 20 ml of DMF. The reaction was warmed to room temperature. After 1 h, a solution of 10.4 g (65.6 mmol) of 2-bromopyrimidine in 20 ml of DMF was added. After 12 h, the reaction mixture was poured into ice water, neutralized with 2 N HCl and extracted with ethyl acetate. The organic phase was dried (MgSO$_4$), concentrated under vacumn and the product was purified by flash chromatography (15% ethyl acetate/hexane) to afford 5.5 g (47%) of 2-bromo-3-[1,1(2-pyrimidinyl)-cyano]methyl-5,5,8,8-tetramethyl-5,6,7,8-tetrahydronaphthalene.

Step C

Preparation of 2-bromo-3-(2-pyrimidinyl)methyl-5,5,8,8-tetramethyl-5,6,7,8-tetrahydronaphthalene.

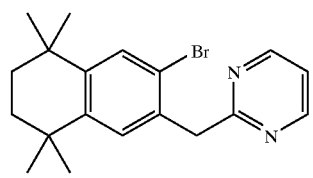

A mixture of 5.5 g (14.3 mmol) of 2-bromo-3-[1,1-(2-pyrimidinyl)-cyano]methyl-5,5,8,8-tetramethyl-5,6,7,8-tetrahydronaphthalene.40 ml concentrated HCl, 20 ml acetic acid and 20 ml of water was heated to reflux. After 15 h, the reaction was poured onto ice, brine added, then extracted with ethyl acetate. The organic phase was dried (MgSO$_4$), concentrated under vacumn and the product purified by flash chromatography (20% ethyl acetate/hexane) to give 2.8 g (54%) of 2-bromo-3-(2-pyrimidinyl)methyl-5,5,8,8-tetramethyl-5,6,7,8-tetrahydronaphthalene.

Step D

Preparation of Methyl-4-[2-5,5,8,8-tetramethyl-3-pyrimidin-2-ylmethyl-5,6,7,8-tetrahydro-naphalen-2-yl)-vinyl]benzoate

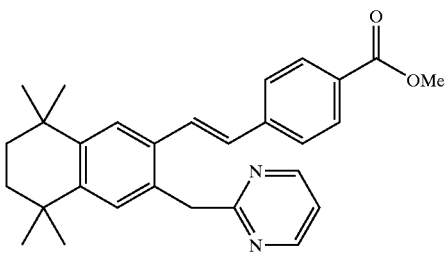

A mixture of 200 mg (0.55 mmol) of 2-bromo-3-(2-pyrimidinyl)methyl-5,5,8,8-tetramethyl-5,6,7,8-tetrahydronaphthalene, 106 mg (0.72 mmol) of vinyltrimethylsilane and 150 μL (1.1 mmol) in 30 ml of NMP was placed under a argon atmosphere and 64 mg (0.22 mmol) of tri-o-tolylphosphine and 24 mg (0.11 mmol) of palladium acetate was added. The reaction was heated to 90. After 2 h, the reaction was cooled to room temperature and 64 mg (0.22 mmol) of tri-o-tolylphosphine, 24 mg of palladium acetate, 106 μl (0.66 mmol) of ethyl-4-bromobenzoate and 900 μL (0.93 mmol) of tetrabutylammonium flouride was added. The reaction mixture was heated at 100. After 6 h, the reaction was cooled to room temperature, poured into brine, extracted with ethyl acetate, dried (MgSO$_4$), concentrated under dryness and purified by flash chromatography (30% ethyl acetate/hexane) to give 38 mg (15%) of Methyl-4-[2-5,5,8,8-tetramethyl-3-pyrimidin-2-ylmethyl-5,6,7,8-tetrahydro-naphalen-2-yl)-vinyl]benzoate. Ester saponification afforded 4-[2-5,5,8,8-tetramethyl-3-pyrimidin-2-ylmethyl-5,6,7,8-tetrahydro-naphthalen-2-yl)-vinyl]benzoic acid (MH$^+$=427).

Example 50

Preparation of Glycerol-4-[(E)-2-(5,5,8,8-tetramethyl-3-pyrzol-1-ylmethyl-5,6,7,8-tetrahydro-naphthalen-2-yl)vinyl]benzoate

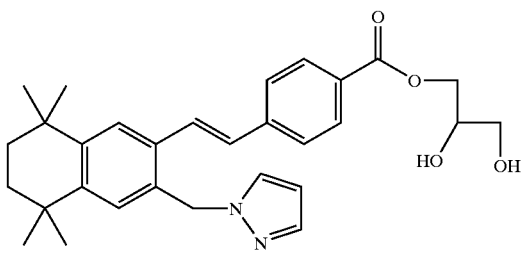

To 200 mg (0.48 mmol) of 4-[(E)-2-(5,5,8,8-tetramethyl-3-pyrzol-1-ylmethyl-5,6,7,8-tetrahydro-naphthalen-2-yl)vinyl]benzoic acid in 30 ml benzene was added 0.17 ml (1.9 mmol) of oxalyl chloride and one drop of diisoproylamine. After 30 minutes, the reaction mixture was concentrated under reduced pressure, additional benzene added and the mixture was concentrated again. The acid chloride was taken up in benzene and added to a mixture of 0.3 ml (2.4 mmol) solketal, 293 mg (2.4 mmol) of DMAP and 0.14 ml (1 mmol) of TEA in benzene. The reaction was stirred at room temperature. After 8 h, the reaction was quenched with 1 N HCl, diluted with brine, the organic layer separated, dried (MgSO$_4$), concentrated under reduced pressure and the product purified by flash chromatography (25% ethyl acetate/hexane). The purified product was taken up in 1:1 methylene chloride, THF and treated with an excess of p-TsOH at room temperature. After 2 h the reaction mixture was concentrated under reduced pressure, diluted with water and extracted with ethyl acetate. The extracts were dried (MgSO$_4$), concentrated under reduced pressure and purified by flash chromatography (5% MeOH/CH$_2$Cl$_2$) to give 62 mg (27%) of Glycerol-4-[(E)-2-(5,5,8,8-tetramethyl-3-pyrzol-1-ylmethyl-5,6,7,8-tetrahydro-naphthalen-2-yl)vinyl]benzoate (MH$^+$=489) 164.

Example 51

Preparation of 4-[(E)-2-(5,5,8,8-tetramethyl-3-pyrzol-1-ylmethyl-5,6,7,8-tetrahydro-naphthalen-2-yl)vinyl]benzamide

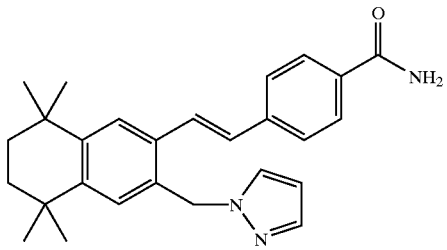

The acid chloride prepared as described in example above for the glycerol ester, on the same scale, in THF, was added to 15 ml concentrated ammonium hydroxide. After 1 h, the reaction mixture was diluted with brine, extracted with EtOAc, dried (MgSO$_4$), concentrated under reduced pressure and purified by flash chromatography (5% methyl alcohol/dichloromethane) to yield 156 mg (78%) of 4-[(E)-2-(5,5,8,8-tetramethyl-3-pyrzol-1-ylmethyl-5,6,7,8-tetrahydro-naphthalen-2-yl)vinyl]benzamide (mp=248–249) 165.

5.52 Example 52: Preparation of 4-[(E)-2-(5,5,8,8-tetramethyl-3-pyrzol-1-ylmethyl-5,6,7,8-tetrahydro-naphthalen-2-yl)vinyl]benzoic acid piperidine amide

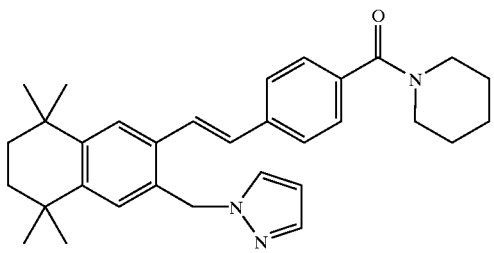

The acid chloride prepared as described in example above for the glycerol ester, on the same scale, in THF, was added to a solution 0.12 ml (1.2 mmol) of piperidine in THF. After 0.5 h, the reaction mixture was diluted with brine, extracted with EtOAc, dried (MgSO$_4$), concentrated under reduced pressure and purified by flash chromatography (60% ethyl acetate/hexane) to yield 125 mg (54%) of 4-[(E)-2-(5,5,8,8-tetramethyl-3-pyrzol-1-ylmethyl-5,6,7,8-tetrahydro-naphthalen-2-yl)vinyl]benzoic acid piperidine amide (mp=171.6–172.5) 166.

Example 53

Preparation of 4-[(E)-2-(3-hexyl-5,5,8,8-tetramethyl-5,6,7,8-tetrahydro-naphthalen-2-yl) vinyl]benzoic acid 2,3-dihydroxy-propylester

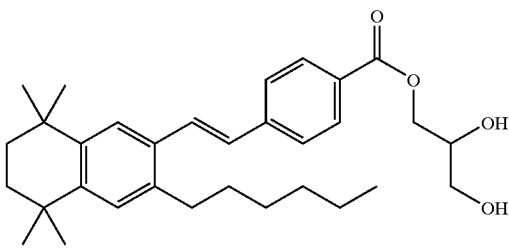

4-](E)-2-(3-Hexyl-5,6,7,8-tetrahydro-5,5,8,8-tetramethyl-2-naphthyl)vinyl]benzoic acid (100 mg) was dissolved in benzene (2.5 ml). To this solution was added oxalyl chloride (44 µl) and dimethylformamide (5 µl) and a rapid outgassing was observed. After the reaction was stirred at room temperature for 1 hour, triethylamine (70 µl) was added followed by a solution of N,N-dimethylaminopyridine (147 mg) and solketal (149 µl) in benzene (3 ml). The reaction mixture was stirred at room temperature overnight. The reaction mixture was acidified with 1M hydrochloric acid and extracted with ethyl ether (2×20 ml). The combined extracts were washed with water, brine, dried and evaporated. The residue was purified by flash chromatography (silica gel, hexane/10% ethyl acetate) to give 97 mg of 4-[(E)-2-(3-hexyl-5,6,7,8-tetrahydro-5,5,8,8-tetramethyl-2-naphthyl)vinyl]benzoic acid 2,24-trimethyl-1,3-dioxalan-4-yl ester as a clear glass. The ester was dissolved in dichoromethane ( 4 ml) and p-toluenesulfonic acid monohydrate (60 mg) was added. The reaction mixture was stirred at room temperature overnight, diluted with water and extracted with ethyl ether. The organic layer was washed with water, 10% sodium bicarbonate, brine, dried and concentrated in vacuo. The crude yellow oil was purified by flash chromatography (silica gel, $CH_2Cl_2$/6% MeOH) to give 49 mg E)-2-(3-hexyl-5,6,7,8-tetrahydro-5,5,8,8-tetramethyl-2-naphthyl)vinyl] benzoic acid 2,3-dihydroxy-propyl ester 56 as a clear glass in 42% yield. ($M^+$492.) 56.

Example 54

Binding Affinity to Retinoid Receptors

The RAR α antagonist selectivity of compounds of the invention was determined by the ligand binding assays described in C. Apfel et al. *Proc. Nat. Sci. Acad. (USA),* 89:7129–7133 (1992). Data for selected compounds from Table 1 are shown below.

| Compound Number | IC50 nM (alpha/beta/gamma) |
| --- | --- |
| 1 | 3600/1600/1700 |
| 2 | 1000/320/190 |
| 3 | 200/100/260 |
| 7 | 260/140/17 |
| 8 | 810/450/26 |
| 11 | 1800/1400/210 |
| 15 | 1000/1000/1800 |
| 20 | 950/620/670 |
| 25 | 190/100/230 |

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

All patents, patent applications and publications cited in this application are hereby incorporated by reference in their entirety for all purposes to the same extent as if each individual patent, patent application or publication were so individually denoted.

What is claimed is:

1. A compound according to structural formula (I):

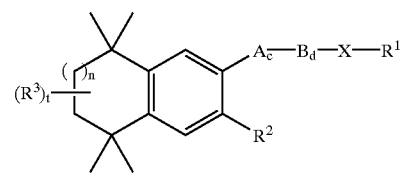

or a pharmaceutically acceptable salt, solvate, hydrate or prodrug thereof wherein:

n is an integer from 0 to 2;

c is 0 or 1;

d is 0 or 1;

A is —C(=O)—, —C($CH_2$)—, —C(=$NR^4$)— or —$CR^5R^6$—;

$R^4$ is hydrogen, alkyl, hydroxy, alkoxy or amino; and $R^5$ and $R^6$ are independently hydrogen, alkyl or $R^5$ and $R^6$ together with the carbon to which they are both attached are a cyclic hydrocarbon of three to seven ring carbons;

B is —C(O)O—, —OC(O)—, —C(O)NH—, —NHC(O)—, —NHC(O)NH—, —$CR^7$=$CR^8$—, —$R^7$C=$CR^8$—C(O)—, —C≡C—, —C≡C—C(O)—, —$CH_2$O—, —$CH_2$S—, —O$CH_2$—, —S$CH_2$—, —CO$CH_2$—, or —$CH_2$CO—;

$R^7$ and $R^8$ are independently hydrogen or alkyl;

with the provisos that:
    when A is —C(=O)—, or —C(=$NR^4$)—, then B is not —OC(O)—; and
    when A is —C(=$CH_2$)—, then B is not —OC(O)—;

X is aryl or a mono- or bicyclic heteroaryl radical said heteroaryl radical containing 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring, said heteroaryl ring being optionally substituted independently with one or more substituents selected from the group consisting of:

(i) acyl,
(ii) acylamino,
(iii) alkyl,
(iv) alkoxycarbonyl,
(v) alkyamino,
(vi) alkylsulfinyl,
(vii) alkylsulfonyl,
(viii) —$SO_2$NR'R" (where R' and R" are independently hydrogen or alkyl),
(ix) alkylthio,
(x) alkoxy,
(xi) amino,
(xii) aryloxy, (xiii) carbamoyl,
(xiv) cyano,
(xv) dialkylamino,
(xvi) ethylenedioxy,
(xvii) halo,
(xviii) thio,
(xix) haloalkyl,
(xx) a heterocycle wherein said heterocycle is a saturated or unsaturated non-aromatic cyclic radical of 3 to 8 ring atoms in which one or two ring atoms are heteroatoms selected from N, O, or S(O)$_n$(where n is an integer from 0 to 2), the remaining ring atoms being C, where one or two C atoms may optionally be replaced by a carbonyl group, said heterocycle may be optionally substituted independently with one, two, or three substituents selected from alkyl, haloalkyl, heteroalkyl, halo, nitro, cyanoalkyl, hydroxy, alkoxy, amino, monoalkylamino, dialkylamino, arylalkyl, —(X)$_n$—C(O)R, -alkylene-C(O)R (where X is O or NR', n is 0 or 1, R is hydrogen, alkyl, haloalkyl, hydroxy, alkoxy, amino, monoalkylamino, dialkylamino or optionally substituted phenyl) or —S(O)$_n$R$^d$ (where n is an integer from 0 to 2, and R$^d$ is hydrogen (provided that n is 0), alkyl, haloalkyl, cycloalkyl, cycloalkyl-alkyl, amino, monoalkylamino, dialkylamino, or hydroxyalkyl,
(xxi) hydroxy,
(xxii) hydroxyalkyl,
(xxiii) methylenedioxy,
(xxiv) nitro, and
(xxv) heteroalkyl wherein said heteroalkyl is an alkyl radical wherein one or more hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkyl-alkyl; R$^b$ and R$^c$ are independently of each other hydrogen, acyl, alkyl, cycloalkyl, or cycloalkyl-alkyl; and when n is 0, R$^d$ is hydrogen, alkyl, cycloalkyl, or cycloalkyl-alkyl, and when n is 1 or 2, R$^d$ is alkyl, cycloalkyl, cycloalkyl-alkyl, amino, acylamino, monoalkylamino, or dialkylamino;

R$^1$ is —C(=O)—R$^9$;
  R$^9$ is (i) alkyl,
    (ii) cycloalkyl,
    (iii) cycloalkyl-alkyl radical —R$^a$R$^b$ where R$^a$ is an alkylene group and R$^b$ is a cycloalkyl group,
    (iv) hydroxy,
    (v) alkoxy,
    (vi) aryloxy,
    (vii) cycloalkyloxy, —OR wherein R is a saturated monovalent cyclic hydrocarbon radical of three to seven ring carbons,
    (viii) cycloalkyl-alkyloxy R$^a$OR$^b$ wherein R$^a$ is alkylene and R$^b$ is cycloalkyl,
    (ix) arylalkyloxy,
    (x) amino,
    (xi) alkylamino,
    (xii) dialkylamino,
    (xiii) heteroalkyloxy, —OR wherein R is alkyl wherein one or more hydrogen atoms of an alkyl group have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, R$^a$ is hydrogen, acyl, alkyl, cycloalkyl, or cycloalkyl-alkyl; R$^b$ and R$^c$ are independently of each other hydrogen, acyl, alkyl, cycloalkyl, or cycloalkyl-alkyl; and when n is 0, R$^d$ is hydrogen, alkyl, cycloalkyl, or cycloalkyl-alkyl, and when n is 1 or 2, R$^d$ is alkyl, cycloalkyl, cycloalkyl-alkyl, amino, acylamino, monoalkylamino, or dialkylamino,
    (xiv) heteroalkylamino, —NHR wherein R is as defined above for heteroalkoxy in xiii,
    (xv) heteroalkylthio, —SR wherein R is as defined above for heteroalkoxy in (xiii),
    (xvi) heterocycle, said heterocycle comprising a three to eight atom saturated or unsaturated non-aromatic cyclic radical in which one or two ring atoms are heteroatoms selected from N, O, or S(O)$_n$ (where n is an integer from 0 to 2), the remaining ring atoms being C, where one or two C atoms may optionally be replaced by a carbonyl group, said heterocyclyl group may be optionally substituted independently with one, two, or three substituents selected from alkyl, haloalkyl, heteroalkyl, halo, nitro, cyanoalkyl, hydroxy, alkoxy, amino, monoalkylamino, dialkylamino, arylalkyl, —(X)$_n$—C(O)R, -alkylene-C(O)R (where X is O or NR', n is 0 or 1, R is hydrogen, alkyl, haloalkyl, hydroxy, alkoxy, amino, monoalkylamino, dialkylamino or optionally substituted phenyl and R' is H or alkyl) or —S(O)$_n$R$^d$ (where n is an integer from 0 to 2, and R$^d$ is hydrogen (provided that n is 0), alkyl, haloalkyl, cycloalkyl, cycloalkyl-alkyl, amino, monoalkylamino, dialkylamino, or hydroxyalkyl), or
    (xvii) heterocyclylalkyl radical —R$^a$R$^b$ where R$^a$ is an alkylene group and R$^b$ is a heterocycle as defined for (xvi) above; and, R$^2$ is:
  (a) —(CR$^{10}$R$^{11}$)$_m$—Y$_p$—R$^{12}$;
    m is an integer from 1 to 10;
    p is 0 or 1;
    R$^{10}$ and R$^{11}$ are independently hydrogen, alkyl, hydroxy or hydroxyalkyl;
    Y is —O—, —S(O)$_q$— or —NR$^{13}$—; and
    q is an integer from 0 to 2; and
    R$^{13}$ is hydrogen or alkyl;
  R$^{12}$ is (i) hydrogen,
    (ii) alkyl,
    (iii) a monovalent cyclic hydrocarbon radical of three to seven ring carbons,
    (iv) cycloalkyl-alkyl radical R$^a$R$^b$ where R$^a$ is an alkylene group and R$^b$ is a monovalent cyclic hydrocarbon radical of three to seven ring carbons,
    (v) aryl,
    (vi) arylalkyl, (vii) heteroaryl wherein said heteroaryl radical is a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring, said heteroaryl radical optionally substituted independently with one or more substituents selected from acyl, acylamino, alkyl, alkoxycarbonyl, alkyamino, alkylsulfinyl, alkylsulfonyl, —SO$_2$NR'R" (where R' and R" are independently hydrogen or alkyl), alkylthio, alkoxy, amino, aryloxy, carbamoyl, cyano, dialkylamino, ethylenedioxy, halo, haloalkyl, heteroalkyl, heterocyclyl, hydroxy, hydroxyalkyl, methylenedioxy, nitro and thio, (viii) heteroarylalkyl wherein said heteroarylalkyl is an alkyl radical wherein one of the hydrogens of an alkyl group has been replaced by a heteroaryl radical as defined in (vii), (ix) acyl, (x) alkoxycarbonyl, (xi) carbamoyl, (xii) heteroalkyl wherein said heteroalkyl is an alkyl moiety wherein wherein one or more hydrogen atoms of an alkyl moiety have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkyl-alkyl; R$^b$ and R$^c$ are independently of each other hydrogen, acyl, alkyl, cycloalkyl, or cycloalkyl-alkyl; and when n is 0, R$^d$ is hydrogen, alkyl, cycloalkyl, or cycloalkyl-alkyl, and when n is 1 or 2, R$^d$ is alkyl, cycloalkyl, cycloalkyl-alkyl, amino, acylamino, monoalkylamino, or dialkylamino, (xiii) heteroalkylsubstituted cycloalkyl wherein one, two or three hydrogen atoms of a cycloalkyl radical have been independently replaced with a heteroalkyl group with the understanding that the heteroalkyl group as defined in (xii) above is attached to the cycloalkyl radical via a carbon-carbon, (xiv) heterosubstituted cycloalkyl wherein one, two or three hydrogen atoms of a C$_{3-7}$ monovalent cyclic hydrocarbon radical have been replaced with a substituent independently selected from the group consisting of hydroxy, alkoxy, amino, acylamino, monoalkylamino, dialkylamino, oxo (C=O), imino, hydroxyamino (=NOH), NR'SO$_2$R$^d$ (where R' is hydrogen or alkyl and R$^d$ is alkyl, cycloalkyl, amino, monoalkylamino or dialkylamino) and —X—C(O)R (where X is O or NR', R is hydrogen, alkyl, haloalkyl, hydroxy, alkoxy, amino, monoalkylamino, dialkylamino, or optionally substituted phenyl, and R' is H or alkyl) or —S(O)$_n$R (where n is an integer from 0 to 2) such that when n is 0, R is hydrogen, alkyl, cycloalkyl, or cycloalkyl-alkyl, and when n is 1 or 2, R is alkyl, cycloalkyl, cycloalkyl-alkyl, amino, acylamino, monoalkylamino or dialkylamino, (xv) a heterosubstituted cycloalkyl-alkyl radical —R$^a$R$^b$ where R$^a$ is an alkylene group and R$^b$ is heterosubstituted cycloalkyl as defined in (xiv), (xvi) heterocycle, said heterocycle comprising a three to eight atom saturated or unsaturated non-aromatic cyclic radical in which one or two ring atoms are heteroatoms selected from N, O, or S(O)$_n$ (where n is an integer from 0 to 2), the remaining ring atoms being C, where one or two C atoms may optionally be replaced by a carbonyl group, said heterocyclyl group may be optionally substituted independently with one, two, or three substituents selected from alkyl, haloalkyl, heteroalkyl, halo, nitro, cyanoalkyl, hydroxy, alkoxy, amino, monoalkylamino, dialkylamino, arylalkyl, —(X)$_n$—C(O)R, -alkylene-C(O)R (where X is O or NR', n is 0 or 1, R is hydrogen, alkyl, haloalkyl, hydroxy, alkoxy, amino, monoalkylamino, dialkylamino or optionally substituted phenyl and R' is H or alkyl) or —S(O)$_n$R$^d$ (where n is an integer from 0 to 2, and R$^d$ is hydrogen (provided that n is 0), alkyl, haloalkyl, cycloalkyl, cycloalkyl-alkyl, amino, monoalkylamino, dialkylamino, or hydroxyalkyl), or (xvii) heterocyclylalkyl wherein said heterocyclylalkyl is a radical —R$^a$R$^b$ where R$^a$ is an alkylene group and R$^b$ is heterocycle as defined in (xvi), with the proviso that when p=0, then R$^{12}$ is not hydrogen or alkyl;

(b) heteroaryl wherein said heteroaryl radical is a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring, said heteroaryl radical optionally substituted independently with one or more substituents selected from acyl, acylamino, alkyl, alkoxycarbonyl, alkyamino, alkylsulfinyl, alkylsulfonyl, —SO$_2$NR'R" (where R' and R" are independently hydrogen or alkyl), alkylthio, alkoxy, amino, aryloxy, carbamoyl, cyano, dialkylamino, ethylenedioxy, halo, haloalkyl, heteroalkyl, heterocyclyl, hydroxy, hydroxyalkyl, methylenedioxy, nitro and thio;

(c) —Z—L;

Z is —CR$^{14}$=CR$^{15}$—, —C≡C—, —O—, —NR$^{16}$—, C(=O) or —S(O)$_q$—;

R$^{14}$, R$^{15}$ and R$^{16}$ are independently hydrogen or alkyl; and

L is (i) heteroaryl as defined in (b) above, (ii) heteroarylalkyl as defined for (viii) of R$^{12}$ above, (iii) heteroalkyl as defined above for (xii) of R$^{12}$, with the added proviso that when Z is O and L is heteroalkyl, R$^a$ is other than alkyl;

with the proviso that when A$_c$—B$_d$ is —C(=O)—CR$^7$=CR$^8$—, then L is not heteroalkyl; or (d) —CR$^{14}$=CR$^{15}$—L$_1$ where L$_1$ is S(O)$_2$R$^{17}$ or SO$_2$NR$^{18}$R$^{19}$ where R$^{17}$ is alkyl and R$^{19}$ are independently hydrogen or alkyl;

each R$^3$ is independently hydrogen, alkyl, hydroxy or oxo; and t is 1 or 2.

2. The compound of claim 1, wherein n is 1 and R$^3$ is hydrogen.

3. The compound of claim 1, wherein A is —C(=O)— and R$^3$ is hydrogen.

4. The compound of claim 1, wherein c is 0 and R$^3$ is hydrogen.

5. The compound of claim 4, wherein B is —NHC(O)NH—, —CR$^7$=CR$^8$—, —R$^7$C=CR$^8$—C(O)—, —C≡C—, —C≡C—C(O)— or —CH$_2$O—.

6. The compound of claim 5, wherein B is trans —CH=CH—.

7. The compound of claim 1, wherein X is phenyl or thienyl.

8. The compound of claim 7, wherein c is 0 and $R^3$ is hydrogen.

9. The compound of claim 1, wherein $R^3$ is hydrogen.

10. The compound of claim 9, wherein c is 0 and B is trans —CH=CH—.

11. The compound of claim 10, wherein $R^9$ is hydroxy.

12. The compound of claim 1, wherein $R^9$ is hydroxy.

13. The compound of claim 1, wherein $R^2$ is —(CR$^{10}$-R$^{11}$)$_m$—Y$_p$—R$^{12}$.

14. The compound of claim 13, wherein $R^{10}$ and $R^{11}$ are hydrogen.

15. The compound of claim 13, wherein m is 1 to 4.

16. The compound of claim 13, wherein p is 1.

17. The compound of claim 13, wherein p is 0.

18. The compound of claim 13, wherein m is 1, p is 1 and $R^{10}$ and $R^{11}$ are independently hydrogen or alkyl.

19. The compound of claim 18, wherein Y is —O—.

20. The compound of claim 19, wherein $R^{12}$ is hydrogen, acyl, alkyl, carbamoyl, cycloalkyl, aryl, heteroaryl or heteroalkyl.

21. The compound of claim 20, wherein c is zero, d is 1, B is trans —CH=CH—, and —X—$R^1$ is 4-carboxyphenyl.

22. The compound of claim 21 having the formula:

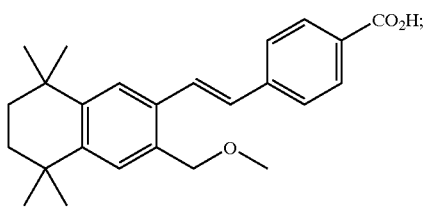

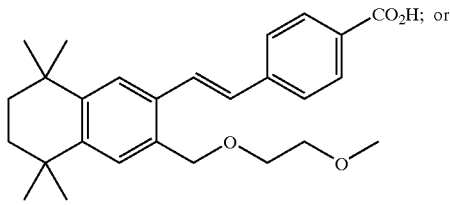

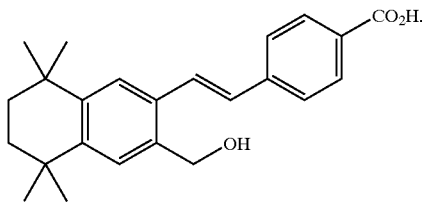

23. The compound of claim 18, wherein Y is —S(O)$_q$—.

24. The compound of claim 23, wherein $R^{12}$ is alkyl, cycloalkyl, heteroalkyl or heterocyclylalkyl.

25. The compound of claim 24, wherein c is zero, d is 1, B is trans —CH=CH—, and —X—$R^1$ is 4-carboxyphenyl.

26. The compound of claim 23 having the formula:

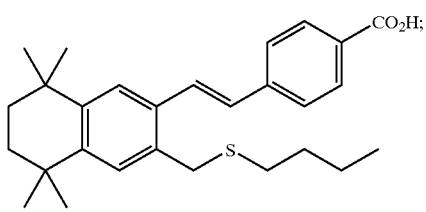

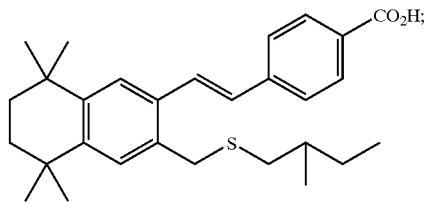

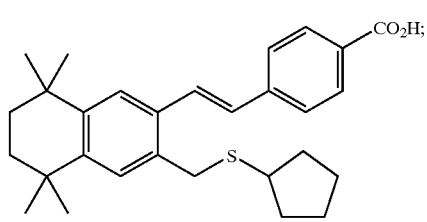

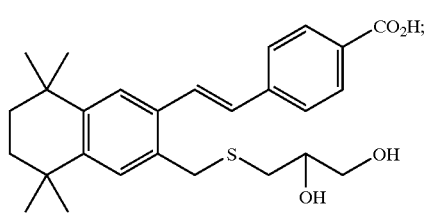

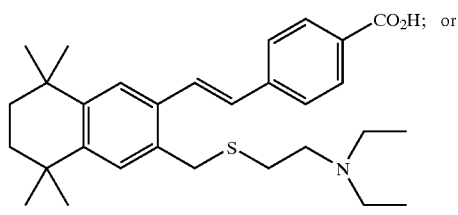

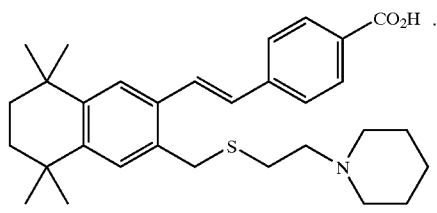

27. The compound of claim 23 wherein $R^{12}$ is heteroaryl, heteroarylalkyl, heterocyclyl or heterocyclylalkyl.

28. The compound of claim 27, wherein c is zero, d is 1, B is trans —CH=CH—, and —X—$R^1$ is 4-carboxyphenyl.

29. The compound of claim 28 having the formula:

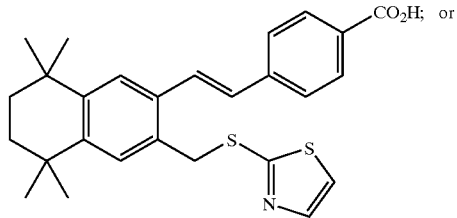

-continued

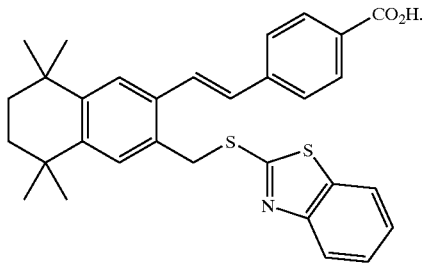

30. The compound of claim 13, wherein m is 3, p is 1 and $R^{10}$ and $R^{11}$ are independently hydrogen or alkyl.
31. The compound of claim 30, wherein Y is —O—.
32. The compound of claim 31, wherein $R^{12}$ is hydrogen, acyl, alkyl, carbamoyl, cycloalkyl, aryl, heteroaryl or heteroalkyl.
33. The compound of claim 32, wherein c is zero, d is 1, B is trans —CH=CH—, and —X—$R^1$ is 4-carboxyphenyl.
34. The compound of claim 33 having the formula:

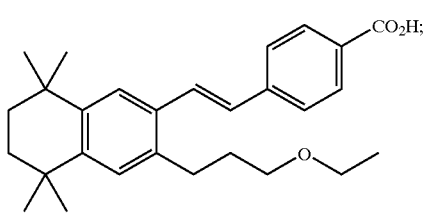

10

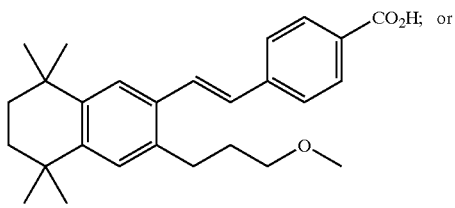

11

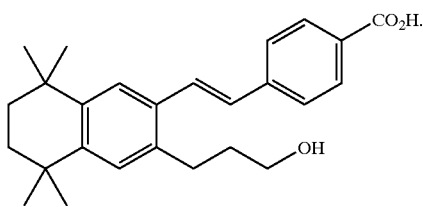

12

35. The compound of claim 30, wherein Y is —$NR^{13}$—.
36. The compound of claim 35, wherein $R^{12}$ is acyl, alkyl, cycloalkyl, aryl, heteroaryl or heterocyclyl.
37. The compound of claim 36, wherein c is zero, d is 1, B is trans —CH=CH—, and —X—$R^1$ is 4-carboxyphenyl.
38. The compound of claim 37 having the formula:

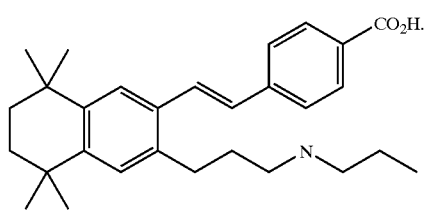

33

39. The compound of claim 30, wherein Y is —$S(O)_q$—.

40. The compound of claim 39, wherein $R^{12}$ is aryl, arylalkyl, heteroaryl, heteroalkyl, heterocyclyl or heterocyclylalkyl.
41. The compound of claim 40, wherein c is zero, d is 1, B is trans —CH=CH—, and —X—$R^1$ is 4-carboxyphenyl.
42. The compound of claim 41 having the formula:

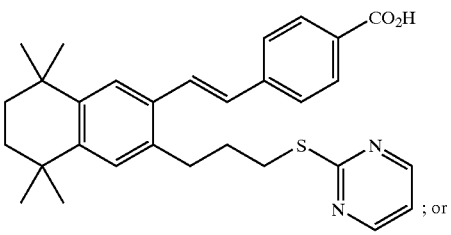

24

; or

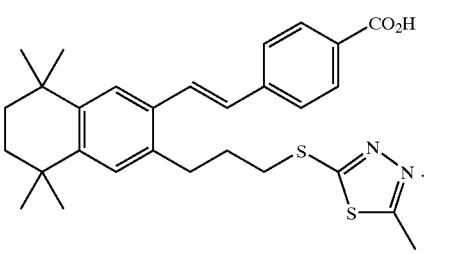

28

43. The compound of claim 13, wherein m is 2, p is 1 and $R^{10}$ and $R^{11}$ are independently hydrogen or alkyl.
44. The compound of claim 43, wherein Y is —O—.
45. The compound of claim 44, wherein $R^{12}$ is hydrogen, acyl, alkyl, carbamoyl, cycloalkyl, aryl, heteroaryl or heteroalkyl.
46. The compound of claim 45, wherein c is zero, d is 1, B is trans —CH=CH—, and —X—$R^1$ is 4-carboxyphenyl.
47. The compound of claim 46 having the formula:

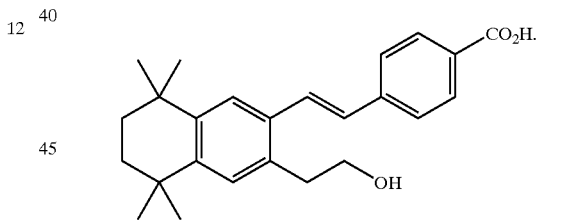

31

48. The compound of claim 43, wherein Y is —$S(O)_q$—.
49. The compound of claim 48, wherein $R^{12}$ is aryl, arylalkyl, heteroaryl heteroarylalkyl, heterocyclyl or heterocyclylalkyl.
50. The compound of claim 49, wherein c is zero, d is 1, B is trans —CH=CH—, and —X—$R^1$ is 4-carboxyphenyl.
51. The compound of claim 50 having the formula:

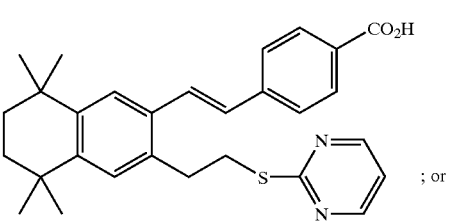

26

; or

27

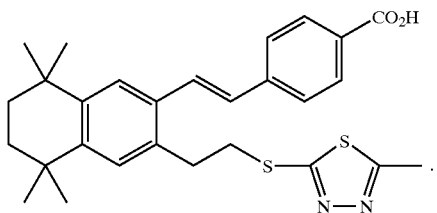

52. The compound of claim 13, wherein m is 4, p is one and $R^{10}$ and $R^{11}$ are independently hydrogen or alkyl.

53. The compound of claim 52, wherein Y is —O— and $R^{12}$ is hydrogen, acyl, alkyl, carbamoyl, cycloalkyl, aryl, heteroaryl or heteroalkyl.

54. The compound of claim 53, wherein c is zero, d is 1, B is trans —CH=CH—, and —X—$R^1$ is 4-carboxyphenyl.

55. The compound of claim 54 having the formula:

51

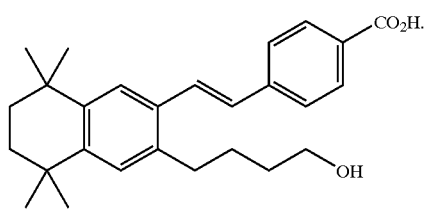

56. The compound of claim 13, wherein m is 1, p is 0 and $R^{10}$ and $R^{11}$ are independently hydrogen or alkyl.

57. The compound of claim 56, wherein $R^{12}$ is heteroaryl, heteroarylalkyl, heterocyclyl or heterocyclylalkyl.

58. The compound of claim 57, wherein c is zero, d is 1, B is trans —CH=CH—, and —X—$R^1$ is 4-carboxyphenyl.

59. The compound of claim 58 having the formula:

47

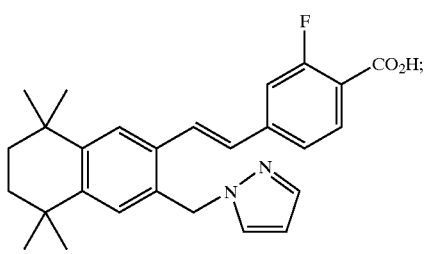

45

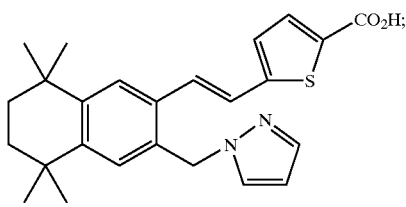

44

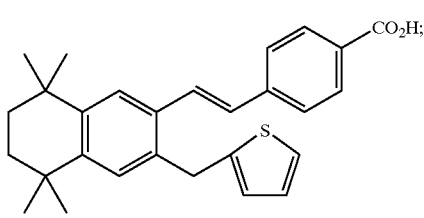

50

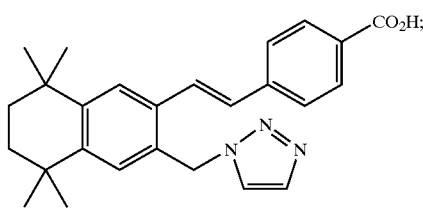

54

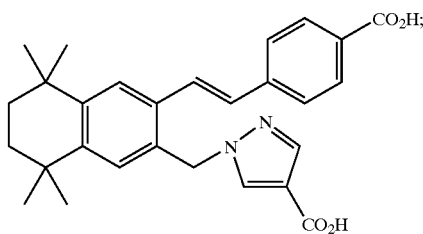

53

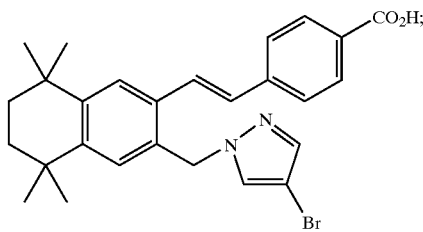

6

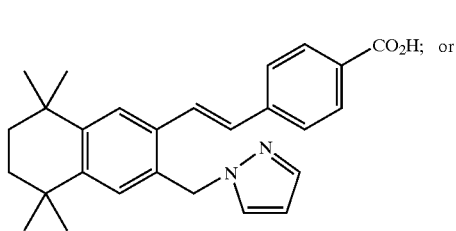

7

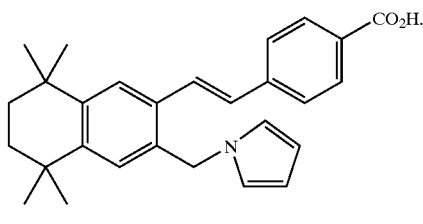

60. The compound of claim 59 having the formula:

6

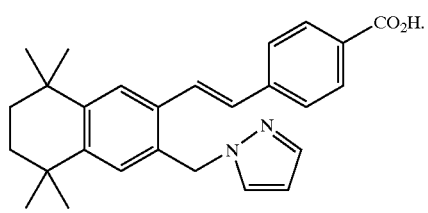

61. The compound of claim 56, wherein $R^{12}$ is aryl, arylalkyl, cycloalkyl or substituted cycloalkyl.

62. The compound of claim 61, wherein c is zero, d is 1, B is trans —CH=CH—, and —X—$R^1$ is 4-carboxyphenyl.

63. The compound of claim 62 having the formula:

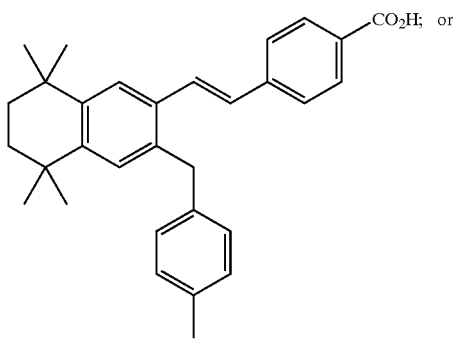
42

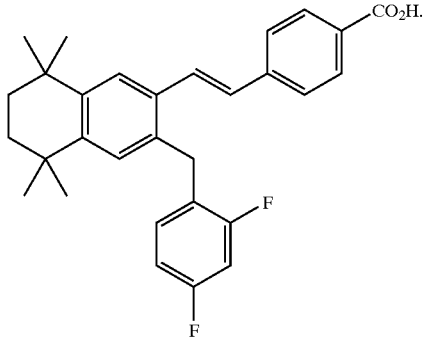
43

64. The compound of claim 13, wherein m is 2, p is 0 and $R^{10}$ and $R^{11}$ are independently hydrogen or alkyl.

65. The compound of claim 64, wherein $R^{12}$ is aryl, arylalkyl, heteroaryl, heteroarylalkyl, heteroalkyl, heterocyclyl or heterocyclylalkyl.

66. The compound of claim 61, wherein c is zero, d is 1, B is trans —CH=CH—, and —X—$R^1$ is 4-carboxyphenyl.

67. The compound claim 64 having the formula:

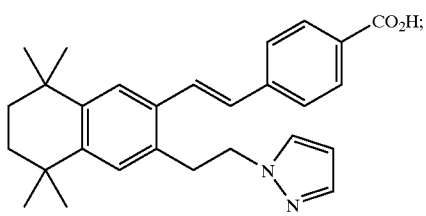
29

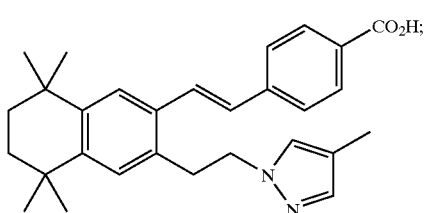
38

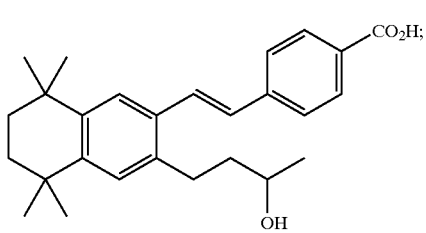
37

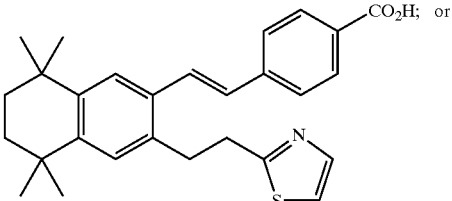
40

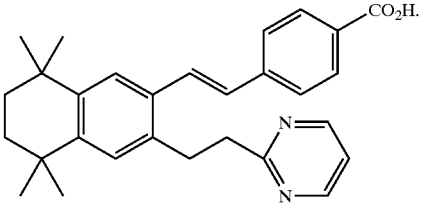
41

68. The compound of claim 13, wherein m is 3; p is 0 and $R^{10}$ and $R^{11}$ are independently hydrogen or alkyl.

69. The compound of claim 68, wherein $R^{12}$ is aryl, arylalkyl, heteroaryl, heteroarylalkyl, heterocyclyl or heterocyclylalkyl.

70. The compound of claim 69, wherein c is zero, d is 1, B is trans —CH=CH—, and —X—$R^1$ is 4-carboxyphenyl.

71. The compound of claim 70 having the formula:

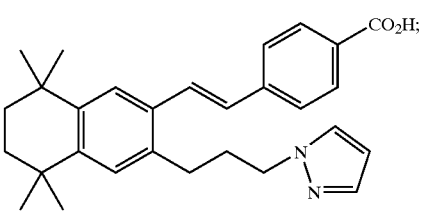
30

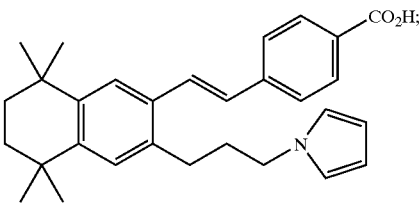
36

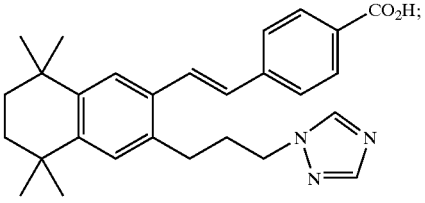
46

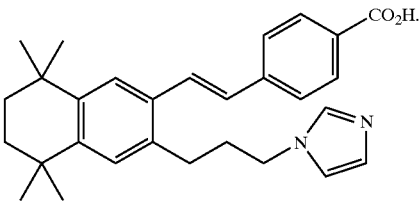
52

72. The compound of claim 4, wherein $R^2$ is heteroaryl.

73. The compound of claim 72, wherein c is zero, d is 1, B is trans —CH=CH—, and —X—$R^1$ is 4-carboxyphenyl.

74. The compound of claim 73 having the formula:

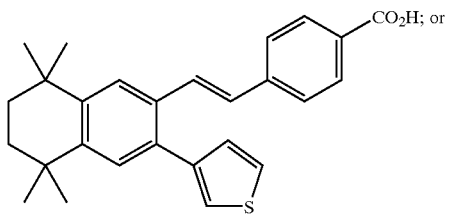

75. The compound of claim 1, wherein $R^2$ is —Z-heteroaryl, —Z-heteroarylalkyl or —Z-heteroalkyl.

76. The compound of claim 75, wherein $R^2$ is —Z-heteroaryl or —Z-heteroarylalkyl.

77. The compound of claim 76, wherein Z is —O—, —C(=O)— or —S(O)$_q$—.

78. The compound of claim 77, wherein c is zero, d is 1, B as trans —CH=CH—, and —X—$R^1$ is 4-carboxyphenyl.

79. The compound of claim 78 having the formula:

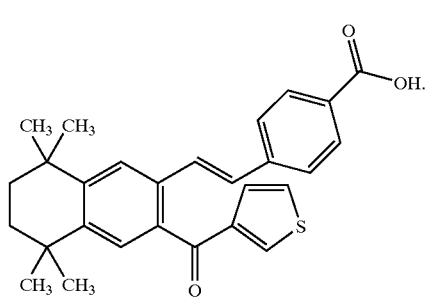

80. The compound of claim 1, wherein c is 0, d is 1 and B is —$CR^7$=$CR^8$—.

81. The compound of claim 80, wherein B is trans —CH=CH—.

82. The compound claim 81, wherein X is aryl.

83. The compound of claim 1 having the structural formula (V): where $R^1$ is —$CO_2H$ and $R^3$ is hydrogen:

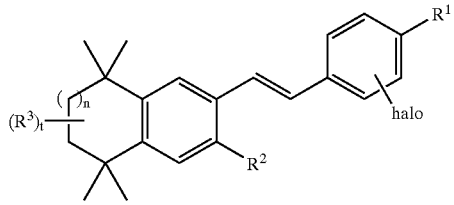

84. The compound of claim 1 having the structural formula (VI):

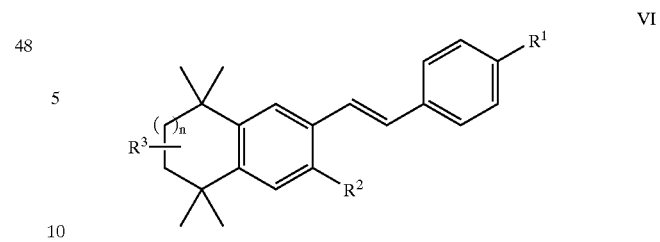

where $R^1$ is —$CO_2H$ and $R^3$ is hydrogen.

85. The compound of claim 81, wherein X is heteroaryl.

86. The compound of claim 1 having the structural formula (VII):

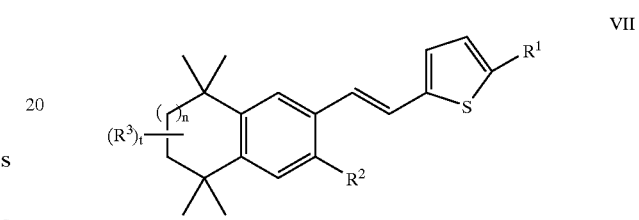

wherein $R^1$ is is —$CO_2H$ and $R^3$ is hydrogen.

87. A compound having the structural formula (VIII):

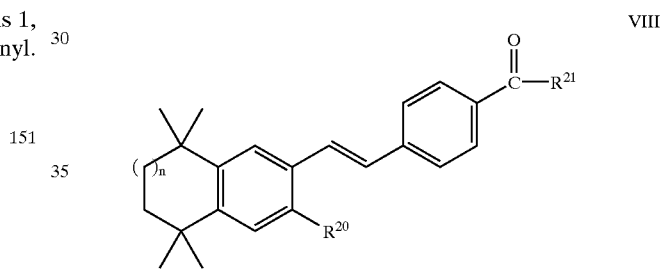

wherein:

$R^{20}$ is alkyl or heteroalkyl wherein one or more hydrogen atoms of an alkyl radical have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkyl-alkyl; $R^b$ and $R^c$ are independently of each other hydrogen, acyl, alkyl, cycloalkyl, or cycloalkyl-alkyl; and when n is 0, $R^d$ is hydrogen, alkyl, cycloalkyl, or cycloalkyl-alkyl, and when n is 1 or 2, $R^d$ is alkyl, cycloalkyl, cycloalkyl-alkyl, amino, acylamino, monoalkylamino, or dialkylamino;

$R^{21}$ is:(a) —$OR^{20}$, —$NHR^{20}$ or —$SR^{20}$ wherein $R^{20}$ is heteroalkyl; or, (b) Q—$R^{22}$ where Q is —O—, —$NR^{23}$— or —S— (where $R^{23}$ is hydrogen or alkyl) and $R^{22}$ is carboxyalkyl;

and n is an integer from 0 to 2.

88. The compound of claim 87 where $R^{20}$ is n-pentyl, $R^{21}$ is heteroalkyloxy and n is 1.

89. A method of treating COPD in a mammal comprising administering to a mammal in need of such treatment a therapeutically effective amount of a compound of claim 1, or a pro-drug thereof, sufficient to alleviate at least one symptom of COPD.

90. The method of claim 89, wherein the COPD is chronic bronchitis or asthma.

91. The method of claim 89, wherein the COPD is emphysema.

92. A method of treating an epithelial cancer in a mammal comprising administering to a mammal in need of such treatment a therapeutically effective amount of a compound of claim 1, or a pro-drug thereof said therapeutically effective amount amount being sufficient to allieviate at least one symptom of said epithelial cancer.

93. A method of treating a dermatological disorder selected from the group consisting of photo-aged skin, psoriasis, seborrhea, acne, acneiform dermatoses, abnormal keratinisation, basal cell carcinoma and cutaneous T-cell lymphoma in a mammal comprising administering to a mammal in need of such treatment a therapeutically effective amount of a compound of claim 1, or a pro-drug thereof said therapeutically effective amount being sufficient to allieviate at least one symptom of said dermatological disorder.

94. A pharmaceutical composition suitable for treating a mammal suffering from emphysema comprising an amount of a compound of claim 1 or a pro-drug thereof, and a pharmaceutically acceptable carrier, said amount being sufficient to alleviate one symptom of emphysema.

95. A pharmaceutical composition suitable for treating a mammal suffering from cancer comprising an amount of a compound of claim 1 or a pro-drug thereof, and a pharmaceutically acceptable carrier, said amount being sufficient to alleviate at least one symptom of cancer.

96. A pharmaceutical composition suitable for treating a mammal suffering from a dermatological disease comprising an amount of a compound of claim 1 or a pro-drug thereof, and a pharmaceutically acceptable carrier, said amount being sufficient to alleviate at least one symptom of the dermatological disease.

97. A method for treating emphysema, chronic bronchitis or asthma in a mammal comprising delivering by orally administering to said mammal a therapeutically effective amount of a compound of claim 1, or a pro-drug thereof, said therapeutically effective amount being sufficient to allieviate at least one symptom of emphysema, chronic bronchitis or asthma.

98. A method of preparing a compound of Formula VI, where m is 1, $R^1$ is $CO_2H$ or $CO_2$-alkyl, $R^2$ is $-(CR^{10}-R^{11})_m-R^{12}$, $R^{10}$ and $R^{11}$ are independently hydrogen, alkyl, hydroxy or hydroxyalkyl and $R^{12}$ is heteroaryl

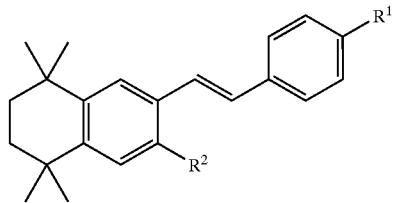

VI comprising: treating a compound of Formula VII

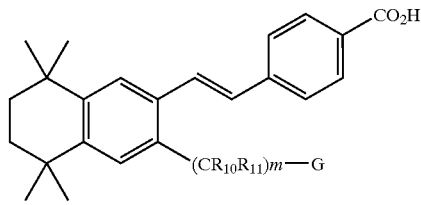

where G is a leaving group with a nucleophile; and when $R^1$ is $CO_2$-alkyl, subsequently hydrolyzing the ester with a base.

* * * * *